US012586325B1

(12) United States Patent
Morgan et al.

(10) Patent No.: US 12,586,325 B1
(45) Date of Patent: Mar. 24, 2026

(54) XR HEALTH PLATFORM, SYSTEM AND METHOD

(71) Applicant: Wellovate, LLC, Boone, NC (US)

(72) Inventors: Joseph W. Morgan, Blowing Rock, NC (US); Nunzio Peter Pagano, II, Asheville, NC (US); Allen Ronald Rufolo, Charlotte, NC (US); Rahul A. Patel, Huntersville, NC (US); Jonathan Jackson, Charlotte, NC (US)

(73) Assignee: Wellovate, LLC, Boone, NC (US)

( * ) Notice: Subject to any disclaimer, the term of this patent is extended or adjusted under 35 U.S.C. 154(b) by 162 days.

(21) Appl. No.: 18/636,841

(22) Filed: Apr. 16, 2024

Related U.S. Application Data

(63) Continuation of application No. 18/127,332, filed on Mar. 28, 2023, now Pat. No. 11,961,197, which is a
(Continued)

(51) Int. Cl.
| | |
|---|---|
| *G06T 19/00* | (2011.01) |
| *G16H 10/60* | (2018.01) |
| *G16H 20/00* | (2018.01) |
| *G16H 30/20* | (2018.01) |
| *G16H 30/40* | (2018.01) |
| *G16H 40/63* | (2018.01) |
| *G16H 50/20* | (2018.01) |
| *G16H 80/00* | (2018.01) |

(52) U.S. Cl.
CPC ........... *G06T 19/006* (2013.01); *G16H 10/60* (2018.01); *G16H 20/00* (2018.01); *G16H*

*40/63* (2018.01); *G16H 50/20* (2018.01); *G16H 80/00* (2018.01); *G16H 30/20* (2018.01); *G16H 30/40* (2018.01)

(58) Field of Classification Search
CPC ...... G06T 19/006; G16H 10/60; G16H 20/00; G16H 40/63; G16H 50/20; G16H 80/00; G16H 30/20; G16H 30/40
See application file for complete search history.

(56) References Cited

U.S. PATENT DOCUMENTS

| | | | |
|---|---|---|---|
| 5,591,409 A | 1/1997 | Watkins |
| 6,149,586 A | 11/2000 | Elkind |
| (Continued) | | | |

FOREIGN PATENT DOCUMENTS

| | | |
|---|---|---|
| CN | 106599558 | 4/2017 |
| EP | 2873444 | 5/2015 |
| (Continued) | | |

*Primary Examiner* — Jeffery A Brier
(74) *Attorney, Agent, or Firm* — Schwartz Law Firm, P.C.

(57) ABSTRACT

A computer-based extended reality health system is adapted for electronically rendering patient sessions within an XR environment incorporating immersive scenes. The XR health system utilizes an XR device adapted for being employed by a patient to visually display the immersive scenes during a patient session within the XR environment. An input device is adapted for electronically interacting with objects, content and features visually displayed in the immersive scenes. A billing module is configured to extract claims data applicable for medical billing claims. The claims data includes billing information associated with the immersive scenes visually rendered to the patient during the patient session within the XR environment.

20 Claims, 56 Drawing Sheets

Related U.S. Application Data continuation of application No. 17/552,067, filed on Dec. 15, 2021, now Pat. No. 11,615,600, which is a continuation of application No. 17/175,033, filed on Feb. 12, 2021, now Pat. No. 11,217,033, which is a continuation of application No. 16/773,432, filed on Jan. 27, 2020, now Pat. No. 10,943,407.

(60) Provisional application No. 62/801,914, filed on Feb. 6, 2019, provisional application No. 62/796,909, filed on Jan. 25, 2019.

(56) References Cited

U.S. PATENT DOCUMENTS

| | | | |
|---|---|---|---|
| 6,425,764 | B1 | 7/2002 | Lamson |
| 8,630,867 | B2 | 1/2014 | Yoo |
| 9,390,630 | B2 | 7/2016 | Daniels |
| 9,814,423 | B2 | 11/2017 | Jain et al. |
| 10,943,407 | B1 | 3/2021 | Morgan |
| 11,217,033 | B1 | 1/2022 | Morgan et al. |
| 11,615,600 | B1 | 3/2023 | Morgan |
| 11,961,197 | B1 * | 4/2024 | Morgan ................. G16H 20/00 |
| 2002/0146672 | A1 | 10/2002 | Burdea et al. |
| 2004/0022349 | A1 | 2/2004 | Hagiwara |
| 2005/0216243 | A1 | 9/2005 | Graham et al. |
| 2007/0006889 | A1 | 1/2007 | Kobal |
| 2012/0108909 | A1 | 5/2012 | Slobounov et al. |
| 2014/0147820 | A1 | 5/2014 | Snow et al. |
| 2014/0287389 | A1 | 9/2014 | Kallmann et al. |
| 2015/0133820 | A1 | 5/2015 | Zohar |
| 2015/0310758 | A1 | 10/2015 | Daddona et al. |
| 2016/0247017 | A1 | 8/2016 | Sareen |
| 2016/0321404 | A1 * | 11/2016 | Ginsburg ............... G16H 10/60 |
| 2017/0150897 | A1 | 6/2017 | Komaki |
| 2017/0323485 | A1 | 11/2017 | Samec et al. |
| 2018/0071425 | A1 | 3/2018 | Jin et al. |
| 2018/0190376 | A1 | 7/2018 | Hill et al. |
| 2018/0263535 | A1 | 9/2018 | Cramer |
| 2019/0176034 | A1 | 6/2019 | Flego |
| 2019/0196576 | A1 | 6/2019 | Saarinen |
| 2020/0077939 | A1 | 3/2020 | Richer et al. |

FOREIGN PATENT DOCUMENTS

| | | |
|---|---|---|
| JP | 2011100413 | 5/2011 |
| WO | WO2008131294 | 10/2008 |
| WO | WO2013054257 | 4/2013 |
| WO | WO2014124002 | 8/2014 |
| WO | WO2015134953 | 9/2015 |
| WO | WO2017115366 | 7/2017 |
| WO | WO2017174466 | 10/2017 |

* cited by examiner

Users:
• Patients
• Clinicians
• Admins

Personalized Regimen for John Doe customized combination of features: Create, configure, and deploy feature, Scene creation and configuration feature, Session creation and configuration feature, Regimen creation and configuration feature, Integration module feature, ML/AI model configuration feature, ML to influence patient behavior feature, Light influence feature, Light alteration and effects feature, Audio ML feature

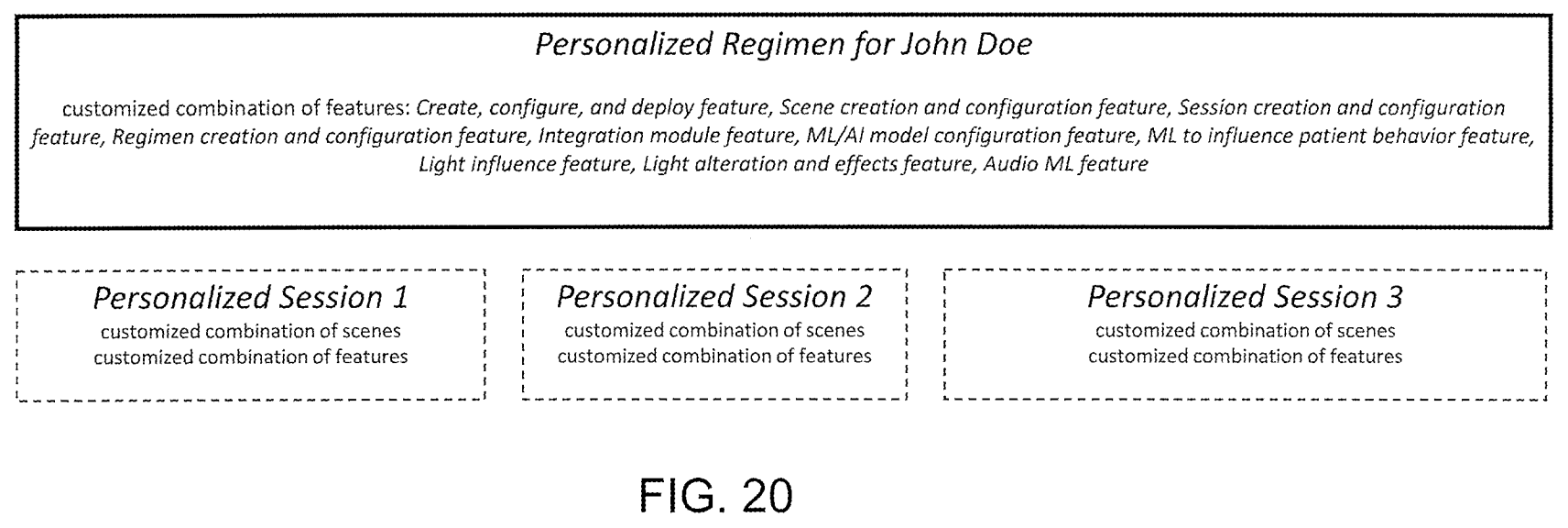

Personalized Session 1
customized combination of scenes
customized combination of features

Personalized Session 2
customized combination of scenes
customized combination of features

Personalized Session 3
customized combination of scenes
customized combination of features

FIG. 20

*Personalized Session 1 for John Doe* customized combination of scenes (below)

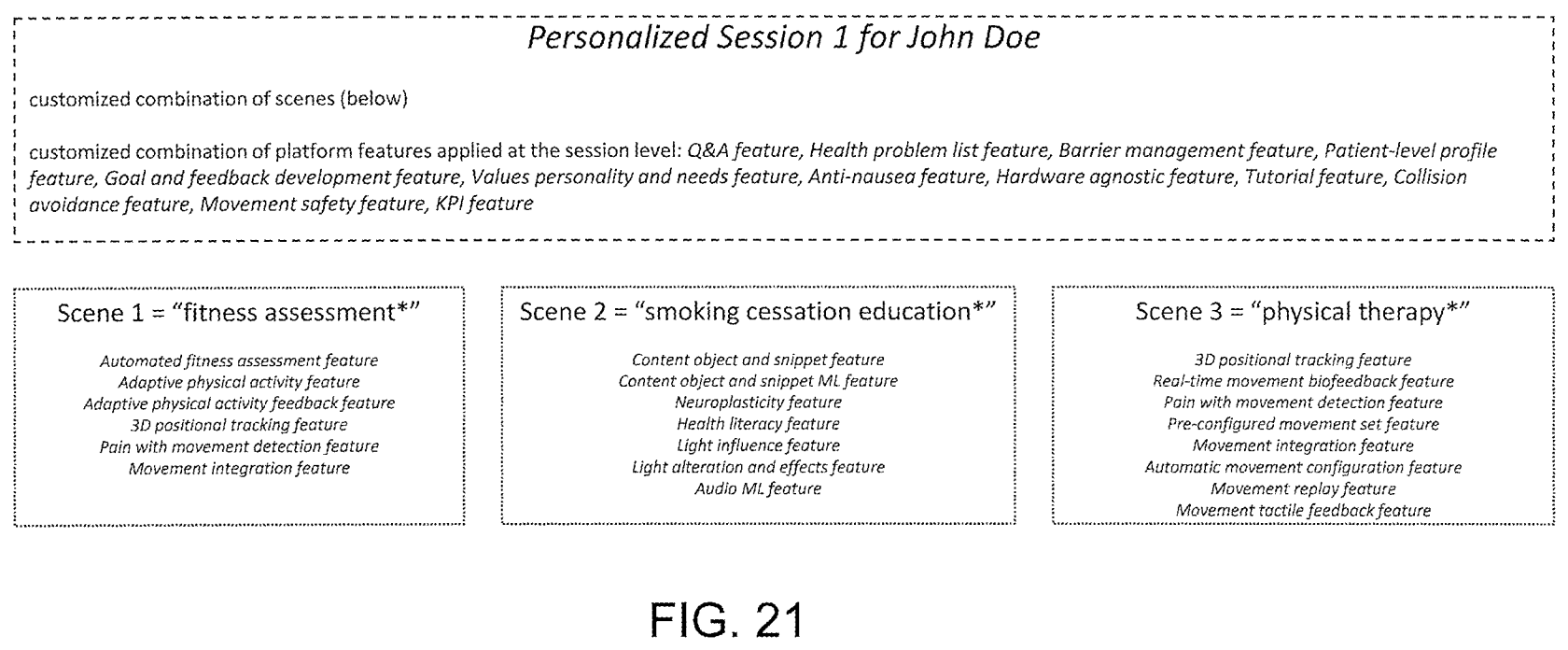

customized combination of platform features applied at the session level: Q&A feature, Health problem list feature, Barrier management feature, Patient-level profile feature, Goal and feedback development feature, Values personality and needs feature, Anti-nausea feature, Hardware agnostic feature, Tutorial feature, Collision avoidance feature, Movement safety feature, KPI feature

**Scene 1 = "fitness assessment*"**

Automated fitness assessment feature
Adaptive physical activity feature
Adaptive physical activity feedback feature
3D positional tracking feature
Pain with movement detection feature
Movement integration feature

**Scene 2 = "smoking cessation education*"**

Content object and snippet feature
Content object and snippet ML feature
Neuroplasticity feature
Health literacy feature
Light influence feature
Light alteration and effects feature
Audio ML feature

**Scene 3 = "physical therapy*"**

3D positional tracking feature
Real-time movement biofeedback feature
Pain with movement detection feature
Pre-configured movement set feature
Movement integration feature
Automatic movement configuration feature
Movement replay feature
Movement tactile feedback feature

FIG. 21

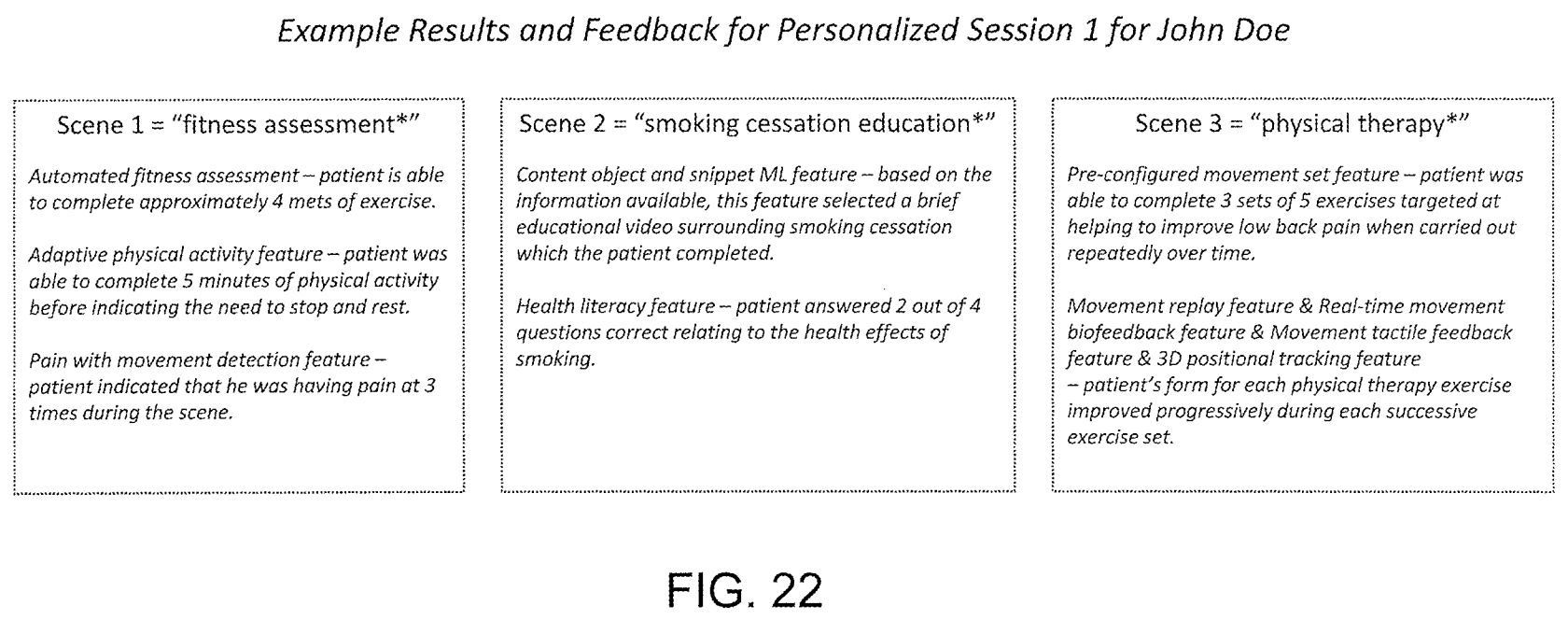

*Example Results and Feedback for Personalized Session 1 for John Doe*

Scene 1 = "fitness assessment*"

*Automated fitness assessment – patient is able to complete approximately 4 mets of exercise.*

*Adaptive physical activity feature – patient was able to complete 5 minutes of physical activity before indicating the need to stop and rest.*

*Pain with movement detection feature – patient indicated that he was having pain at 3 times during the scene.*

Scene 2 = "smoking cessation education*"

*Content object and snippet ML feature – based on the information available, this feature selected a brief educational video surrounding smoking cessation which the patient completed.*

*Health literacy feature – patient answered 2 out of 4 questions correct relating to the health effects of smoking.*

Scene 3 = "physical therapy*"

*Pre-configured movement set feature – patient was able to complete 3 sets of 5 exercises targeted at helping to improve low back pain when carried out repeatedly over time.*

*Movement replay feature & Real-time movement biofeedback feature & Movement tactile feedback feature & 3D positional tracking feature – patient's form for each physical therapy exercise improved progressively during each successive exercise set.*

FIG. 22

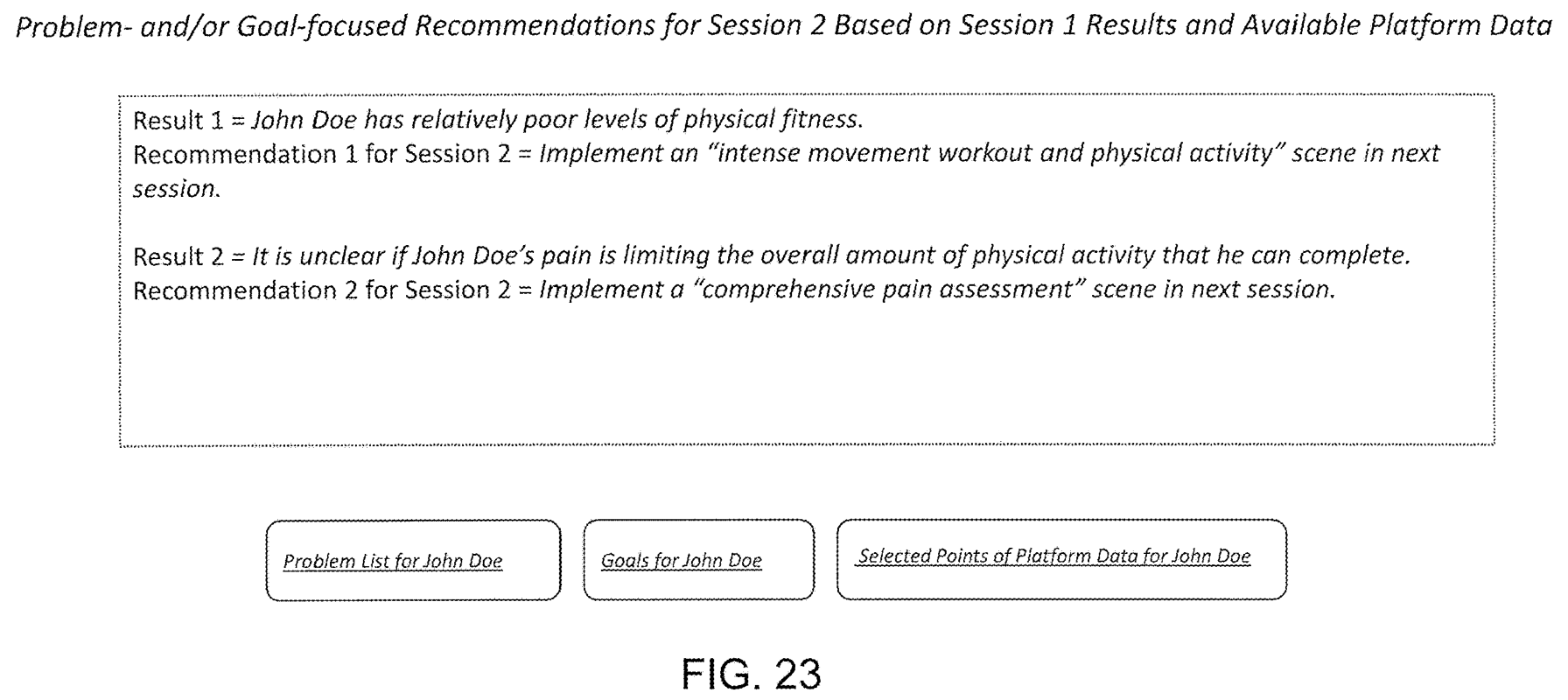

*Problem- and/or Goal-focused Recommendations for Session 2 Based on Session 1 Results and Available Platform Data*

Result 1 = *John Doe has relatively poor levels of physical fitness.*
Recommendation 1 for Session 2 = *Implement an "intense movement workout and physical activity" scene in next session.*

Result 2 = *It is unclear if John Doe's pain is limiting the overall amount of physical activity that he can complete.*
Recommendation 2 for Session 2 = *Implement a "comprehensive pain assessment" scene in next session.*

*Problem List for John Doe*

*Goals for John Doe*

*Selected Points of Platform Data for John Doe*

FIG. 23

*Personalized Session 2 for John Doe* customized combination of scenes (below)

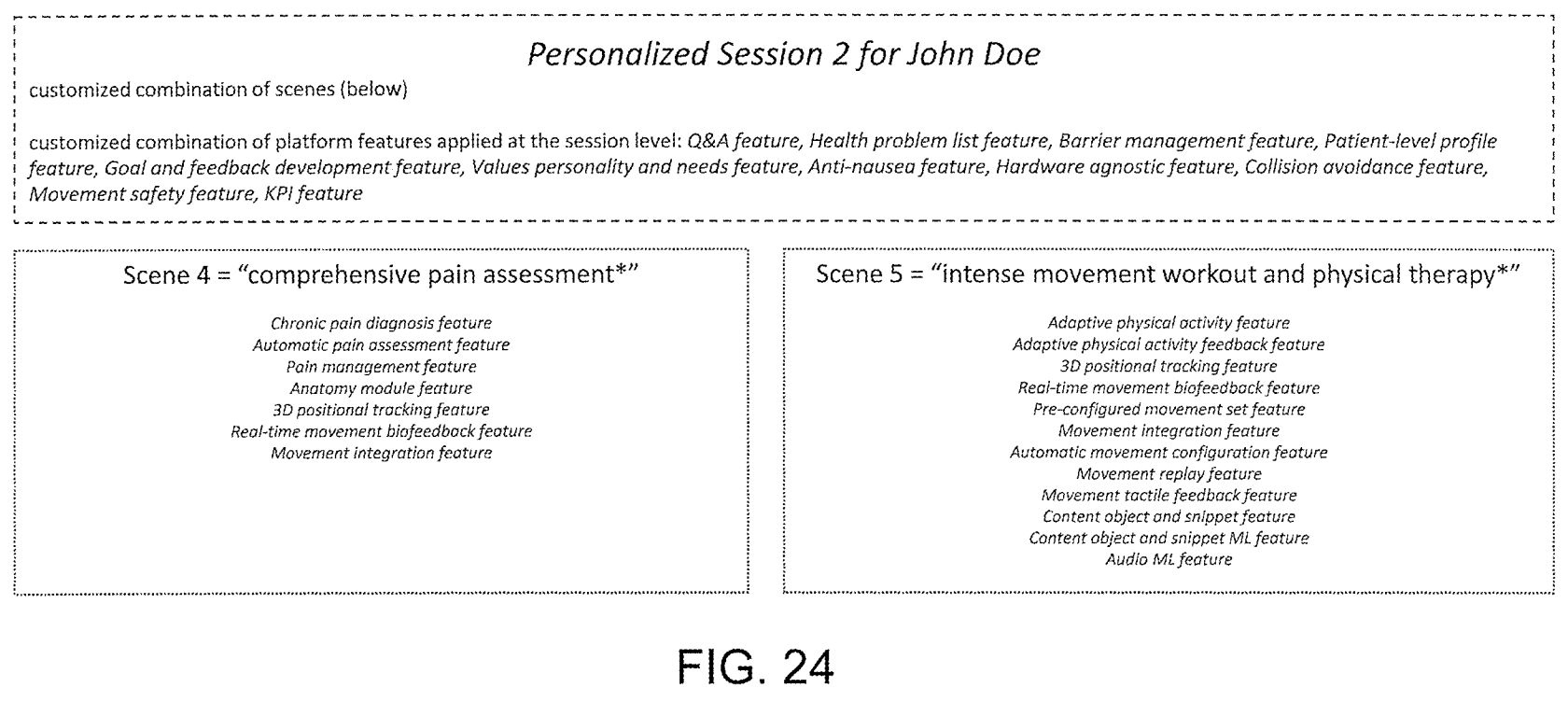

customized combination of platform features applied at the session level: Q&A feature, Health problem list feature, Barrier management feature, Patient-level profile feature, Goal and feedback development feature, Values personality and needs feature, Anti-nausea feature, Hardware agnostic feature, Collision avoidance feature, Movement safety feature, KPI feature Scene 4 = "comprehensive pain assessment*"

Chronic pain diagnosis feature
Automatic pain assessment feature
Pain management feature
Anatomy module feature
3D positional tracking feature
Real-time movement biofeedback feature
Movement integration feature Scene 5 = "intense movement workout and physical therapy*"

Adaptive physical activity feature
Adaptive physical activity feedback feature
3D positional tracking feature
Real-time movement biofeedback feature
Pre-configured movement set feature
Movement integration feature
Automatic movement configuration feature
Movement replay feature
Movement tactile feedback feature
Content object and snippet feature
Content object and snippet ML feature
Audio ML feature

FIG. 24

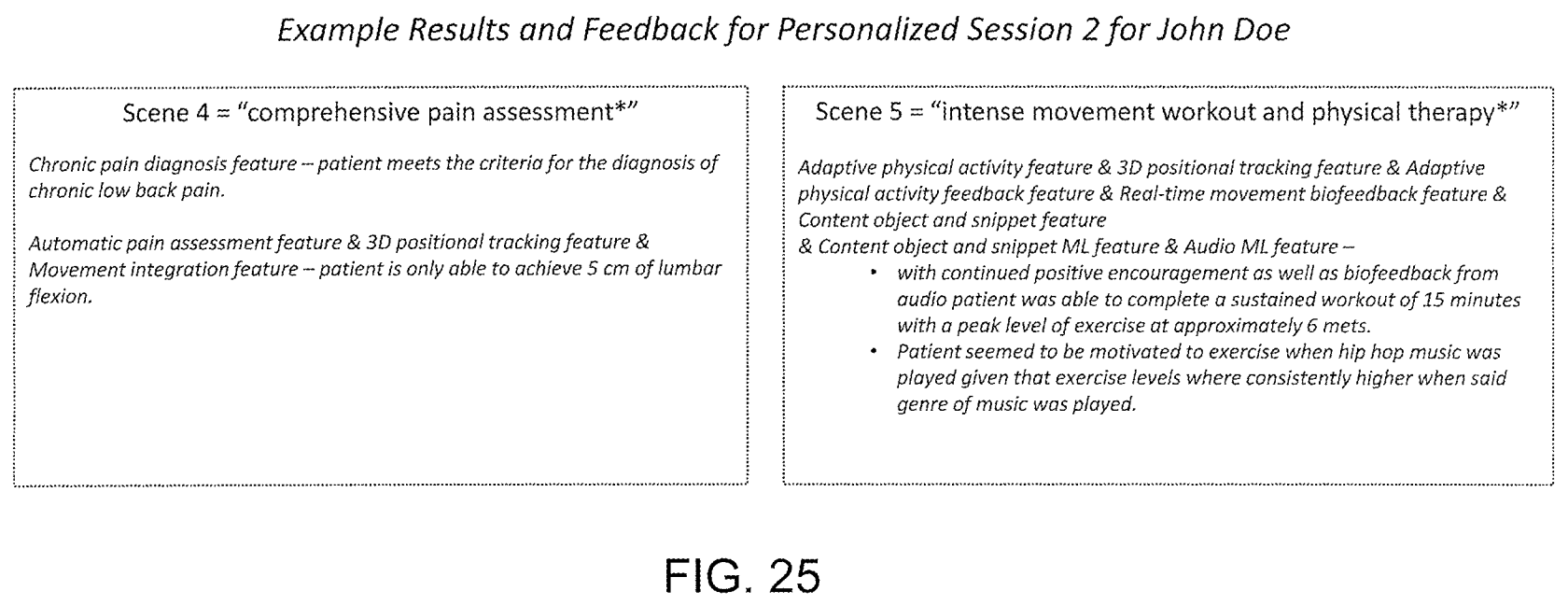

*Example Results and Feedback for Personalized Session 2 for John Doe*

Scene 4 = "comprehensive pain assessment*"

*Chronic pain diagnosis feature -- patient meets the criteria for the diagnosis of chronic low back pain.*

*Automatic pain assessment feature & 3D positional tracking feature & Movement integration feature -- patient is only able to achieve 5 cm of lumbar flexion.*

Scene 5 = "intense movement workout and physical therapy*"

*Adaptive physical activity feature & 3D positional tracking feature & Adaptive physical activity feedback feature & Real-time movement biofeedback feature & Content object and snippet feature & Content object and snippet ML feature & Audio ML feature --*

- *with continued positive encouragement as well as biofeedback from audio patient was able to complete a sustained workout of 15 minutes with a peak level of exercise at approximately 6 mets.*
- *Patient seemed to be motivated to exercise when hip hop music was played given that exercise levels where consistently higher when said genre of music was played.*

FIG. 25

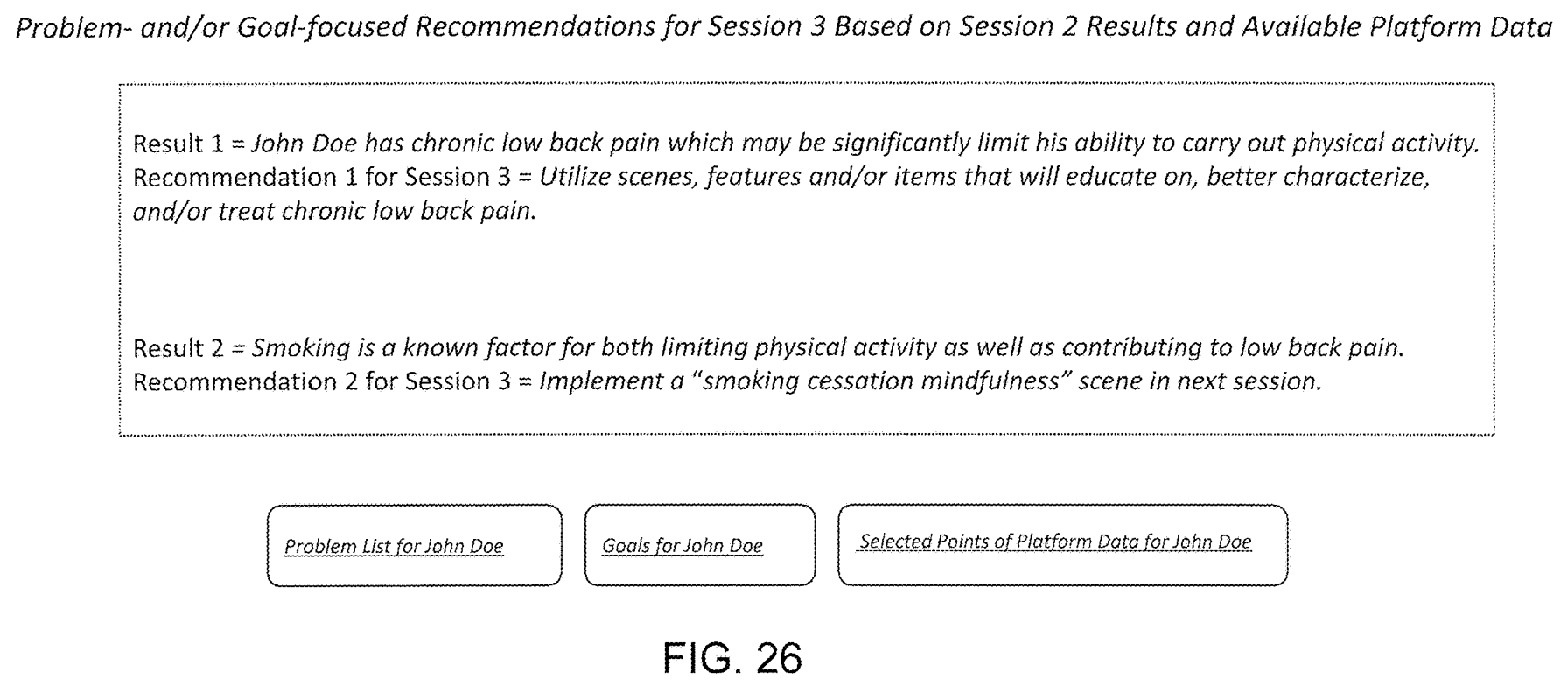

*Problem- and/or Goal-focused Recommendations for Session 3 Based on Session 2 Results and Available Platform Data*

Result 1 = John Doe has chronic low back pain which may be significantly limit his ability to carry out physical activity. Recommendation 1 for Session 3 = Utilize scenes, features and/or items that will educate on, better characterize, and/or treat chronic low back pain.

Result 2 = Smoking is a known factor for both limiting physical activity as well as contributing to low back pain. Recommendation 2 for Session 3 = Implement a "smoking cessation mindfulness" scene in next session.

*Problem List for John Doe*

*Goals for John Doe*

*Selected Points of Platform Data for John Doe*

FIG. 26

*Personalized Session 3 for John Doe* customized combination of scenes (below)

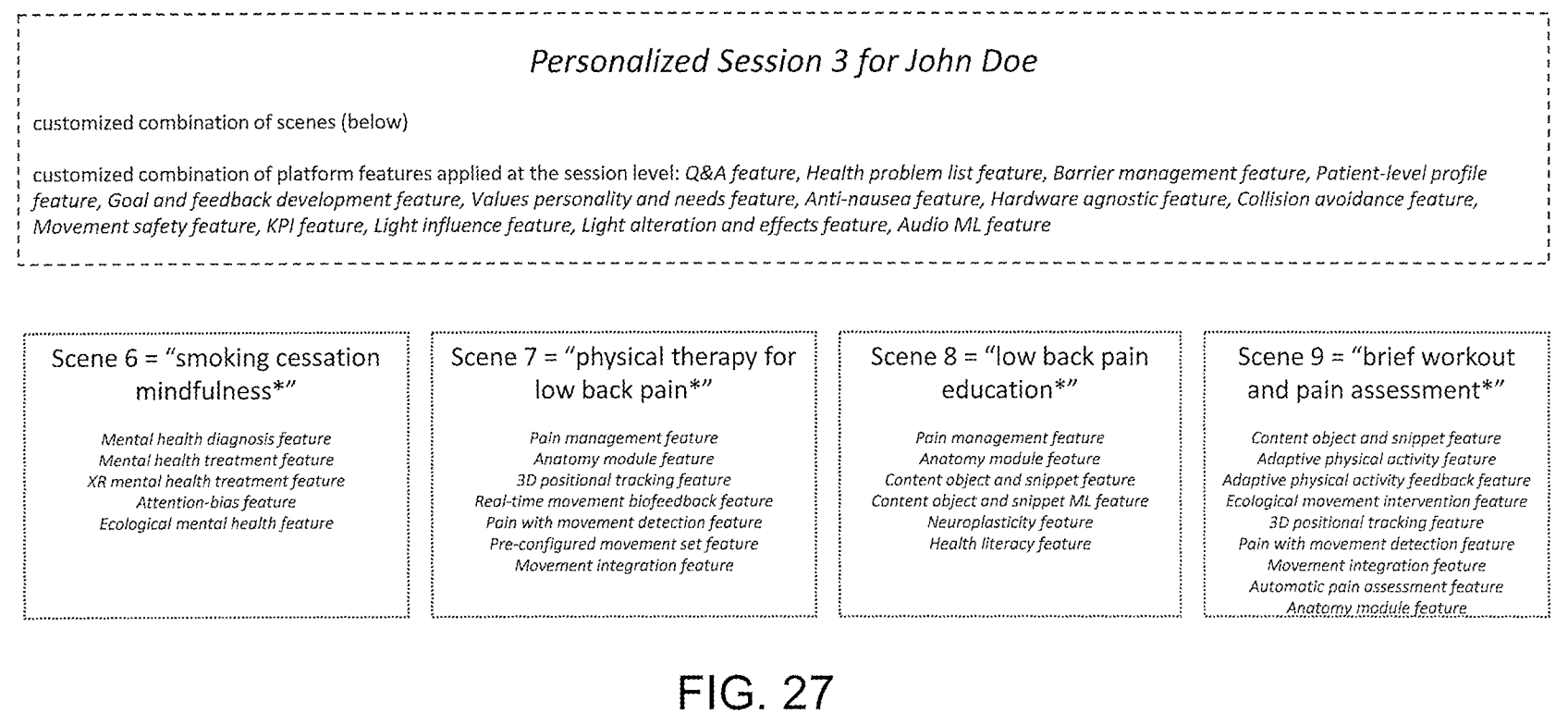

customized combination of platform features applied at the session level: Q&A feature, Health problem list feature, Barrier management feature, Patient-level profile feature, Goal and feedback development feature, Values personality and needs feature, Anti-nausea feature, Hardware agnostic feature, Collision avoidance feature, Movement safety feature, KPI feature, Light influence feature, Light alteration and effects feature, Audio ML feature Scene 6 = "smoking cessation mindfulness*"

Mental health diagnosis feature
Mental health treatment feature
XR mental health treatment feature
Attention-bias feature
Ecological mental health feature Scene 7 = "physical therapy for low back pain*"

Pain management feature
Anatomy module feature
3D positional tracking feature
Real-time movement biofeedback feature
Pain with movement detection feature
Pre-configured movement set feature
Movement integration feature Scene 8 = "low back pain education*"

Pain management feature
Anatomy module feature
Content object and snippet feature
Content object and snippet ML feature
Neuroplasticity feature
Health literacy feature Scene 9 = "brief workout and pain assessment*"

Content object and snippet feature
Adaptive physical activity feature
Adaptive physical activity feedback feature
Ecological movement intervention feature
3D positional tracking feature
Pain with movement detection feature
Movement integration feature
Automatic pain assessment feature
Anatomy module feature

FIG. 27

Key:
Ⓐ Data obtained through the Q&A feature
Ⓑ Related to the use of one or more platform features
Ⓒ Related to one or more points of platform data
Ⓓ Logic and/or math operations

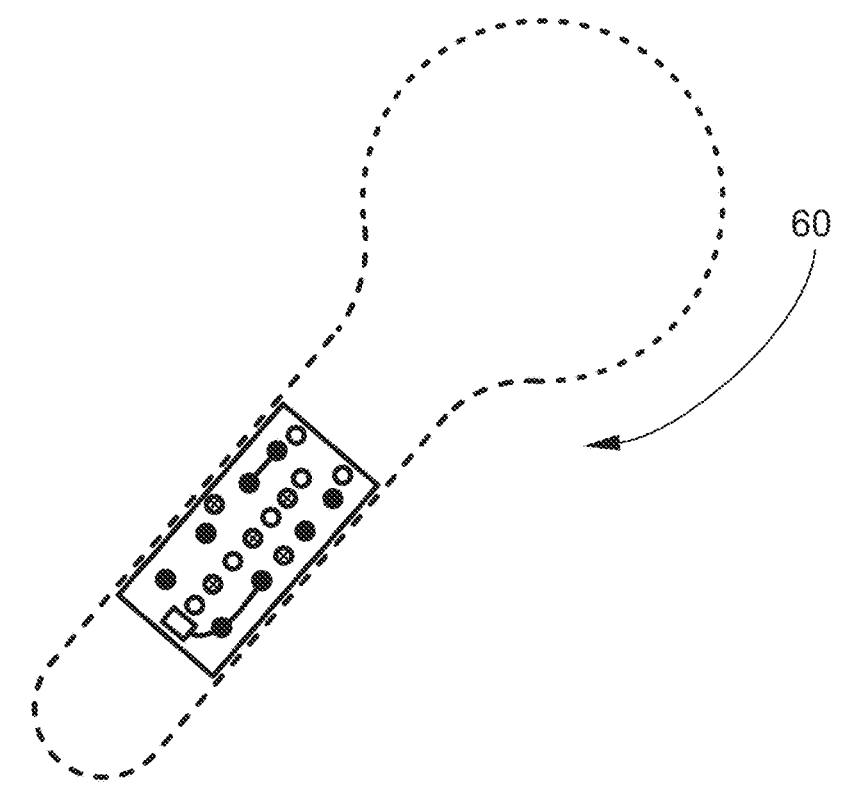
60
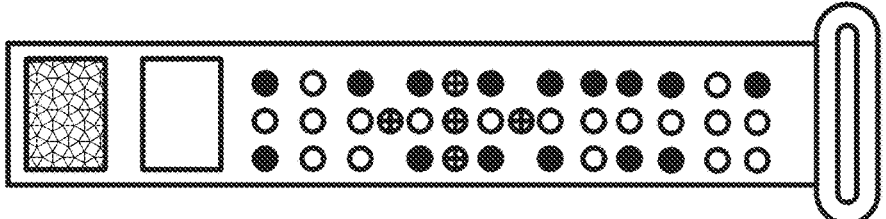
FIG. 56

XR HEALTH PLATFORM, SYSTEM AND METHOD

TECHNICAL FIELD AND BACKGROUND OF THE DISCLOSURE

The present disclosure relates broadly and generally to an extended reality health platform, system and method referred to broadly and collectively herein as "XR Health Platform" or "XR Platform" or "Platform" or the like.

SUMMARY OF EXEMPLARY EMBODIMENTS

Various exemplary embodiments of the present disclosure are described below. Use of the term "exemplary" means illustrative or by way of example only, and any reference herein to "the invention" is not intended to restrict or limit the invention to exact features or steps of any of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may. Any reference herein to "patient", "user", "clinician", and any other individual is intended as gender neutral notwithstanding use of the words "he", "him", "himself" or the like, or any singular possessive use of the word "his" or the like.

It is also noted that terms like "preferably", "commonly", and "typically" are not utilized herein to limit the scope of the invention or to imply that certain features are critical, essential, or even important to the structure or function of the invention. Rather, these terms are merely intended to highlight alternative or additional features that may or may not be utilized in a particular embodiment of the present invention.

According to one exemplary embodiment, the present disclosure comprises an extended reality (XR) health platform, system and method.

Abbreviations and Definitions

All claim terms used herein are intended to be given their broadest reasonable meaning in their ordinary usage as these terms would be understood by one of ordinary skill in the art, and consistent with their ordinary and customary meaning in the art while taking into account the following definitions and written description contained in the present specification.

"ID" refers to an identification and/or identifier.

"GUID" means a globally unique identifier.

"UI" means user interface.

"2D" means two-dimensional.

"3D" means three-dimensional.

"API" means Application Programmer Interface.

"Extended reality (XR)" refers to any real-world-and-virtual combined environment and human-machine interactions generated by technology, including any two-dimensional (2D) and/or three-dimensional (3D) content and/or features. XR includes virtual reality (VR), augmented reality (AR), mixed reality (MR), 2D content (including through the use of a computer monitor, television, and/or any other 2D viewing device), 3D content, the use of platform features, and/or any use of the XR platform. For clarity, XR also includes any platform features, scenes, sessions, regimens, content and/or features which may be simulated, accessed, viewed, and/or interacted with through the use of XR devices, web portals, and/or companion applications.

"XR device" refers to any device that can be used for simulating, viewing, engaging, experiencing, controlling and/or interacting with XR. This includes headsets, head-mounted displays (HMD), augmented reality glasses, 2D displays viewing XR content, 2D displays, 3D displays, computers, controllers, projectors, other interaction devices, mobile phones, speakers, microphones, cameras, head-phones, haptic devices, and the like.

"Clinician application" refers to one embodiment of the companion application described herein. Where mentioned, "clinician application" describes a clinician-facing portion of the system used to control, observe, monitor, and/or interact with instances of the patient-facing portion(s) of the XR platform. The clinician application may run on XR devices.

"HMD" means head-mounted display.

"Supervised" means requiring the input of and/or evaluation by humans.

"Semi-supervised" (synonymous with "semi-autonomous") means may or may not require the input of and/or evaluation by humans.

"Unsupervised" (synonymous with "autonomous") means not requiring human input and/or evaluation. Use of the term "unsupervised" includes its use in the context of ML/AI models, where it may additionally refer to the use of these models to identify and/or characterize signals, patterns, and/or results from sets of data without requiring human input.

"Scene" means a single XR environment with objects, content and/or features.

"Session" means one continuous usage period of XR, one continuous usage of a web portal, and/or one continuous usage of a companion application.

"Scene data" refers to all measurable and/or available data from scenes.

"Session data" refers to all measurable and/or available data from sessions.

"Platform" means the entire software and hardware ecosystem described herein.

"Platform data" means any and/or all data within the entire software ecosystem described herein. May be generated and/or modified manually (e.g. by clinicians, clinical providers, caregivers, patients, administrators), in an autonomous/unsupervised fashion (e.g. by ML model and/or programmatically), and/or in a semiautonomous/semi-supervised fashion (a combination of automatic and manual generation and/or modification).

"Platform data point(s)" (synonymous with "point(s) of platform data") refers to item(s) of platform data.

"Platform data field" refers to the "empty box" occupied by platform data of a speciated type.

"Derived data" means any new and/or novel platform data and/or data fields created by combining sets of platform data fields and/or by applying machine learning, artificial intelligence, mathematical, and/or logical operations on platform data.

"Platform actions" refers to measurable and/or configurable actions or capabilities of the XR platform.

"Patient platform actions" refers to actions and/or interactions between a patient using the XR platform and objects, content items, platform features, scenes, and/or clinicians.

"Patient behaviors" refers to measurable patient actions tracked over time.

"Clinician" means any individual licensed and/or authorized by a regulatory body and/or authorized by patients to perform and/or carry out appropriate items described herein. This definition of clinician may include any of the following: a physician, nurse, therapist, clinical provider, provider, advanced practice nurse, physician assistant, dentist, chiropractor, caregiver, allied health professional, family member, friend, loved one, and/or technologist.

"Care delivery" (synonymous with "care" unless otherwise specified) refers to the application and/or utilization of platform features in patients.

"JSON" means JavaScript Object Notation.

"Camera" refers to a real-world or virtual object that may produce images, renderings, and/or videos.

"Tag" (synonymous with "tagging", "label(s)", and/or "annotation(s)") refers to a tag, label, and/or annotation applied to features and/or content, platform features, and/or any other item(s) within the XR Health Platform as described herein.

"HIPPA" means of and/or relating to the Health Insurance Portability and Accountability Act of 1996.

"Snippet" (synonymous with "content object") means a single continuous piece and/or item of text, audio, image, video, rendered object, and/or other forms of media and/or content. A snippet may include an instructional, educational, feedback, and/or therapeutic statement, and/or a diagnostic, rhetorical, and/or thought-provoking question. A snippet may also be an input and/or output for ML/AI models.

"Virtual human avatar" refers to a humanoid virtual avatar which may be animated, simulated, programmatically controlled (using ML/AI models, for example), and/or represented through other types of rendered content and/or other media, and is designed to interact with, educate, instruct, demonstrate, advise, assist, guide, escort, diagnose, screen, test, treat, and/or manage disease(s) and/or health-related issues for patients in XR. Virtual human avatars may interact with patients and/or clinicians through spoken dialogue, text, rendered content, through visual means, and/or through any other method of communication. Virtual human avatars may possess characteristics that are virtual approximations and/or facsimiles of characteristics of real-world clinicians and/or patients. When used in this context, the term "virtual human avatar(s)" is synonymous with "digital twin(s)".

"Portion of virtual human avatar" refers to one continuous area on a virtual human avatar.

"Disease" (synonymous with "diseases") means any disease and/or illness and/or disorder and/or syndrome and/or ailment and/or sickness and/or condition and/or disability and/or health-related issue.

"ML/AI model" (also ML/AI) includes any models, functions, algorithms, code, and/or programming that involve machine learning, artificial intelligence, mathematical, statistical, logic-based processes, and/or control functionalities. Some examples include any model and/or algorithm that includes and/or is related to the following: arithmetic, calculus, matrices, linear algebra, differential equations, discrete math, logic, regression, decision forests, neural networks, recurrent neural networks, convolutional neural networks, adversarial learning, generative adversarial networks, capsule networks, reinforcement learning, transfer learning, computer vision (CV), object identification, object recognition, activity recognition, key point detection, pose recognition, spatial recognition, spatial contextualization, spatial understanding, optical character recognition (OCR), object segmentation, mask segmentation, instance segmentation, text-based (sentiment, content, feature extraction, etc.), natural language processing, natural language understanding, text to speech (may also be referred to as "text-to-speech" or "TTS"), speech to text (may also be referred to as "speech-to-text" or "STT"), and/or collaborative filtering.

"Q&A" refers to one or more elements of the question and answer feature as described herein.

"Interaction" (synonymous with "interactions") means any interaction occurring between a patient and any feature, item, or element within the XR Health Platform, and/or any interaction occurring between a patient and a clinician. An interaction may be spoken, audio-based, text-based, visually-based, tactile-based, and/or movement-based. For clarity, any encounter, scene, session, and/or regimen involving a patient is a type of interaction.

"Safety prompt" refers to a visual, auditory, and/or text-based message that delivers safety-related instructions, safety-related educational points, and/or evokes safety-related actions (for example, an audio message "please remove the HMID").

"Patient input methods" (synonymous with "patient input(s)") refers to patient interactions with platform features which may be accomplished using one or more of the following: controller inputs (which includes controller buttons, joysticks, and/or touch sensors, and/or any other controller functionalities), keyboard inputs, computer mouse inputs, touchscreen inputs, physical movements, spoken voice/verbal inputs, gaze inputs, text inputs, question response inputs, communication inputs, and/or by any other visual, tactile, movement-based, and/or auditory means, and/or by any other means described herein.

"Positional tracking" includes two-dimensional positional tracking data, three-dimensional positional tracking data, two-dimensional rotational tracking data, and/or three-dimensional rotational tracking data. Positional tracking may also include points of data obtained through the use of items of XR hardware, cameras, microphones, and/or any other type of sensor, either with or without the use of ML/AI models.

"Game engine" refers to any third-party software used to create XR content and/or XR applications.

"Metadata" means data that describes and/or relates to points of platform data.

"Platform feature(s)" refers to any one or more of the features and/or items described herein. For clarity, the definition of "platform feature(s)" includes any feature described herein as well as any item(s) within and/or related to any feature described herein.

"Content and/or feature(s)" (synonymous with "content", "feature(s)", and/or "XR program" unless otherwise specified) refers to any object, lighting condition, audio element, video element, animation element, rendered element, sensing element, programmatic functionality, software, programming, code, user interface, user experience, menu, text element, any element within XR, any element interacted with using XR, other platform features, and/or other items relating to XR. For clarity, this includes the use of XR devices to view, experience, engage in and/or interact with any item described herein.

"XR hardware data" includes points of data produced by, and/or delivered to, any device with XR functionalities.

"Eye tracking data" includes positional eye tracking data, gaze tracking data, retinal data, data relating to images of the eye, and/or pupil data obtained from one or both eyes of individuals.

"Peri operative" (synonymous with "periprocedural", "procedural", "procedure", "operation", and/or "surgery" unless otherwise specified) refers to the period of time before, during, and after any medical procedure, surgical procedure, health-related procedure and/or surgery.

"Biometric data" means data points obtained from any wearable, medical, and/or health-related sensor, device, and/or item of hardware. For clarity, data obtained from ML/AI models may be considered biometric data (for example, when this data relates to health-related characteristics of an individual). Biometric data also includes any of electrocardiogram data (EKG); heart rate data; heart rate variability data (HRV), and/or any derivative of RR and/or NN interval; pulse wave velocity; laser doppler vibrometry data; ultrasound data; x-ray and/or other radiographic imaging data; electroencephalogram data (EEG); electromyography data (EMG); electrooculography data (EOG); galvanic skin response (GSR); impedance data; electrodermal data; accelerometry/IMU data (other than data from XR controllers or HMD); pupil diameter; blood pressure; respiratory rate; pulse oximetry; oxygen consumption; grip strength; blood glucose; points of anthropometric data including height, weight, waist circumference, bust circumference, thigh circumference, bicep circumference, body fat percentage; capnography including end-tidal CO2; lung volumes and/or lung capacities; data points relating to measurements of respiratory and/or pulmonary flow; data points relating to eye tracking; range of motion data for skeletal joints; data points produced by and/or derived from real-world or virtual cameras; points of activity data including active minutes, cadence, calories burned, distance, exercise minutes, floors and/or flights climbed, inactivity and/or sitting time, minutes of moderate-to-vigorous physical activity, peak acceleration, speed, step count; points of sleep data including number of awakenings per sleep session, number of restless periods, sleep duration, sleep latency, sleep position, time awake per restless period, length of time in bed, wake-up time, time out of bed.

BRIEF DESCRIPTION OF THE DRAWINGS

Exemplary embodiments of the present disclosure will hereinafter be described in conjunction with the drawing figures described briefly below.

6 progress, and the facilitation of goal achievement through iterative and/or incremental gains using XR.

Figure 8:
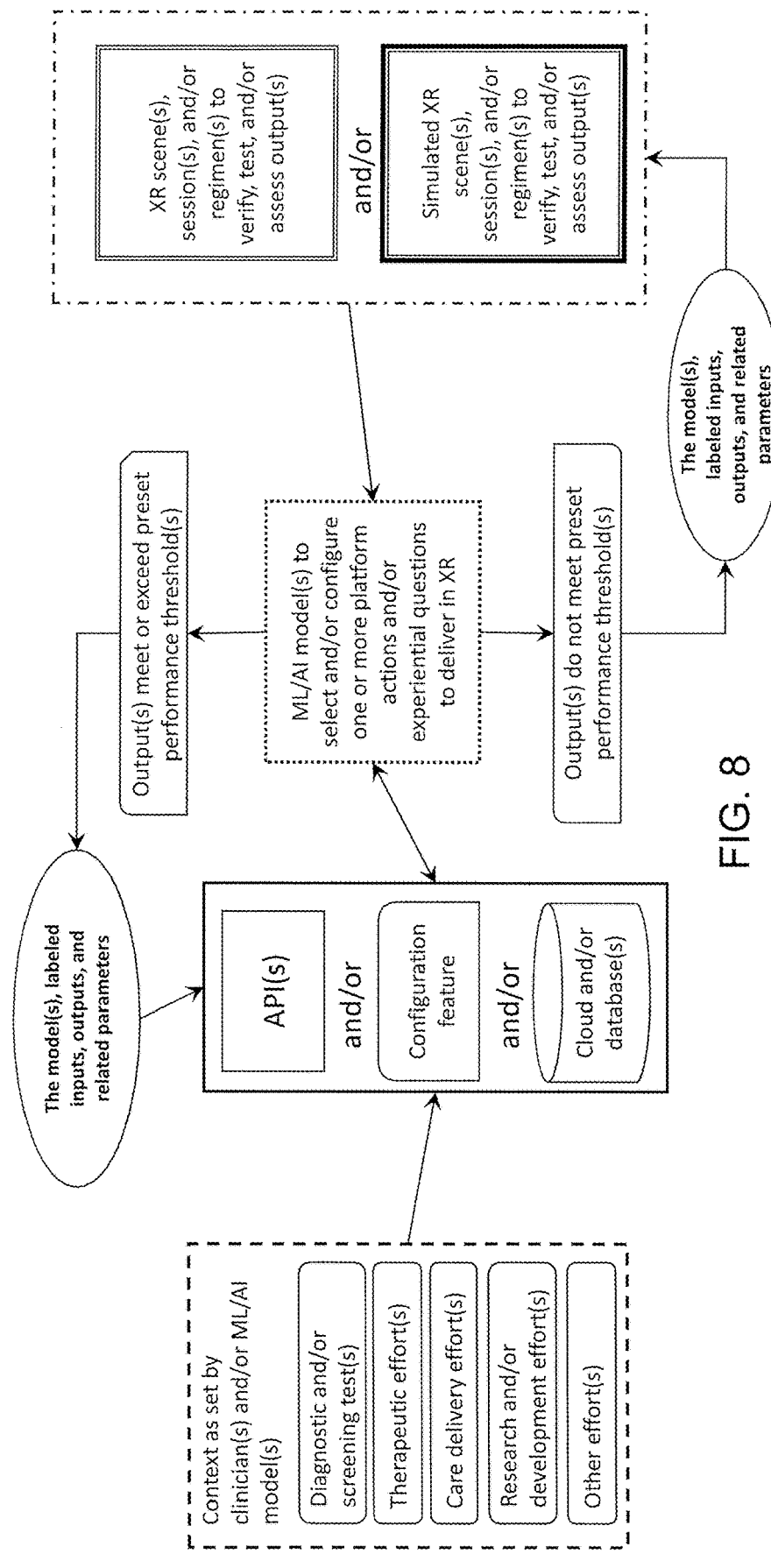

FIG. 8 is a diagram illustrating one embodiment of the iterative ML/AJ feature.

Figure 9:
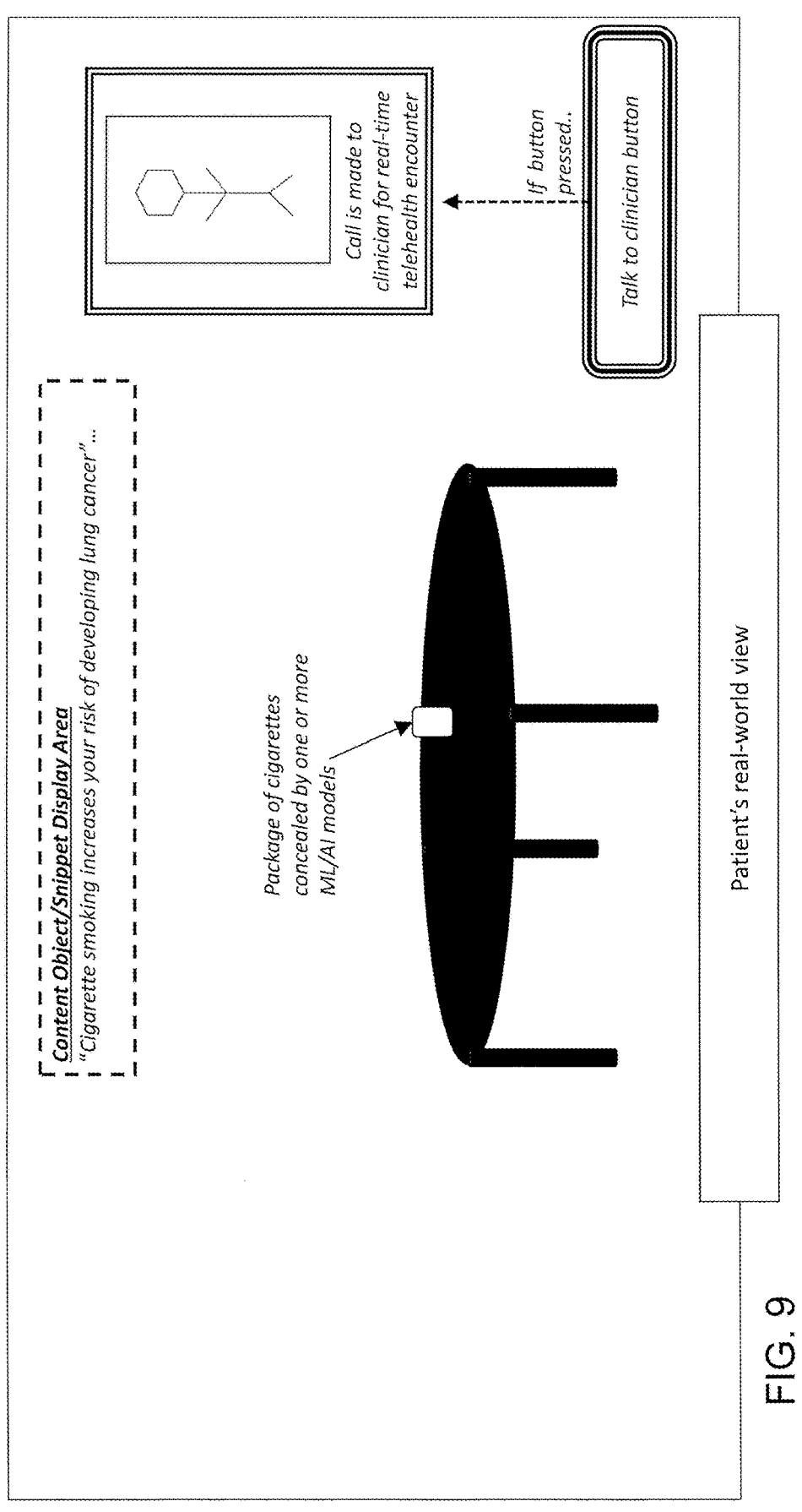

FIG. 9 is a diagram illustrating one embodiment of a patient-facing XR program.

Figure 10:
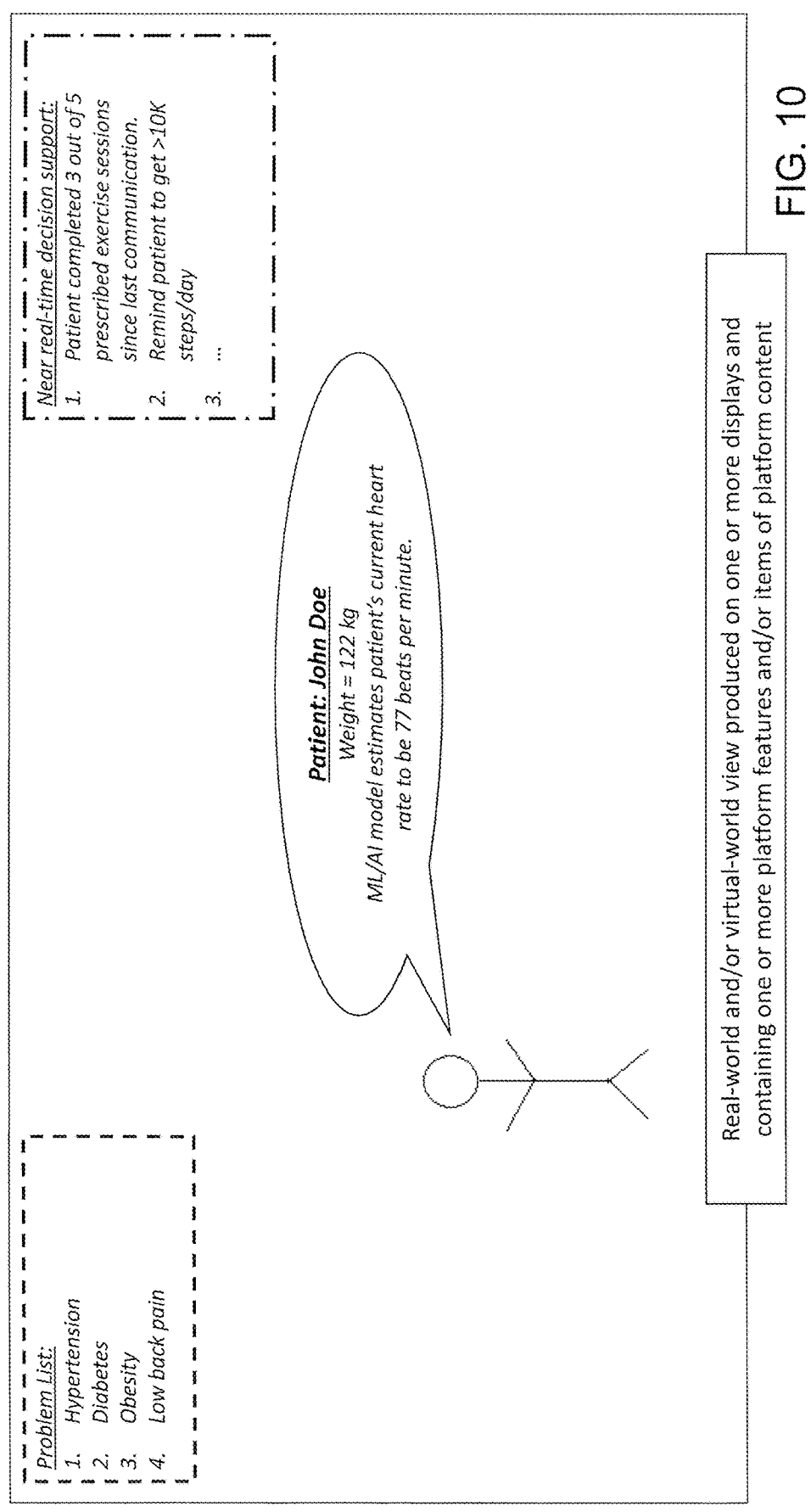

FIG. 10 is a diagram illustrating one embodiment of a clinician-facing decision support XR program.

Figure 11:
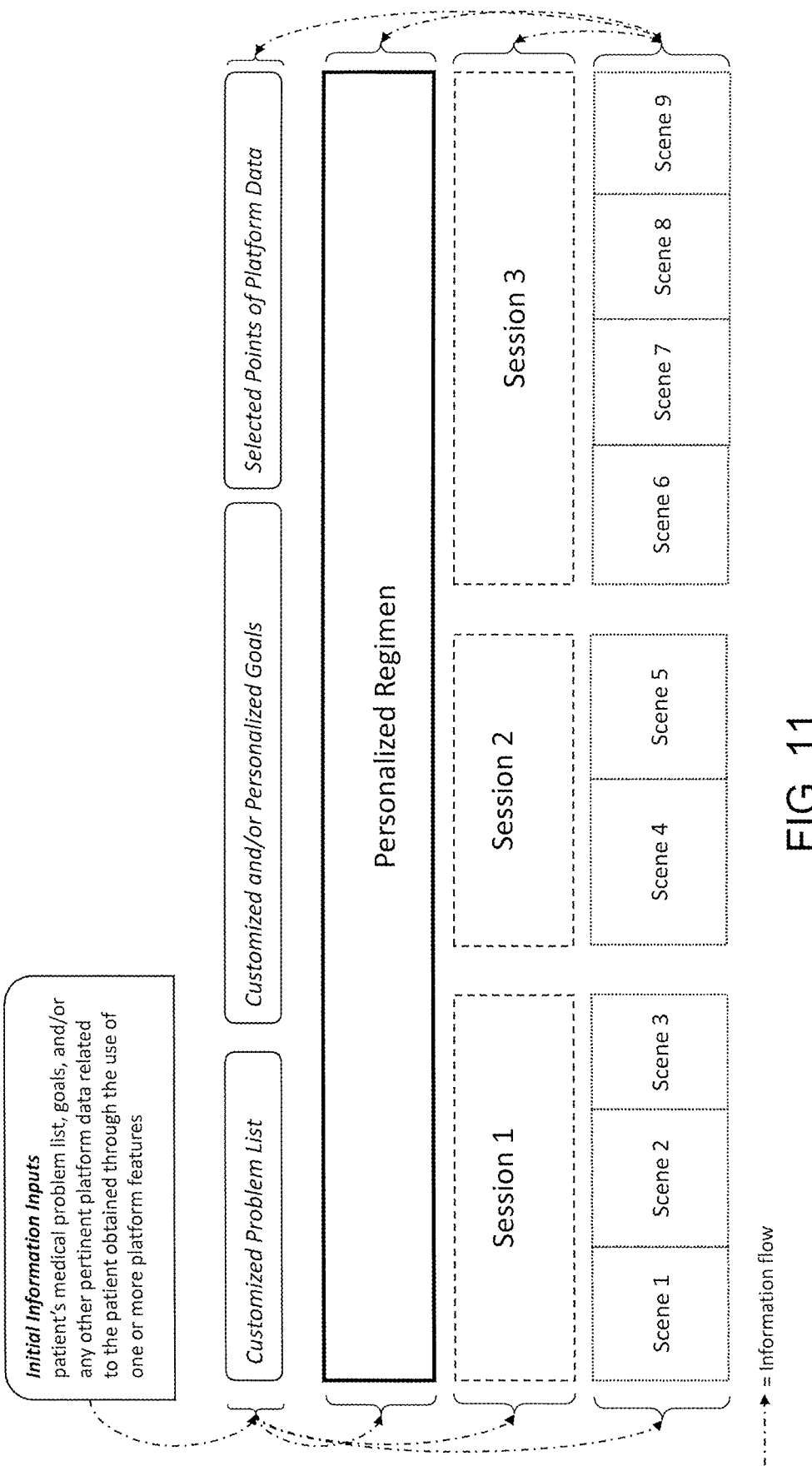

FIG. 11 is a diagram illustrating information flow for a first exemplary personalized regimen.

Figure 12:
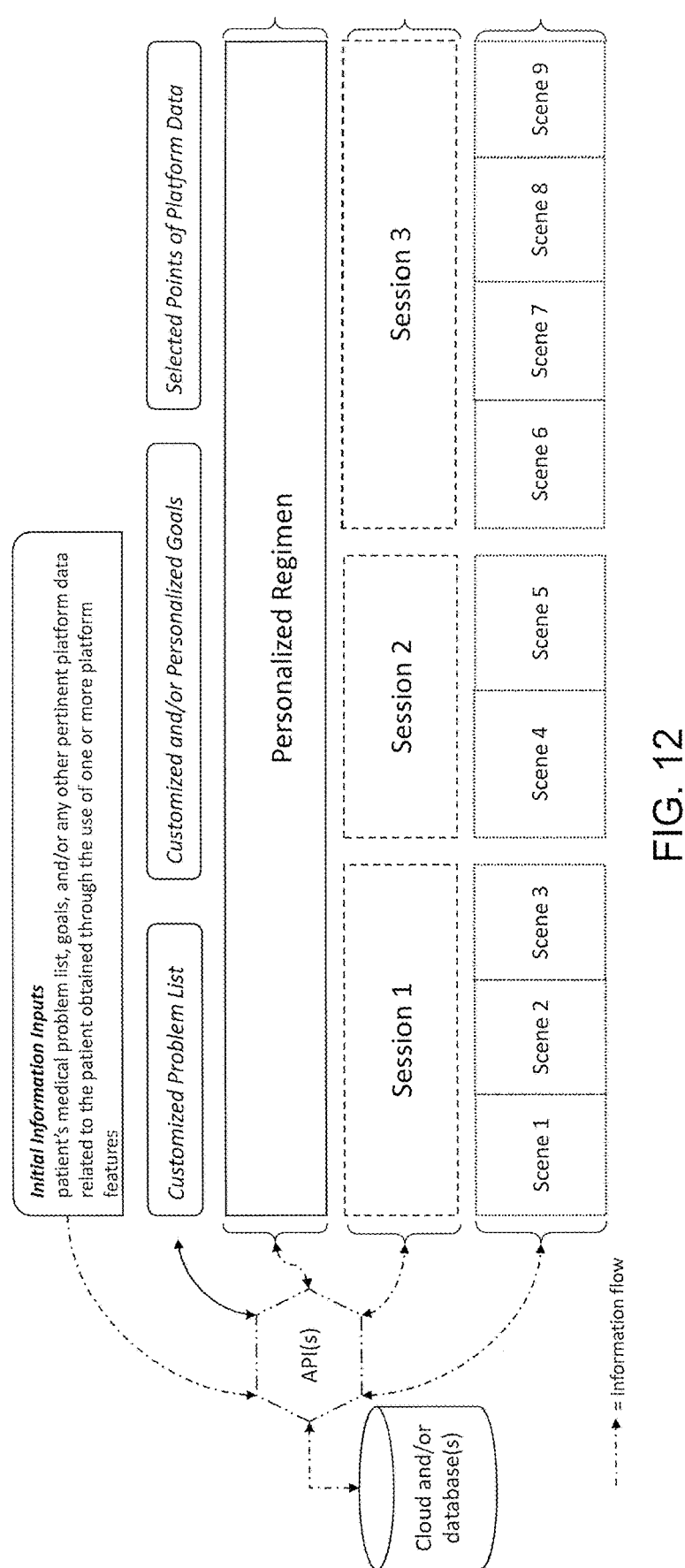

FIG. 12 is a diagram illustrating information flow for a second exemplary personalized regimen.

Figure 13:
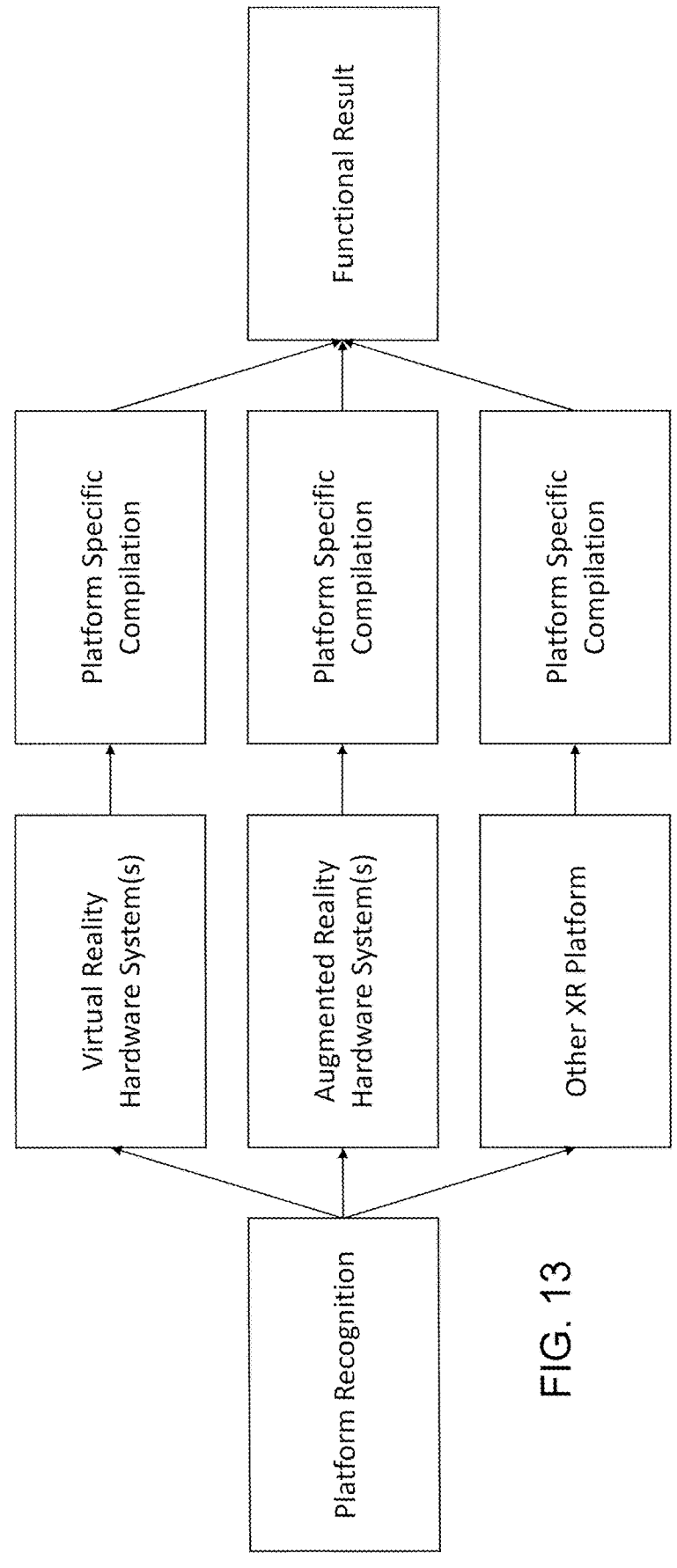

FIG. 13 is a diagram illustrating an exemplary hardware agnostic feature.

Figure 14:
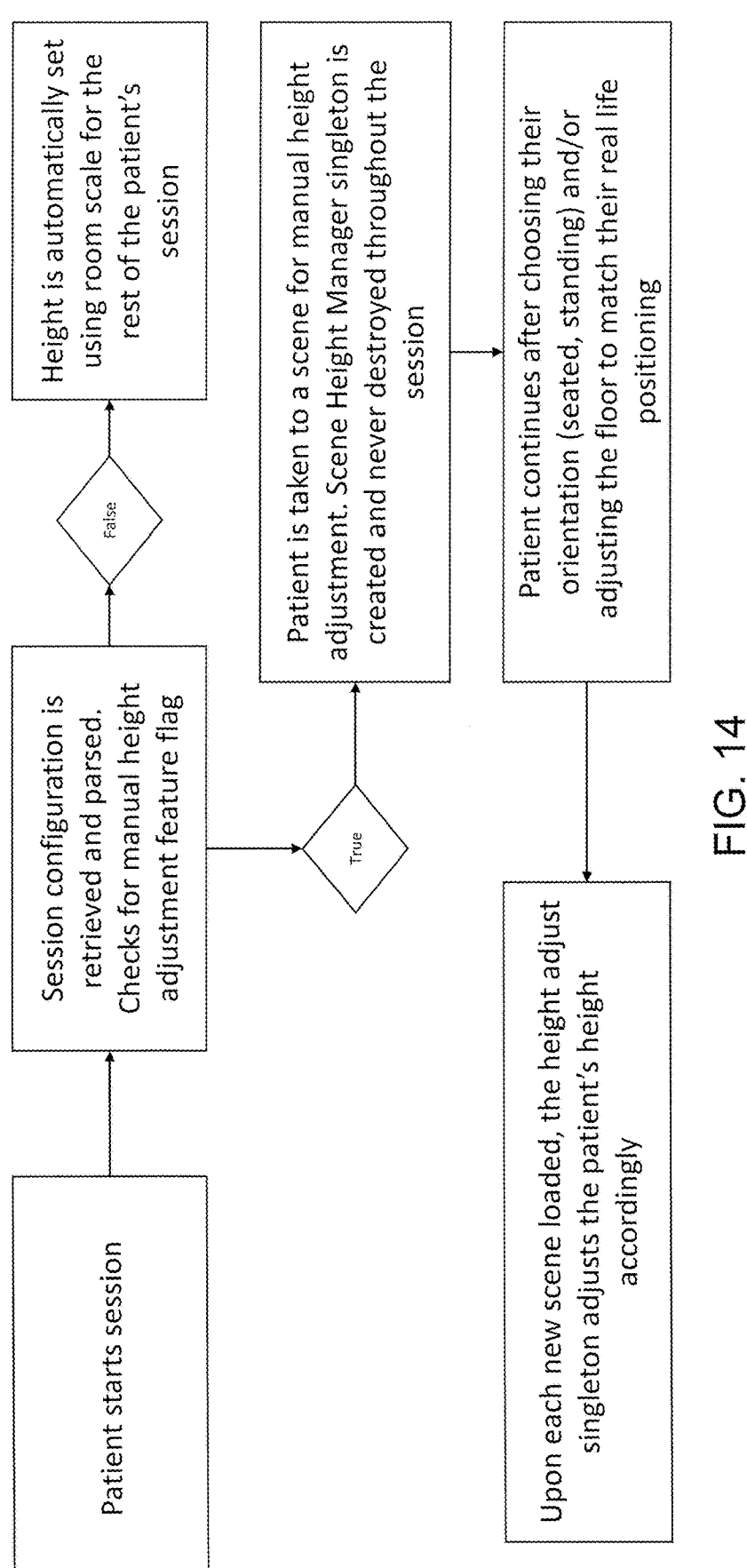

FIG. 14 is a diagram illustrating an exemplary height adjust feature.

Figure 15:
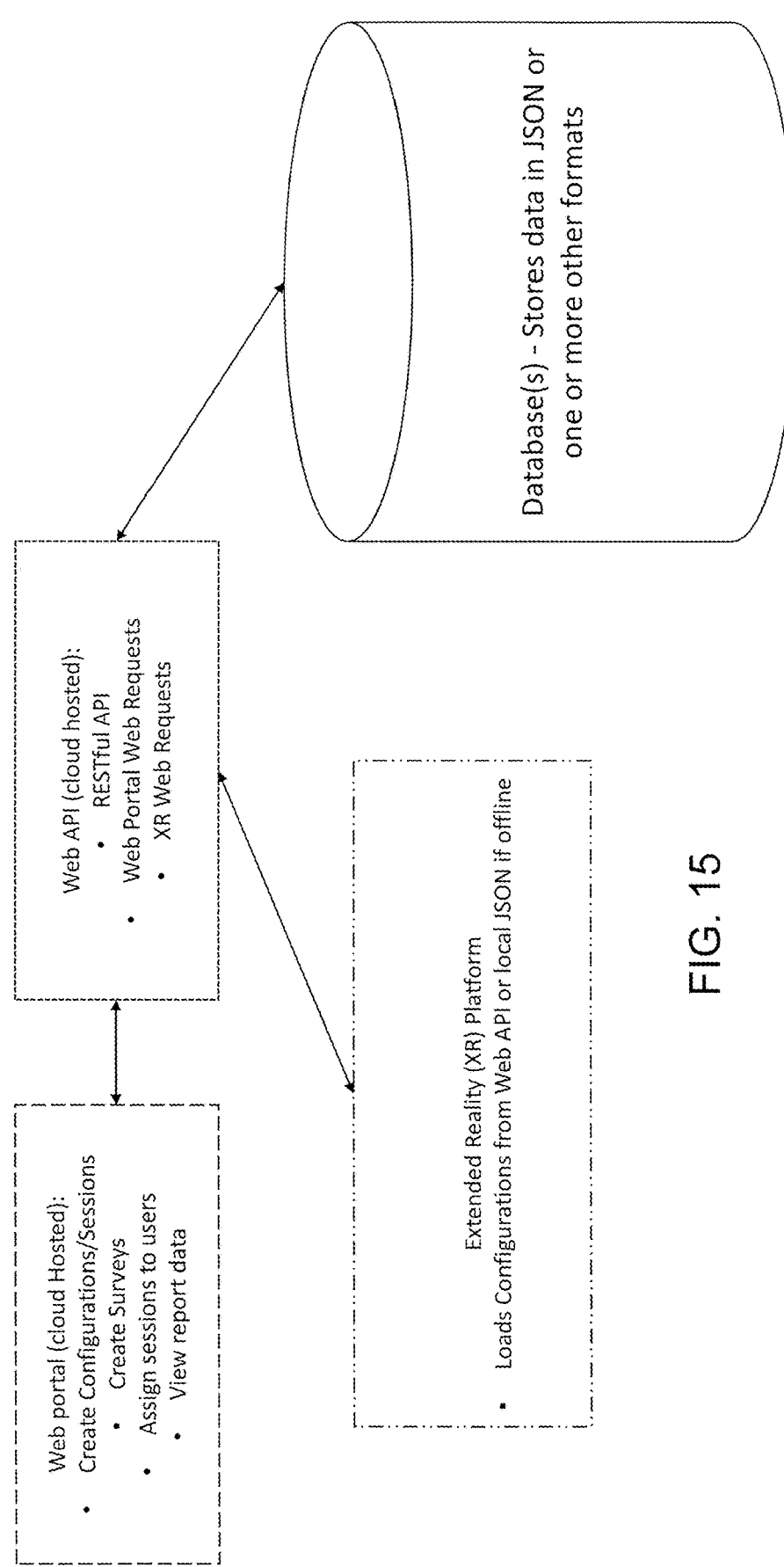

FIG. 15 is a diagram illustrating architecture of the exemplary XR Health Platform using configuration capabilities.

Figure 16:
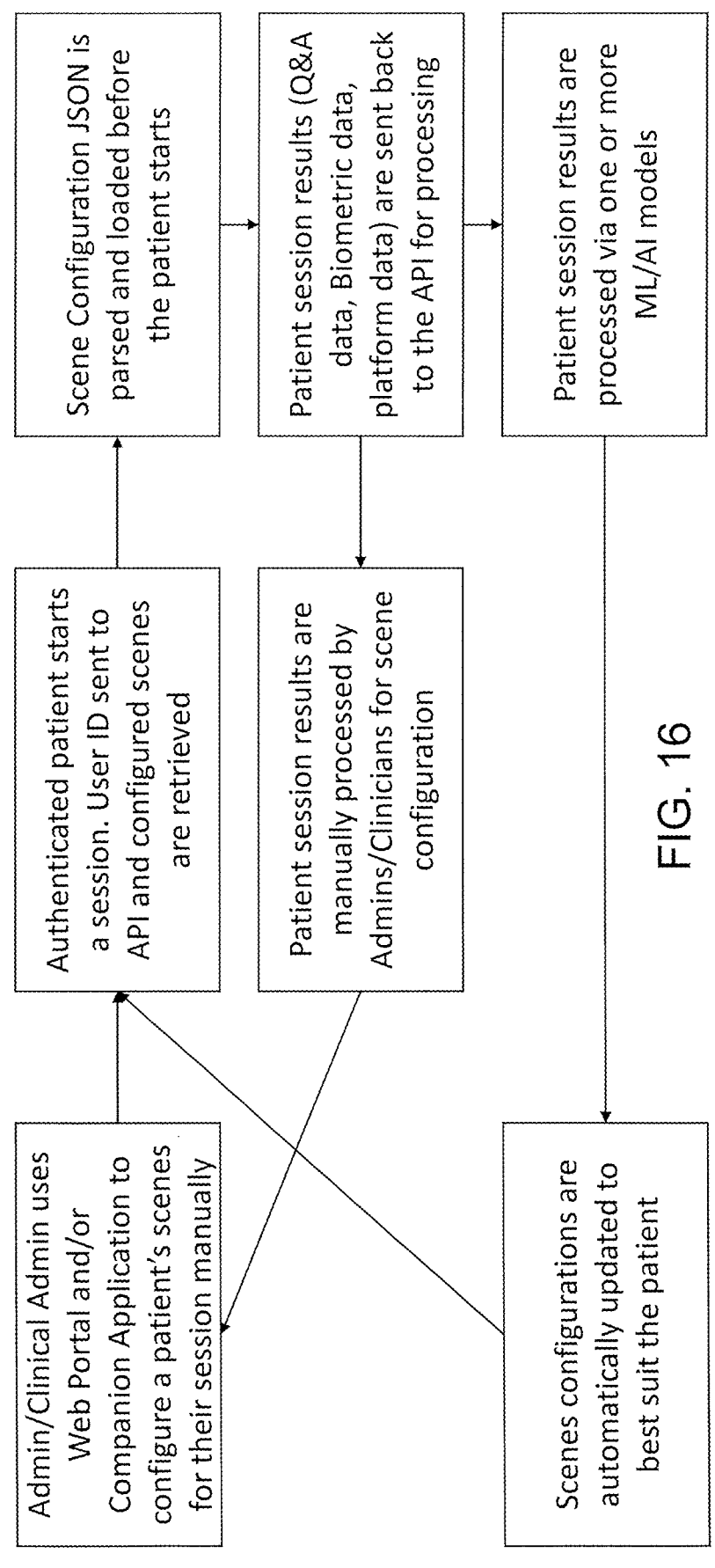

FIG. 16 is a diagram illustrating an exemplary configuration driven experiences workflow.

Figure 17:
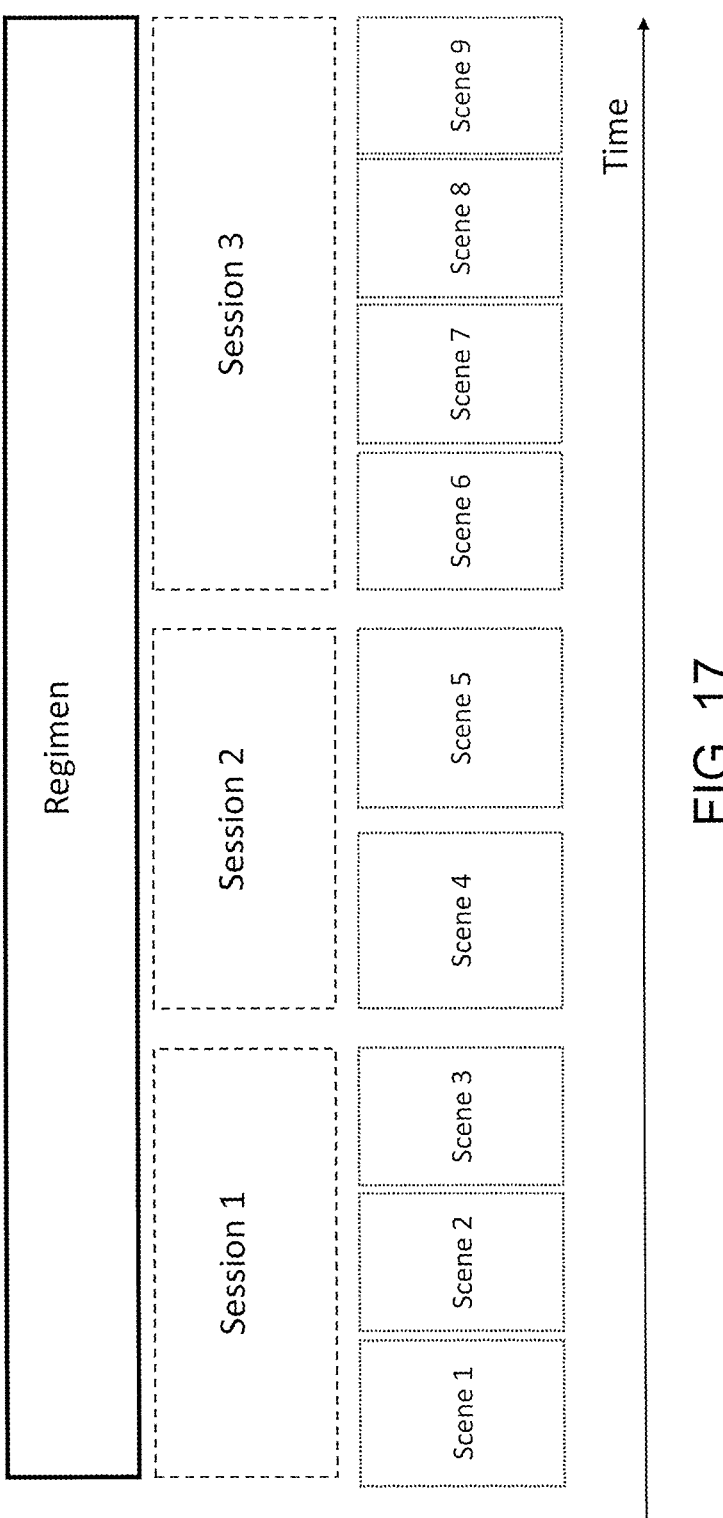

FIG. 17 is a diagram illustrating an exemplary hierarchy of scene(s), session(s), and/or regimen(s).

Figure 18:
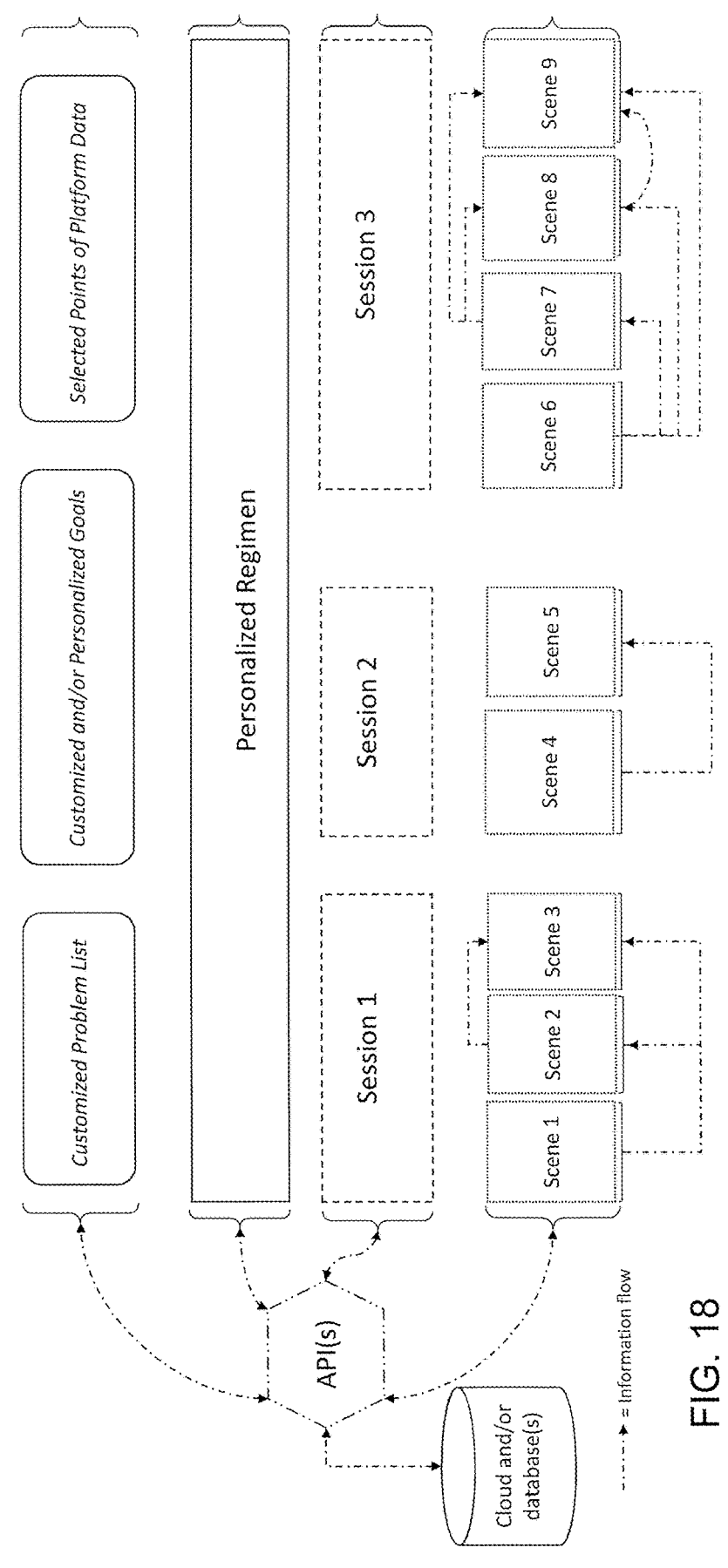

FIG. 18 is a diagram illustrating information flow for an exemplary personalized regimen.

Figure 19:
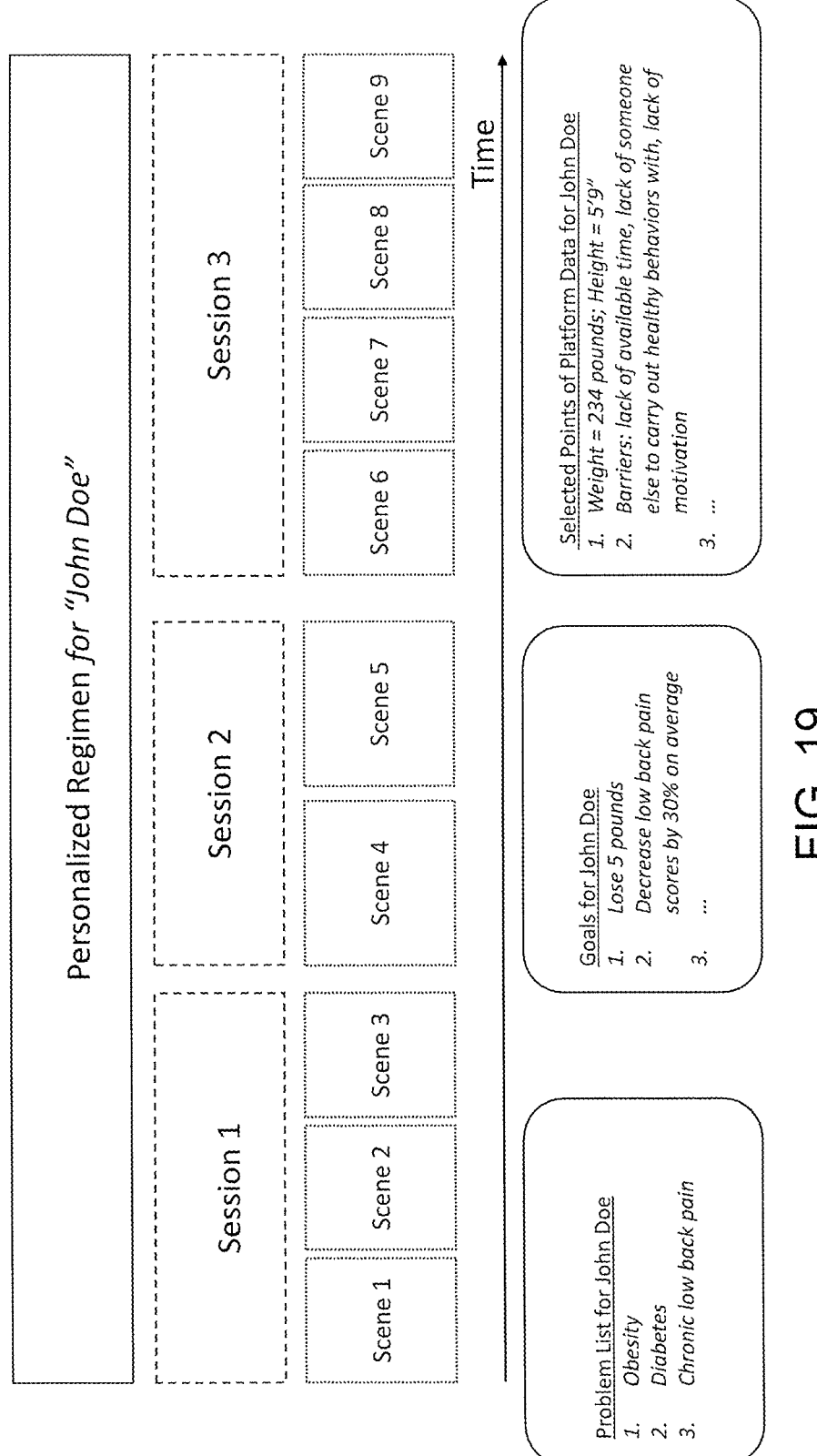

FIG. 19 is a diagram illustrating one example of a personalized regimen. Italicized font represents one or more points of platform data and/or platform features that are created, populated, modified, and/or configured by one or more clinicians, ML/AI models and/or other platform feature(s). The names of the scenes presented in this diagram are for descriptive purposes only and are simply meant to describe the functional purpose of the scene.

FIG. 20 is a diagram illustrating another example of a personalized regimen. Italicized font represents one or more points of platform data and/or platform features that are created, populated, modified, and/or configured by one or more clinicians, ML/AI models and/or other platform feature(s). The names of the scenes presented in this diagram are for descriptive purposes only and are simply meant to describe the functional purpose of the scene.

FIG. 21 is a diagram illustrating yet another example of a personalized regimen. Italicized font represents one or more points of platform data and/or platform features that are created, populated, modified, and/or configured by one or more clinicians, ML/AI models and/or other platform feature(s). The names of the scenes presented in this diagram are for descriptive purposes only and are simply meant to describe the functional purpose of the scene.

FIG. 22 is a diagram illustrating yet another example of a personalized regimen. Italicized font represents one or more points of platform data and/or platform features that are created, populated, modified, and/or configured by one or more clinicians, ML/AI models and/or other platform feature(s). The names of the scenes presented in this diagram are for descriptive purposes only and are simply meant to describe the functional purpose of the scene.

FIG. 23 is a diagram illustrating yet another example of a personalized regimen. Italicized font represents one or more points of platform data and/or platform features that are created, populated, modified, and/or configured by one or more clinicians, ML/AI models and/or other platform feature(s). The names of the scenes presented in this diagram are for descriptive purposes only and are simply meant to describe the functional purpose of the scene.

FIG. 24 is a diagram illustrating yet another example of a personalized regimen. Italicized font represents one or more points of platform data and/or platform features that are created, populated, modified, and/or configured by one or more clinicians, ML/AI models and/or other platform feature(s). The names of the scenes presented in this diagram are for descriptive purposes only and are simply meant to describe the functional purpose of the scene.

FIG. 25 is a diagram illustrating yet another example of a personalized regimen. Italicized font represents one or more points of platform data and/or platform features that are created, populated, modified, and/or configured by one or more clinicians, ML/AI models and/or other platform feature(s). The names of the scenes presented in this diagram are for descriptive purposes only and are simply meant to describe the functional purpose of the scene.

FIG. 26 is a diagram illustrating yet another example of a personalized regimen. Italicized font represents one or more points of platform data and/or platform features that are created, populated, modified, and/or configured by one or more clinicians, ML/AI models and/or other platform feature(s). The names of the scenes presented in this diagram are for descriptive purposes only and are simply meant to describe the functional purpose of the scene.

FIG. 27 is a diagram illustrating yet another example of a personalized regimen. Italicized font represents one or more points of platform data and/or platform features that are created, populated, modified, and/or configured by one or more clinicians, ML/AI models and/or other platform feature(s). The names of the scenes presented in this diagram are for descriptive purposes only and are simply meant to describe the functional purpose of the scene.

Figure 28:
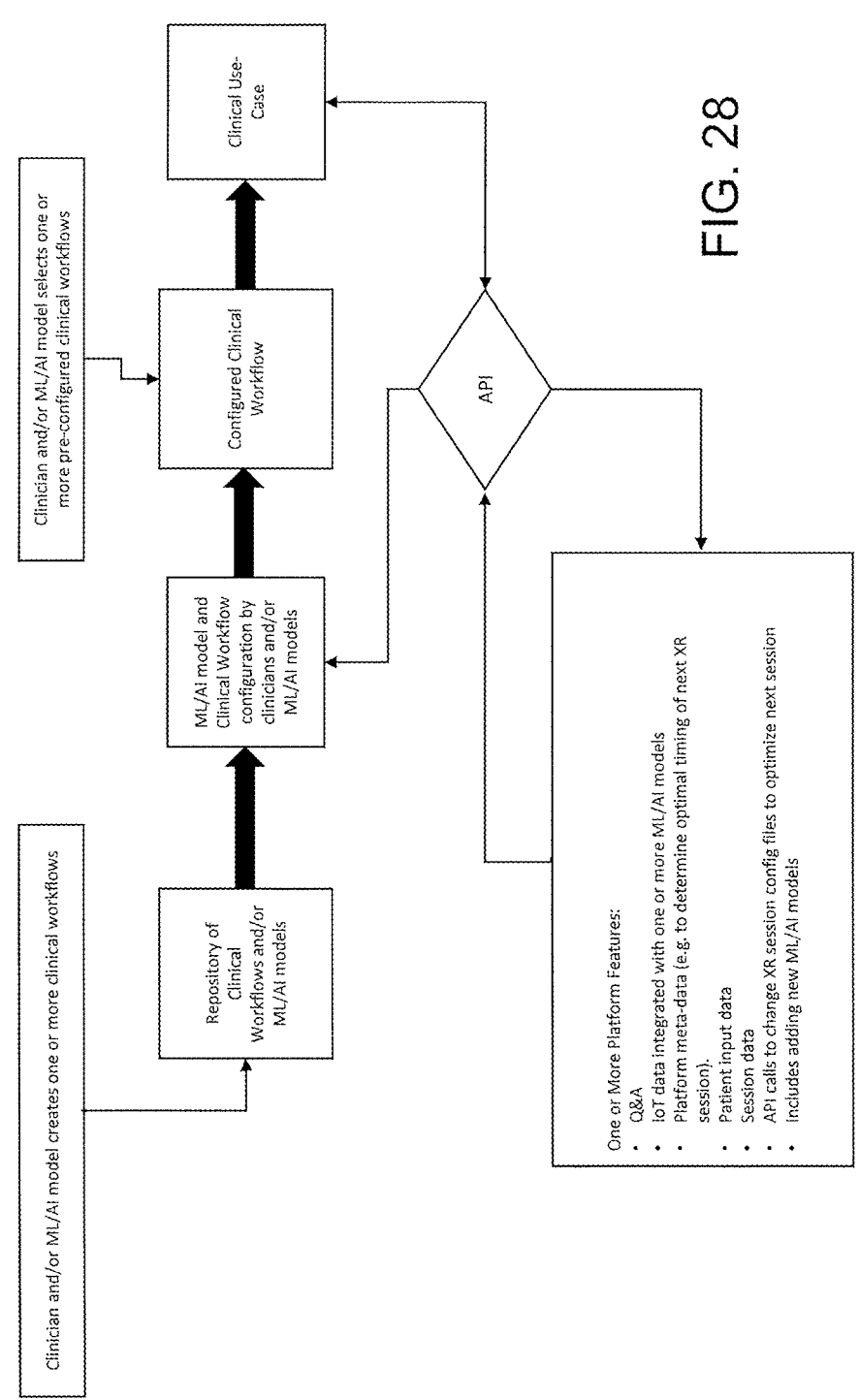

FIG. 28 is a diagram illustrating one example of a system to create, and/or integrate clinical workflows for diagnostic, therapeutic, and/or care delivery purposes.

Figure 29:
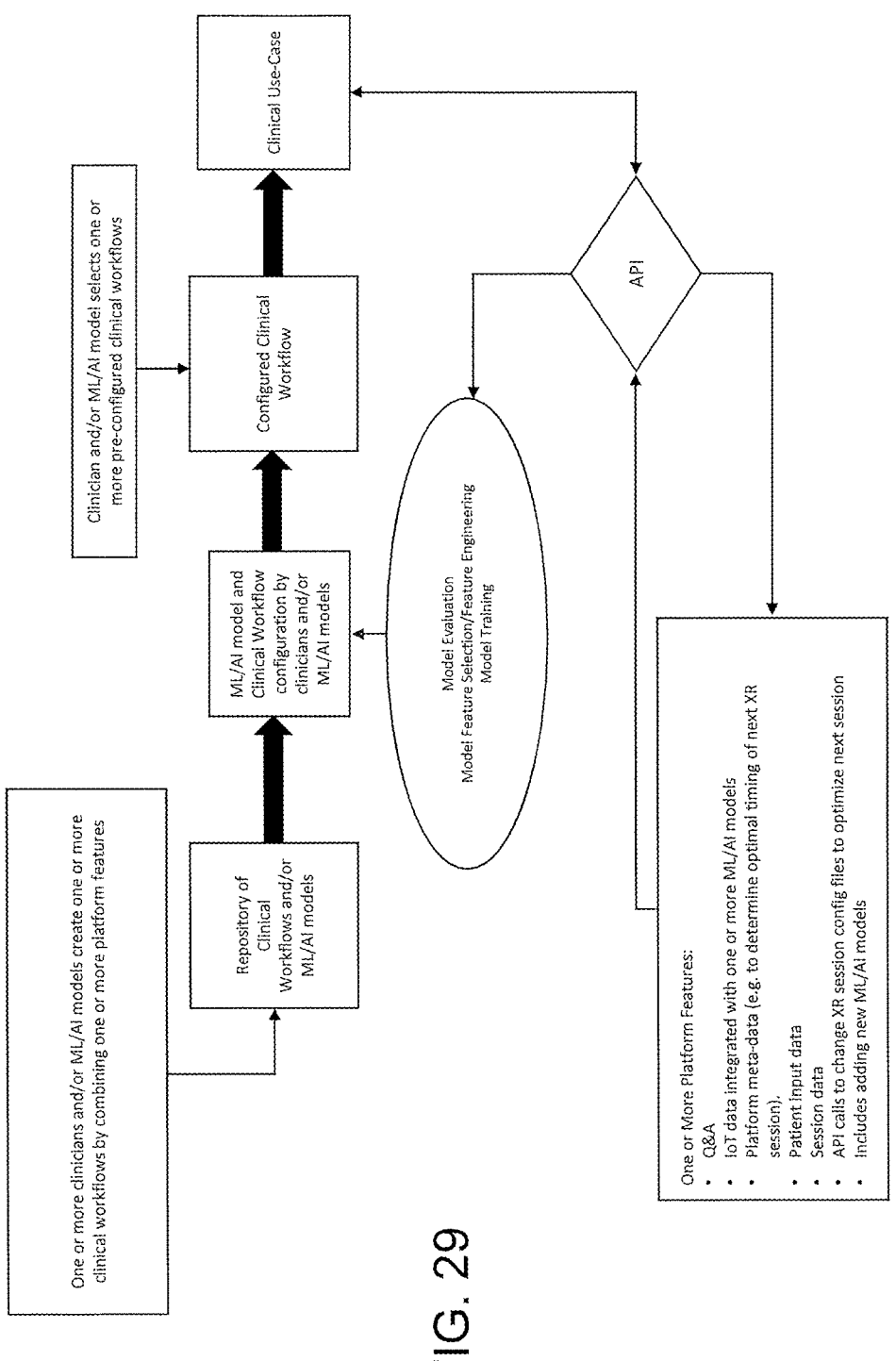

FIG. 29 is a diagram illustrating another example of a system to create, and/or integrate clinical workflows for diagnostic, therapeutic, and/or care delivery purposes.

Figure 30:
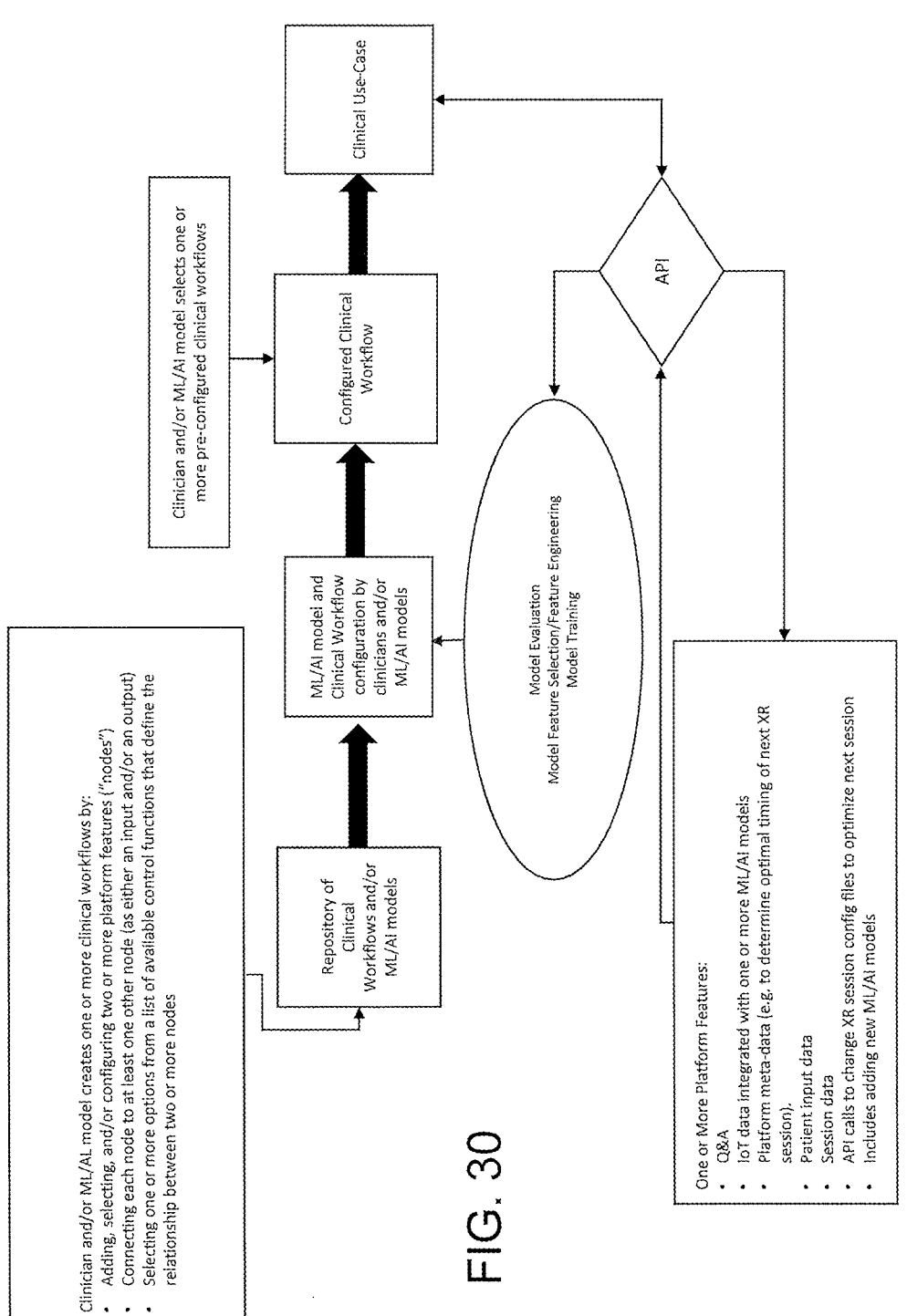

FIG. 30 is a diagram illustrating yet another example of a system to create, and/or integrate clinical workflows for diagnostic, therapeutic, and/or care delivery purposes.

Figure 31:
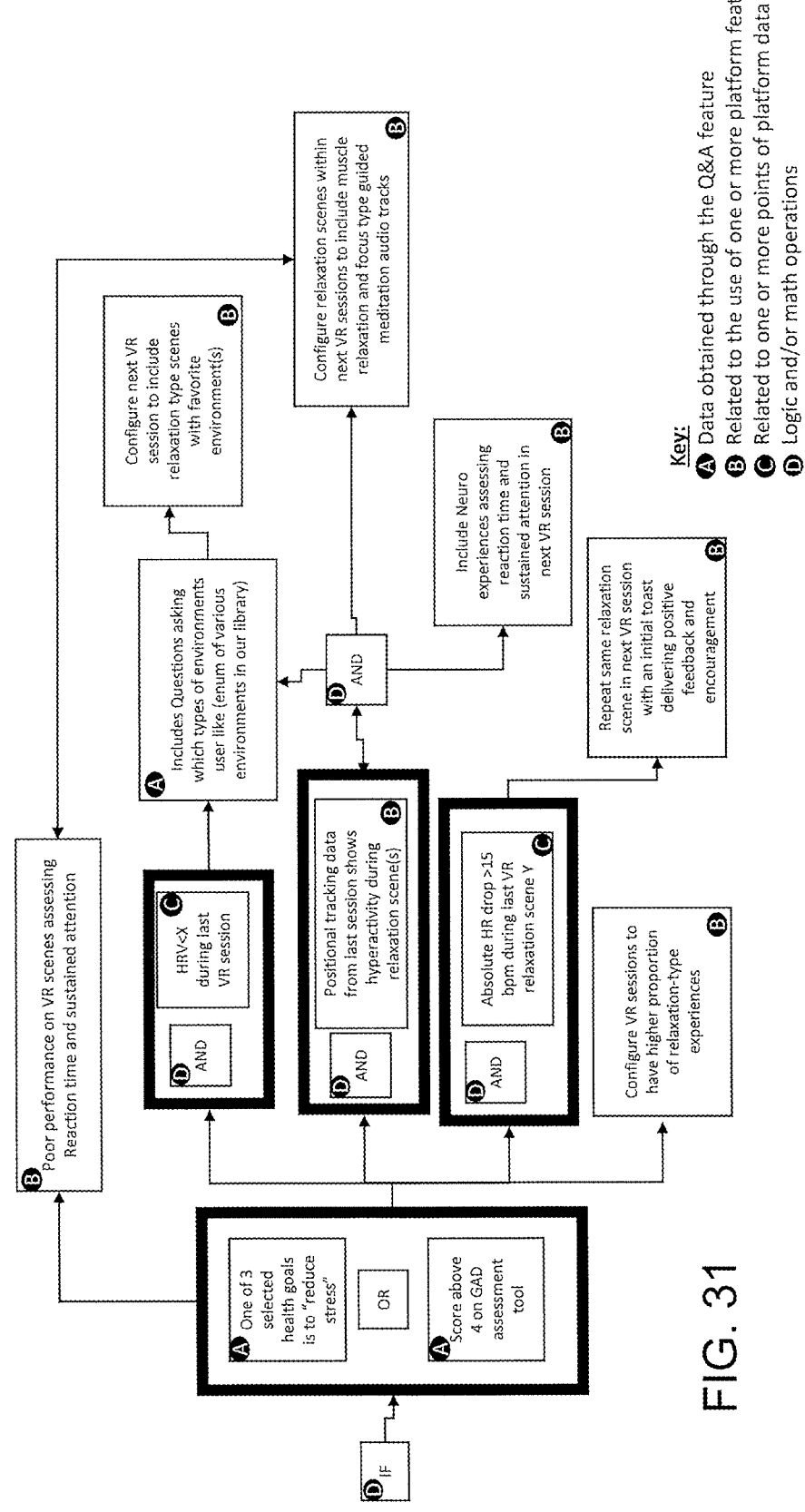

FIG. 31 is a diagram illustrating a clinical workflow example for anxiety produced using an exemplary clinical workflow feature.

Figure 32:
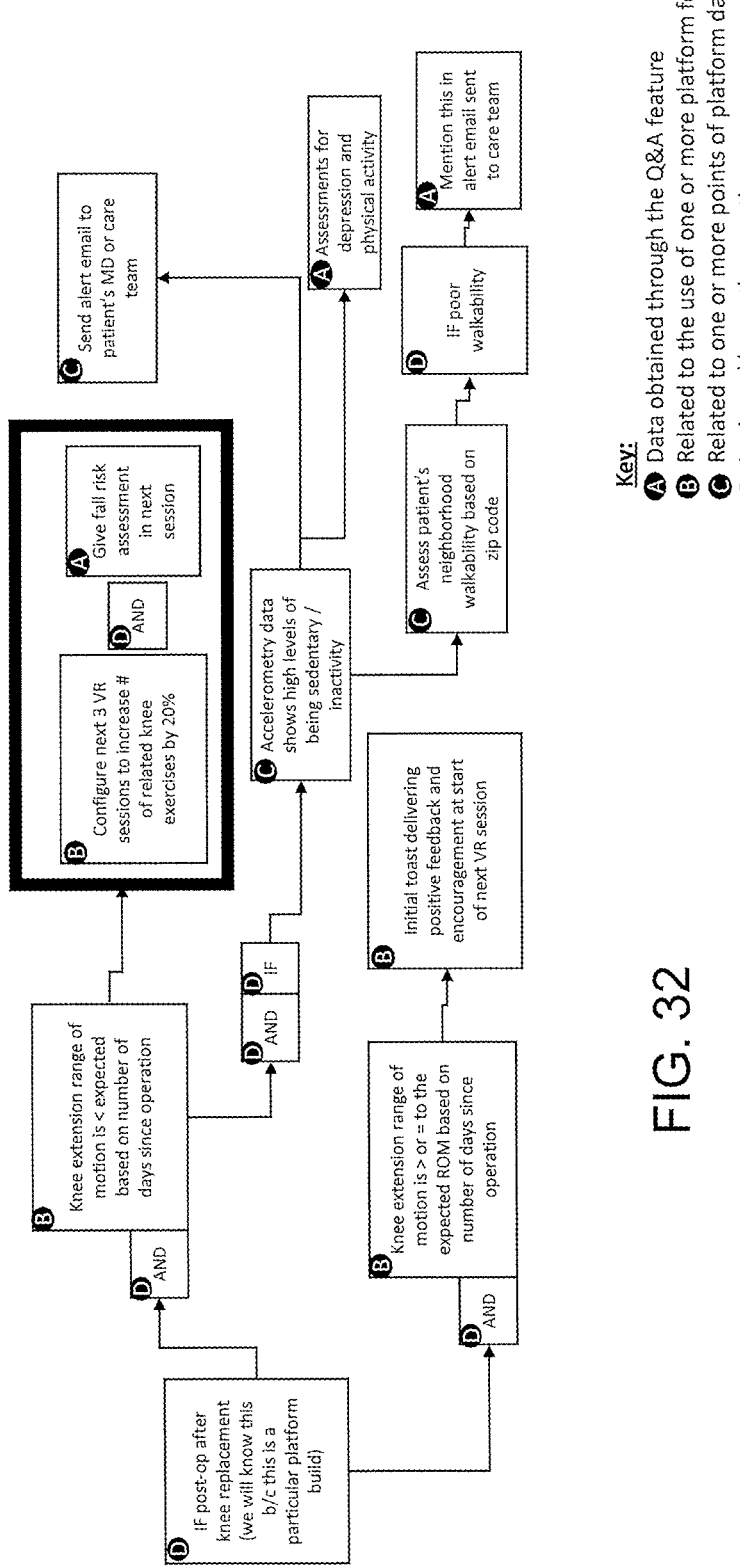

FIG. 32 is a diagram illustrating a clinical workflow example for post-op knee replacement produced using the exemplary clinical workflow feature.

Figure 33:
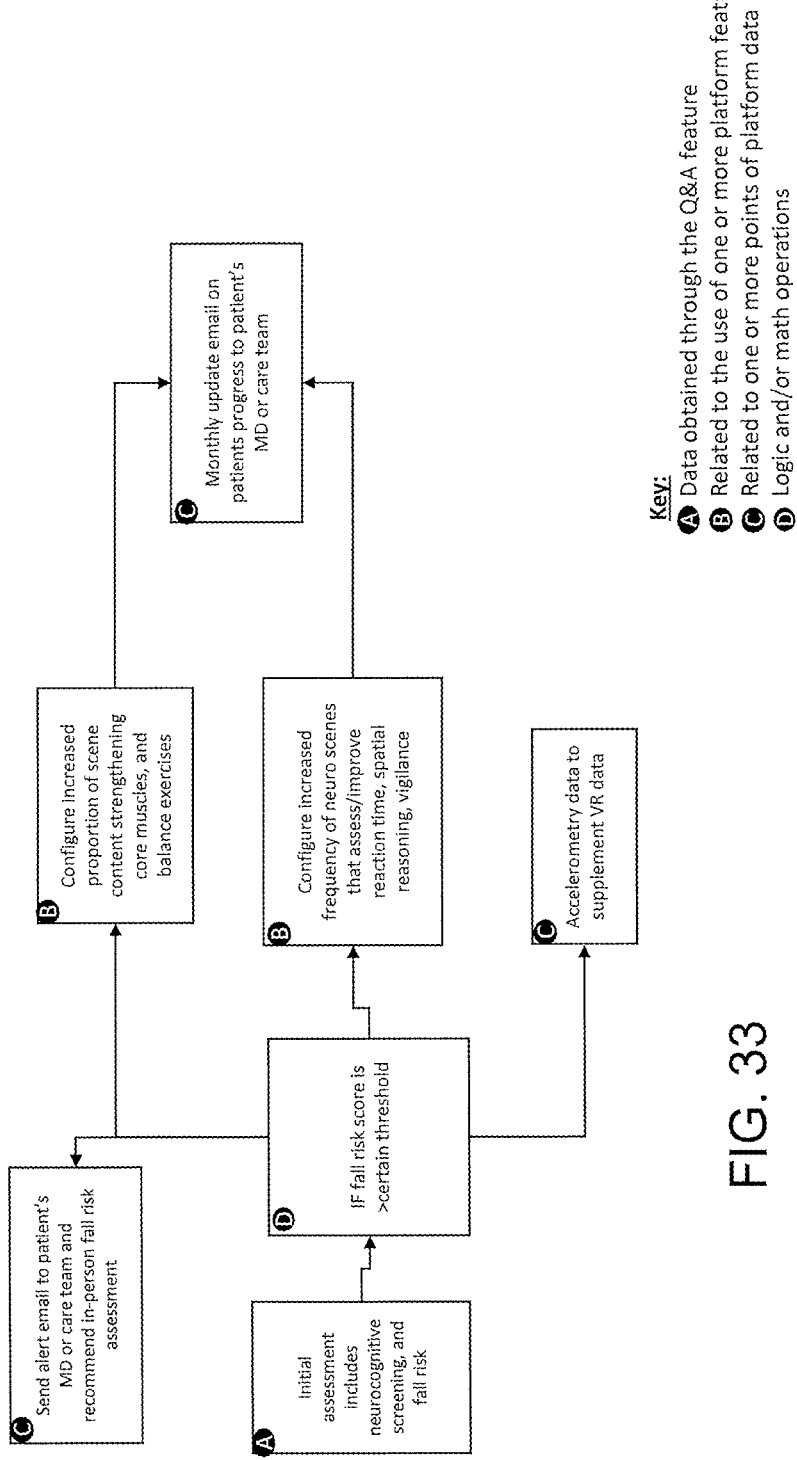

FIG. 33 is a diagram illustrating a clinical workflow example for fall risk assessment and mitigation produced using the exemplary clinical workflow feature.

Figure 34:
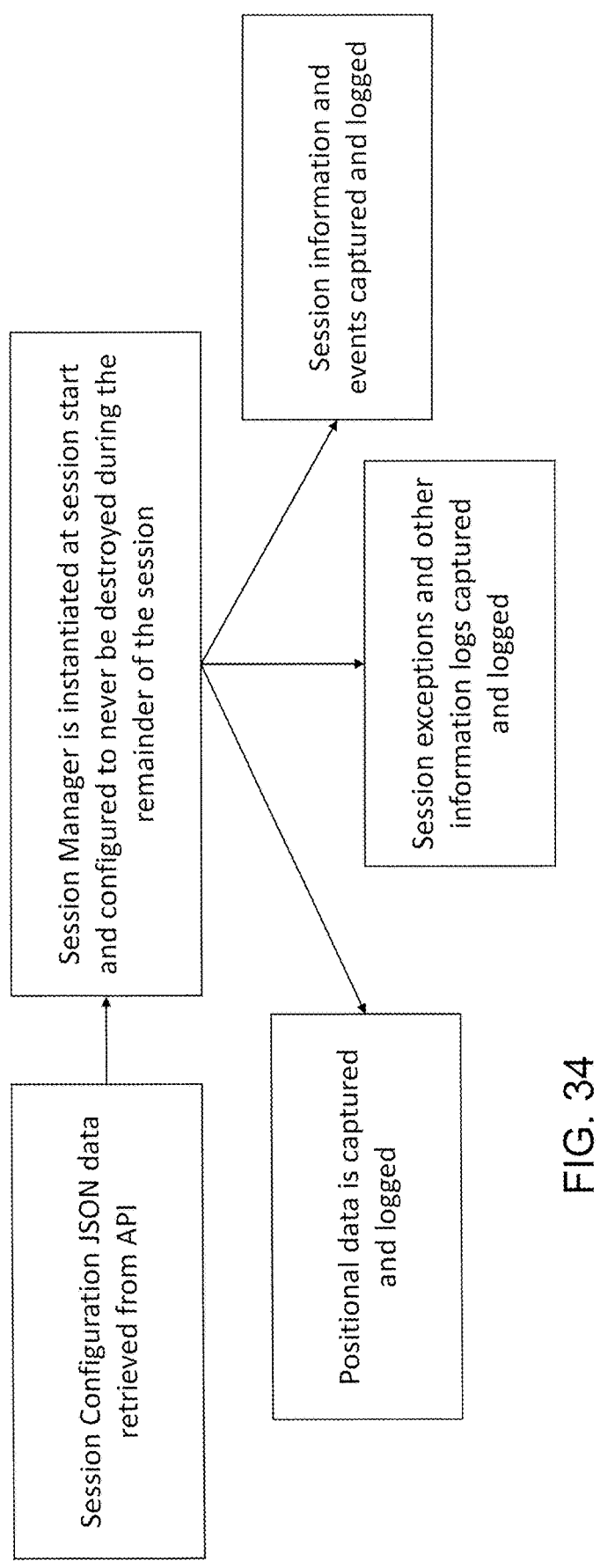

FIG. 34 is a diagram illustrating one embodiment of an exemplary session configuration feature.

Figure 35:
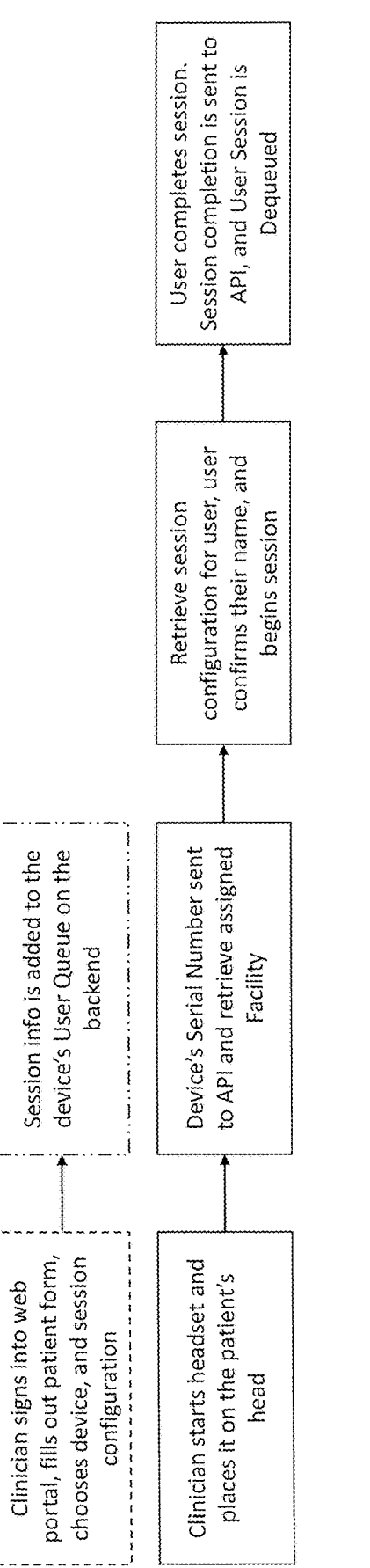

FIG. 35 is an exemplary facility session diagram.

Figure 36:
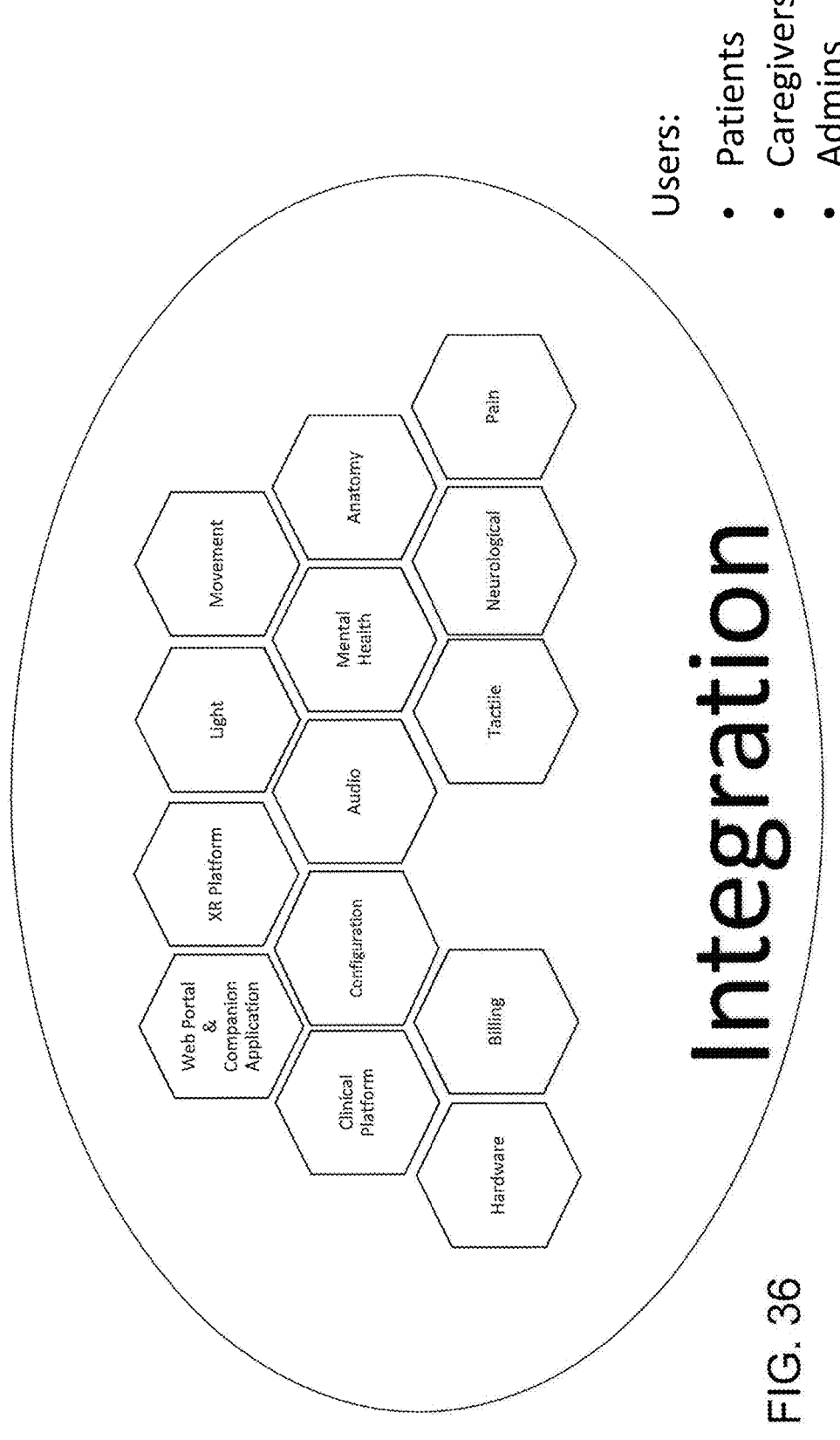

FIG. 36 is a diagram illustrating an embodiment of the XR Health Platform demonstrating one role of the exemplary Integration Module.

Figure 37:
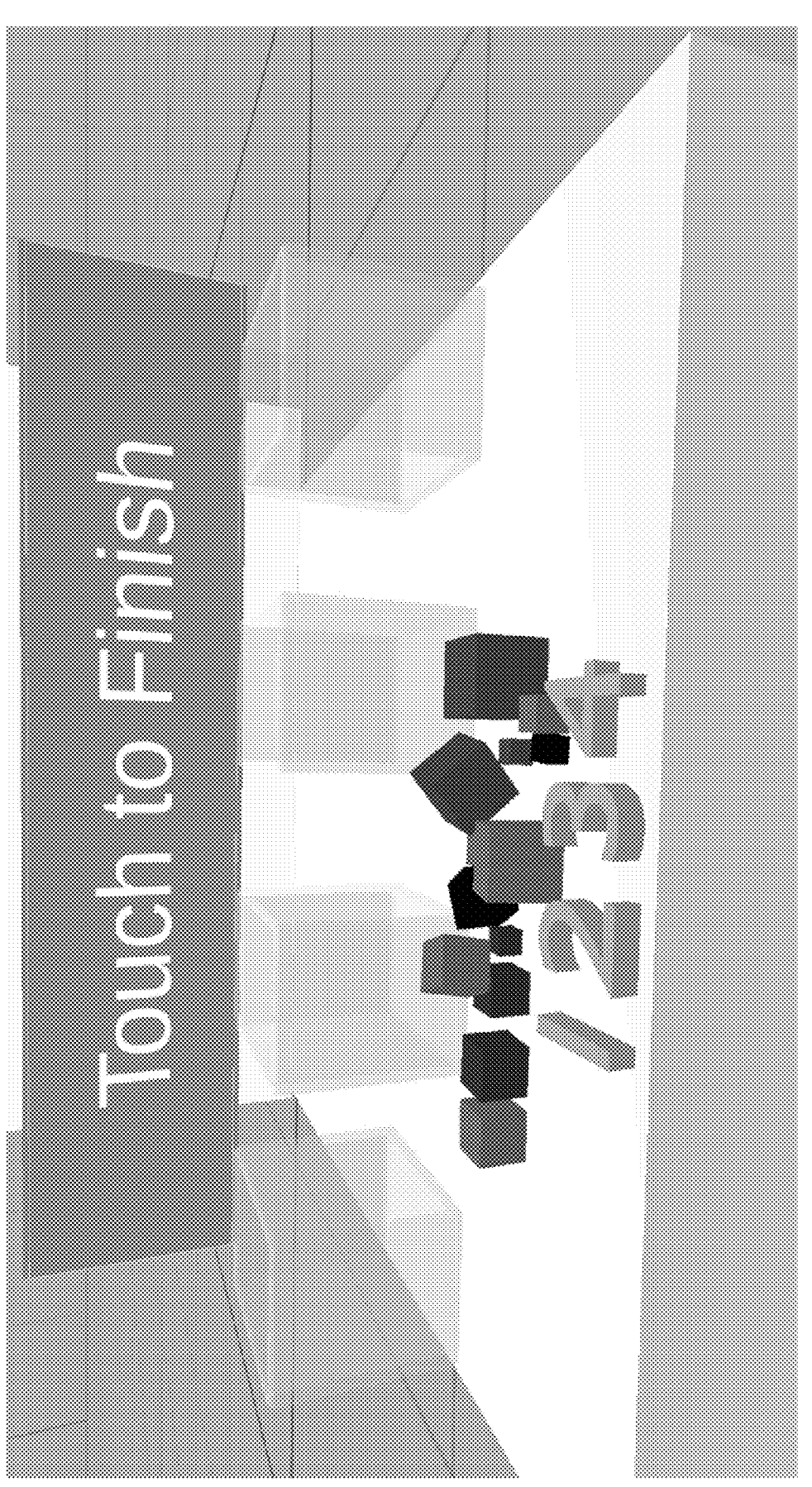

FIG. 37 is a diagram illustrating one example of a 3D sorting test.

Figure 38:
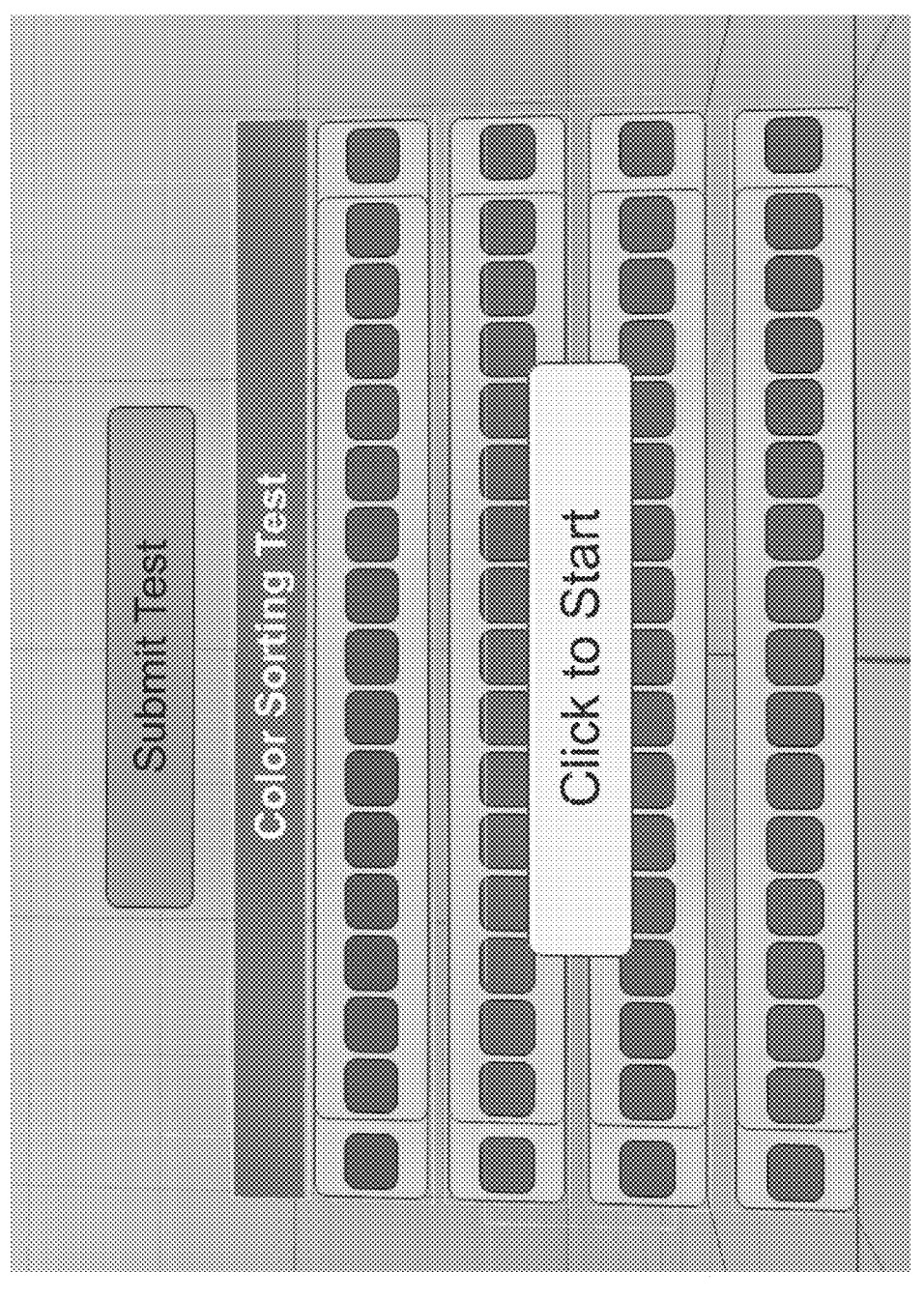

FIG. 38 is a diagram illustrating one example of a color sorting test.

Figure 39:
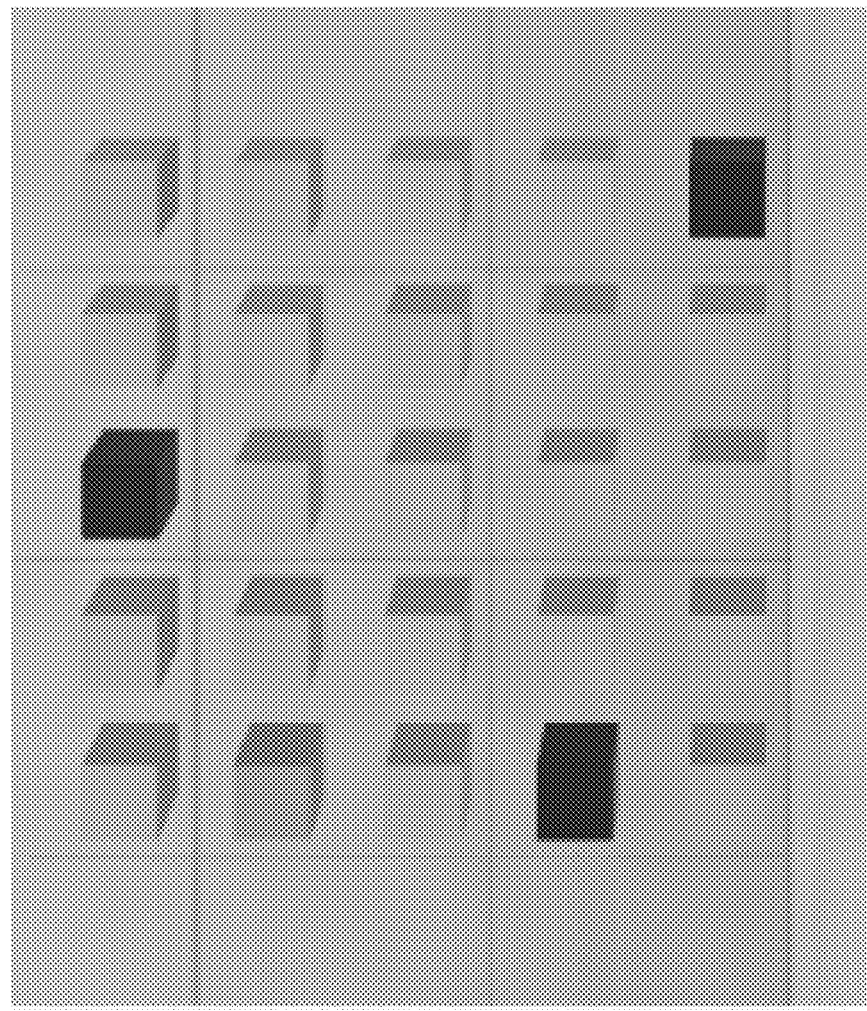

FIG. 39 is a diagram illustrating one example of an episodic memory test.

Figure 40:
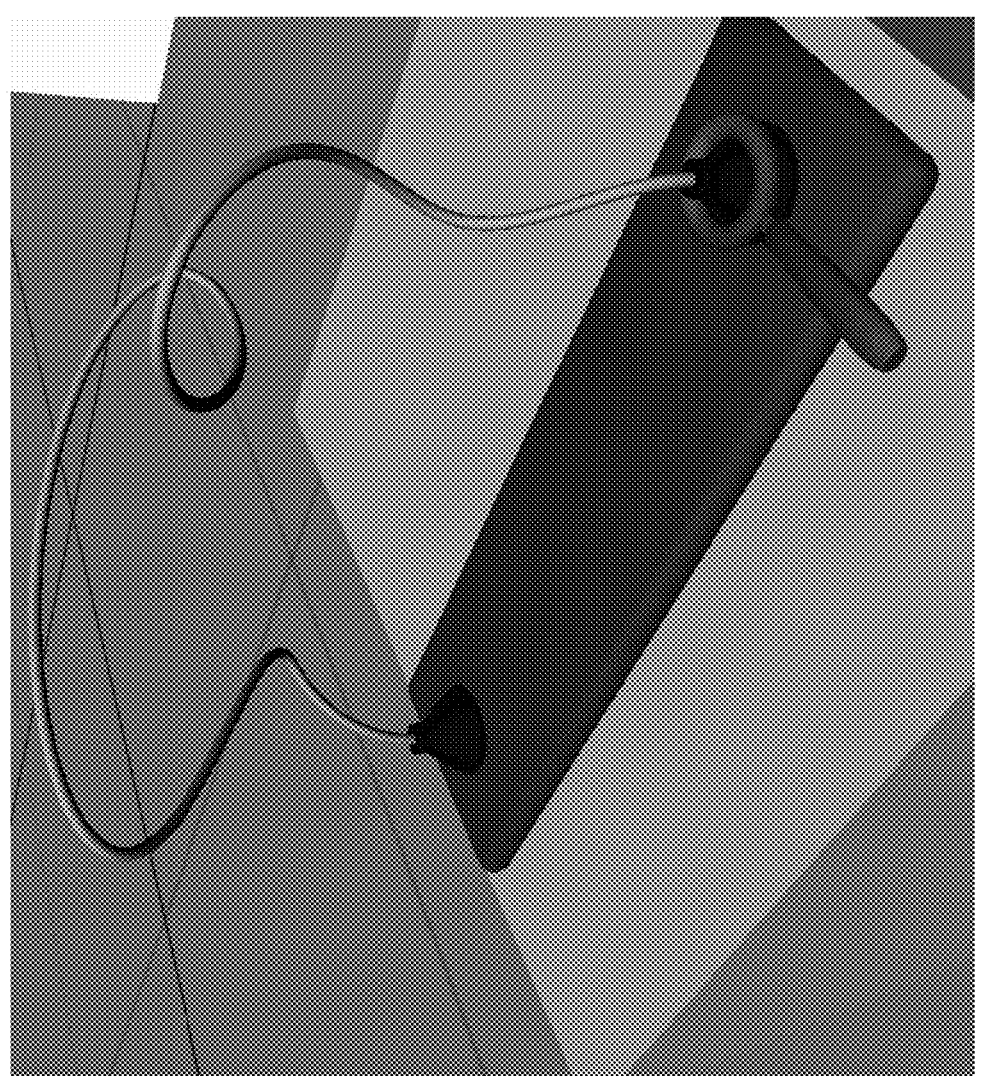

FIG. 40 is a diagram illustrating one example of a loop and wire test.

Figure 41:
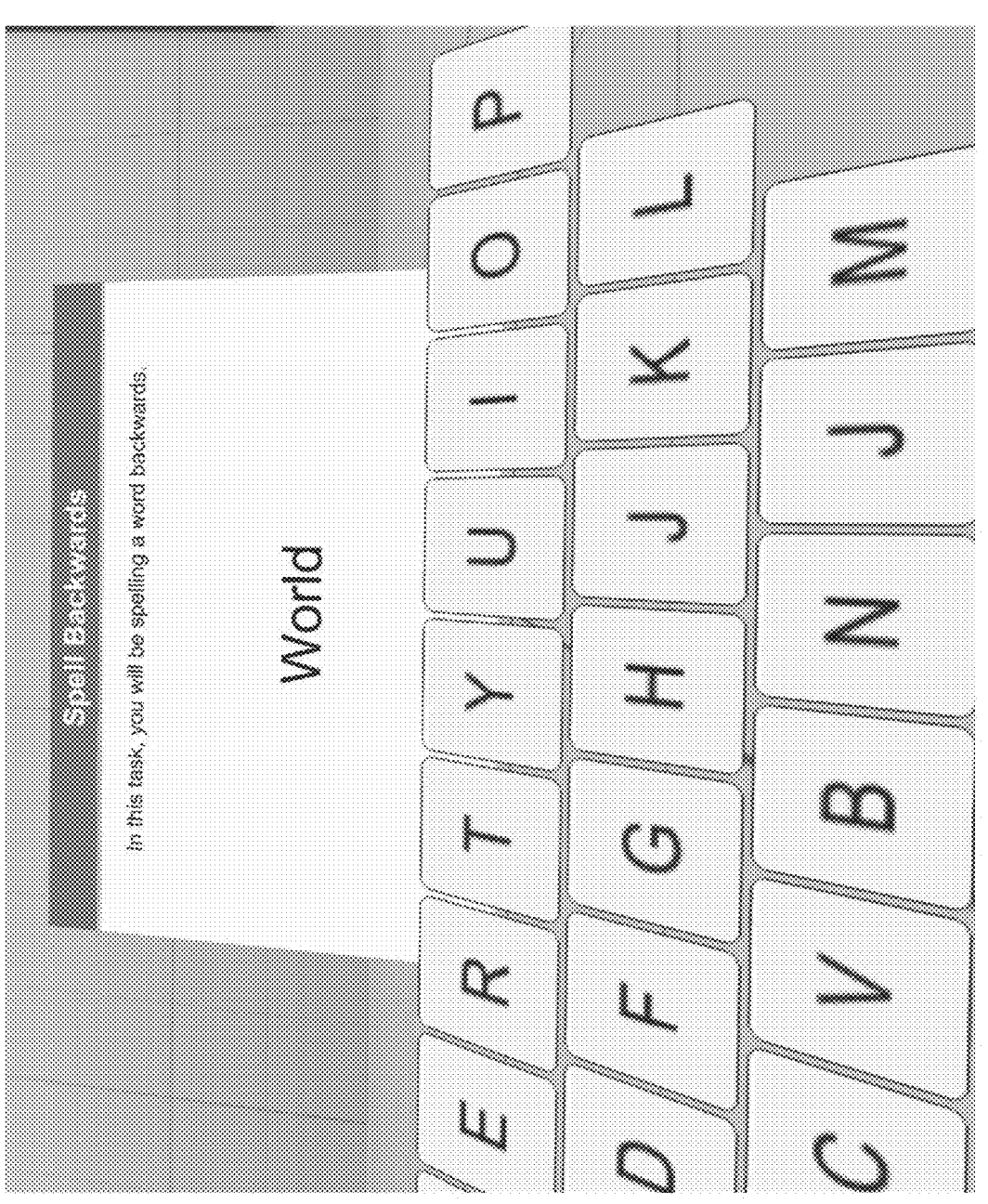

FIG. 41 is a diagram illustrating one example of a spell backwards test.

Figure 42:
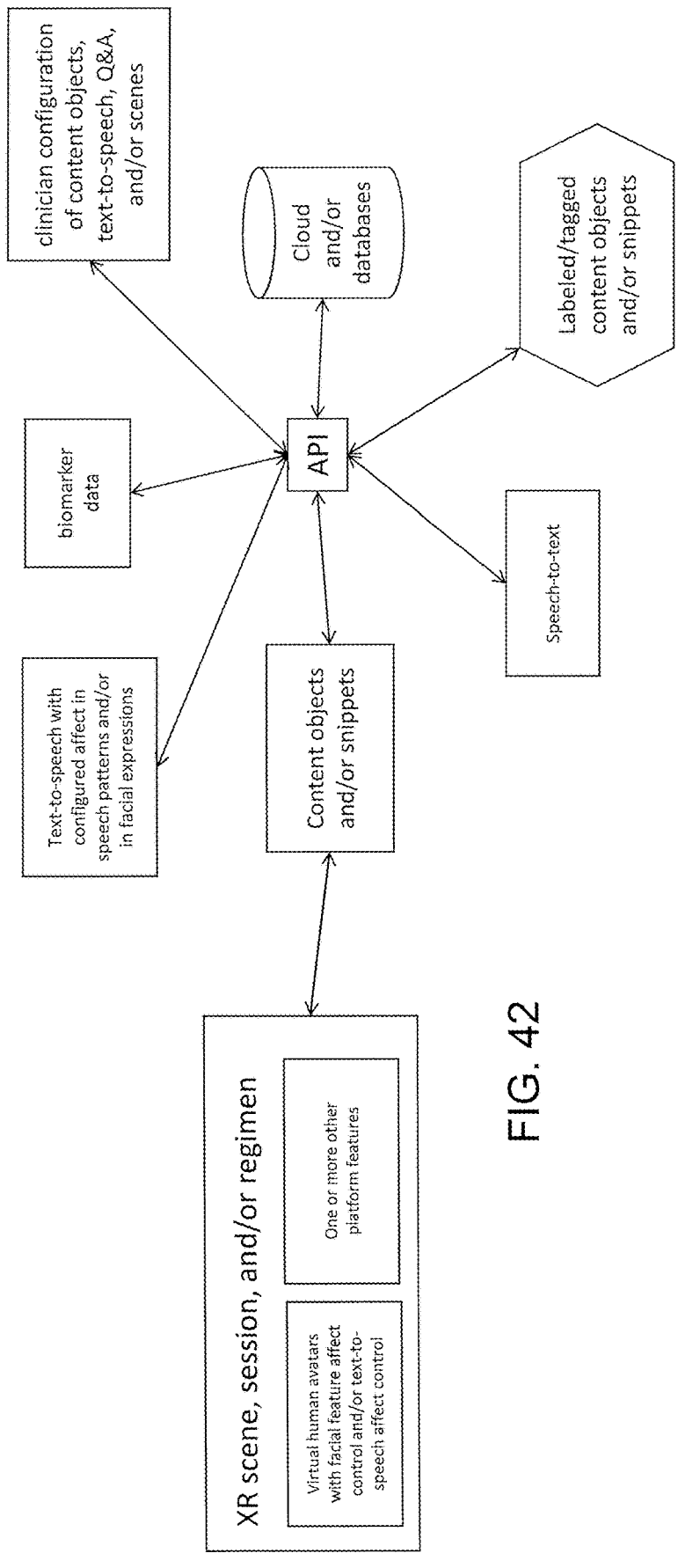

FIG. 42 is a diagram illustrating one mental health-related embodiment of the exemplary XR Health Platform.

Figure 43:
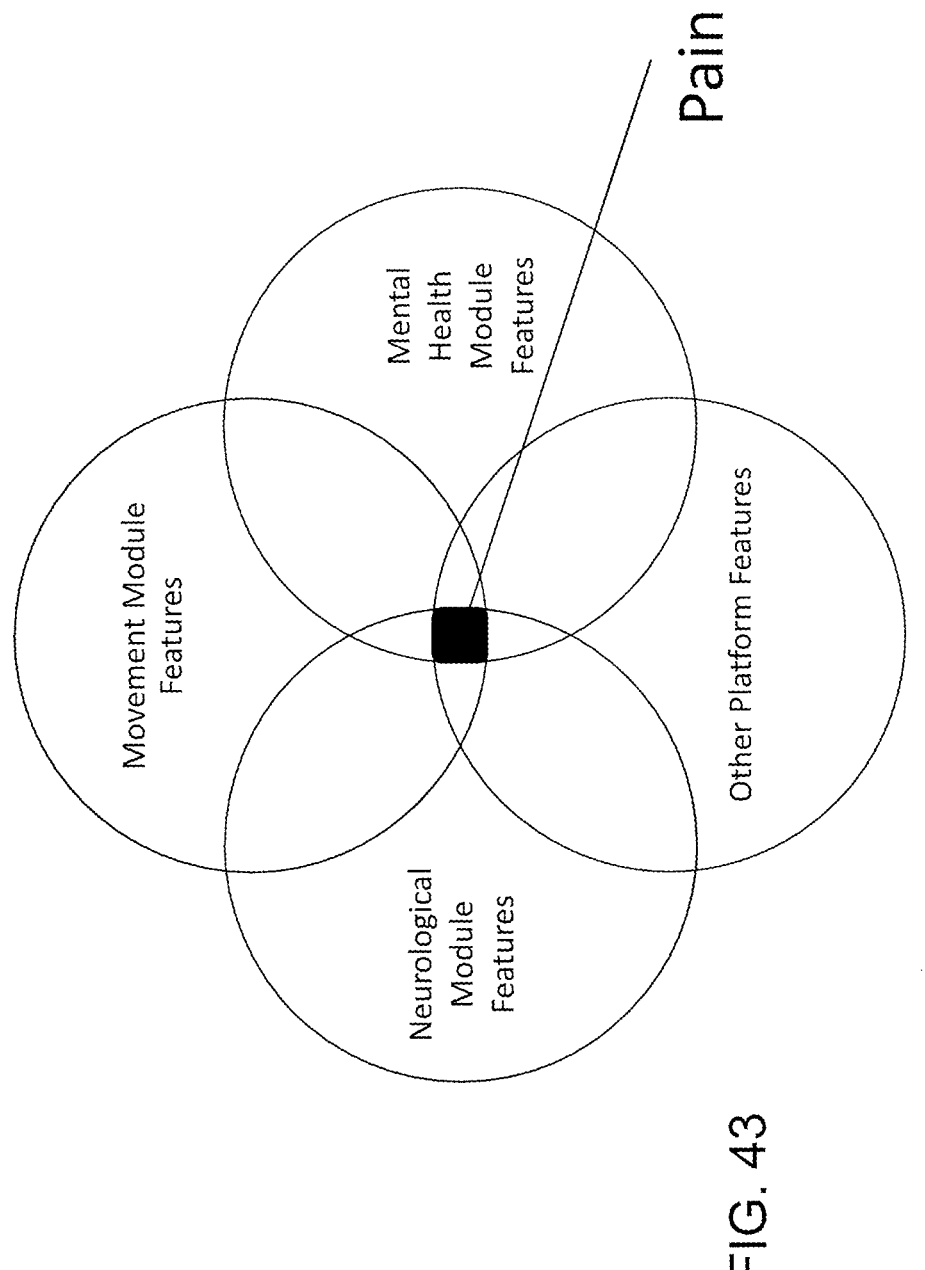

FIG. 43 is a diagram illustrating the clinical capabilities of the platform with regard to pain.

Figure 44:
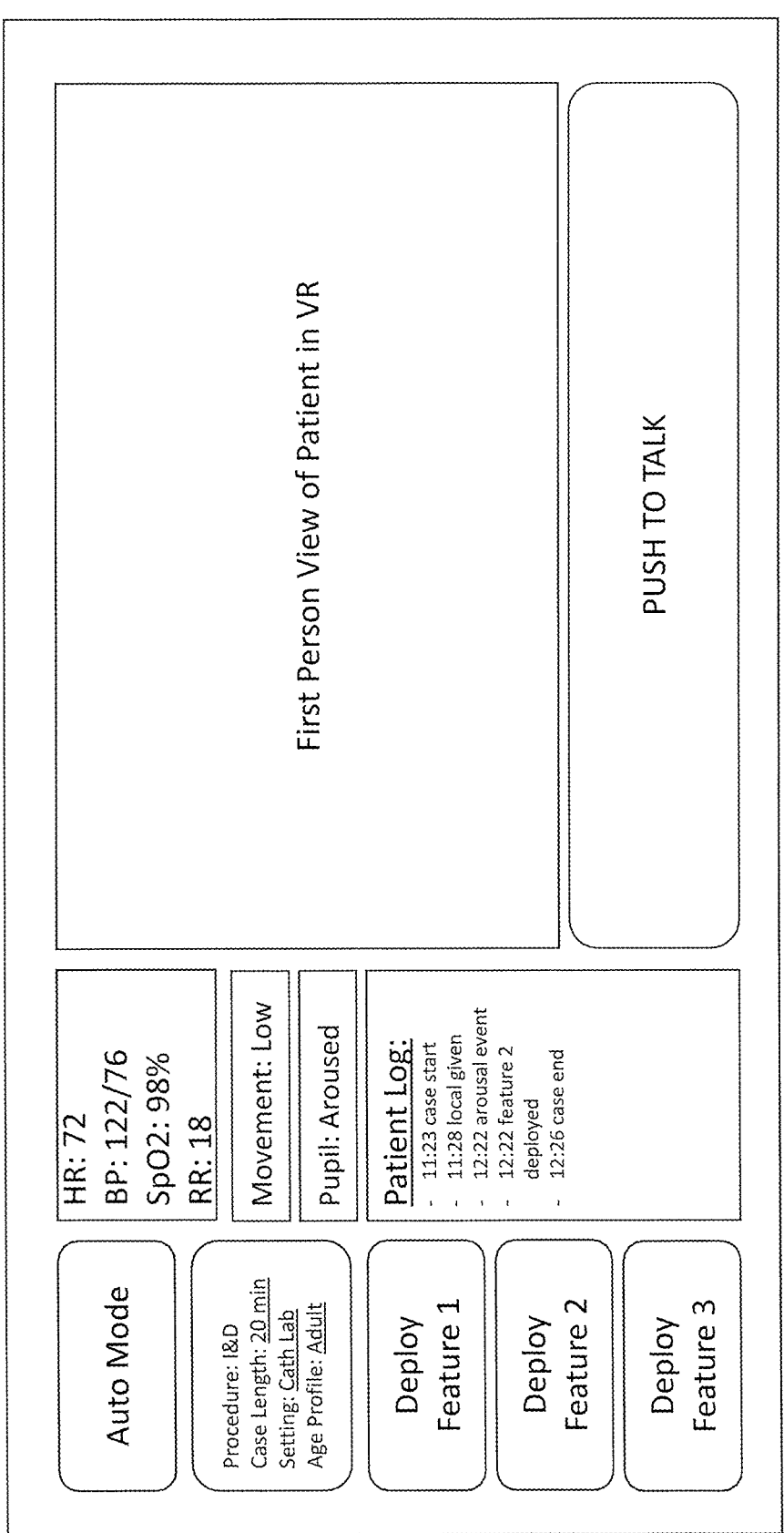

FIG. 44 is a diagram illustrating one embodiment of an XR companion application.

Figure 45:
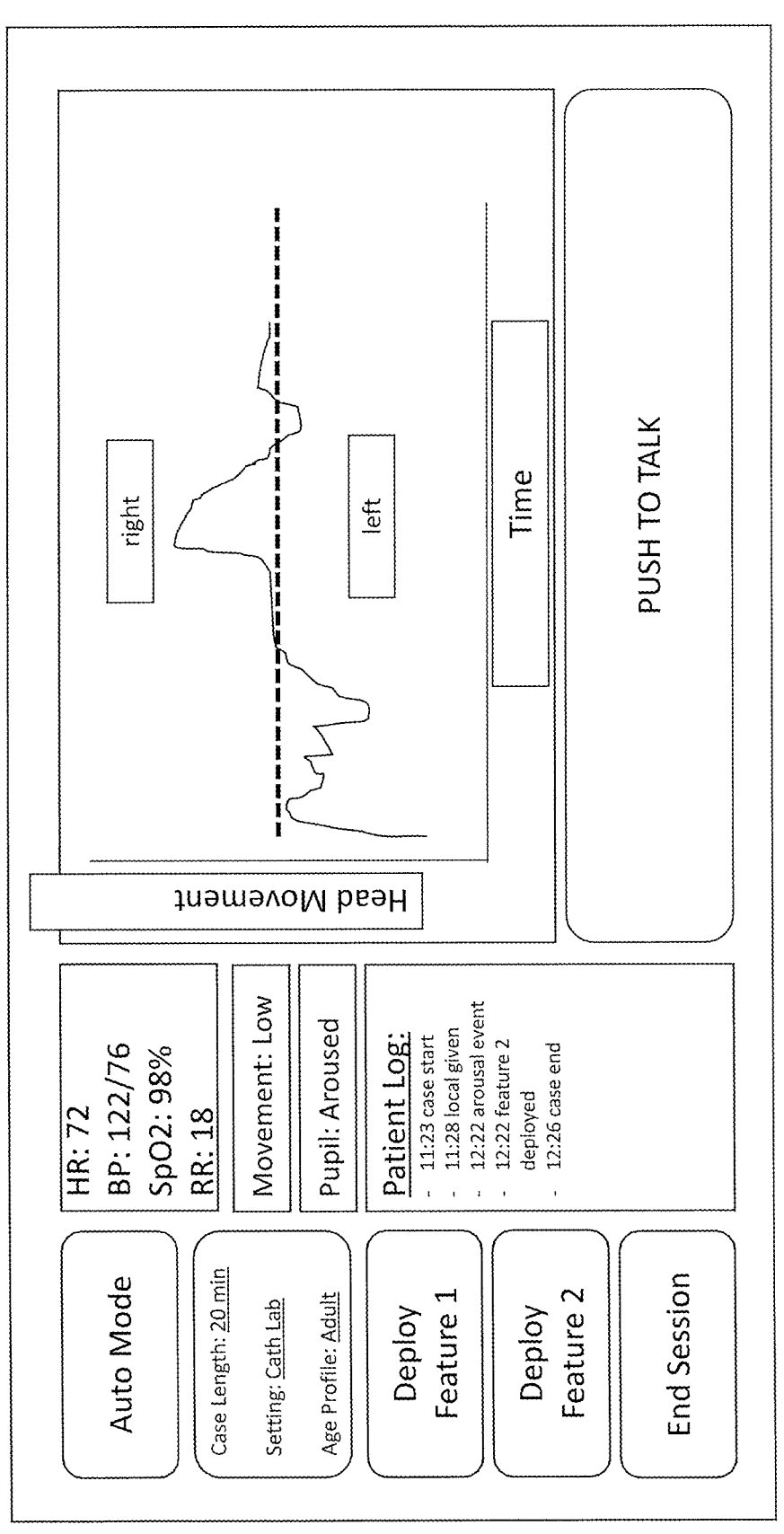

FIG. 45 is a diagram illustrating another embodiment of the provider application.

Figure 46:
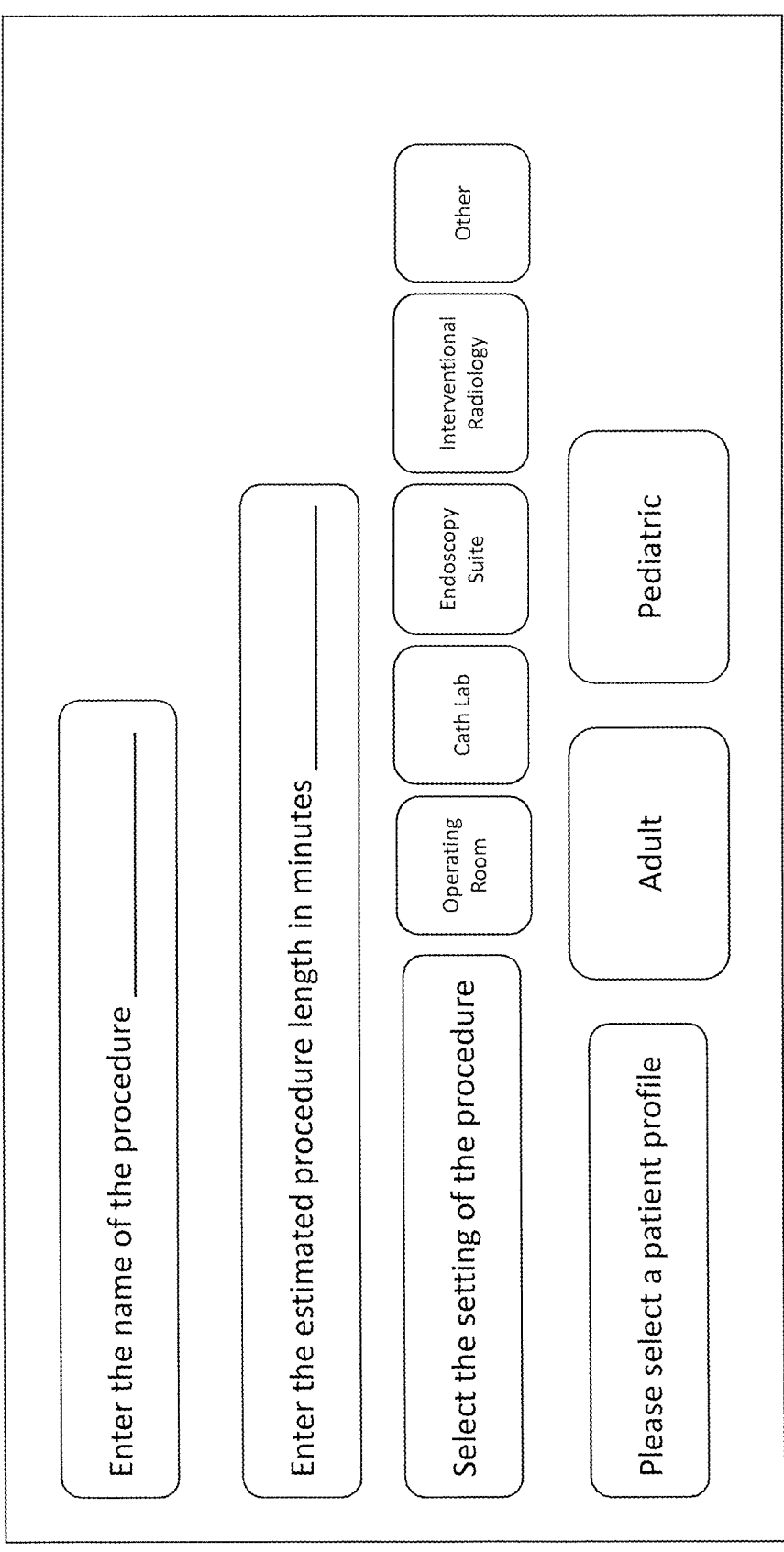

FIG. 46 is a diagram illustrating one embodiment of a pre-procedure form.

Figure 47:
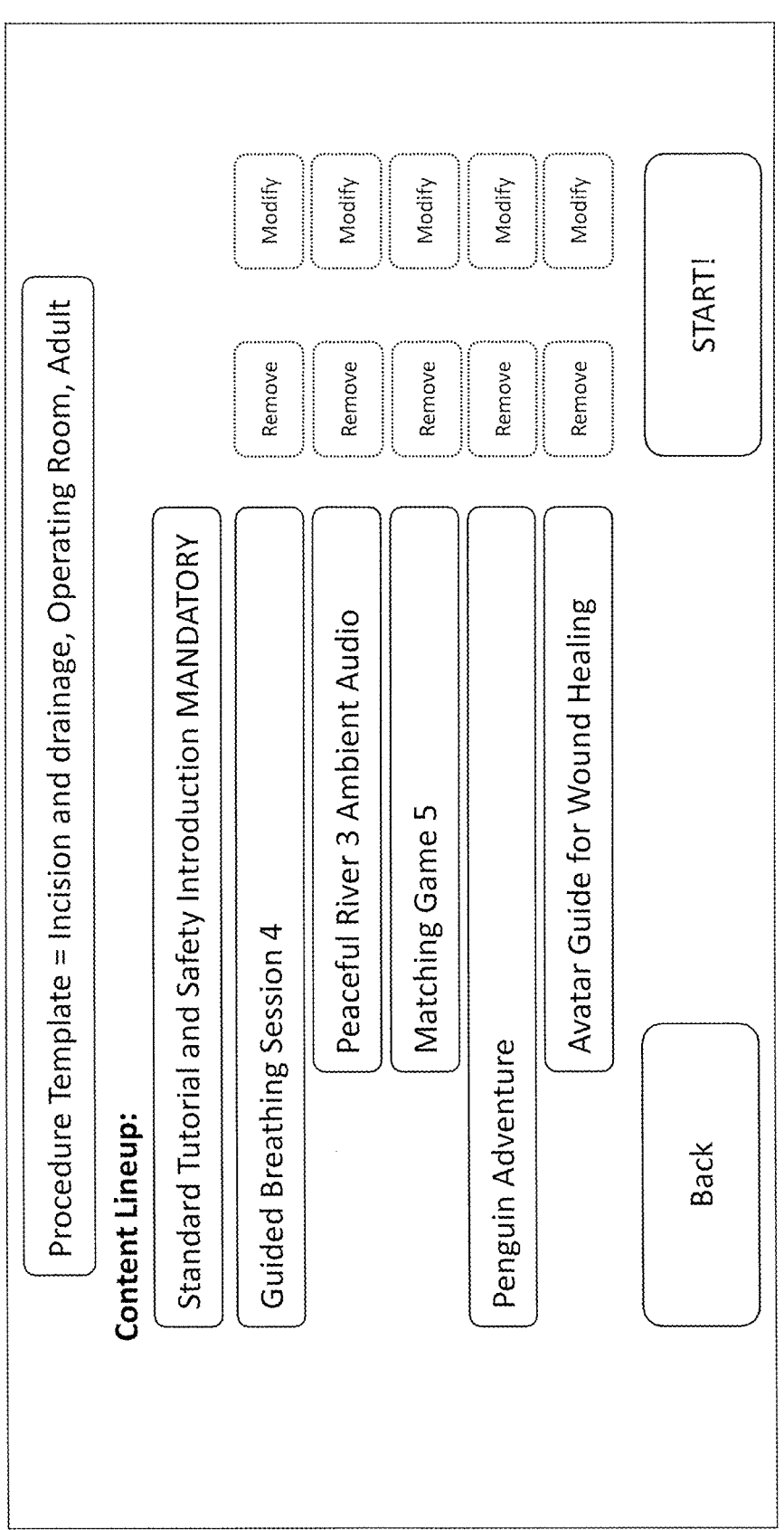

FIG. 47 is a diagram illustrating one embodiment of a procedure template.

Figure 48:
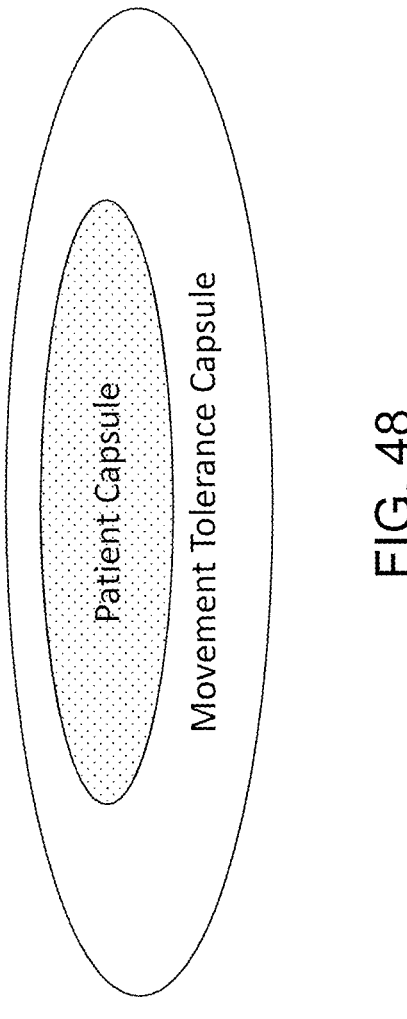

FIG. 48 is a diagram illustrating proper alignment of patient and movement tolerance capsules.

Figure 49:
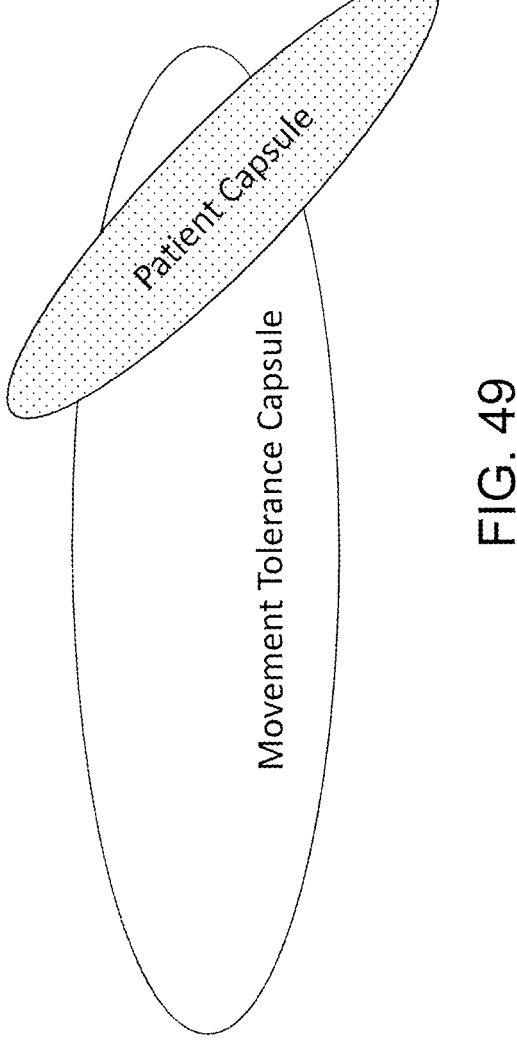

FIG. 49 is a diagram illustrating an example of improper patient alignment and movement tolerance capsules.

Figure 50:
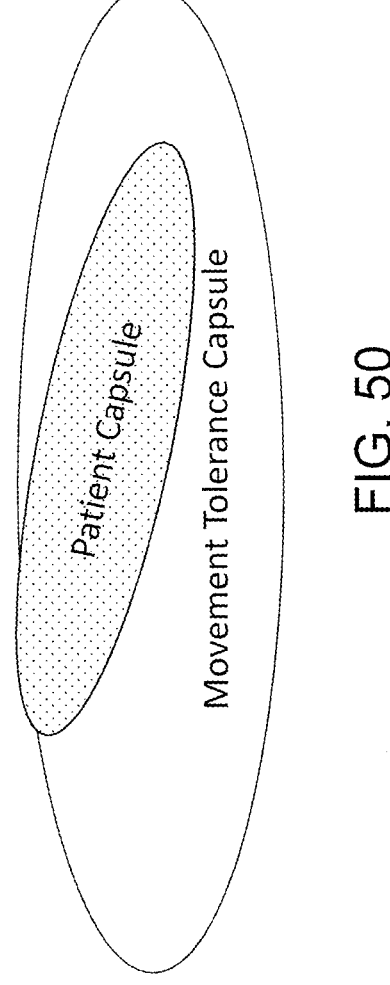

FIG. 50 is a diagram illustrating another example of improper patient alignment and movement tolerance capsules.

Figure 51:
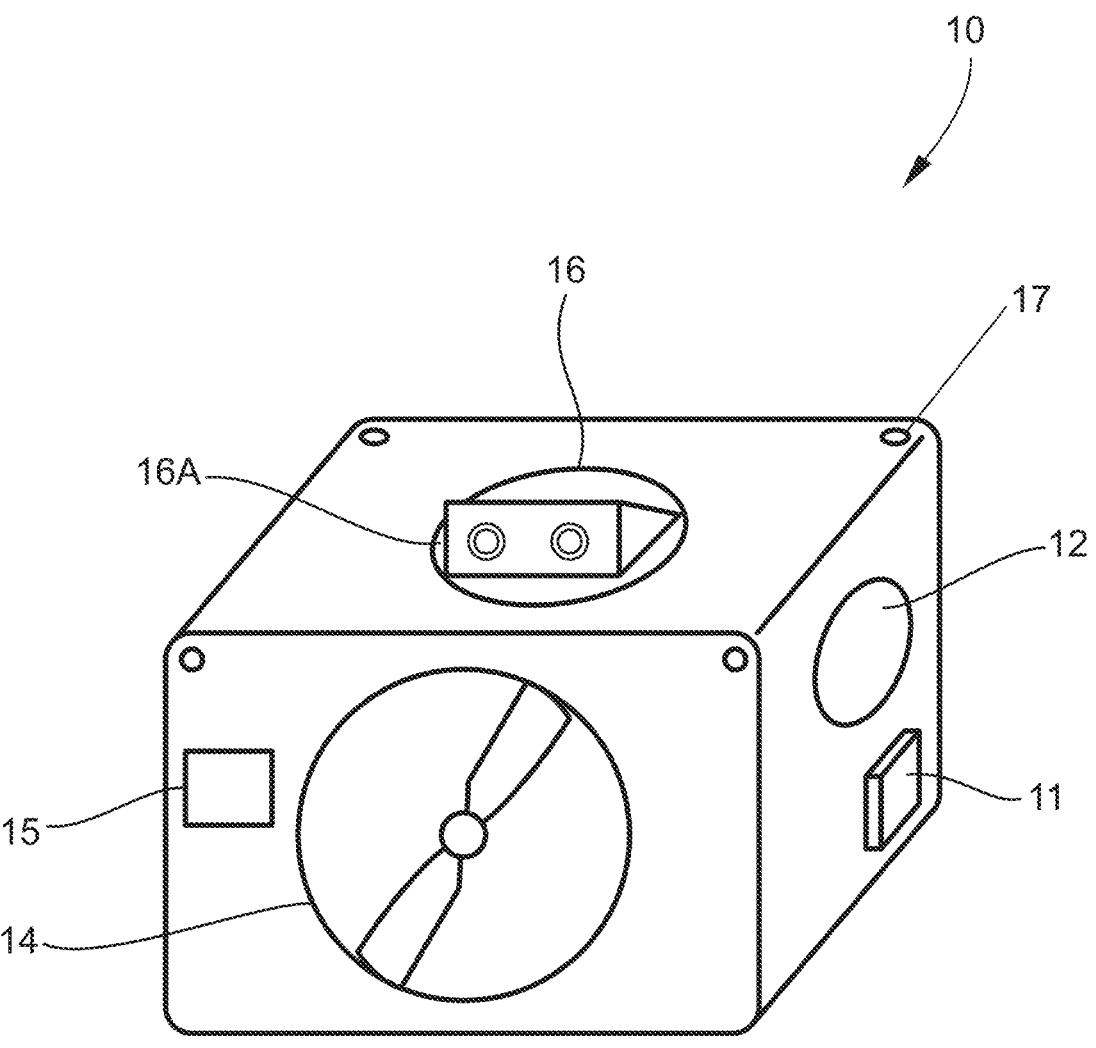

FIG. 51 is a diagram illustrating an exemplary "Box" device of the present disclosure.

Figure 52:
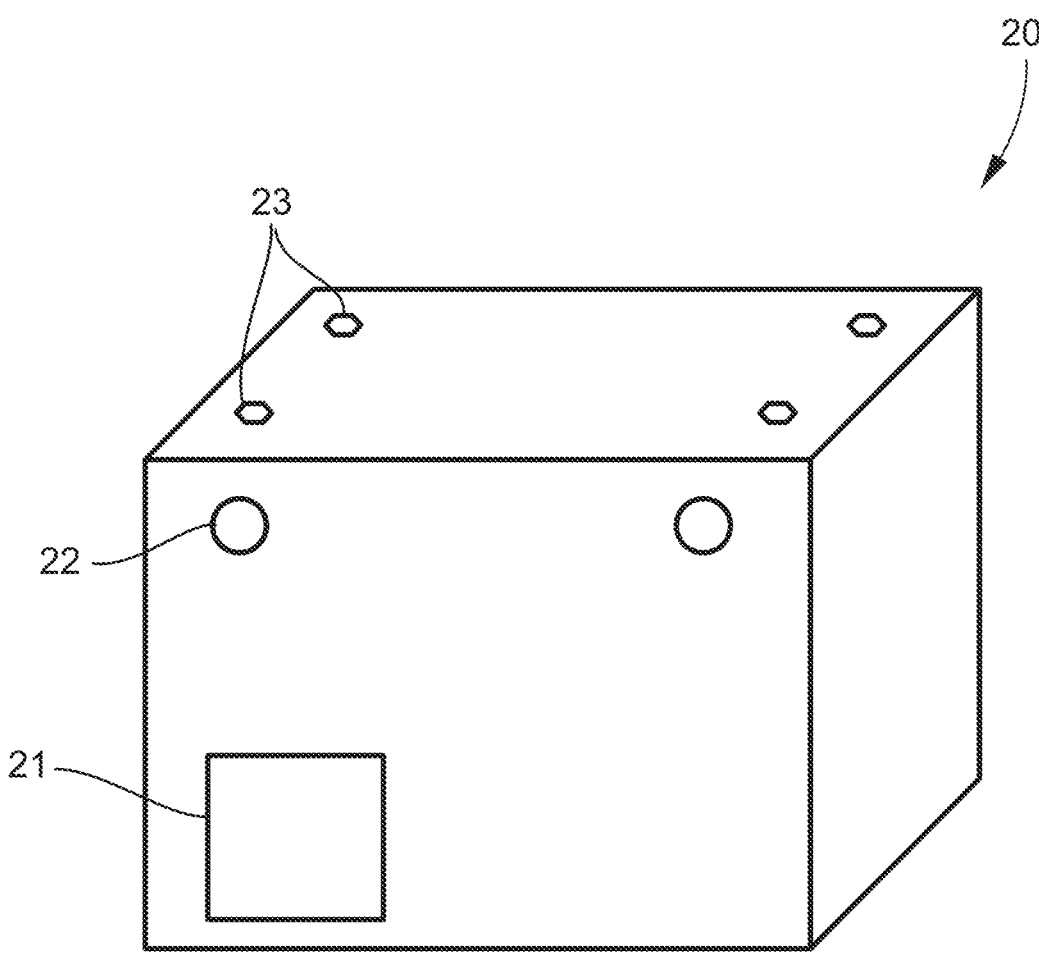

FIG. 52 is a diagram illustrating an exemplary "O.R. Box" device.

Figure 53:
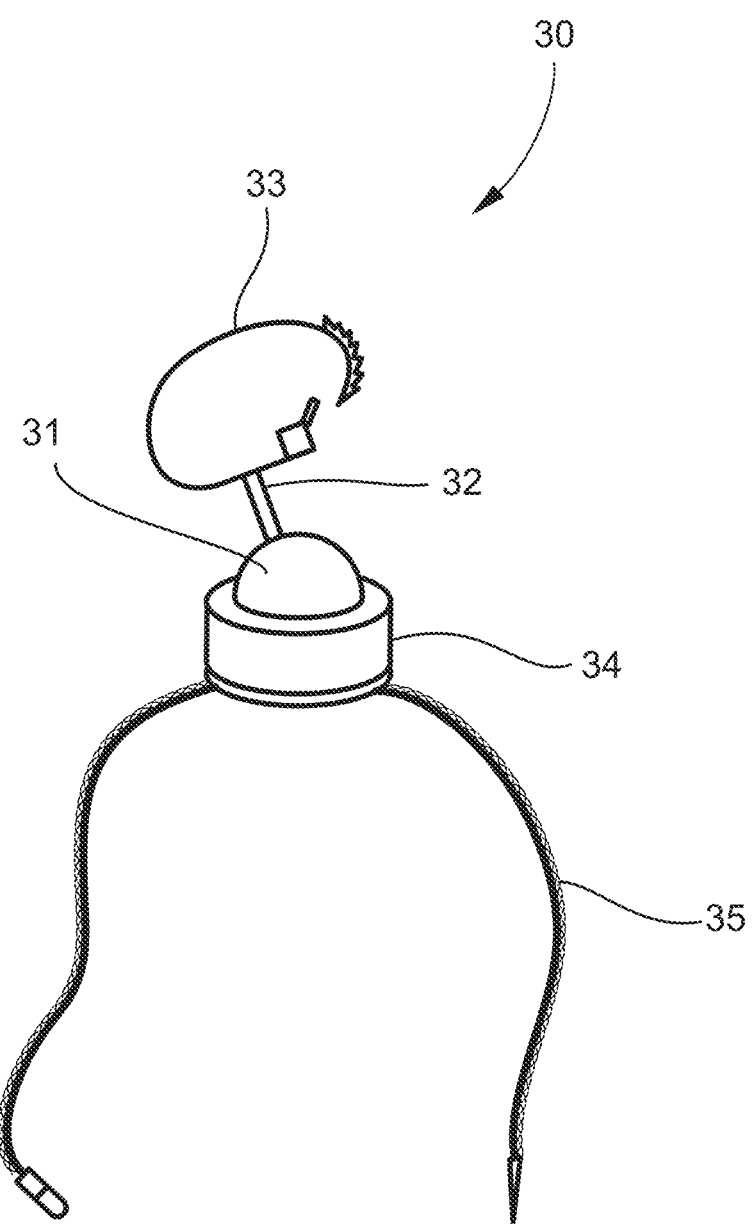

FIG. 53 is a diagram illustrating an exemplary controller clip/harness.

Figure 54:
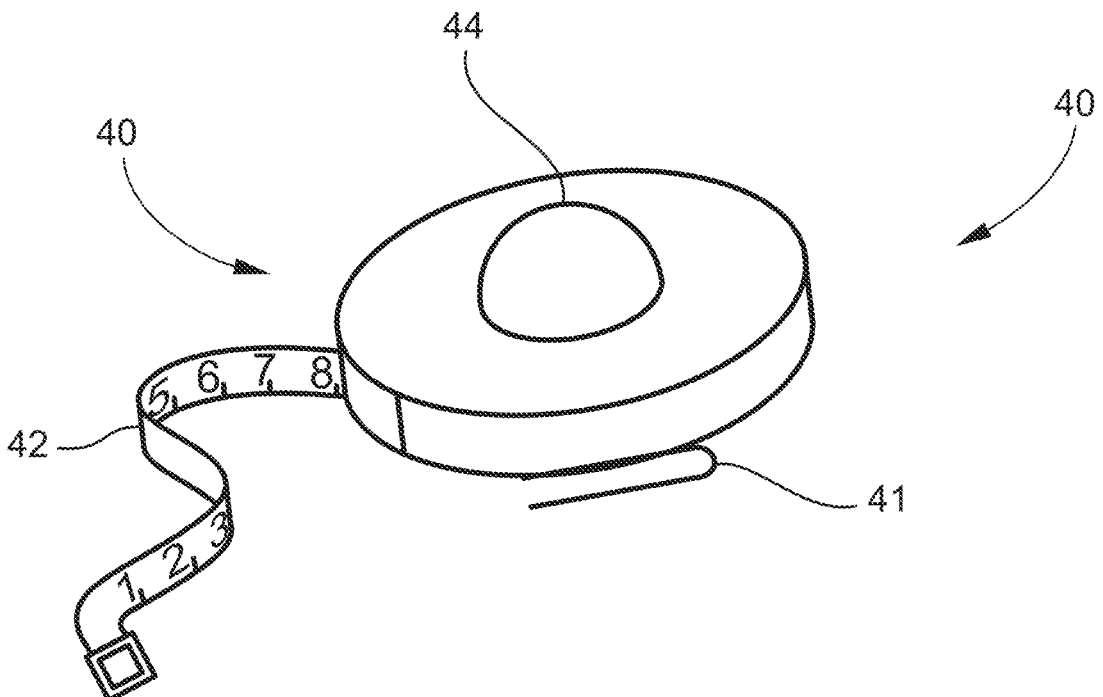

FIG. 54 is a diagram illustrating an exemplary measuring tape.

Figure 55:
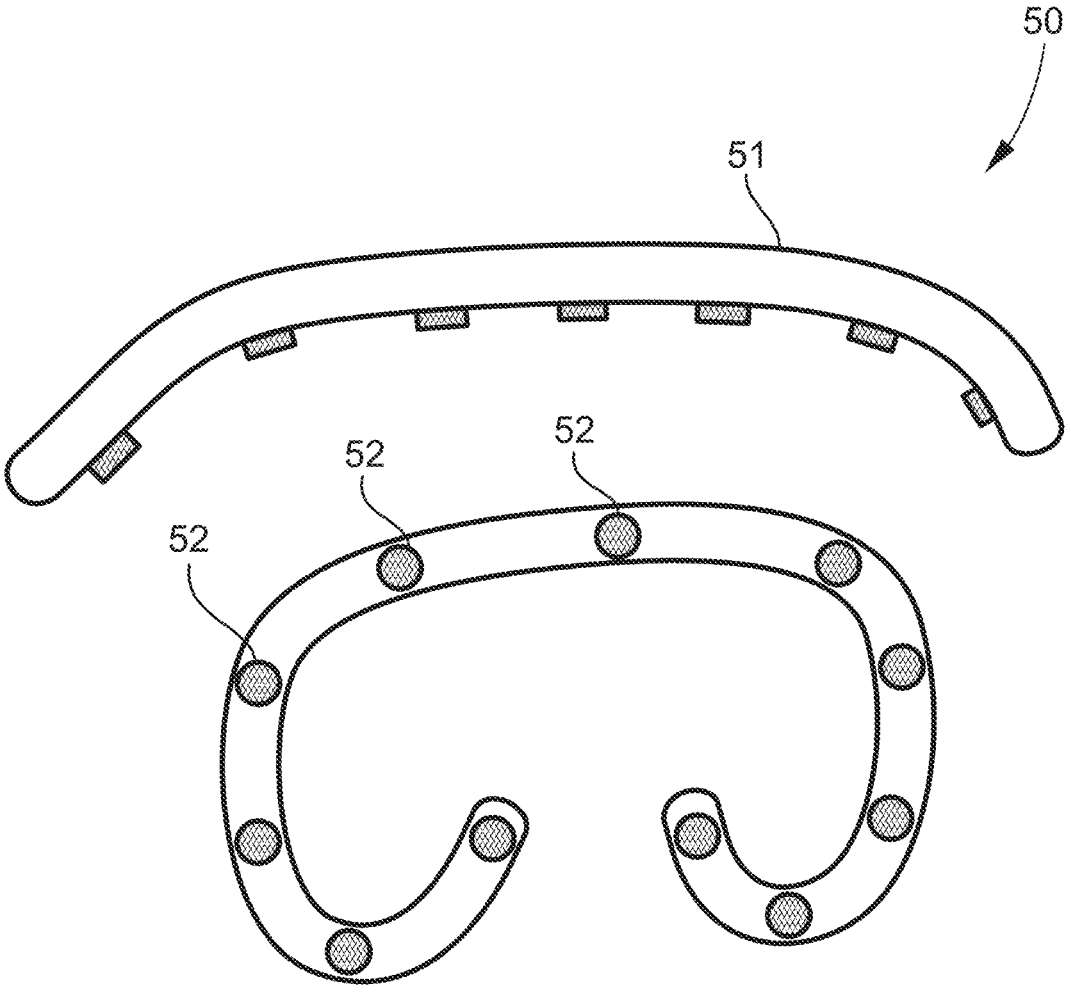

FIG. 55 is a diagram illustrating an exemplary HMD cushion.

FIG. 56 is a diagram illustrating one embodiment of the controller handle sensor device.

DESCRIPTION OF EXEMPLARY EMBODIMENTS AND BEST MODE

The present invention is described more fully hereinafter with reference to the accompanying drawings, in which exemplary embodiments of the invention are shown. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, and any and all equivalents thereof.

Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Referring now specifically to the drawings, the present disclosure comprises an extended reality health platform, system and method also referred to broadly and collectively herein as "XR Health Platform" or "XR Platform" or "Platform" or the like.

The exemplary XR Platform of the present disclosure may be implemented via a computer program product (e.g., software application or "mobile app") comprising program instructions tangibly stored on a computer-readable medium, and operable to cause a computing device to execute the present XR Health Platform. The present disclosure further comprises a computer-readable storage medium storing computer-executable instructions, executable by processing logic of a computing device, including instructions, that when executed by the processing logic, cause the processing logic to perform the present XR Health Platform. In yet another exemplary embodiment, the present disclosure comprises an article of manufacture including a computer-readable storage medium, and executable program instructions embodied in the storage medium that when executed by processing logic of a computing device causes the processing logic to perform the present XR Health Platform. The computing device may incorporate or comprise any general or specific purpose machine with processing logic capable of manipulating data according to a set of program instructions. Examples of computing devices include standalone virtual reality devices, standalone augmented reality devices, standalone mixed reality devices, high-end mobile phones or "smartphones", tablet computers, laptops, personal computers, and others.

Exemplary Standalone Extended Reality (XR) Device

In one exemplary embodiment, the present XR Health Platform utilizes a combined extended reality head-mounted display and computing device (referred to herein as "HMD and Computing Device"). The exemplary HMD and Computing Device comprises a standalone (meaning wireless and untethered) extended reality system using an operating system such as Google's Android, Apple's iOS, and others. The exemplary HMD and Computing Device may include a virtual reality head-mounted display, an augmented reality head-mounted display, or a mixed reality head-mounted display. The HMD and Computing Device may also include a web browser, high-speed data access via Wi-Fi and mobile broadband, Bluetooth capability, an expandable memory slot for micro SD cards, built-in eye tracking capabilities, front-facing and rear-facing cameras, video mirroring and video output support, built-in speaker and microphone, built-in rechargeable lithium-polymer battery, a USB-C or Micro USB port for connecting to a PC for debugging or file transfer, built-in stereo speakers, 3.5 mm headphone jack, advanced application programming interfaces (APIs) for running third-party applications, and various sensors including three-axis gyro, accelerometer, inertial measurement unit, ambient light sensor, and/or other sensors.

Exemplary Tethered Extended Reality (XR) Device

In one exemplary embodiment, the present XR Health Platform utilizes a wearable head mounted display (referred to herein as "HMD"). The exemplary HMD comprises a wired unit that is connected to a PC that runs on the Windows 10 operating system, or another operating system. The exemplary HMD is powered and managed via the Windows Mixed Reality software (which employs the HMD with the ability to run Universal Windows Platform (UWP) applications), but may be powered and managed by other software packages. The HMD may include a high-resolution display screen. The HMD may further include built-in Bluetooth capability for pairing controllers directly to the HMD. If the HMD does not include Bluetooth, other software may by utilized to manage controller pairing through other means. The exemplary HMD may also include a web browser, high-speed data access via Wi-Fi and mobile broadband, Bluetooth capability, built-in eye tracking capabilities, front-facing and rear-facing cameras, video mirroring and video output support, built-in speaker and microphone, built-in stereo speakers, 3.5 mm headphone jack, advanced application programming interfaces (APIs) for running third-party applications, and various sensors including three-axis gyro, accelerometer, inertial measurement unit, infrared sensor, ambient light sensor, and/or other sensors.

Exemplary Two-dimensional Display Device

In one exemplary embodiment, the present XR Health Platform utilizes a two-dimensional display and computing device (referred to herein as "2D Device"). The exemplary 2D Device comprises a two-dimensional display and computer, tablet computer, and/or mobile computing device such as a mobile phone. The 2D Device may also include a web browser, high-speed data access via Wi-Fi and mobile broadband, Bluetooth capability, an expandable memory slot for micro SD cards, built-in eye tracking capabilities, cameras, video mirroring and video output support, built-in speaker and microphone, USB ports for connecting to other devices for debugging or file transfer, HDMI ports for connecting a two-dimensional display to a computer, built-in stereo speakers, 3.5 mm headphone jack, advanced application programming interfaces (APIs) for running third-party applications, and various sensors including three-axis gyro, accelerometer, inertial measurement unit, infrared sensor, ambient light sensor, and/or other sensors.

Exemplary Virtual Reality Device Tracking Mechanisms

The exemplary HMD, HMD and Computing Device, and/or 2D Device may also include different versions of positional tracking in the form of either Orientation Tracking (3 degrees of freedom) or Inside out tracking (6 degrees of freedom). Positional tracking may be achieved using cameras and/or sensors. The exemplary HMD and Computing Device, HMD, and/or 2D Device may include different versions of input in the form of either one controller (3 degrees of freedom), two controllers (6 degrees of freedom), hand tracking (controllerless and 6 degrees of freedom), and/or other method of input.

Exemplary Web Browser

In one exemplary embodiment, the web portal and/or companion application may be accessed through one of the following web browser versions: Chrome, Chromium, Firefox, Edge, Internet Explorer (IE), IE Mobile, Safari, iOS, Android, Nougat, Marshmallow, Lollipop, and KitKat.

Exemplary Computing Environment

In an exemplary implementation discussed further below, the present XR Health Platform operates in an environment utilizing a client device, such as the HMD and Computing Device, the HMD, the 2D Device, and/or the Web Browser described above, in communication with a host server (e.g., cloud server) over a computer network, such as the Internet. The exemplary computing environment utilizes and incorporates all necessary hardware components and software to support the various wireless or wired communication functions as part of a network communication system.

The host server communicates with the XR Platform, the web portal and/or companion application, and any other involved systems including ML/AI models, and/or other third-party software libraries or applications. The host server Web API application exposes a finite list of API (Application Programming Interfaces) endpoints that utilize GET, POST, PUT, PATCH, DELETE, and any other HTTP Verbs to transfer data to/from the client application. The endpoints may also only be accessed once the user is properly authenticated with a third-party authentication system (e.g. OAuth2).

The host server communicates with the application's database (e.g. SQL, CosmosDB) via SQL commands, document queries (no SQL), and third-party system HTTP requests. The communication with the database includes a series of CRUD commands (Create, Read, Update, Delete) to modify the contents of the database.

In other embodiments, the present XR Health Platform may utilize other computer networks; for example, a wide area network (WAN), local area network (LAN), or intranet. The host server may comprise a processor and a computer readable medium, such as random access memory (RAM). The processor is operable to execute certain programs for performing the present XR Health Platform and other computer program instructions stored in memory. Such processor may comprise a microprocessor (or any other processor) and may also include, for example, a display device, internal and external data storage devices, cursor control devices, and/or any combination of these components, or any number of different components, peripherals, input and output devices, and other devices. Such processors may also communicate with other computer-readable media that store computer program instructions, such that when the stored instructions are executed by the processor, the processor performs the acts described further herein. Those skilled in the art will also recognize that the exemplary environments described herein are not intended to limit application of the present XR Health Platform, and that alternative environments may be used without departing from the scope of the invention. Various problem-solving programs incorporated into the present XR Health Platform and discussed further herein, may utilize as inputs, data from a data storage device or location. In one embodiment, the data storage device comprises an electronic database. In other embodiments, the data storage device may comprise an electronic file, disk, or other data storage medium. The data storage device may store features of the disclosure applicable for performing the present XR Health Platform. The data storage device may also include other items useful to carry out the functions of the present XR Health Platform. In one example, the exemplary computer programs may further comprise algorithms designed and configured to perform the present XR Health Platform.

Exemplary XR Health Platform

Figure 1:
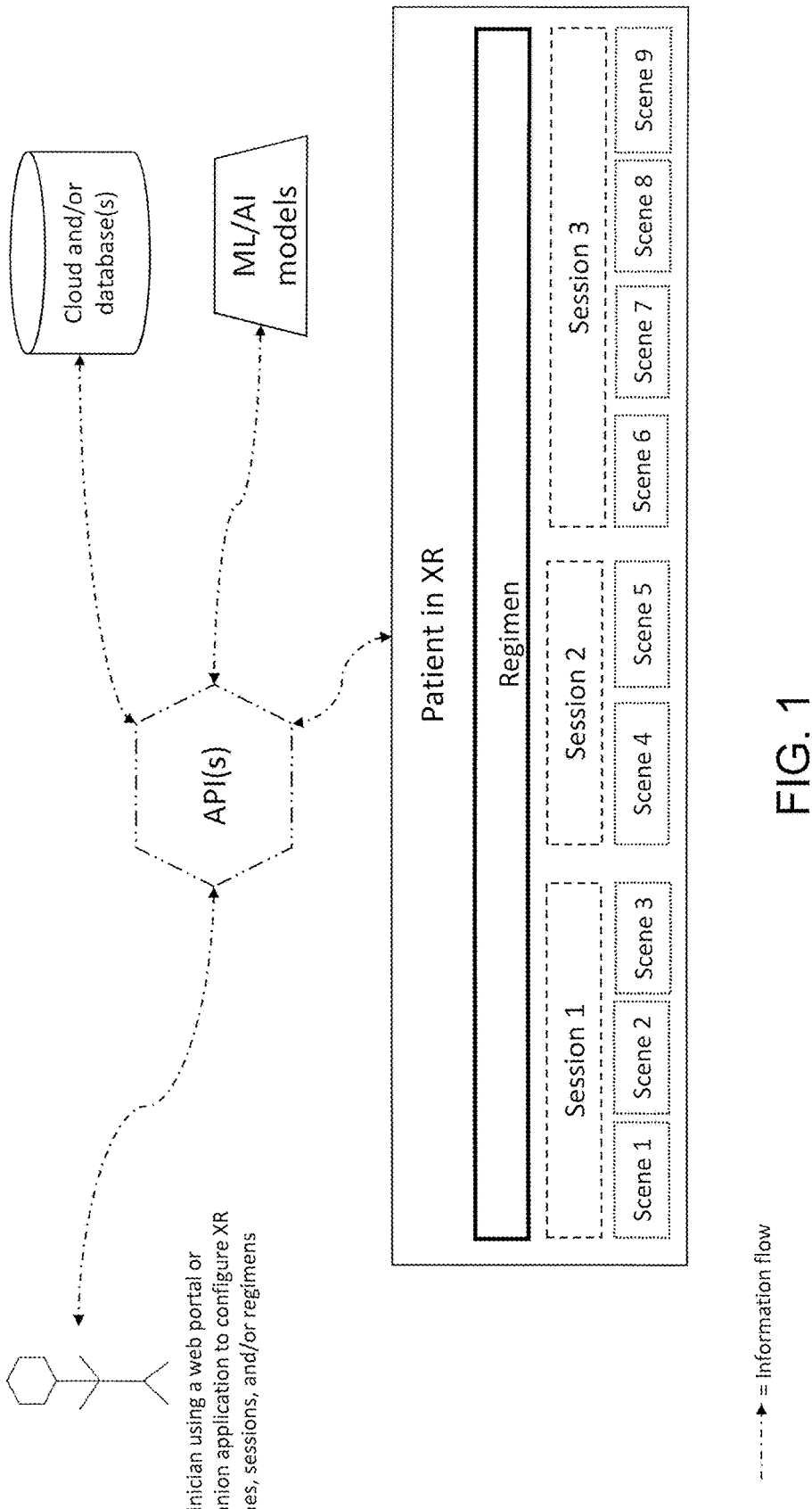
FIG. 1 is a diagram illustrating a first overview of the exemplary XR Health Platform of the present disclosure.
Figure 2:
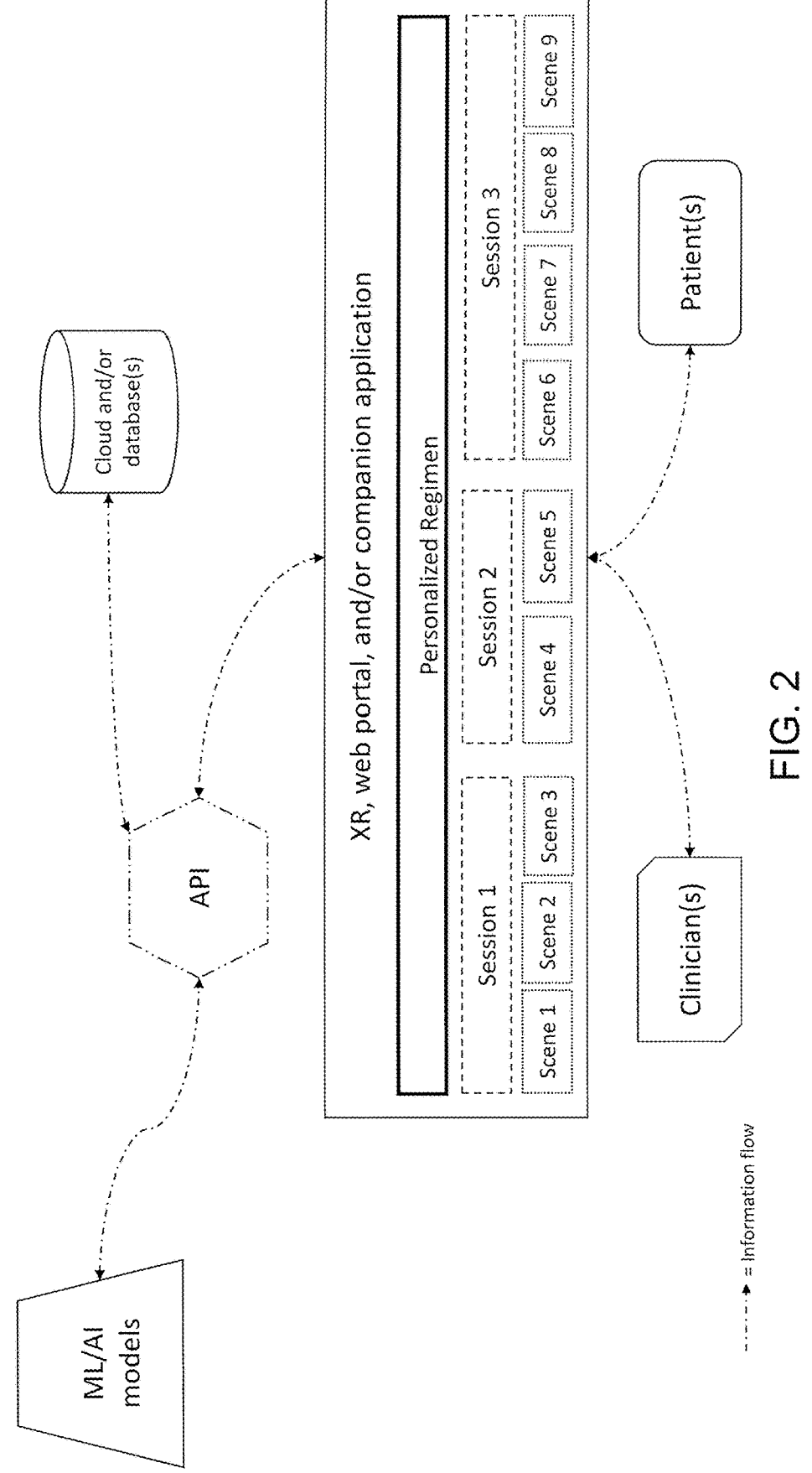
FIG. 2 is a diagram illustrating an overview of platform data inputs and/or outputs in the exemplary XR Health Platform.

In exemplary embodiments described herein, the present XR Health Platform is a modular, scalable, and broadly capable diagnostic, therapeutic, and care delivery system. It empowers clinicians to create, develop, modify, automate and/or deploy diagnostic, therapeutic, care delivery solutions, and/or care delivery end-to-end workflows and/or a portion of diagnostic, therapeutic, care delivery solutions, and/or care delivery workflows relating to patients. The exemplary platform leverages the motivational, experiential, and immersive properties of XR. Its modular framework allows for both individual solutions as well as complete care systems. ML/AI models, points of platform data, as well as information and communication technologies may be integrated to allow for personalized, tailored, iterative, actionable, and/or distributed care solutions. FIG. 1 depicts a high-level overview of one embodiment of the XR Health Platform allowing for the aforementioned capabilities. FIG. 2 depicts a high-level overview of one embodiment of the XR Health Platform that illustrates how clinicians and/or patients may utilize an XR application, a web portal, or a companion application, and additionally shows a high-level depiction of data inputs and outputs.

Any of the content, methods, systems and/or platform features described herein are intended to be applied, accessed, viewed, and/or interacted with using subtypes of XR, either with or without accompanying audio, haptic, and/or other types of media. For example, an implementation to manage chronic low back pain may utilize virtual reality for pain distraction, augmented reality for decision support to identify objects that may be too heavy to pick up, mixed and extended reality for either the distraction or decision support, and/or a 2D application for instructed exercise to prevent worsening of pain.

Any of the exemplary platform features may be applied as any portion of applications relating to the health, wellness, and/or health education of individuals. For example, features within the Anatomy Module discussed below may be used for having an individual identify the location of a symptom (as part of a diagnostic), may be used to identify an area in need of strengthening (as part of a therapeutic), may be used by clinicians in documenting changes in symptoms over time (as part of care delivery), as an anatomy simulator, and/or to educate patients regarding anatomy-related subject matter. Additionally, any of the platform features may be combined with any other set of platform features to form applications of the exemplary XR Health Platform. Additionally, any set of items (any item within any module, feature, or sub-feature) may be combined with any other set of items for any implementation(s) of the XR Health Platform.

Figure 3:
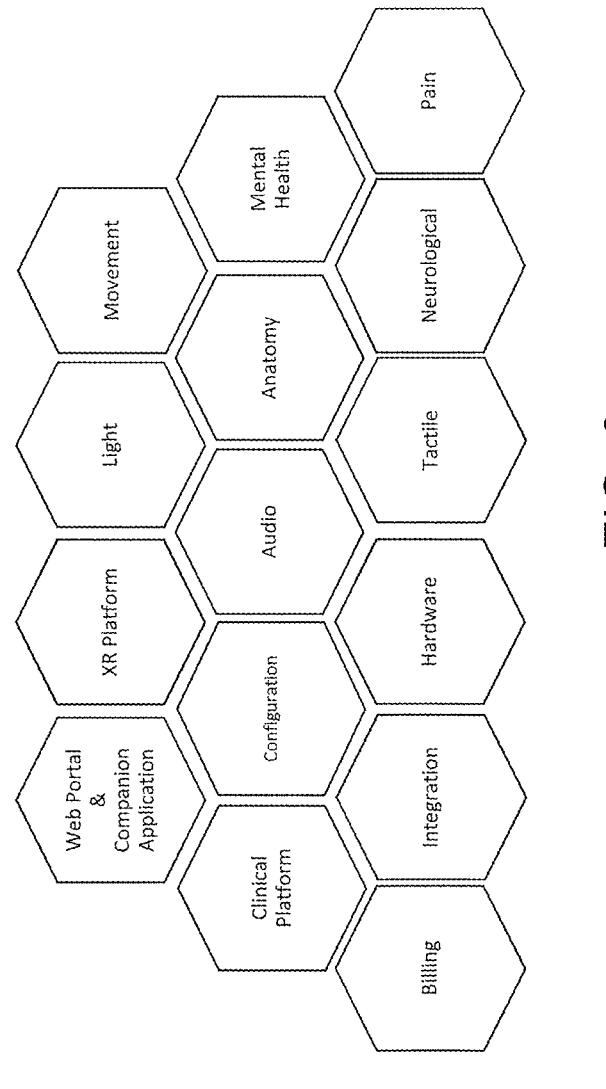
FIG. 3 is a diagram illustrating exemplary modules within the XR Health Platform.

In one exemplary implementation, the present XR Platform may be employed by three types of users: patients, clinicians (also referred to as "caregivers"), and administrators (also referred to as "admins"). The term "user" or "users" may mean admin(s), patient(s), and/or clinician(s). Admins are a user class with all of the access and/or privileges of clinicians and/or patients, and in addition, admins also have access to otherwise restricted areas, features, and/or functionalities. FIG. 3 illustrates all of the categories of platform features within the exemplary XR Health Platform ("the modules"), and also lists the different types of users of the XR Platform.

Any mentioning of "configure", "configured", "pre-configured", "pre-configure", and/or "configuration" refers to the utilization of functionalities and/or features described in the Configuration Module discussed further herein (unless explicitly stated otherwise).

Platform features may exist within HIPPA compliant systems.

All items described herein as well as any combination of items described herein are intended to be utilized in any health-related and/or wellness-related setting including, for example: inpatient care settings, outpatient care settings, home care settings, telehealth and/or remote care settings, post-acute care settings, skilled nursing care settings, nursing home settings, rehabilitation settings, pre-operative care settings, intraoperative care settings, post-operative care settings, palliative care settings, any medical practice setting, any residential setting, dentistry, orthodontic, optometry, chiropractic, and/or podiatry settings.

Figure 4:
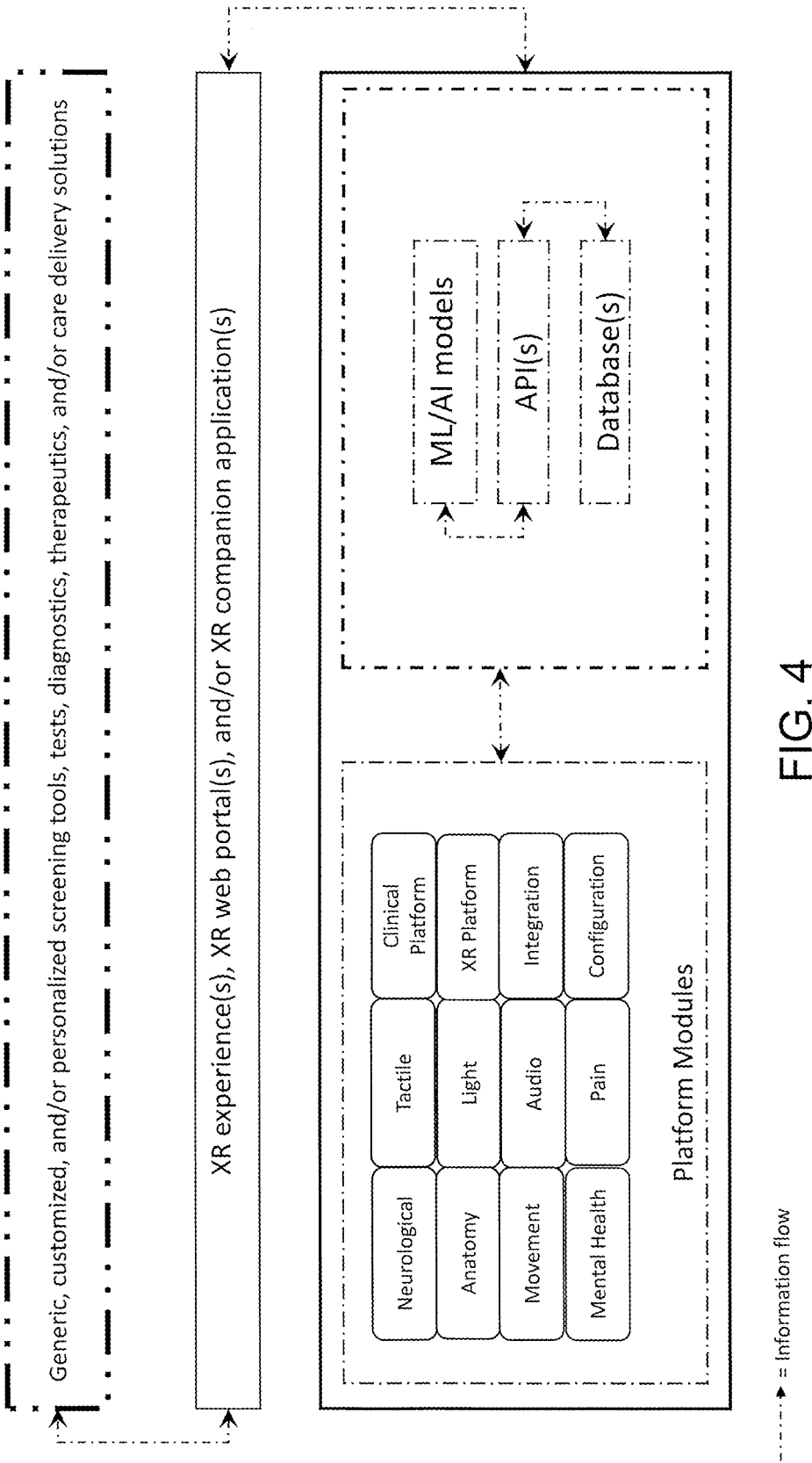
FIG. 4 is a diagram illustrating an overview of one embodiment of the XR Health Platform.

The exemplary XR Health Platform includes features which are organized into different "modules" described further below. These exemplary modules are for organizational purposes only, and any set of features and/or any set of items within features may be combined with any set of other features and/or items described herein, irrespective of module(s). Each of the exemplary modules may comprise features applicable for creating, configuring, and/or deploying tailored, personalized, adaptive and/or problem-focused scenes, sessions, and/or regimens to deliver, perform, and/or deploy diagnostic tests, screening tests, therapeutic features, and/or care delivery features. These features enable clinicians and/or ML/AI models to create, modify, configure, administer, and/or orchestrate diagnostic, therapeutic, and/or care delivery solutions in XR. FIG. 4 provides a high-level overview of one embodiment of the XR Platform.

ML/AI models may be used to create, control, identify, assess, deploy, instantiate, deliver, configure, modify, interact with, and/or remove points of platform data and/or platform features. ML/AI models may have multiple purposes and/or uses within the XR Platform, and the table below titled "Some Examples of ML/AI Model Uses within The Platform" provides a non-comprehensive list of such uses.

Some Examples of ML/AI Model Uses Within the XR Health Platform (a) Virtual human avatars or virtual avatars controlled by ML/AI models (such as generative adversarial networks, reinforcement learning, decision forests, and the like) to interact with and/or influence the actions of patients in XR.

(b) Collaborative filtering to determine preferences.

(c) Natural language processing and/or natural language understanding to assess patient and/or provider sentiment, symptoms, history of present illness items, emotions and/or feelings expressed by a patient.

(d) Natural language processing and/or natural language understanding to utilize and/or apply corpora of medical specific terminology in diagnosis, treatment, and/or care delivery.

(e) Natural language processing and/or natural language understanding to determine and/or identify patient and/or provider sentiment, symptoms, history of present illness, emotions and/or feelings expressed by a patient.

(f) Computer vision models to identify facial and/or any anatomic topologic features for the diagnosis of disease.

(g) Computer vision models to characterize and/or measure wounds and/or skin lesions.

(h) Computer vision models to determine positional data given the data from cameras.

(i) Computer vision models as an overlay on top of or more medical images.

(j) Computer vision instance segmentation masks to determine anthropometric features.

(k) Computer vision models for facial tracking and facial expression analysis.

(l) Approaches to identify vocal biomarkers from text and/or audio.

(m) Activity recognition computer vision models to identify healthy and/or unhealthy actions and/or behaviors.

Exemplary modules of the present XR Health Platform are discussed individually below.

a. Clinical Platform Module

Figure 5:
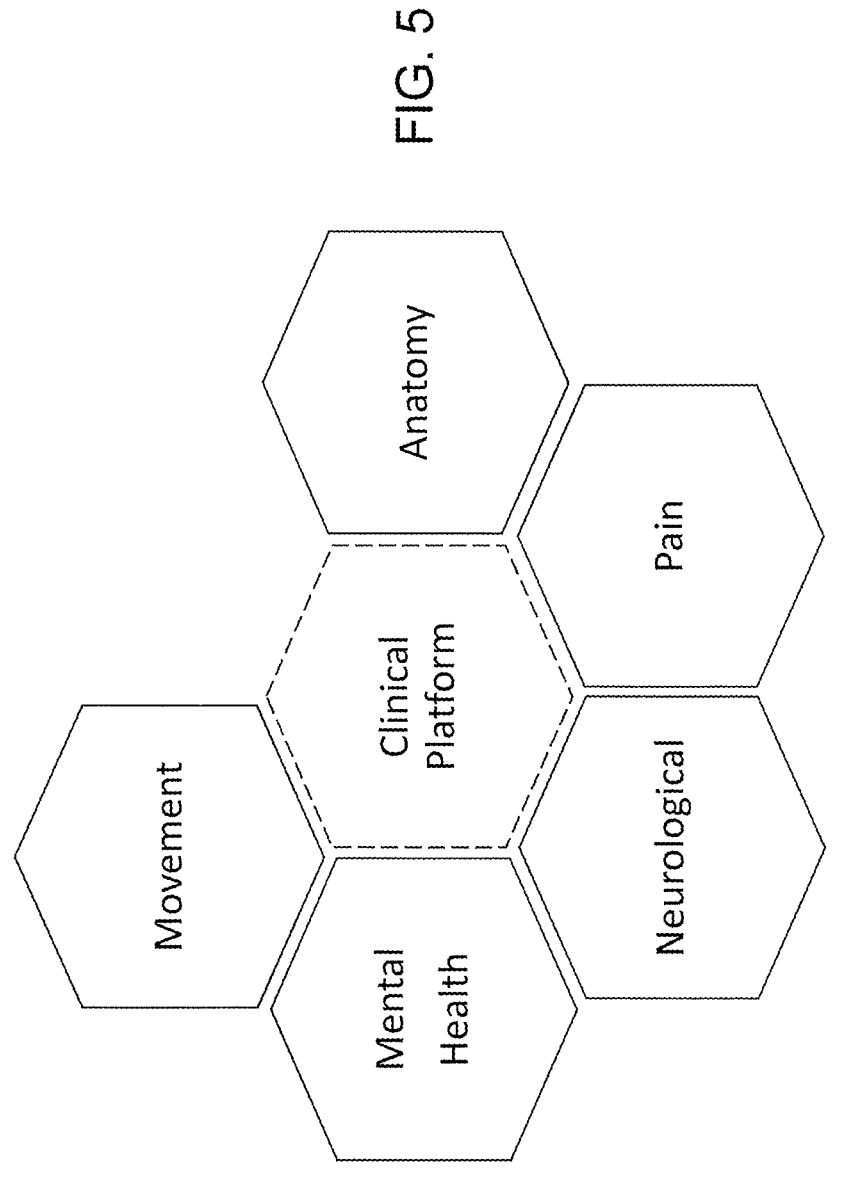
FIG. 5 is a diagram illustrating a relationship between care modules and the clinical platform module.

The Clinical Platform Module of the exemplary XR Health Platform contains features and/or items applicable for diagnosing, treating, and/or delivering care irrespective of medical specialty or discipline. These features and/or items may have universal clinical utility, and as such, they may be combined with other more specific clinical features and/or items from other modules within specific use-cases and/or implementations. See attached FIG. 5. Features and/or items within the module may also contribute to the autonomous, semi-autonomous, and/or manual recognition and/or identification of items on a health history, health-related problems, goals, barriers, and/or priorities for patients. Further, features and/or items within this module may contribute to the autonomous, semi-autonomous, and/or manual determination of appropriate actions for patients to take. Several features and/or items within this module may additionally contribute to the completion of items relating to medical encounters including the completion of items in a health-related history and/or physical exam, and/or items constituting any portion of health-related interventions. Exemplary items within the Clinical Platform Module may utilize, may be utilized as part of, and/or may be combined with other platform features, points of platform data, ML/AI models, and/or one or more other applications of the exemplary XR Health Platform.

The exemplary Clinical Platform Module may comprise one or more of the following features below.

Communications Feature

Figure 6:
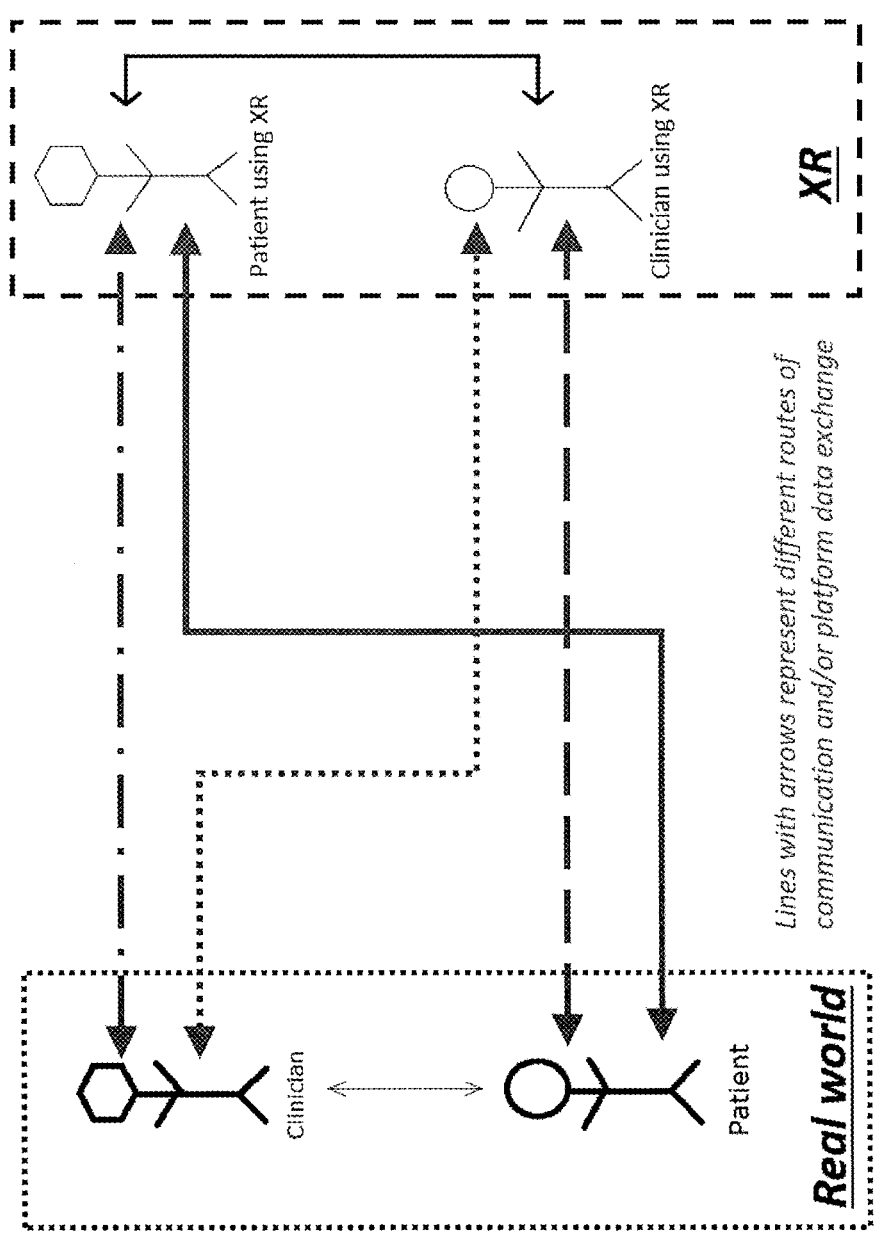
FIG. 6 is a diagram illustrating an embodiment of the disclosure wherein any combination of one of more patient(s) and/or clinician(s) may exchange communication(s) and/or platform data either in the real world and/or in XR. Italicized font represents one or more points of platform data and/or platform features that may be created, populated, modified, and/or configured by one or more clinicians, ML/AJ models and/or other platform feature(s).

A communications feature of the exemplary Clinical Platform Module includes the system and programming necessary for patients and/or clinicians to interact and/or communicate with one another, either asynchronously and/or in real-time, and using any combination of XR and/or any other method of communication. See FIG. 6. These interactions and/or communications enable the combination and integration of platform features with real-time telehealth encounters. The interactions and/or communications also enable telehealth encounters to occur between individuals appearing in the real-world and virtual facsimiles of other individuals appearing in the virtual-world.

Additionally, the above interactions and/or communications may occur through the use of one or more of the following:

(i) Email, text (SMS), video, video chat, videoconference, voice (phone and/or internet, protocol-based voice communications (VOIP)), Bluetooth, and/or any other method of communication not otherwise mentioned. In addition, communications may be initiated using one of several different methods. For example, clinicians may search through a list of patients and select a patient to connect with using one of the above communication modalities, and/or patients may search through a list of available clinicians using patient input methods and select any available clinician to connect with; however patients cannot see any information relating to any other patients.

(ii) Using a HIPPA compliant "file vault" whereby clinician-patient communications can take place involving protected health information and/or items of other personal information.

(iii) For clarity, any incoming and/or outgoing communication and/or the application of any items within the communications feature may take place using any combination of instances of XR and/or using any combination of XR devices (including HMDs, augmented reality glasses, any 2D displays including desktop computers, televisions, mobile phones, tablets, and/or laptop computers).

Patient-level Profile Feature

In exemplary embodiments, the present Clinical Platform Module further includes a patient-level profile feature which maintains an up-to-date record of goals, outcome-focused patient characteristics, and/or other points of relevant platform data between scenes, sessions, and/or regimens to enable personalized, dynamic, and/or adaptive applications of platform features for individual patients. Data within such feature may be encrypted and/or may or may not contain points of protected health information (or any information falling under HIPPA or similar regulations). Data within a patient-level profile may include, for example, points of information relating to a patient's available time, physical capabilities, health history, desirable activities, disabilities, level of knowledge, level of education, goals, values, personality, barriers to achieving goals, and the like. This feature may also incorporate items and/or platform data points described within the "values personality and needs feature" within the Mental Health Module discussed below.

Initial Visit Feature

An initial visit feature of the exemplary Clinical Platform Module allows for the distributed, supervised, semi-supervised and/or unsupervised patient self-completion of items in an "initial visit" type medical encounter, including items in a medical history and/or physical exam, and/or items that are part of any other type of medical encounter. Certain pre-configured initial and/or other assessments are completed by patients using ML/AI models, by clinicians, by using other platform features, and/or by using other points of platform data. Exemplary assessments include:

(a) A general health assessment system for patients comprising items described within the Q&A feature discussed below, one or more other items of XR content and/or features, and/or other platform features to assess items relating to and/or comprising any portion of the following: past medical history, family history, past surgical history, patient allergies, past substance abuse history, current medications and/or medication adherence assessment, personality assessment, needs assessment, assessment of values, assessment of motivators and/or motivations, assessments of social determinants of health, identify the activities or types of activities an individual finds fun and/or enjoyable, identify an individual's current level of social support, identify an individual's current stage of behavior change with respect to behaviors relating to health, a "barriers" assessment to determine what (if any) barriers may be standing in the way for an individual with respect to one or more behaviors relating to health, an assessment of what motivates an individual, screening for diseases.

(b) Assessments, features, and/or items described within the Movement Module, either with or without the integration of one or more other platform features.

(c) Assessments, features, and/or items described within the Neurological Module, either with or without the integration of one or more other platform features. For example, this may include a neurocognitive assessment comprised of the following: vision assessments such as the vision tests described herein, hearing assessments such as the hearing tests described herein, cranial nerve assessments, language and/or speech assessments, motor assessments, sensory assessments, coordination assessments, assessment of cognitive domains, assessment of Activities of Daily Living (ADLs), assessment of Instrumental Activities of Daily Living (IADLs), and other features described within the Neurological Module.

(d) Assessments, features, and/or items described within the Mental Health Module, either with or without the integration of one or more other platform features. For example, this may include a mental health assessment comprised of the following: Emotional Intelligence (EQ), screening for and/or assessment of depression, screening for and/or assessment of anxiety, screening for and/or assessment of mixed mood disorders, screening for and/or assessment of unspecified mood disorders, screening for and/or assessment of sleep disturbances, assessments relating to cognitive distortions and/or negative thoughts, other features described within the Mental Health Module.

Any of the items described within this feature may utilize direct and/or asynchronous patient-clinician interactions using exemplary features described in the communications feature. Clinicians may create, modify, re-configure, and/or deploy pre-configured initial assessments for patients using a web portal and/or a companion application and/or in XR as described herein. The aforementioned assessments, encounters, exam features, and/or other items may be administered and/or repeated multiple times in order to monitor a patient's health over time as part of scenes, sessions, and/or regimens. For example, the "initial visit"-type medical encounter may be repeated on a regular basis as a "regular checkup", "annual checkup", and/or at any time as a "checkup" or "acute care assessment". Points of platform data produced through scenes, sessions, regimens, interactions, and/or encounters may be transmitted to APIs for subsequent analysis by ML/AI models, by clinicians, and/or by other platform features.

History of Present Illness Feature

A history of present illness feature of the exemplary Clinical Platform Module allows for a distributed, supervised, semi-supervised and/or unsupervised patient self-completion of items related to and/or included in a "history of present illness" assessment by assisting in the determination of and/or determining the onset, location, duration, character or nature, alleviating factors, aggravating factors, radiating factors, temporally associated factors, severity and/or subjective inputs relating to symptoms, issues, problems, and/or complaints of a patient. Each of the aforementioned factors relating to a symptom, issue, problem, and/or complaint may be ascertained using patient input methods. The items otherwise comprising the history of present illness feature may include, for example:

(a) patient voice inputs and/or interactions with or without speech to text (STT) and/or natural language processing and/or natural language understanding;

(b) spoken or other interactions with a virtual human avatar;

(c) patient actions and/or behaviors in XR;

(d) findings from vocal biomarker analyses of patient voice and/or vocal biomarker time series analyses of patient voice either with or without temporally correlated logged actions occurring in XR; for clarity, patient voice and/or vocal biomarker data may include mono, stereo, and/or three-dimensional sound, and/or audio data of any type;

(e) patient response(s) to questions using items within the Q&A feature discussed below;

(f) manual data entry by patient and/or clinician either in XR, a companion application, and/or using a web portal;

(g) any combination of platform data and/or ML/AI model(s) where the outputs of data and/or model(s) reliably identify items related to and/or comprising the onset, location, duration, character or nature, alleviating factors, aggravating factors, radiating factors, severity and/or temporally associated factors related to symptoms, issues, problems, and/or complaints;

(h) patient indicating the locations of health-related items, symptoms, issues, problems, and/or complaints on anatomical model(s) using items within the Anatomy Module, and/or using other platform features;

(i) patient selection from a finite list of symptom character descriptions either with or without indicating one or more anatomical locations on anatomical model(s) and/or indicating one or more anatomical locations using any other platform feature(s);

(j) patient indication of a symptom severity on anatomical model(s) using one or more patient input methods, color coding, voice input, text, and/or selecting from a list of possible choices using other functionalities within the Anatomy Module;

(k) facial analysis using ML/AI models with or without temporal correlations with logged actions occurring in XR to determine and/or contribute to the determination of symptom onset, location, duration, alleviating and/or aggravating factors of one or more symptoms and/or health-related issues;

(l) analysis of body language using ML/AI models with or without temporal correlations with logged actions occurring in XR to determine and/or contribute to the determination of symptom onset, location, duration, alleviating factors and/or aggravating factors of symptoms and/or health-related issues;

(m) direct and/or asynchronous patient-clinician interactions using features described in the communications feature; and (n) any of the above items may be combined with other platform features either in time series or as a single measurement to derive one or more points of platform data.

Medical Image Integration Feature

A medical image integration feature of the exemplary Clinical Platform Module may be utilized for medical image platform integration to incorporate one or more relevant findings obtained from analyses performed on medical images and/or videos, using computer vision and/or ML/AI models. Examples of such medical images and/or videos include: DICOM and/or radiological images (including x-rays, ultrasound, DEXA, CT and MRI); images and/or videos obtained from medical procedures and/or surgeries (for example, images obtained from a colonoscopy); images of the retina, sclera, and/or images relating to the eye; images of and/or including patients; and videos of and/or including patients.

Health Problem List Feature

A health problem list feature of the exemplary Clinical Platform Module may be utilized for determining, helping to determine, identifying, selecting, categorizing, classifying, suggesting and/or prioritizing of an individual's health-related problems, symptoms, health risks, health-related predispositions, patient actions, patient platform actions, patient behaviors, health-related goals, health-related priorities prognoses, and/or other health-related factors and/or issues by completing and/or using the following items, platforms, interactions, and data described below.

Through the use of the exemplary XR Health Platform, and/or through interactions, a patient completes medical encounters and/or completes scenes, sessions, and/or regimens as described herein. Platform data obtained through encounters and/or interactions are analyzed using clinicians, ML/AI models, and/or other platform features to populate items on the "problem list" of an individual with each item on the problem list including, for example: symptoms, diseases, disease risks and/or predispositions, injury risks and/or predispositions (for example "high risk for falls"), personal safety risks and/or predispositions (for example "lack of smoke alarm in house" for fire safety), and health-related issues. The problem list is then further analyzed using points of platform data, and/or ML/AI models, to identify priority items on the problem list with each priority item being based on and/or determined by biopsychosocial factors, specific patient concerns, other points of platform data, and/or other platform features. Identified problems for which a patient is determined to be in the pre-contemplation state (also called "stage") of behavior change are given special prioritization.

Figure 7:
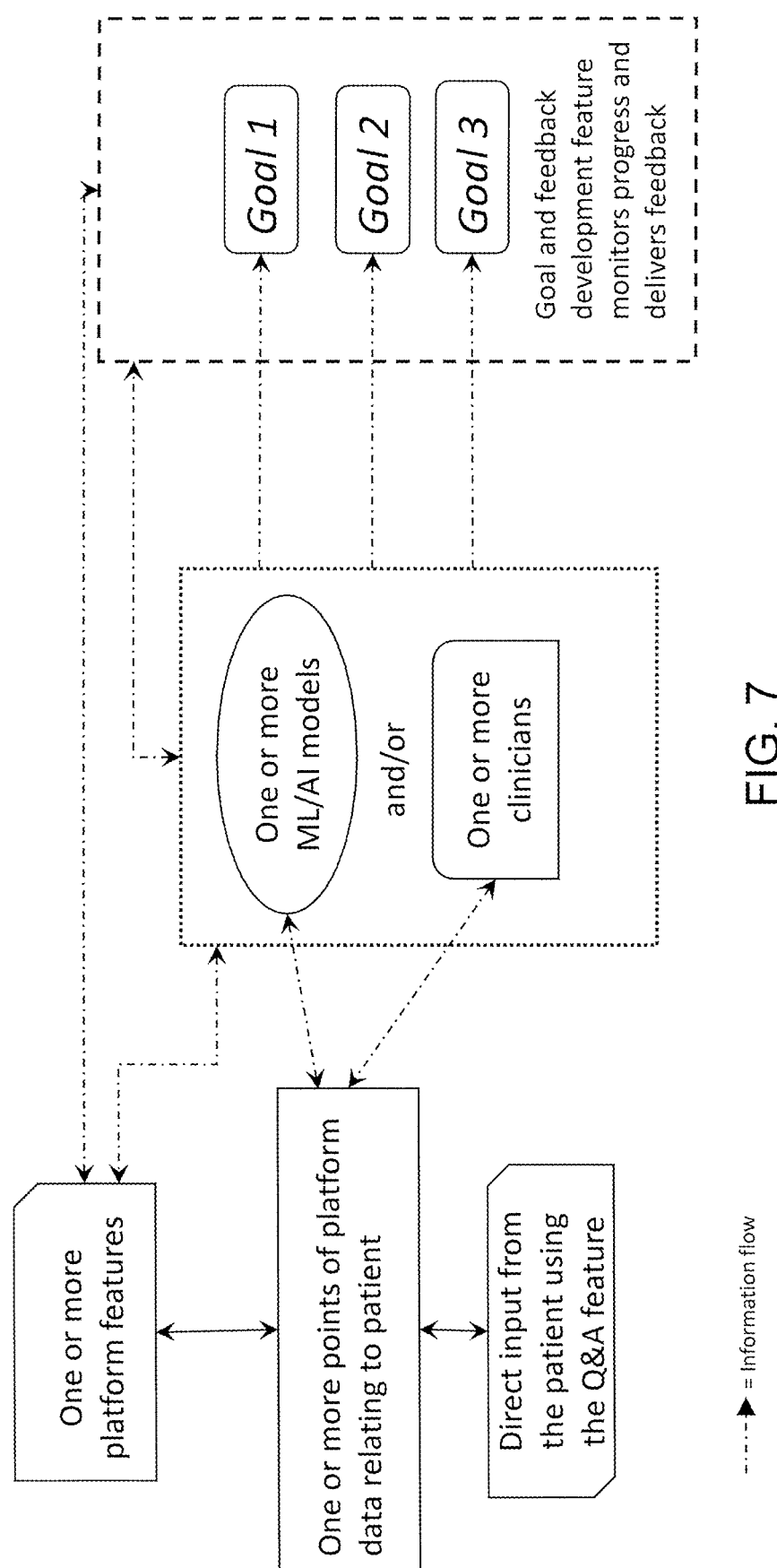
FIG. 7 is a diagram illustrating the development of prioritized and/or personalized goals, the monitoring of goal

Using points of platform data and/or ML/AI models, one or more goals are developed, determined, suggested, selected, and/or updated to address each priority with each goal having one or more of the following characteristics: goal must be specific; goal must have measurable health-related outcomes; goal must be actionable for the patient; goal must be attainable and/or realistic for the patient; goal must be relevant to the patient and/or his/her health; and goal must have a specific deadline and/or timeframe for completion. Goals are prioritized and/or personalized based on a determination of the highest clinical-yield action(s) that require the lowest amount of patient effort and/or are most likely to be carried-out, as determined through the application of platform features, points of platform data, one or more platform inputs, and/or using ML/AI models. See FIG. 7 for an illustration showing one example of how goals are determined, developed, monitored, and/or achieved using the exemplary XR Health Platform.

The problem list, priority items list, goals, as well as the names and configurations of any ML/AI models, any points of platform data, and/or any clinician inputs utilized in creating these lists may be logged and saved into a database for later use. Upon the completion of encounters, the above process may be repeated and the problem list, priorities, and/or goals may be updated to reflect newly available platform data points. Other points of platform data, and/or other platform features may also be used as any portion of the items described within this feature.

Re-Admission Prevention Feature

The exemplary Clinical Platform Module may further comprise a re-admission prevention feature intended to prevent (or reduce) re-admissions at health-related facilities by predicting, monitoring, assessing, and/or treating one or more health-related factors and/or issues in patients using points of platform data, platform features, ML/AI models, and/or clinicians. Examples of health-related issues that this feature may be applied to include: preventing re-admissions after open heart surgery, after total knee replacement surgery, after total hip replacement surgery, and/or after a medically-related health facility admission such as may occur with a CHF exacerbation, COPD, pneumonia, and/or after a heart attack.

Reinforcement Learning Feature

A reinforcement learning feature of the exemplary Clinical Platform Module may be used to implement one or more reinforcement learning models and/or other ML/AI models to influence patient actions or behaviors in XR using platform features and one or more of the following:

(a) virtual human avatars within XR that are controlled by ML/AI models and/or by other platform features, with the ML/AI models and/or other platform features being designed to influence actions and/or behaviors of patients in XR;

(b) rendered elements within XR that are controlled by one or more ML/AI models and/or by other platform features designed to influence actions and/or behaviors of patients in XR;

(c) ML/AI models utilizing reinforcement learning algorithms with reward functions that are defined by desirable actions and/or behaviors of patients; and (d) ML/AI models utilizing adversarial learning algorithms (including the use of generative adversarial network algorithms) designed to influence actions and/or behaviors of one or more patients in XR.

Barrier Management Feature

A barrier management feature of the exemplary Clinical Platform Module may be utilized for determining, helping to determine, identifying, selecting, categorizing, classifying, suggesting, prioritizing, managing, and/or helping individuals overcome health-related barriers through the use of items in the Q&A feature (discussed below), items of XR content, using one or more scenes, sessions, regimens, and/or configurations, and/or through the use of other platform features. The items within this feature relate to one or more of the following: barriers as they relate to health-related issues, lack of someone else to carry out the healthy behaviors with, lack of enough time, lack of enough money and/or healthy behaviors are too expensive, having family obligations (including having to care for children or a loved one), lack of enough energy (including feeling too tired or fatigued), lack of self-management skills, being self-conscious or lack thereof, lack of equipment, lack of a place to carry out healthy behaviors, inconveniences associated with carrying out healthy behaviors, being too stressed out, lack of social support, being discouraged from healthy behaviors, not being healthy enough and/or having an underlying health condition, lack of interest and/or finding exercise to be boring and/or do not find healthy behaviors to be fun or enjoyable, lack of knowledge and/or not knowing what to do, lack of skills to carry out healthy behaviors, lack of motivation and/or laziness, pain disease-specific barriers (other than pain), fear of being injured and/or having a recent injury, bad weather, and other health-related issues, symptoms, problems, predispositions, behaviors, and/or risks.

Patient Action Management Feature

A patient action management feature of the exemplary Clinical Platform Module may be utilized for determining, helping to determine, identifying, selecting, categorizing, classifying, suggesting, prioritizing and/or recommending a set of patient actions, patient platform actions, and/or patient behaviors to help patients achieve health-related goals, address health-related priorities, address health problems, address health-related issues, and/or treat diseases using platform features, and/or using one or more of the following: items on a health problem list, health-related goals and/or priorities, health-related barriers, and any item on a list of health-related issues.

The health-related issues, goals, priorities, and/or barriers may be pre-populated within configuration options in XR (including a web portal, companion application, and/or any other form of XR as defined herein). These goals and/or priorities may also be populated either manually by one or more clinicians, and/or automatically using ML/AI models.

For each goal, a list of platform actions that work towards and/or address the goal are pre-populated as well as pre-populated within configuration options in XR (including a web portal, companion application, and/or any other form of XR as defined herein) using features and/or functionalities of the Configuration Module, the Integration Module, and/or other platform features. Goal customization, modification, deployment, and/or orchestration are then implemented by clinicians, ML/AI models, one or more features of the Configuration Module and/or Integration Module, and/or one or more other platform features.

For each priority, a list of platform actions that address the priority are pre-populated within configuration options in XR (including a web portal, companion application, and/or any other form of XR as defined herein) using one or more features of the Configuration Module and/or Integration Module, and/or other platform features. Action customization, modification, deployment, and/or orchestration may then be implemented by clinicians and/or ML/AI models using features of the Configuration Module and/or Integration Module, and/or using other platform features.

Actions or sets of actions to address goals and/or priorities may be created, modified, selected and/or pre-configured by clinicians and/or ML/AI models in XR (including a web portal, companion application, and/or any other form of XR as defined herein) via the Configuration Module described below. Each action may have one or more of the following characteristics: action is specific; completion of and/or performance during the action is measurable; action is attainable and/or realistic for the patient; action suggestion is temporally related to patient actions, patient platform actions and/or events that prompted the suggestion; action is an example of strategies and/or methodologies to modify and/or change health-related behaviors; action is at least partially determined and/or approved by clinicians.

For each goal and/or priority, a schedule of automated re-assessments, scenes, and/or sessions may be configured and/or pre-populated to track any actionable platform data. The exemplary schedule may also identify the behavior change state or stage relating to goals and/or priorities, and/or the presence of any barriers standing in the way of achieving one or more goals, priorities, health problems, and/or health-related issues.

For each goal and/or priority, "feedback items" (platform data fields for desirable and/or undesirable points of feedback data) are pre-configured to populate with points of platform data to be utilized for feedback. When a patient engages with the exemplary XR Health Platform, a feedback report is automatically populated with points of such data such that when a patient completes related scenes, sessions, and/or regimens, a personalized and actionable feedback report is available which contains points of relevant feedback for an individual patient. This report may be sent to the patient and/or clinicians at a timing, frequency, and/or schedule set by the patient, clinicians, and/or by ML/AI models. Items on a feedback report may be recited out loud to the patient while in XR, displayed through visual means, conveyed using one or more tactile/haptic methodologies, communicated using items within the communications feature, and/or conveyed using other platform features.

For each goal and/or priority, "feedback items" (platform data fields for desirable and/or undesirable points of feedback data) may also be pre-configured to populate with points of platform data that may be utilized for feedback. When a patient engages with the exemplary XR Health Platform, if the data fields are populated then feedback messages are automatically generated such that a personalized and actionable feedback snippet and/or content object may be delivered to the patient. The feedback message(s) may be sent to the patient and/or clinicians at a timing, frequency, and/or schedule set by the patient, one or more clinicians, and/or by ML/AI models. Feedback messages may be recited out loud to the patient while in XR, displayed through visual means, conveyed using tactile/haptic methodologies, communicated using items within the communications feature, and/or conveyed using other platform features.

Clinicians and/or ML/AI models may set and/or modify the scheduling, timing, and/or frequency of future assessments and/or one or more future feedback reports to follow progress towards meeting goals and/or to follow how well health-related priorities are being addressed.

Where multiple actions and/or sets of actions are recommended, a decision support layer may be applied wherein ML/AI models are utilized to favorably leverage positive and/or negative behavioral network characteristics.

Positive network characteristic example: If a patient is trying to diet, the decision support layer may suggest for the use of scenes, sessions, and/or regimens focused on exercise, as combined diet and exercise result in superior results compared to either health intervention alone.

Negative network characteristic example: If a patient is attempting smoking cessation, the decision support layer may advise against the simultaneous use of scenes, sessions, and/or regimens focused on weight loss, as trying to lose weight and quit smoking at the same time results in inferior results compared to either health intervention alone.

Q&A Feature

The Q&A feature of the exemplary Clinical Platform Module is applicable for creating, modifying, configuring, selecting, and/or deploying questions to individuals in XR. Clinicians using a web portal, companion application, and/or XR, may create, modify, and/or configure certain questions in a variety of different formats, such as open-ended, short answer, single response multiple choice, multiple response-type, single response grid-type, multiple response grid-type, true/false type, dichotomous-type, rank order-type, Likert-type, rating scale-type, slider-type, dropdown-type, and/or semantic differential-type questions, and/or other types of question.

Clinicians using a web portal, companion application, and/or XR, and/or ML/AI models may control, modify, and/or configure the following: which question(s) appear, where within a particular scene question(s) appear, and when during particular scenes and/or sessions question(s) appear. The timing of questioning can be controlled through multiple methods including, for example: time after scene and/or session start, upon collisions between virtual objects in XR, upon patient inputs and/or patient input methods, upon other events related to platform features and/or other events related to XR.

Alternatively or in addition, one or more ML/AI models may create, generate, modify, pre-populate, and/or configure certain questions in a variety of different formats, including: open-ended, short answer, single response multiple choice, multiple response-type, single response grid-type, multiple response grid-type, true/false type, dichotomous-type, rank order-type, Likert-type, rating scale-type, slider-type, drop-down-type, semantic differential-type questions, and/or any other type of question. Alternatively or in addition, one or more clinicians and/or ML/AI models may create, modify, and/or configure one or more question groups with each question group being comprised of selected questions. Alternatively or in addition, clinicians and/or ML/AI models may create, modify, configure, and/or deploy assessments with each assessment being comprised of selected question groups. The questions and/or assessments are answered by one or more specific patients and/or clinicians in XR.

Questions, answer fields, and/or assessments may utilize forms of input validation, conditional branching, Boolean type logic, and/or ML/AI models to control the flow, configuration, and/or distribution of questions with regards to individual patients using the exemplary XR Health Platform.

Once deployed to patients and/or clinicians, question and associated answer choices are conveyed in XR as a combination of items of text, images, videos, haptic stimuli, and/or through spoken/voice interactions (where the question and/or answer selections are recited out loud), and/or using other patient input methods (including through spoken or text-based dialogue, for example).

Experiential Data and Question Feature

An experiential data and question feature of the exemplary Clinical Platform Module is applicable for completing tasks related to data generation, data labeling, data collection/data capture, question generation, and/or question answering through simulation of and/or participation in scenes, sessions, and/or regimens. Any of these tasks may be completed in a supervised, semi-supervised, unsupervised, manual, and/or automated manner.

"Synthetic" data sets may be generated, labeled, and/or collected through the use of ML/AJ models in simulations.

An "experiential question" may be generated by clinicians using items within the Q&A feature above. The question is then answered through simulation, and/or by patients, clinicians, and/or through passive means via participation in interactive scenes, sessions, and/or regimens. This includes interactions with items of content and/or features in scenes, sessions, regimens, and/or through other interactions and/or simulations in XR.

An "automated experiential question" may be generated automatically from generic question templates (which may or may not require the utilization of items within the Q&A feature) using data obtained passively thorough simulations, through patient participation in interactive scenes, sessions, and/or regimens, and/or through interactions with items of content and/or features. In one example, clinicians and/or ML/AJ models create and/or modify generic question templates. Clinicians and/or ML/AJ models configure generic question templates with the configuration parameters indicating which specific data fields are to be obtained, and/or when, where, and/or how completed generic question templates are to be deployed if and/or when the data fields are passively populated through platform use by patients and/or through simulations.

In the next session in the simulation and/or for the patient (and/or in one or more later sessions as configured per items within this feature), specific data fields on each applicable question template are automatically populated using, for example: patient's and/or virtual object's proximity and/or position relative to one or more 2Dand/or 3D virtual objects and/or features; data captured through interactions between a patient and 2D and/or 3D virtual objects and/or features; data captured through interactions between a patient and virtual human avatars; data captured through simulated interactions between a platform feature and 2D and/or 3D virtual objects and/or other platform features; data captured through the use of scene and/or session metadata; data captured through the use of biometric data; data captured through the use of any other platform data; and data captured through the use of data from other interactions and/or simulations.

When the patient's next participate in platform use (or as per any configuration), completed question templates (question templates that are now populated with specific data) are automatically deployed at a time, frequency, virtual location, and/or using forms of media that are determined, configured, modified, and/or triggered by the following, for example: patient's and/or virtual object's proximity and/or position relative to one or more 2D and/or 3D objects, content and/or features; interactions between a patient and 2D and/or 3D objects, content and/or features; items and/or responses contained within interactions occurring between a patient and 2D and/or 3D virtual objects, content, and/or virtual human avatars; data captured through simulated interactions between a platform feature and 2D and/or 3D virtual objects and/or other platform features; data captured through the use of points of scene, session, and/or regimen metadata; data captured through the use of other platform features; data captured through the use of other points of platform data. Clinicians and/or ML/AI models may create, select, modify, and/or configure generic question templates at any time after they are created.

As a variation of the above "experiential question" and/or "automated experiential question" items, the question(s) to be answered within XR may relate to data labeling tasks and wherein the data to be labeled may appear in XR as items of text, images, video, audio, haptic, and/or rendered content.

A "synthetic data" generation capability may comprise ML/AI models and/or virtual human avatars controlled by ML/AI models which simulate participation in scenes, sessions, and or regimens, and wherein items of platform data generated by the simulation(s) may be utilized by the platform features, by other ML/AI models, by administrators, by one or more clinicians, and/or by patients.

The experiential data and question feature may further comprise other items within the Q&A feature. The experiential data and question feature may further comprise other platform features.

A-B Testing Feature

An A-B testing feature of the exemplary Clinical Platform Module suggests and/or identifies which platform features, and/or which features and/or content within a scene, session, and/or regimen a patient and/or clinician finds to be positive, negative, fun, enjoyable, useful, efficacious, and/or serving other purposes using points of platform data, items in the above Q&A feature, ML/AI models, and/or other platform features.

Serial A-B testing of two or more scenes, sessions, and/or regimens may be implemented such that two variants ("A" and "B", respectively) of the scene, session, and/or regimen are created. The patient and/or clinician subsequently completes variant A followed by variant B in series with items within the Q&A feature being utilized at points during the aforementioned serial A-B testing.

Sentiment testing of scenes, sessions, and/or regimens may be implemented such that variants of the scenes, sessions, and/or regimens are created. The patient and/or clinician subsequently completes the variants with items within the above Q&A feature being utilized to assess sentiment or other characteristic(s) at points during the scenes, sessions, and/or regimens.

Clinical Research Feature

The exemplary Clinical Platform Module may further comprise a clinical research feature wherein a specific question (as opposed to a generic question template) is entered by clinicians, ML/AI models, and/or by one or more other platform features. Using features in the Configuration Module discussed below and items within the above Q&A feature, questions are created to address research and/or development related issues ("research-type questions") with at least one of the questions relating to the assessment of clinical outcomes, categorical outcomes, and/or qualitative outcomes. The questions may be created, modified, and/or configured, and the questions and related responses may be tagged, labeled, and/or annotated with all of these functions being performed by clinicians, ML/AI models, and/or through the utilization of one or more other platform features. In addition, the clinicians, ML/AI models, and/or other platform features may create, modify, and/or configure the timing and/or frequency at which the question(s) may appear in XR, the medium (text vs audio vs visual content, etc.) through which the question(s) are conveyed, as well as any other related content and/or features to be utilized in related scenes, sessions, and/or regimens.

Using an in-scene button panel, clinicians and/or patients may control and/or configure research efforts using XR. The buttons may include in-scene buttons with functionalities to "Start Trial" and/or "Stop Trial".

In one embodiment, once a "Start Trial" button is activated using patient input methods, one or more points of platform data are recorded for later analysis. These data may include points of the following: positional tracking data, biometric data, video data recorded from cameras, audio data recorded from cameras, audio data recorded from microphones, audio data recorded from other objects with audio recording functionalities within XR, points of data produced by actions and/or behaviors of clinicians and/or patients while in XR, responses to other questions, other items from the Q&A feature, other platform features, and other points of platform data. Other points of platform data may comprise items of content and/or features within XR. These items may be instantiated, modified, initialized, displayed, stopped and/or destroyed, and these functionalities may have in-scene buttons to control such functionalities.

Upon activating the "Stop Trial" button using patient input methods the platform data recording is stopped, and the data that was recorded may be sent to forms of electronic storage via APIs and/or using functionalities of the Integration Module. A within-scene question panel user interface element appears within XR scenes (the "outcomes question panel") displaying research-type questions as configured by clinicians and/or patients. One or more answer selections may be made using patient input methods with each response being saved and/or logged. Other platform features that were instantiated, modified, initialized, displayed, stopped and/or destroyed after "Start Trial" button was activated may now be instantiated, modified, initialized, displayed, stopped and/or destroyed again.

Desirable Scene Based on Thoughts or Destinations Feature

In this feature of the exemplary Clinical Platform Module, a scene is procedurally generated based on desirable thoughts (that are expressed) and/or desirable destinations for individuals. The destinations may be real-world destinations that are identified by a patient, clinician, and/or ML/AI models, or they may be fictitious destinations with characteristics that are described, derived, and/or inferred by a patient, clinician, and/or ML/AI models.

Using clinicians, ML/AI models, virtual human avatars, and/or other platform features, a patient is asked to described one or more desirable thoughts and/or destinations using patient inputs. The thoughts and/or destinations may be identified and/or described using one or more speech-to-text ML/AI models to convert spoken words into a text-based representation of the inputs. This text-based representation may be utilized in or as part of items within this feature as well as one or more other platform features. The thoughts, destinations, and/or related characteristics may be identified, derived and/or inferred by ML/AI models.

Patient-generated, clinician-generated, and/or ML/AI model-generated text, image, video, rendered, and/or audio objects are obtained which in some way describe the desirable thoughts and/or destinations. The objects may be obtained after visual, auditory, and/or haptic prompts are delivered to patients and/or clinicians in XR.

The patient-generated text, image, video, rendered, and/or audio objects and any subsequent text, audio, image, rendered objects, and/or video are combined with zero or more points of other platform data and parsed for relevant features and/or keywords using ML/AI models and/or other platform features.

Using this parsed output, ML/AI models extract key features to yield a list of virtual environments and/or virtual object characteristics from which one or more elements of an XR scene are procedurally and/or programmatically created. The parsed output may be used as a direct input to other ML/AI models which generate or select virtual objects and/or virtual environment characteristics within a procedurally created and/or programmatically created XR scene. The parsed output is utilized by other platform features to produce virtual environment characteristics, and/or virtual objects, and/or a procedurally created virtual scene.

One Embodiment of the Question and Answer (Q&A) Feature

In one exemplary embodiment of the present Q&A feature, users can answer questionnaires that are assigned to him through a web portal. User specific surveys can be retrieved via API using a logged in user's current authentication token as structured JSON. Default survey JSON can also be loaded if the XR Health Platform is configured for offline use or if the device is offline. A survey's JSON may comprise one or more of an ID, a user ID, title, and a collection of questions. The questions may comprise: an ID, the question itself which is referred to as a title, and a format. Exemplary formats include: slider wherein the response can be a configurable range of numbers; dropdown wherein the response can be a single choice from a dropdown list of options; single response selection wherein the response can be a single choice from a list of options; multi response selection wherein the response can be multiple choice from a list of options; single response grid wherein the response can be one selection each for a subset of questions; and multi response grid wherein the response can be multiple selections each for a subset of questions.

A slider's responses will have the range of numbers. Dropdown, single choice selection, and multi choice selection will have a collection of individual choices. Single choice grid and multi choice grid will have a collection of potential responses to each individual sub-question. Single choice and multi choice grid format questions will have a collection of sub-questions.

Once a user's assigned questionnaire is retrieved from the API, the JSON is then parsed and displayed to the user in XR for answering. The parser checks the format of each question object, then procedurally generates the appropriate UI Canvas with the question at the top, the ability to respond in the center, and a button to move onto the next question at the bottom.

The user will then use the pointer on his controller as well as the trigger for a pointer and click interface to answer each question individually. For slider, the user will click on a slider handle and drag left or right until the numerical indicator above the slider displays his desired answer. For dropdown, the user will click on the dropdown and the available responses will appear. They will then click on the appropriate response. The list of responses will disappear, and his chosen response will be displayed in the dropdown. For single response selection and multiple response selection, a list of responses with checkboxes next to them will appear. The user will click on the checkbox next to his desired response(s). If it is single response and a new selection is made, the previous selection will be cleared. For single response grid and multiple response grid, a grid will appear with a list of sub-questions along the left-hand side of the UI Canvas as well as their potential responses across the top. There is a checkbox for each possible sub-question/response combination. The user will select for his desired responses. If it is single choice, if the user has already made a selection for a sub-question before selecting another response for the same sub-question, his previous selection will be cleared upon making a different selection.

Once the user has reached the end of the survey, his responses will be parsed and formatted as JSON and sent via API to the server using a POST request. If the XR Health Platform is configured for offline use, or the device is offline, the JSON will be stored locally to the device in the Session Storage folder.

Clinical Computer Vision Feature

An exemplary clinical computer vision feature of the exemplary Clinical Platform Module is applicable for combining mask and/or instance segmentation computer vision models, and/or other ML/AI models with points of platform data (such as anthropometric data), and/or other platform features to derive therapeutic, diagnostic, prognostic, and/or disease risk prediction data for diseases and/or disease-related outcomes.

A camera is used to take photographs, images, and/or videos of a patient and/or relating to the health of patients. Using the "measuring tape" (as described in the hardware section below) and/or using one or more other measurement scales and/or methods of evaluation, one or more of the following are obtained for an individual: height, waist circumference, hip circumference, bust circumference, thigh circumference, calf circumference, neck circumference, mid-brachial circumference, and knee-to-heel length. Using a scale and/or the Q&A feature, the weight of an individual is obtained. Mask and/or instance segmentation computer vision models and/or one or more other ML/AI models are applied to photographs, images, platform data, and/or videos of the patient and/or frames extracted from a video of a patient. The photo, image, platform data, and/or frame outputs of the model are modified versions of the input photo, image, platform data, and/or frame with pixels belonging to an area, characteristic, volume, and/or other measurement of the patient being delineated. The area, volume, and/or other measurement of the patient is estimated and/or calculated from a set of the model outputs either by themselves or when combined with other points of platform data and/or other platform features. The morphology, shape, body habitus, postural data, and/or anthropometric data are derived using other ML/AI models from estimates and/or calculations of area, volume, and/or other measurement related to the patient. Different ML/AI models may be applied to the photos, images, points of platform data, and/or frames to determine and/or validate points of derived data, morphological data, postural data, anthropometric data, and/or other points of platform data.

Data points obtained through this feature may be recorded and stored in a database. Points of the derived data may be combined with other points of platform data, which may then be analyzed by ML/AI models and/or one or more other platform features to derive therapeutic, diagnostic, prognostic, and/or disease risk prediction data relating to diseases and/or disease-related outcomes.

ML/AI to Influence Patient Behavior Feature

The exemplary Clinical Platform Module may further comprise a ML/AI to influence patient behavior feature which uses ML/AI models combined with points of platform data to influence a patient's and/or clinician's behavior and/or influence the patient to carry out desirable actions in XR by creating, deriving, configuring, triggering, modifying, deploying and/or controlling platform content and/or by utilizing other platform features. Points of platform data for a given patient are used as inputs for ML/AI models and/or one or more other platform features. Code and/or configuration instructions may be used to programmatically or otherwise modify, configure, instantiate, and/or control "non-player characters", virtual human avatars, content and/or features, objects, and/or other features within scenes, sessions and/or regimens. The exemplary feature may use specific measurable and desirable platform actions and/or series of desirable and measurable platform actions over time ("platform behaviors"). For the purpose of this feature, "desirable actions" above also includes mitigating, decreasing, and/or eliminating undesirable actions (for example, decreasing the amount or frequency of cigarette smoking). Inputs or outputs for other ML/AI models, and/or inputs or outputs for one or more iterations of the same ML/AI model(s) may also be utilized within this feature.

Anti-Nausea Feature

An anti-nausea feature of the present Clinical Platform Module is applicable to identify, diagnose, quantify, assess, mitigate, and/or treat nausea by creating, deriving, configuring, triggering, modifying, deploying and/or controlling items of platform content and/or features using ML/AI models, and/or points of platform data, and features described in one or more modules of the exemplary XR Health Platform. As indicated previously, each of the various modules is described in further detail separately herein.

Iterative ML/AI Feature

An iterative ML/AI feature of the exemplary Clinical Platform Module allows for the iterative testing, assessment, verification and/or improvement of ML/AI model(s) and/or inputs and/or outputs of ML/AI models using either actual XR and/or simulated XR. One embodiment of the iterative ML/AI feature is outlined in FIG. 8. The embodiment allows for the iterative testing, assessment, verification and/or improvement of ML/AI model(s) and/or inputs and/or outputs of ML/A models.

The input(s) and/or output(s) of ML/AI models (the "model of interest") comprises at least part of diagnostic tests, screening tests, therapeutic efforts, care delivery efforts, research efforts, development efforts, and/or other clinically-related efforts are created, selected, modified, and/or configured by clinicians and/or by other ML/AI models. The outputs from the model of interest are generally utilized for selecting and/or configuring platform actions and/or experiential questions to deliver in XR, but the outputs may be a set of items which may be evaluated and/or appreciated in XR experiences and/or in XR simulations.

Clinicians and/or ML/AI models determine preset performance thresholds by which the outputs of the model of interest will be evaluated in the context of the aforementioned particular clinical effort. All parameters, inputs, outputs, model features, as well as the preset thresholds are labeled, and a log of this data is stored in database(s).

The model of interest is run in a development environment. If the output(s) meet or exceed the preset performance threshold(s), the model(s), his performance with respect to the aforementioned clinical effort, all labeled parameters, inputs, outputs, model features, as well as the preset thresholds utilized are logged and stored in database(s) for future use. If the output(s) do not meet the preset performance threshold(s), the model(s), his performance with respect to the aforementioned clinical effort, all labeled parameters, inputs, outputs, model features, as well as the preset thresholds are logged, and the model outputs are then tested, assessed, verified, and/or improved through their application and/or implementation in XR experiences and/or in XR simulations. The testing, assessment, verification, and/or improvement in XR and/or XR simulations may be achieved by:

i. Using items in the above Q&A feature, patient action management feature, experiential data and question feature, A-B testing feature, barrier management feature, reinforcement learning feature, clinical research feature, ML/AI to influence patient behavior feature, patient decision support feature, any features within the Configuration Module, and/or using other platform features;

ii. Using other ML/AI models;

iii. Using the input of clinicians;

iv. Using patient input methods; and v. Using points of platform data.

Anytime the outputs of a model of interest are attempted to be tested, assessed, verified, and/or improved in XR experiences and/or in XR simulations, the above steps in this process are carried out or repeated until either the model of interest output(s) meet or exceed the preset performance threshold(s), or the process is terminated by clinician(s), admin(s), and/or by one or more other ML/AI model(s).

Patient Decision Support Feature

The patient decision support feature utilizes XR for individualize health-related decision support in real-world everyday life and/or in XR by combining XR (including augmented reality) with platform features, ML/AI models, points of platform data, and/or items of content in such a way to influence a patient's actions and/or behaviors. FIG. 9 comprise a schematic of one embodiment of the XR Health Platform that utilizes several items within the patient decision support feature. Specific use-cases/embodiments of this feature include the following:

1. Using the system to avoid injuries and/or falls.

2. Using the system as a dietary guide and/or assistant.

3. Using the system as an exercise and/or physical activity guide, personal trainer, and/or assistant.

4. Using the system to help with and/or assist in smoking cessation and/or avoiding, quitting, and/or abstaining from substances specifically using of the following items:

(i) Positive reinforcement upon successful avoidance delivered through the use of voice, audio, video, rendered, and/or text-based content, including snippets and/or content objects as described herein; and (ii) the delivery of timely and actionable recommendations, facts, and/or educational points to increase the odds or likelihood of abstaining from the substance.

5. Using ML/AI models such as mask segmentation, instance segmentation activity recognition, object identification, and/or object recognition, either with or without other platform features to "black out", associate a negative stimulus with, and/or deliver educational facts related to identified objects and/or substance(s). For example, showing an image of lungs affected by long term cigarette smoking and/or delivering educational content objects when a patient is about to pick up a pack of cigarettes, and/or using other platform features to "black out" a pack of cigarettes. FIG. 9 illustrates an example that utilizes the aforementioned "black out" capability to "black out" a package of cigarettes when encountered, and then subsequently deliver one or more educational content objects in the context of a smoking cessation effort. In addition, the diagram also illustrates how other platform features may be integrated into any such implementation, where in this example, the patient may initiate a video conference with a clinician using items within the communications feature.

6. Using the system to assess, help with and/or assist in medication adherence, and/or giving medication reminders. This may include the completion of simulations in XR requiring the patient to complete medication adherence-related tasks such as ordering a medication refill and/or appropriately sorting and organizing one week's worth of a mock medication regimen.

7. Using the system to help with and/or assist in remembering important people, places, and/or things.

8. Using object segmentation, instance segmentation, activity recognition, facial recognition, object identification, object recognition, and/or other ML/AI models, with or without the use of other platform features to identify important people, places, and/or things for an individual, and then subsequently assist the individual in remembering the important people, places, and/or things through the use of items of voice, audio, video, rendered, and/or text-based content and/or snippets.

9. Using the system either with or without ambient audio data and/or the use of an integrated food and nutritional content database and/or API to perform diet logging, monitoring, management, and/or dietary decision support for individuals.

10. Using the system to assess and/or assist with wayfinding or navigational tasks.

11. Using the system to assess, help with and/or assist with ADLs and/or IADLs. In addition to all of the other elements described herein, this feature may additionally include the following tasks to be simulated and/or completed in XR simulating house cleaning, such as loading and/or starting a dishwasher; making a shopping list from a recipe, purchasing the items on the shopping list from a virtual store, and/or carrying out cooking simulations wherein the recipe is followed; pill sorting tasks and/or simulations; having a patient write a mock check to pay a mock utility bill; carrying out a simulation wherein the patient makes an appointment and then appropriately marks the appointment on a virtual calendar; and making a mock phone call to accomplish simulated tasks.

12. Using ML/AI models with data from cameras resulting in an XR rendered image with real-world and/or virtual objects being completely removed and/or with attenuated visual characteristics compared to the original image ("the masking sub-feature"). For example, the masking sub-feature may be utilized to "black out" cigarettes and/or cigarette packages in individuals attempting smoking cessation.

13. Using ML/AI models combined with data from cameras resulting in an XR rendered image with real-world and/or virtual objects being visually highlighted and/or with visual characteristics that are emphasized compared to the original image ("the object emphasis sub-feature"). For example, the object emphasis sub-feature may be utilized to highlight one or more fall risks and/or hazards that exist in the real-word environment in order to assist individuals with avoiding injuries and/or falls. One variation may combine the object emphasis and/or masking sub-features above, along with other platform features to enable the emphasis and/or the attenuation of stimuli to positively influence an individual's health.

One specific embodiment utilizes these combined object emphasis and/or masking sub-features with other platform features to enable an intelligent diet tracking and management system that does one or more of the following: reduces triggers for cravings for unhealthy foods; masks and/or visually attenuates poor food choices; visually highlights and/or emphasizes positive food choices; gives goal-focused, actionable, and timely reminders, recommendations, facts, and/or educational points to increase the odds of accomplishing goals using items of voice, audio, video, rendered, and/or text-based content and/or snippets; and guides, simulates, reminds, advises, and/or educates an individual with respect to healthy ingredient selection, healthy meal planning, healthy cooking techniques, and/or healthy meal preparation.

One variation that allows the patient to load any recipe himself and uses ML/AI models to deliver ratings, modifications, educational points, and/or recommendations relating to the composition and/or quality of items within the loaded recipe.

Another variation allows the patient to select from a predefined list of healthy recipes.

Yet another variation allows for an individual to get assistance in adhering to disease-specific healthy diets and/or healthy diet choices (examples include a low sodium diet for individuals with hypertension, a low potassium diet for individuals with kidney disease, a low vitamin K diet for individuals taking the drug warfarin, and/or a low carbohydrate diet for individuals with diabetes).

Any of the above items may be combined with the addition of instances of haptic, visual, olfactory, and/or auditory feedback and/or biofeedback. Any of the above items may be combined with other platform features and/or use points of platform data.

Any and/or all of the aforementioned items may be utilized by either patients and/or clinicians. FIG. 10 provides one example of what the decision support capabilities may look like when utilized by a clinician during a patient encounter.

FIGS. 11 and 12 illustrate two examples of the flow of information related to the creation, modification, configuration, and/or implementation of scenes, sessions, and/or regimens. In these embodiments, the creation of personalized scenes, sessions, and/or regimens starts with platform features being utilized to curate, collect, modify, and/or create points of platform data to be used as initial information inputs. In these embodiments, items within the patient-level profile feature, initial visit feature, history of present illness feature, health problem list feature, barrier management feature, Q&A feature, and/or within the goal and feedback development feature are utilized in curating, collecting, modifying, and/or creating initial information inputs. In these embodiments, after the initial information inputs are set, clinicians, ML/AI models, and/or other platform features then use the initial information inputs to populate a curated problem list, a set of customized and/or personalized goals, and/or other selected points of platform data. The curated problem list, set of customized and/or personalized goals, and/or other selected points of platform data are then subsequently utilized to inform the creation and/or initial configuration of the personalized scenes, sessions, and/or regimens by clinicians and/or by ML/AI models. Then, whenever a patient next engages in the scenes, sessions, and/or regimens, any one or more points of platform data generated and/or modified during the engagement may be utilized to update and/or configure other points of platform data, platform features, as well as any content and/or features comprising subsequent scenes, sessions, and/or regimens. In this embodiment, this iterative process continues until goals are achieved, until there are no remaining scenes, sessions, and/or regimens available for the patient, and/or until this process is terminated by clinicians, admins, and/or ML/AI models. FIG. 12 illustrates all of the same characteristics of the diagram of FIG. 11 and additionally illustrates how the data enabling these characteristics is routed and/or stored using one or more API(s) and/or database(s), respectively. FIGS. 11 and 12 also illustrate two examples of how scenes, sessions, and/or regimens are comprised of content and/or platform features which are customized for individual patients by way of features described within the Configuration Module described herein, and/or, by other platform features.

B. XR Platform Module

The XR Platform Module of the exemplary XR Health Platform contains features that, either alone, or in combination with other platform features, enable platform features to work in a hardware agnostic manner, makes the platform safe, comfortable, and easy to use, and/or allows the XR Health Platform to be built in a way that allows it to be distributed at scale. One or more of the features within the XR Platform Module may utilize other platform features, other points of platform data, and/or one or more ML/AI models. The exemplary XR Platform Module itself may comprise one or more of the features described below.

Hardware Agnostic Feature

A hardware agnostic feature of the exemplary XR Platform Module allows systems within the XR Health Platform to work in a hardware agnostic manner and/or to be distributed at scale (see FIG. 13) and consists of one or more of the following items described below. The XR Health Platform may be paid for, downloaded, and/or updated remotely using XR and/or other web-based interface. Tooltips may be provided for showing patients how to use patient input methods with the tooltips automatically adjusting to point to the correct locations on the virtual representations of one or more real-world input devices. Deep links and/or other methods may be utilized to recognize a user's hardware device(s) and/or facilitate the remote delivery of compatible platform/software package(s). A floor recognition feature may be utilized whereby the location and/or shape of a real-world floor is determined and integrated into XR using ML/AI models and/or sensors and/or one or more other platform features. A spatial understanding feature may be utilized whereby the real-world space and/or objects within the real-world space surrounding an individual are identified, recognized, and/or contextualized using ML/AI models, other platform features, and/or other points of platform data. The exemplary module may also comprise health-related spatial understanding feature whereby health-related objects, people, places, and/or activities within the real-world space surrounding an individual are identified, recognized, and/or contextualized using ML/AI models for the purposes of improving aspects relating to the health of individuals. The exemplary platform features conditional compilation in necessary areas to account for differences in platform specific libraries. These areas may include threading, data persistence and input/output, and Bluetooth and communications library usage.

Height Adjust Feature

The height adjust feature of the exemplary XR Platform Module allows for XR hardware systems that use inside-out tracking to be used in novel real-world environments without having to go through a setup and/or configuration procedure (see FIG. 14).

The exemplary platform features the ability to use both room-scale tracking and non-room scale tracking positioning. The Non-Room Scale Tracking positioning option is used for scenarios where Room Scale Tracking is unavailable and/or undesirable. If this is the case, the user is taken to the manual height adjustment scene preemptive to the rest of his session.

The manual height adjustment scene features several items that the user and/or clinician can modulate. Selecting the default seated position will move the position of the camera to 46 inches above the virtual floor. This is said to be the average seated height of a human's eyes. This number is configurable (may be modified).

Selecting the standing position will move the position of the camera to 60 inches above the virtual floor. This is said to be the average standing height of a human's eyes. This number is configurable. Once the user has selected seated or standing, they can move the virtual floor up as needed if it is too low. This "floor adjustment up" item will move the camera down by a configurable amount to give the appearance that the virtual floor is moving up. Once the user has selected seated or standing, they can move the virtual floor down as needed if it is too high. This "floor adjustment down" item will move the camera up by a configurable amount to appear that the virtual floor is moving down. Once the user has adjusted his height in XR to a comfortable position which closely matches his position in real life, they can click the "start" item to start the rest of his session.

After completing this scene, there is a HeightAdjustment script that is never destroyed for as long as the session is going. The script stores the user's position in memory upon completion. The script subscribes to Game engine's scene loading events and on scene load, adjusts the User's scene camera and/or the rendered visual elements of XR experiences to the correct stored position so the user remains comfortable in each scene they load.

Tutorial Feature

An exemplary tutorial feature of the exemplary XR Platform Module functions to teach the patient and/or clinician how to use the XR Health Platform and may incorporate the various items described herein. The tutorial system may be used for first time users and/or repeat users to get familiar with the platform controls and/or patient input methods. One embodiment of the tutorial system teaches users how to complete and/or participate in assessments, tests, tasks, exercises, screening tests, diagnostic tests, therapeutic experiences, and/or other platform features relating to, and/or contained within, XR scenes, sessions, and/or regimens. The system may deliver instructions and/or teach users how to complete the items through various modalities.

In exemplary embodiments, the feature may use auditory means including voiceover instructions, through verbal responses, through spoken interactions and/or dialogue type interactions with virtual human avatars, ML/AI models, and/or other platform features.

In other exemplary embodiments, the feature may also use visual means including text-based, image-based, video-based, and/or rendered content-based instructions delivered by virtual human avatars, ML/AI models, and/or other platform features, and delivered either as a screen overlay, a "heads-up display", and/or within any other location within XR.

In further exemplary embodiments, the feature may also use tactile means including the use of haptic biofeedback to indicate one or more of the following: the correctness and/or incorrectness of movements, the correctness and/or incorrectness of patient inputs, to nudge the user in the right virtual direction and/or towards the correct method of patient input(s) in order to complete learning tasks, and to prompt the user to take other actions.

One embodiment of the tutorial system features a hierarchical structure comprising (a) the overall tutorial, (b) tutorial steps, (c) completion steps.

The overall tutorial comprises a TutorialManager class including configurable properties such as:

(i) public TutorialStep[ ] Tutorial Steps—A collection of TutorialStep Objects that are necessary to complete the tutorial;

(ii) public string NextSceneName—The next scene to go to once the tutorial has been completed by the user;

(iii) public float CompletionDelay—The time it takes to go to the next scene once the tutorial is complete; and (iv) public GameObject[ ] CompletionObjects—A collection of GameObjects to show once the tutorial is complete.

The TutorialManager manages which Tutorial Step is active and whether or not all tutorial steps have been completed.

The tutorials steps comprise a TutorialStep class including configurable properties such as:

(i) public TutorialManager TutorialManager—A reference to the TutorialManager object;

(ii) public CompletionStepBase[ ] CompletionSteps—A collection of all CompletionStepBase objects that are necessary to complete the tutorial step;

(iii) public GameObject RightControllerPrefab—The controller configuration for the right hand that will be used during this tutorial step;

(iv) public GameObject LeftControllerPrefab—The controller configuration for the left hand that will be used during this tutorial step;

(v) public Material HighlightButtonMaterial—The material that will be applied to buttons on the controller when they need to be highlighted by a completion step;

(vi) public GameObject [ ] StepObjects—A collection of game objects that should be enabled while this step is active.

Tutorial steps manage which completion step is active and whether or not all completion steps are complete. Once tutorial step complete, the TutorialStep class notifies the tutorial manager the tutorial step is complete.

The completion steps comprise a CompletionStepBase class including configurable properties such as:

(i) public TutorialStep TutorialStep—A reference to the TutorialStep this completion step belongs to;

(ii) public ControllerElement [ ] ButtonsToHighlight—A collection of buttons that should be highlighted while this step is active; and (iii) public GameObject [ ] StepObjects—A collection of game objects that should be enabled while this step is active.

The CompletionStepBase class is meant to be derived by another class that implements the logic for step completion. Once the action is completed, the deriving class must call a protected method called CompleteStep. The CompleteStep method will notify the appropriate TutorialStep of completion step completion.

The overall user experience of the aforementioned and described embodiment proceeds through a series of sequential steps as follows:

1. User opts-in to the tutorial.
2. Tutorial is separated into groups of 'Tutorial Steps' which comprise a collection of 'Completion Steps'.
3. The first Tutorial Step is started, starting the first completion step of the tutorial step.
4. User is instructed to complete certain task.
5. User completes task (i.e. Button Press).
6. Tutorial step moves to the next completion step, until all completion steps are exhausted.
7. Tutorial goes to next Tutorial step.
8. Process is repeated until all steps are completed.
9. Once tutorial is complete user starts his XR session.

Box Integration Feature

The exemplary XR Platform Module Platform may further utilize an integration of "Box" hardware feature (hardware is as described below) comprising a fan and various scents. The fan helps to reduce and/or prevent nausea. The fan speed, angle, position, and/or direction may be adjusted by patients, clinicians, and/or ML/AI models to optimize XR content and/or features for greater immersiveness and/or patient comfort. The various scents shown to have an anti-nausea effect help to reduce nausea via the integrated aroma diffuser. The selection and/or intensity of deployable scents may be modified by patients, clinicians, and/or ML/AI models to optimize immersiveness and/or patient comfort. Both features above may be controlled by ML/AI models to achieve synergistic benefit.

Collision Avoidance Feature

A collision avoidance feature of the exemplary XR Platform Module assists in avoiding collisions with real world objects in XR and may comprise: relative distance, absolute distance and/or real-world positional thresholds are set by a clinician and/or admin using the Configuration Module; movement beyond a virtual collider, and/or past a certain absolute or relative real-world distance after starting XR, and/or a signal is received from an external camera or any other device indicating that a user's real-world position has exceeded preset thresholds. This may trigger one or more of the following for the user in XR:

(i) A pop-up of passthrough video and/or augmented reality overlay showing an external/real-world view through an XR device with items of text, images, and/or rendered content overlaid on top of the real-world view. The image(s) of passthrough video and/or augmented reality overlay may be enhanced by effects and/or by ML/AI models to clearly outline and/or highlight real-world hazards (for example a real-world object that represents a fall risk).

(ii) A camera filter and/or graphical overlay is applied to the user's field of view to instruct, prompt, persuade and/or influence a patient to take appropriate actions in XR and/or in the real-world.

(iii) An audio warning message with or without voice instructions to carry out appropriate actions in XR and/or in the real-world.

(iv) Text pop-up warnings with or without instructions to carry out one or more appropriate actions in XR and/or in the real-world.

Additional elements of the collision avoidance feature may comprise warnings delivered through tactile (or haptic) stimulation, re-orientation of scene in a way that minimizes the likelihood of a collision with real world objects, or cessation of an XR session. A clinician observing, supervising and/or interacting with an individual in XR may also trigger any of the above actions at any time via a web portal, companion application, and/or in XR.

Accessibility Feature

An accessibility feature of the exemplary XR Platform Module enables the XR Health Platform and/or XR for individuals with disabilities, to accommodate individuals with disabilities, and/or to assist in the rehabilitation from and/or treatment of disabilities. An individual with disabilities either self-identifies as such and/or a clinician identifies the disabilities. Clinicians and/or ML/AI models utilize items in the clinician Configuration Module to alter XR scenes and/or features within the scenes to help an individual rehabilitate from and/or to accommodate for disabilities. Clinicians and/or ML/AI models may select from one or more global XR pre-configurations that alter XR scenes and/or features within the scenes to accommodate common disabilities. Specific embodiments of the rehabilitative and/or accommodative features include: a global volume adjustment to better accommodate for individuals with conductive hearing loss, and a visual magnifier feature that magnifies image(s) rendered to the users XR hardware for individuals with vision-related issues. The magnification may be globally applied to all rendered material and/or images, may be applied on-demand, and may be applied based on a patient's head position, gaze, eye position, points of biometric data, points of other platform data, and/or based on other platform features.

Clinician Supervision Feature

A clinician supervision feature of the exemplary XR Platform Module is applicable for clinician supervision of one or more patients in medically-related and/or health-related XR scenes, sessions, and/or regimens and may comprise the following: clinicians may supervise, observe, and/or interact with a patient in XR through the use of a web portal and/or a companion application and/or in XR, using avatars and/or through other features described in the communications feature; clinicians may supervise, interact with, and/or observe patients in XR from either the first or third-person perspectives; and clinicians, ML/AI models, and/or other platform features may create, modify, and/or deploy safety prompts as described herein.

User Interface Gaze Follow Feature

A user interface gaze follow feature of the exemplary XR Platform Module may comprise one or more of the elements discussed below. Within the XR Health Platform, several UI Canvases (menus) including the start menu include an implementation of a Gaze Follow feature that is used to keep any menu element in front of a user without causing any nausea or discomfort. The Gaze Follow feature translates and rotates any menu by using a series of configurable fields to smoothly move the canvas as a user starts to look or move away from it, as well as keep it a preferred distance away if they move closer to it. The Gaze Follow Feature may be modified and/or configured by altering parameters, including:

(a) A reference to the user interface (menu) that will be following the gaze of the user.

(b) The virtual distance (in meters) the menu will appear in front of the user.

(c) The speed at which the menu follows the user's gaze.

(d) The speed at which the menu rotates with the user's gaze.

(e) A threshold value—If this threshold is less than the absolute value of the menu virtual distance minus the actual virtual distance of the menu from the user, the menus' position is always translated/rotated. This is to account for the user's actual position moving, not just users gaze.

(f) A snap parameter where a menu automatically updates to the preferred position and rotation, without having to translate, and also allows for the menu to appropriately update position and/or rotation upon a "teleport" with XR.

(g) A hide parameter which disables the menu such that it is no longer rendered in XR.

C. Configuration Module

The Configuration Module of the exemplary XR Health Platform allows for platform objects, content objects, platform features, platform data, content elements, scenes, sessions, and/or regimens to be created, configured, and/or deployed by clinicians and/or by using ML/AI models. It allows for either the real-time and/or near-real-time creation of one or more tailored, personalized, adaptive and/or problem-focused scenes, sessions, and/or regimens containing diagnostic, screening, therapeutic, and/or care delivery features. It is the clinical workflow engine containing the back-end programming that enables clinicians and/or ML/AI models to create modify, administer, and/or orchestrate diagnostic, therapeutic, and/or other health-related systems. It is how the XR Health Platform leverages platform data to deliver customized and/or personalized care to patients. Clinicians and/or patients utilize and/or experience Configuration Module features and/or functionalities through using a web portal, companion application, and/or XR.

FIG. 15 provides a high-level depiction of the architecture underlying one embodiment of the XR Health Platform that utilizes configuration-related items and/or features described herein. FIG. 16 further provides an illustration of one workflow involving items and/or features within the Configuration Module.

Example types of platform actions configured by clinicians, admins and/or by ML/AI models using of the features within the Configuration Module include: changing question content and/or timing of question(s); email notification; text/SMS notification; changing audio content, and/or how, and/or when audio is delivered; feedback reports; asynchronous communication with other individuals; real-time communication with other individuals; near-real-time communication with clinicians; changing aspects of ML/AI models (including his inputs and/or outputs); changing what ML/AI model(s) are used; changing what scene(s) are utilized in next session; changing the order in which scenes are utilized in next session; change in content and/or features in scenes; change in sequence of events within scenes; change in the timing, speed, or duration of scenes; and change in virtual location within scenes.

XR content and/or platform features may be applied in the context of a scene, session, and/or regimen, with multiple scenes typically comprising a session, and multiple sessions typically comprising a regimen. FIG. 17 illustrates this hierarchy. In this embodiment, scenes, sessions, and/or regimens may contain any combination of sets of customized platform features and/or platform content. Although scenes and/or sessions may be applied in a standalone manner, the aforementioned hierarchy allows for multifactorial and/or multimodal approaches to health-related issues which otherwise may be difficult to diagnose, manage, and/or treat. The aforementioned organizational structure and the platform features described herein provide for granular control over clinical workflows, yet also give clinicians the ability to longitudinally follow patients and allow for the continuous development of systems that iteratively improve for the benefit of individual patients over time. FIG. 18 also illustrates the aforementioned hierarchy, and the information flow outlined on this diagram illustrates one example of how platform data is used within scenes, sessions, and/or regimens to iteratively address and/or improve specific health related issues for individual patients.

This overall approach of utilizing a session comprised of personalized and interactive scenes, delivering personalized feedback and/or educational information, and then iteratively adapting subsequent sessions and/or scenes based on previous results can be appreciated when reviewing FIGS. 19-27. In these diagrams, note how the composition of each session is influenced by platform data related to the patient and by the patient's performance and/or behavior in previous scenes and/or sessions. This series of diagrams illustrate one embodiment of how a personalized regimen may be constructed and/or carried out for a hypothetical patient "John Doe", given his particular problem list, goals, and/or other pertinent points of platform data. FIG. 19 illustrates how platform features and/or items of platform content may be distributed in particular scenes, sessions and/or regimens. In addition, this diagram also illustrates how the XR Health Platform is able to be personalized and is designed to address clinical issues that are multi-factorial in nature. FIG. 20 illustrates how any combination of platform features may be combined and/or utilized at the session and/or regimen level. FIGS. 21-27 walk through a series of three sessions for "John Doe" with each session, and all the scenes comprising each session utilizing combinations of platform features that are germane to the health of this particular patient. The patient's participation in each session yields a "results report" containing points of personalized educational information and/or feedback (as depicted in FIGS. 22 and 25). Using the results obtained for each scene or session, and/or using points of other platform data available, a set of problem-focused and/or goal-focused recommendations to carry out and/or address in subsequent scenes and/or sessions are developed by clinicians and/or by ML/AI models (as depicted in FIGS. 23 and 26).

Various features within the Configuration Module may utilize other platform features, one or more other points of platform data, and/or ML/AI models. In exemplary embodiments, the Configuration Module may further comprise one or more of the features described below.

Patient Behavior and Action Configuration Feature

A patient behavior and action configuration feature of the Configuration Module enables the ability to select desirable actions, behaviors, outcomes, and/or points of derived data. Combined with the integration of other platform features, the patient behavior and action configuration feature facilitates the ability of clinicians and/or ML/AI models to create, modify, configure, trigger, track, influence, deploy and/or iteratively develop one or more patient actions, patient platform actions, patient behaviors, platform actions, platform outcomes, and/or points of derived data.

Using this feature, clinicians and/or ML/AI models may select items from predefined lists of patient actions, patient platform actions, patient behaviors, platform actions, platform outcomes, and/or derived data fields to utilize, configure, modify, trigger, track, influence, discourage, and/or promote in individual patients, with the items otherwise being implemented through the use of other platform features. Novel patient actions, patient platform actions, patient behaviors, platform actions, platform outcomes and/or derived data fields may be created by combining or utilizing sets of one or more platform data fields and/or platform data points, with these platform data fields and/or platform data points being selected and/or utilized by clinicians and/or by applying ML/AI models.

Content Object and Snippet Feature

The exemplary Configuration Module may also comprise a content object and snippet feature which allows users to create, label, tag, annotate, configure, trigger, and/or deploy content objects and/or snippets. This exemplary feature may comprise a sub-feature for creating and/or tagging snippets and/or content objects. Using XR (including a web portal and/or a companion application), clinicians and/or ML/AI models may enter instructional, educational, diagnostic, feedback, and/or therapeutic snippets and/or content objects, and may additionally apply clinically related tags, labels, and/or annotations to each snippet entered. Tags, labels, and/or annotations may be text, audio, images, rendered objects, or other media. For clarity, "diagnostic snippets" refers to snippets and/or content objects that are designed to elicit and/or provoke patient responses, actions, and/or behaviors that may contain one or more points of diagnostic information. For clarity, "feedback snippets" refers to snippets and/or content objects that are designed to deliver items of feedback to patients and/or clinicians. For clarity, "therapeutic snippets" refers to snippets and/or content objects that are designed to deliver items of therapeutic value to patients and/or clinicians. Each snippet and/or content object may be assigned GUIDs or other identifiers, and the snippet/content objects along with all associated labels, tags, and/or annotations are saved in database(s).

In other exemplary embodiments, the feature further comprises a sub-feature for selecting from already created snippets and/or content objects. Clinicians and/or ML/AI models search for any available instructional, educational, diagnostic, feedback, and/or therapeutic snippets and/or content objects. Searching is accomplished either via a search function and/or by going through a list of all tag entries via a dropdown menu, scrollable element, search box, and/or other methods of querying, searching and/or selecting. Searching may also be carried out by ML/AI models. The search string entered may be used to query against the list of tags, labels, and/or annotations, and clinicians and/or ML/AI models may select items appearing in the search results to deploy to patients and/or clinicians in XR.

In other exemplary embodiments, the feature further comprises a sub-feature to configure and deliver selected snippets and/or content objects to patients. Clinicians and/or ML/AI models set one or more of the following configuration parameters for each selected snippet/content object: (a) what scene(s) snippet will be used in, and when during the scene to utilize the snippet (triggered by certain action(s) vs specific time after scene start); (b) whether the item will be conveyed in XR as text, read aloud using text-to-speech models, using other audio and/or visual means of communication, and/or other ML/AI models; (c) if the item will appear as text in XR, selecting which virtual objects will display the text; (d) if the item will be read aloud in XR, indicating from which virtual objects and/or features the audio will emanate from (e.g., an avatar, the virtual environment, or other object(s)); and (e) to which patient(s) or devices will the snippet(s) and/or content object(s) be deployed.

Once the above configuration steps are completed, the selected configuration choices may be saved as a "preset" and later re-deployed to users in XR per the configuration.

Content Object and Snippet ML Feature

A content object and snippet ML feature of the Configuration Module may be used to create, label, tag, annotate, configure, trigger, and/or deploy snippets and/or content objects for the purpose of creating, iterating upon, training, and/or developing ML/AI models. This feature uses points of platform data, platform features, and a variation of the above content object and snippet feature wherein content objects and/or snippets utilized for these purposes have labels, tags, and/or annotations that additionally reference characteristics of the ML/AI models. These references may be later programmatically called, selected by clinicians, or selected by other ML/AI models for the purpose of creating or altering inputs, outputs, training characteristics, or other characteristics of ML/AI models.

Voice-Based Clinical Application Feature

A voice-based clinical application feature of the exemplary Configuration Module is applicable for voice-based clinical applications via the creation, entry, modification, configuration, selection and/or deployment of voice-type snippets and/or applicable content objects by clinicians and/or ML/AI models. This feature enables entry of text snippets and/or entry of snippets using one or more speech-to-text (STT) models, using the content object and snippet feature as described herein.

Using the present feature, a clinician and/or ML/AI models select snippets to deliver to a patient using the content object and snippet feature as described herein. Any selected text snippets are converted to audio files containing spoken language using text-to-speech models (TTS). Audio voice over(s) of text snippets may be configured to be recited out loud to patients in XR. Patient voice response(s) may be entered using patient input methods. STT models are applied to audio to convert the audio into text. Patient audio and/or text transcripts of patient voice may be saved in database(s) and/or application(s) for later analysis. Natural language processing (NLP) models may be applied to either the text and/or original audio with feature extraction and/or analysis results of text and/or audio (vocal biomarkers, semantics, sentiment, clinical meaning, and the like) being saved. The most appropriate snippet(s) are then selected to deliver to the patient next using one or more platform features.

Goal and Feedback Development Feature

The exemplary Configuration Module may further comprise a goal and feedback development feature. According to this feature, clinicians and/or ML/AI models may create, generate, modify, configure, and/or deploy concise, goal-focused, actionable, and/or personalized feedback as items of text, audio, images, video, and/or rendered content. The exemplary feature is enabled through one or more of the items and/or steps described below.

Clinicians may create, generate, modify, configure, and/or deploy personalized goals using methods and/or features described herein. Clinicians and/or ML/AI models create a "templated goal-based feedback snippet" for a specific goal. This feature may also configure platform data fields to be used for the feedback, and/or any visualizations to be used to convey the platform data. The feature may also configure positive and/or encouraging snippets to address certain scenarios using an embedded embodiment of the snippet feature described herein. Exemplary scenarios include (a) if goal was not met, a positive statement encouraging continued participation; and (b) if goal was met, a positive congratulatory/celebratory snippet to be delivered at the time a goal is met or thereafter. The feature may further comprise any additional and/or already existing snippets that educate and/or instruct patients to breed autonomy and competence in the knowledge and/or skills needed to accomplish the goal.

In one exemplary embodiment, the present feature includes a sub-feature to create personalized feedback reports. Clinicians and/or ML/AI models select a patient. A template feedback report is pre-populated with a "templated goal-based feedback snippet" for each of the patient's goals. Based on the available platform data as well as the specific metrics comprising each goal, performance-based statements populate the appropriate areas of each goal-based feedback snippet. Clinicians and/or ML/AI models may modify any statements within the pre-populated report. Clinicians and/or ML/AI models configure how and/or when visualizations and snippets are delivered.

In another exemplary embodiment, the present feature includes sub-feature to generate personalized feedback. Personalized feedback reports may be generated using supervised, unsupervised, and/or semi-supervised methods. For supervised and/or semi-supervised methods, reports may be created using the subsystem described above. For unsupervised and/or autonomous methods, ML/A models are combined with the goals as well as available platform data to generate feedback content for an individual patient. The feedback content may be positively framed, detailed, specific, actionable, and goal-focused. The content itself may reward increased frequency of participation whenever applicable. The feedback content may be pre-configured to be delivered concurrent with triggering actions or as soon as possible thereafter. The feedback content may be delivered through greater than 1 modality (e.g., visual, text-based, audio, tactile, smell).

In yet another exemplary embodiment, the present feature includes a sub-feature allowing patients to adjust the timing and/or frequency of feedback to better suit preferences. This sub-feature is enabled through the use of XR, patient input methods, and/or through the use of email and/or text messages.

In yet another exemplary embodiment, the present feature includes a sub-feature that allows for the personalized, timely, and actionable delivery of feedback through points of other platform data. Exemplary points of data include biometric data, data from neuro-behavioral and/or cognitive assessments, data from compliance monitoring systems, imaging studies, data produced by one or more computer vision algorithms, vocal biomarker data, and/or data from diagnostic studies. For clarity, this feature also may utilize data points produced by the use of scenes, sessions, and/or regimens.

In yet another exemplary embodiment, the present feature includes an "experience-based feedback" sub-feature that monitors a patient in XR and identifies positive actions and/or negative actions. Upon completion of a session, this sub-feature delivers tailored education and feedback based on the individual's actions or behaviors in XR.

ML/AI Model Configuration Feature

A ML/AI model configuration feature of the exemplary Configuration Module is applicable for configuring ML/AI models for use within XR scenes, sessions, and/or regimens to address, improve, influence and/or mitigate health-related aspects of an individual. According to this feature, admins select model inputs and/or outputs from the master lists of available platform data fields and/or derived data fields. Admins and/or clinicians select which model(s) to use for any given use case from a list of available ML/AI models. The admins and/or clinicians configure any selected ML/AI models and select one or more platform features, platform data, scenes, sessions, and/or regimens to which the selected ML/AI models will be applied and/or integrated with.

One variation of this exemplary feature includes the coding and/or programming necessary to enable ML/AI models to determine and select a predicted optimal set of inputs and/or outputs for other ML/AI models, and/or select which ML/AI model(s) are to be used in given scenarios. All ML/AI model outputs along with a detailed description of the specific configurations of all models used to derive the outputs are logged and saved in a database. A further variation may incorporate the GUI-based system to config-ure, train, modify, and/or deploy conversational agents (the bot GUI feature), as described below. A further variation may incorporate the method and/or system for clinical workflow creation, modification and/or configuration (the clinical workflow feature) as described below.

Bot GUI Feature

The exemplary Configuration Module may also include a Bot GUI feature. This feature comprises a GUI-based sys-tem for clinicians to configure, train, modify, and/or deploy text, voice, and/or avatar-based diagnostic and/or therapeu-tic conversational agents (referred to as "bots") by combin-ing platform features with the application of ML/AI models. According to this feature, clinicians, admins, and/or ML/AI models create, select, modify, and/or configure appropriate "pattern/template"-type responses or other responses, given points of platform and/or hypothetical data. ML/AI models may be created and/or configured, and may subsequently train the input data as model inputs, and the response data as model outputs. After training of the ML/AI models, the feature can be utilized to derive text, audio/voice, and or visually-based responses for patients, given a set of patient specific inputs. The ML/AI models may be utilized in patient care simulations and/or one or more actual patient care scenarios.

In the patient care simulation scenarios, the steps outlined for this feature may be repeated for ML/AI model perfor-mance assessment, validation, and or improvement. The ML/AI models that have been previously validated and/or assessed may be utilized in ongoing decision support capaci-ties wherein they are used to derive an appropriate and/or personalized list of potential text, audio/voice, image, and/or rendered object responses given a set of platform data. In each patient care simulation or real patient care scenario, a set of "best responses" are chosen by clinicians and/or ML/AI models which may then be deployed to patients. One example implementation of this feature is as a part of a set of features for engaging one or more patients in a Socratic dialogue (see related descriptions within the Mental health module).

Clinical Workflow Feature

A clinical workflow feature of the exemplary Configura-tion Module is applicable for clinical workflow creation, modification and/or configuration. This feature addresses particular health-related use-cases, and/or may be used to construct clinical testing, diagnostic, therapeutic and/or care delivery solutions.

In exemplary embodiments, a "workflow" may be created by adding, selecting, and/or configuring two or more plat-form features (each referred to as a "node") using a GUI-based layout (and/or other features for platform feature selection and/or configuration), by connecting each node to at least one other node (as an input and/or an output), and by selecting options from a list of available control functions and/or weights which define the relationship between two or more nodes. A node represents at least one platform feature and a node performs operations on points of platform data, with the platform data fields containing these points of platform data being selected by ML/AI models and/or by clinicians using a GUI. The operations may include any of the features and/or functionalities fitting within the defini-tion of "ML/AI model(s)" as described herein.

When the platform data is sent to a node as an input, the operations are performed either with or without results being evaluated against pre-configured thresholds. The outputs of the node may activate and/or have a weighted influence over configured control functions. These configured control func-tions may then subsequently influence other nodes and/or control platform actions as described below. The influence of nodes may include triggering, inhibiting, and/or serving as an input to other nodes. The control of platform actions may include triggering, inhibiting, deploying, configuring, modifying, and/or serving as an input to platform actions as defined herein.

Control functions may be based on the inputs and/or outputs from ML/AI models as defined herein (which, for clarity, includes mathematical and/or logic-based opera-tions). Control functions may be applied (a) to incorporate control functionalities and/or operations into processes within a clinical workflow node, (b) to control and/or influence the programmatic and/or operational flow between two or more nodes in a clinical workflow, and/or (c) to control and/or influence the programmatic and/or opera-tional flow between nodes in a clinical workflow and the execution of resulting platform actions.

Workflows are created, configured and/or deployed either asynchronously and/or in near-real-time. The workflows may be created manually via a GUI within a web portal, a companion application, and/or in XR. The workflows may also be created automatically using ML/AI model(s) and/or via previously configured workflows. The workflows may also be created in a manner wherein the "automatic" con-figurations above are instead created, selected, and/or modi-fied manually by clinicians.

The inputs and/or outputs of any portion of workflows may be populated, modified, configured, and/or removed by ML/AI models, clinicians, points of platform data, and/or by other platform features.

FIGS. 28, 29 and 30 illustrate three different examples of how platform features, ML/AI models, and items within the clinical workflow feature may be utilized to create, modify, and/or configure workflows for clinical testing, diagnostic, therapeutic, and/or care delivery solutions that iteratively improve. These diagrams also serve to illustrate how an entire clinical workflow may itself be constructed, modified, configured, and/or deployed by clinicians and/or by ML/AI models, either with or without the utilization of other platform features.

FIGS. 31, 32, and 33 offer specific clinically-oriented examples of the types of clinical workflows and related feature integrations that may be created and/or configured using the clinical workflow feature with other platform features and/or using platform data.

Peri-Procedural Feature

The exemplary Configuration Module may further include a "peri-operative" and/or "peri-procedural" feature wherein clinicians and/or ML/AI models select, modify, configure, and/or utilize platform features and/or a subset of platform features described herein.

This exemplary feature may be used by clinicians in preoperative planning, such as for a surgeon to utilize when planning the specifics of his surgical technique and/or surgical approach prior to an operation. The exemplary feature may also be used by surgeons in intra-operative guidance and/or surgical planning. The exemplary feature may also be used by clinicians in creating, modifying, configuring, and/or deploying rehabilitative scenes, sessions, and/or regimens. The exemplary feature may also be used by clinicians in creating, modifying, configuring, and/or deploying scenes, sessions, and/or regimens designed to identify, mitigate, treat, and/or prevent post-operative complications (such as blood clot). The exemplary feature may also be used for patient education either preoperatively, immediately after an operation, and/or for rehabilitation education after an operation. The exemplary feature may also be used for patient analgesia either preoperatively, immediately after an operation, and/or to better tolerate post-operative rehabilitation regimens or components of the regimens. The exemplary feature may also be used for patient anxiolysis either preoperatively, immediately after an operation, and/or to better tolerate post-operative rehabilitation regimens or components of the regimens. The exemplary feature may also be used by patients in carrying out post-operative rehabilitation scenes, sessions, and/or regimens. The exemplary feature may also be used by patients in carrying out scenes, sessions, and/or regimens designed to identify, mitigate, treat, and/or prevent post-operative complications (such as a scene, session, and/or regimen containing exercises to mitigate and/or prevent blood clot). The exemplary feature may also be used by patients in carrying out, and/or as part of, post-operative home health efforts. The exemplary feature may also be used by patients in carrying out pre-operative rehabilitation ("pre-habilitation" or "prehab") scenes, sessions, and/or regimens.

KPI Feature

A KPI feature of the exemplary Configuration Module may be utilized to create, configure, modify, and/or capture Key Performance Indicators (referred to as "KPIs") relating to health and/or health care. According to this feature, clinicians and/or systems administrators may create KPI objects by selecting one or more platform data fields to track over time with the resulting time series of platform data being populated to the KPI object. KPI objects may be configured to track KPIs in specific patients and/or specific groups of patients. Each KPI object may be labeled/tagged/annotated with billing codes for integration with Billing Module functionalities. KPI objects may be inputs, outputs, and/or triggers for ML/AI models or the creation and/or modification of other KPIs.

Scene Creation and Configuration Feature

A scene creation and configuration feature of the exemplary Configuration Module may be utilized to create, improve, develop, and/or configure one or more scenes. This feature uses clinicians, ML/AI models, points of other platform data, and/or patient input methods to set configuration parameters. The configuration parameters may be set using a graphical user interface (GUI) located in a web portal, a companion application, and/or in XR. This feature gives clinicians/admins the ability to customize features, objects, and/or other aspects of scenes, including any content objects to be utilized within such scenes.

In one exemplary embodiment, configurable parameters include a patient's regimen comprising a collection of sessions for a patient. In another exemplary embodiment, configurable parameters include a patient's session comprising scenes a patient has access to and the order of scenes experienced during a session. In yet another exemplary embodiment, configurable parameters include a patient's scenes. The scenes may comprise rendered 2D and/or 3D objects in a scene. The scenes may further comprise scene specific features. Other exemplary embodiments may further comprise content in scene and any needed configuration for each of audio, images, video, text, rendered objects, and/or animations. Other exemplary embodiments may comprise scene agnostic features including integration of ML/AI models, biometric data, platform data, and Q&A. Other exemplary embodiments may comprise weather, sky, and/or time parameters for a scene. Other exemplary embodiments may comprise duration, timing, frequency of events which may occur while in a scene. Other exemplary embodiments may comprise difficulty and/or intensity of features within a scene.

Exemplary configurable parameters may further comprise a patient's Q&A configuration. This may include when assessments appear during a scene, and the questions/potential responses that appear within an assessment.

One Exemplary Embodiment of the Scene Creation and Configuration Feature:

In an exemplary embodiment of the scene creation and configuration feature, configurations can be made via a web portal, a companion application, and/or in XR. Clinicians and/or admins can specify the scenes comprising a session. On the server side, a many-to-many relationship will be established between the patient's ID and the ID of the scenes, as well as ordinality and any other necessary metadata. Clinician and/or admin can specify objects, features, and configurations that are within a scene. Options for a scene may include configurations specific to that scene, objects/features that are compatible with that scene, and scene agnostic objects/features. On the server side, a one-to-one relationship will be established between a patient's scene and a scene configuration object. A one-to-one relationship will be established between a patient's scene and scene objects configuration.

To load patient specific configurations in the platform for the end patient an authenticated request is made before the first scene to the server to retrieve scenes configured for the patient's ID. This call will load JSON which may contain a collection of scene configuration objects. Each scene configuration object may contain scene specific configurations (i.e. weather, time) and a collection of scene specific objects/features and scene agnostic objects/features.

When loading a scene, a customized SceneManager class will parse the scene information and load scene configurations as well as spawn scene objects/features. Scenes may or may not include the integration of adaptive elements that automatically influence patients to carry out actions necessary to achieve goals throughout the same scene and/or within or throughout other scenes. Clinicians and/or ML/AI models, with or without the use of platform data and/or patient input methods, may be used to select one or more pre-configured scenes. Experiential type question features may be configured by adding the experiential features to a scene.

One Exemplary Embodiment of the Code in the Scene Creation and Configuration Feature:

In an exemplary embodiment of the scene creation and configuration feature, the XR Health Platform uses a customized Scene Manager for switching scenes as well as other scene management activities. The Scene Manager works with Scene Configurations, which are collections of metadata to fully configure any scene type available. Scene Configurations are specific to a single scene, and while they can be duplicated and reused, their purpose is for them to be customized to the specific scenario to maximize the efficacy of the XR session. Scenes can be configured statically, i.e. default scenes. Scenes can also be configured dynamically by the user either via controller input, voice input, question responses, etc. Scenes can also be configured dynamically by the clinician through the companion application. Scenes can also be configured dynamically by the system through AI/ML means to detect sub-optimal experiences and compensate. This uses biometric, positional, and other sensor inputs to determine the configuration changes needed.

Scenes can also be configured and/or queued for future runs, and this configuration may include goal-based scene selections, clinician made scene selections, user based scene configuration, and/or scheduling for users. The exemplary XR Platform may make scene selections and configurations using the workflow engine, ML/AI models, clinician inputs, patient inputs, Q&A results, platform data, and/or using other platform features.

The configuration of scenes allows a single experience to broadly represent many different scenarios. An example would be the preference of day or night cycles in the scene and the effect it has on the user. If relaxation is the goal and the user is afraid of the dark, the scene configuration would be changed as it is going against the goal of the session. However, if the goal is to be used in an immersion therapy situation, that could actually be the desired state. The desired state may be mediated by direct input of a clinician, or by using ML/AI models to trigger a desired state when platform data thresholds are exceeded for one or more preset platform data fields. The Session Manager is responsible for delivering the assigned post-scene and post-session surveys.

Another Embodiment of the Scene Creation and Configuration Feature:

Another embodiment of the scene creation and configuration feature comprises a series of steps that are completed programmatically. Clinicians, ML/AI models, and/or other platform features configure scenes as described herein. When a user next engages with the platform, the platform makes a request to the API and a configuration JSON is retrieved. Scene agnostic configurations are parsed and loaded by the universal scene manager. Items within the Q&A feature are utilized to set and load the configured set of questions, the appropriate question types, and the appropriate answer choices. Loading configurations are set and loaded (e.g. text to load during the loading scene). Scene specific configurations are parsed and loaded by a scene manager (e.g. scene lighting, in scene objects, and scene event timing). Scene agnostic object configurations are parsed and loaded by a universal object loader (e.g. content objects and/or snippets). After completing the above, the scene starts.

Session Creation and Configuration Feature

A session creation and configuration feature of the exemplary Configuration Module may be utilized to create, improve, develop, and/or configure one or more sessions using clinicians, ML/AI models, points of platform data, and/or using patient input methods to create sessions and/or to set parameters relating to session configurations. When applicable, clinicians create sessions and/or set configuration parameters using a graphical user interface (GUI) located in a web portal and/or a companion application, and/or in XR (see FIG. 34).

According to this exemplary feature, sessions may or may not include the integration of adaptive elements that automatically influence patients towards achieving goals throughout scenes and/or sessions. Clinicians, ML/AI models, points of platform data, and/or patient input methods may be used to select pre-configured sessions. Experiential type question scenes may be configured by adding one or more experiential scenes to a session. Options relating to whether a session is to be conducted online and/or offline may also be provided.

One Exemplary Embodiment of Session Configuration:

In the exemplary XR Health Platform, a session is considered a patient's entire time spent in the platform during one continuous period of usage. A Session Manager is created per session which manages the session and all its data gathering and configuration capabilities. The Session Manager is responsible for session length, notifications to the user about the state of the session, loading the default scene from the Scene Manager, logging data about the session, and loading other scenes via the Scene Manager upon scene completion, a requested scene change (e.g. by a patient or clinician), or as determined by ML/AI models.

Exemplary positional data for analysis and replay may include time stamp, scene time, scene position, scene rotation, head position, head rotation, left hand position, left hand rotation, right hand position, and righthand rotation.

Exemplary session information comprising metadata about the current session may include event type (an enum data type—session start, session end, scene start, or scene end), time stamp, event description, scene name, scene time, and total session time.

Exemplary session logs may include any system level events, whether low level state change or high-level API calls, user triggered events, or other integration events.

Other configuration elements may procedurally generate destination portals in the Lobby based on the selected scene list in a configuration. The exemplary configuration elements may also procedurally generate Start Menu options based on the selected scene list in a configuration. The exemplary configuration elements may also implement a custom configured session length (the maximum amount of time the user can spend in a session before an ending survey is launched or before the session ends). The exemplary configuration elements may also implement an option to reset the session on the final scene so a clinician may easily reset everything for the next patient. The exemplary configuration elements may also implement a facility session including various steps, as outlined in FIG. 35.

In one exemplary implementation of the facility session, admins assign a XR device's serial number to a facility. A clinician fills out a form on a web portal or using a companion application to configure a session on a particular device for a patient, and the configured session is added to a queue for that device. When a session is started by the patient, the patient and/or a clinician confirms the patient's information and the appropriate session configurations are loaded for the patient. Caregivers can login to a web portal and/or companion application and view dynamically created reports based on the scenes that were assigned to the user via the session configuration. Upon session completion, the currently set configuration is de-queued and the next patient may use the system per the previous steps above.

Result reporting may be implemented as described below.

The facility ID is gathered at the beginning of the session based on the device's serial number (see "facility session" item(s) above). A session ID is also generated at the start of the session. Assessment data is sent to an API along with the facility ID and session ID as the user completes assessments. The dynamic objects "test result objects" are stored in a database as JSON, with a few common properties used for parsing. Clinicians can log in to the web portal and/or companion application front end and view the results of the assessments as reports. Each individual assessment has a correlated front-end web component for parsing and displaying the data. The final report is a compilation of the individual assessments the users completed during the facility session. The report can be viewed in a print friendly view and printed and/or shared.

Regimen Creation and Configuration Feature

A regimen creation and configuration feature of the exemplary Configuration Module may be utilized to create and/or configure regimens that comprise sessions. The feature allows clinicians, ML/AI models, and/or one or more points of platform data, and/or patient input methods to select, schedule, and/or configure sessions for a patient. Clinicians may set the configuration parameters using a graphical user interface (GUI) located in a web portal, a companion application, and/or in XR.

In one exemplary embodiment, regimens may or may not include the integration of adaptive elements that automatically adjust scenes, sessions, and/or the regimen itself to influence patients towards specific actions or behaviors related to his goals. Clinicians and/or ML/AI models, with or without the use of platform data and/or patient input methods, may be used to select one or more pre-configured sessions.

D. Web Portal & Companion Application Module

In exemplary embodiments, the present XR Health Platform may further comprise a Web Portal & Companion Application Module. This module serves as the front end/web-based graphical user interface (GUI) for creating, viewing, selecting, configuring, modifying, and/or interacting with items of platform content and/or platform features. For clarity, any embodiment of the companion application and/or web portal may be mobile application(s), web application(s), web page(s), "web view" application(s), and/or any type of computer application(s).

The exemplary Web Portal & Companion Application Module may include an application feature comprising a front end and/or graphical user interface. In one embodiment, the front end and/or graphical user interface is employed by clinicians and/or patients to view the results and/or reports generated for a scene, session, and/or regimens (multiple sessions) over time. In another embodiment, the front end and/or graphical user interface is used for all features listed in the clinician Configuration Module. In yet another embodiment, the front end and/or graphical user interface is employed for clinicians and/or patients to utilize items in the communications feature described above. In yet another embodiment, the front end and/or graphical user interface is employed by clinicians and/or patients to utilize items in the Q&A feature described above. In yet another exemplary embodiment, the front end and/or graphical user interface is employed by clinicians and/or patients to utilize any two-dimensional versions of any XR content and/or features, platform features, modules, scenes, sessions, and/or regimens. The exemplary feature may further comprise code and/or programming necessary to render the above graphical user interfaces, and populate them with the appropriate data, features, and/or functionalities. The exemplary feature may further comprise code and/or programming necessary to transfer data between a web portal, a companion application, and/or other platform features.

E. Integration Module

In exemplary embodiments, the present XR Health Platform may further comprise an Integration Module. The Integration Module includes the code and/or programming necessary for handling, storing, retrieving, extracting, formatting, parsing, displaying, provisioning, logging, transmitting, transferring, deploying, distributing, tagging, labeling, and/or annotating points of platform data. This exemplary module may additionally handle, store, retrieve, extract, format, parse, display, provision, log, transmit, transfer, deploy, distribute, tag, label, and/or annotate points of platform data with respect to one or more platform features and/or ML/AI models. This exemplary module orchestrates and manages the data flow within the XR Health Platform, and as such, it may control, utilize, or interact with any platform data. Similarly, this exemplary module may control, utilize, or interact with any set of platform features and/or any set of items within any module. FIG. 36 illustrates how this exemplary module may interact with any platform features or any platform data.

One exemplary embodiment of the Integration Module features cloud-based and/or local databases to store platform data, logs, and one or more points of any other platform data requiring storage.

Another exemplary embodiment of the Integration Module features an Application Programmer Interface (API). The exemplary API may comprise code to import, "clean", preprocess format, and/or harmonize points of platform data for storage in the databases. The exemplary API may further comprise code and/or programming to retrieve, properly format, and/or transmit one or more points of platform data between API(s) and database(s). The exemplary API may further comprise code to retrieve, properly format, harmonize, and/or transmit points of appropriate platform data at appropriate points in time to appropriate platform features and/or other destinations. This includes the code and/or programming needed to retrieve, properly format, and/or transmit points of ML/AI model input and/or output data, and/or points of data relating to the usage, configuration, creation, modification, and/or deployment of ML/AI models as described herein.

The exemplary module may further comprise code and/or programming to retrieve, properly format, and/or transmit ML/AI model inputs and/or outputs to and/or from API(s). The exemplary module may further comprise code and/or programming to retrieve, properly format, and/or transmit ML/AI model inputs and/or outputs between instances of XR (including instances of a web portal and/or companion application) and APIs. The exemplary module may further comprise code and/or programming to extract points of platform data representing one or more features from voice, audio, video, image, text, rendered data, and/or items of other media, and transfer the platform data between platform features and/or databases and API(s). The exemplary module may further comprise code and/or programming to import, parse, clean, pre-process and/or harmonize data from a variety of 3rd party hardware and/or software sources such as IoT, biometric, and other data from 3rd parties and transfer the data between API(s). The exemplary module may further comprise code and/or programming to import, harmonize and/or display platform data as 2D and/or 3D visualizations in XR (including on a web portal, and/or on a companion application). The exemplary module may further comprise code and/or programming for handing, appropriately distributing, and/or streaming one or more items of XR content and/or platform content to patients and/or clinicians in XR and/or between XR devices. The exemplary module may further comprise code and/or programming for integrating interactive capabilities between two or more XR devices allowing for the users of the devices to interact with one another. The exemplary module may further comprise code and/or programming for integrating interactive capabilities between two or more XR simulations allowing for the simulations to interact. The exemplary module may further comprise code and/or programming for integrating interactive capabilities between one or more XR devices and XR simulations allowing for the devices and the simulations to interact with one another. The exemplary module may further comprise code and/or programming to handle and/or manage creating and/or maintaining accurate and detailed logs of ML/AI model inputs and input labels, outputs and output labels, the models used, training parameters, and/or any other information that may be useful for data integrity, transparency, validation, and/or later analysis. The exemplary module may further comprise code and/or programming to carry out and/or manage the modeling, training, and/or evaluation processes of ML/AI models within isolated virtual testing environments. The exemplary module may further comprise code and/or programming to carry out and/or manage the provisioning, governance, and/or deployment of ML/AI models. Specifically, this feature may include the code and/or programming to ensure that ML/AI models are supported by the proper provisioning of computer resources, ensure that any governance policies are enacted within the code and/or programming, and/or to manage the deployment of ML/AI models from development environments to production environments.

In another exemplary embodiment, the present module comprises a globally unique ID (GUID) and tagging system that allows for the indexing, labeling, annotation, storage, and/or retrieval of points of information (and/or one or more points of platform data) associated with and/or related to, unique objects, ML/AI models, content elements, content objects, snippets, platform features, clinicians, patients, scenes, sessions, regimens, and/or clinical workflows. Each time a new and/or novel GUID is created, the associated novel item may be assigned tags, and the novel item (a unique object, ML/AI model, content element, snippet, platform feature, clinician, patient, scene, session, regimen, clinical workflow, and/or other item) along with any assigned tags are then appended to master lists and/or databases for later modification and/or retrieval. Tagging involves adding tags, labels, and/or annotations to one or more items as described herein (e.g. any set of items within any platform feature, any point of platform data, any platform data field, any item of platform content and/or features, any item related to any ML/AI model, and the like). Tagging is carried out by ML/AI models and/or by clinicians using a web portal, companion application, and/or in XR.

F. Light Module

The exemplary XR Health Platform may also incorporate a Light Module. The Light Module allows for the delivery and/or modulation of features relating to light within XR. These features include intensity/brightness, contrast, color, saturation, wavelength, hue, temperature, and/or albedo. The Light Module may be used in the diagnosis, assessment, and/or treatment of acute pain, chronic pain, depression, post-partum depression, anxiety, seasonal affective disorder, sleep disruption, sleep disturbance, sleep deprivation, and partial sleep deprivation. The exemplary Light Module may also be used to optimize sleep, to mitigate circadian disruption and/or jet lag, and to hasten wound healing.

Light Trigger Feature

Using a light trigger feature of the exemplary Light Module, points of platform data and/or changes in platform data and/or patient platform interactions trigger changes on light sources within a scene. Such changes may involve light intensity/brightness, contrast, color, saturation, wavelength, hue, temperature, albedo, and/or any other feature relating to light. Such light changes may be configured by clinicians and/or ML/AI models.

Color Preference Feature

Using a color preference feature of the exemplary Light Module, platform features and/or features within a scene and/or session are used to determine the color preferences of an individual. Such preferences may include preferred colors, preferred levels of color brightness, preferred levels of saturation, preferred levels of color contrast, and/or color temperature preferences. This feature may also log points of platform data and/or patient platform interactions.

Light Emotion Feature

A light emotion feature of the exemplary Light Module combines other platform features with features within the Light Module to determine how characteristics of light influence the emotional state and/or mental health of an individual. Platform features may be combined with features within the Light Module to leverage characteristics of light (intensity/brightness, contrast, color, saturation, wavelength, hue, temperature, albedo, and/or any other feature relating to light) to positively influence the emotional state and/or mental health of an individual.

Light Influence Feature

A light influence feature of the exemplary Light Module combines platform features with features within the Light Module to leverage characteristics of light (intensity/brightness, contrast, color, saturation, wavelength, hue, temperature, albedo, and/or any other feature relating to light) to influence behaviors, the level of arousal, ability to concentrate, and/or level of wakefulness of an individual.

Light Alteration and Effects Feature

A light alteration and effects feature of the exemplary Light Module uses platform data points, changes in platform data points, ML/AI models, and/or patient platform interactions (including the use of patient input methods) to trigger changes to light characteristics and/or to light sources and/or cameras within a scene. These changes may be configured by clinicians and/or ML/AI models to help achieve patient goals, help achieve patient-related objectives, to address health-related issues, and/or to influence health-related behaviors.

Exemplary changes may include the application and/or termination of camera filters; the application and/or termination of light filters; the application and/or termination of camera effects; the application and/or termination of light effects; changes in the frequency, color, brightness and/or intensity of lights; the position of lights and/or cameras; the number of instances and/or the 3D position of any such instance of lights and/or cameras within scenes; the 3D position as a function of time for any instances of lights and/or cameras within scenes; changes in other parameters relating to lights and/or cameras not otherwise mentioned herein.

G. Audio Module

The exemplary XR Health Platform may also incorporate an Audio Module comprising one or more of the features discussed below.

Audio Trigger Feature

Using an audio trigger feature of the exemplary Audio Module, platform data points, changes in one or more platform data points, ML/AI models, and/or patient platform interactions (including the use of patient input methods), to trigger changes in audio characteristics, audio sources, and/or items of audio content within a scene. Such audio changes may be configured by clinicians and/or ML/AI models to achieve patient goals, patient-related objectives, address one or more health-related issues, and/or to influence health-related behaviors.

Exemplary changes in audio may involve one or more of use of monaural beats and/or monaural audio content, use of binaural beats and/or binaural audio content, changes in audio content, the application of audio effects and/or filters, changes in audio volume and/or amplitude and/or intensity, changes in audio tone and/or timbre and/or bass, changes in audio frequency and/or pitch, changes in audio envelope, changes in audio location, changes in audio tempo, or the position of sources of audio content within XR. In another exemplary embodiments, changes in audio may further involve the number of instances and/or the 3D position of any such instance of audio content within scenes. This may include the spatial arrangement of two or more items of audio content within any particular scene. In yet another exemplary embodiment, changes in audio may further involve the 3D position of any instances of audio content as a function of time in any particular scene, the audio channel to through which to play and/or assign any instances of audio content, and changes in other audio parameters not otherwise mentioned.

Audio Visualization Feature

Using an audio visualization feature of the exemplary Audio Module, platform data points and/or changes in platform data and/or patient platform interactions may trigger changes in 2D and/or 3D audio visualizations within a scene. The changes may be configured by clinicians and/or ML/AI models.

Audio Changes and Foreshadow Feature

Using an audio changes and foreshadow feature of the exemplary Audio Module, platform data points and/or changes in platform data points and/or patient platform interactions may trigger pleasant changes in audio. This may in turn foreshadow positive changes in features and/or objects within a scene. Such changes may be configured by clinicians and/or ML/AI models.

Audio ML Feature

Using an audio ML feature of the exemplary Audio Module, platform data points and/or changes in platform data points and/or elements comprising interactions may trigger the utilization (and/or prevention of utilization) of ML/AI models (such as text-to-speech (TTS) models) and/or result in changes to these models. Such changes may be configured by clinicians and/or other ML/AI models.

H. Tactile Module

In exemplary embodiments, the present XR Health Platform may also include a Tactile Module comprising one or more of the features discussed below.

Tactile Configuration and Delivery GUI Feature

A tactile configuration and delivery GUI feature of the exemplary Tactile Module may be used to remotely configure and/or deliver tactile (or haptic) stimuli to patients where a patient wears and/or uses devices capable of delivering a tactile or haptic stimulus from items of XR hardware. Examples of tactile stimuli include haptic stimuli, vibratory stimuli, proprioceptive stimuli, thermal stimuli, pressure stimuli, and/or touch stimuli. Through the use of a GUI, clinicians may configure various characteristics with respect to tactile stimuli delivered.

Exemplary characteristics may include if the stimuli are delivered or not, the number of stimuli to be delivered, the frequency of stimuli to be delivered, the duration of stimuli to be delivered, the intensity of stimuli to be delivered, the nature and/or character of stimuli to be delivered, and the anatomic locations of where the stimuli are to be delivered on a patient's body where a clinician selects the locations on a 2D and/or 3D human model within a GUI.

Automatic Tactile Configuration and Delivery Feature

Using an automatic tactile configuration and delivery feature of the exemplary Tactile Module, platform data points and/or changes in platform data and/or elements comprising interactions may trigger the remote delivery of tactile stimuli to patients. According to this feature, the patient wears and/or uses devices capable of delivering a tactile stimulus as well as integrating with the platform. Clinicians and/or ML/AI models may configure certain characteristics including if the stimuli are delivered or not, the number of stimuli to be delivered, the frequency of stimuli to be delivered, the duration of stimuli to be delivered, the intensity of stimuli to be delivered, the nature and/or character of stimuli to be delivered, and the anatomic locations of where the stimuli are to be delivered on a patient's body.

Certain features to detect and/or identify changes in tactile sensitivity and/or to assess characteristics of the human sense of touch and related characteristics are described below within the sensory assessment feature of the Neurological Module.

I. Anatomy Module

The exemplary XR Health Platform may further comprise an Anatomy Module featuring the various code and programming described below.

In one embodiment, the Anatomy Module comprises code and/or programming for the use of marking tools such as "highlighters" and "pins" for use on 2D and/or 3D anatomic models and/or virtual human avatars by one or more clinicians, ML/AI models, and/or patients. The exemplary code and/or programming may also feature an animation clip and/or simulation selection tool to select animation clips and/or simulations for use on 2D and/or 3D anatomic models and/or virtual human avatars by clinicians, ML/AI models, and/or patients. The exemplary code and/or programming may also feature an animation clip and/or simulation loading system to load animation clips and/or simulations for animating and/or simulating 2D and/or 3D anatomic models and/or virtual human avatars. The exemplary code and/or programming may also function to map and/or render points of platform data onto specific points on 2D and/or 3D anatomic models and/or virtual human avatars. The exemplary code and/or programming may also comprise the use of images (including DICOM images), animations, simulations, and/or videos alongside, in tandem with, and/or overlaid upon 2D and/or 3D anatomic models and/or virtual human avatars.

The exemplary code and/or programming may also comprise an annotation system for playing or displaying text, video, images, animations, simulations, audio files, rendered content, content objects, and/or snippets upon selection of various different features on an anatomical model. The annotation system may feature the use of a web portal and/or companion application for the addition/creation, modification, and/or selection of voice, video, image, text, snippet, content object, rendered object, 2D object, and/or 3D object annotations to be played, displayed, and/or instantiated upon selection of various anatomical structures by patient(s) in XR. The annotations and/or snippets can be tagged by clinical use case, by a patient, by a clinician, by ML/AI models, and/or by other platform features.

Any of the features described within the Anatomy Module may be created, selected, configured, modified, and/or deployed by clinicians and/or using ML/AI models, through the use of applicable platform features described herein. Any features described within the Anatomy Module may additionally utilize the features, code, and/or programming of other platform features within other modules (e.g. platform features within the Configuration Module, the Integration Module, and the like) to carry out the functionalities described herein.

Movement Module

In exemplary embodiments, the present XR Health Platform may also include a Movement Module comprising one or more of the features discussed below. The movement module contains features that, either alone, or in combination with other platform features, enable the screening for, assessment of, detection of, diagnosis of, treatment of, optimization of, and/or rehabilitation from issues and/or diseases relating to the musculoskeletal system. One or more of the items and/or features within the movement module may utilize platform features, points of platform data, and/or ML/AI models.

Movement Safety Feature

A movement safety feature of the exemplary Movement Modules comprises a multi-modal assessment that utilizes platform features and/or points of platform data to determine which XR scenes, sessions, and/or regimens involving physical movements may be safe for an individual to participate in.

Automated Fitness Assessment Feature

Automated fitness assessment feature of the exemplary Movement Module comprises a system for an automated, semi-automated, clinician-supervised, and/or patient-self-directed physical fitness assessment. The exemplary assessment may comprise a pre-test safety assessment and/or other assessments completed using the Q&A feature discussed above. The exemplary assessment may further comprise a pre-configured and/or standardized set of physical tasks completed in scenes, sessions, and/or regimens using items within the movement module, ML/AI models, and/or other platform features. The exemplary assessment may further comprise a pre-configured feedback/results report that automatically populates with any relevant data obtained during the assessment.

Automated Stress Test Feature

An automated stress test feature of the exemplary Movement Module may be utilized for an automated, semi-automated, clinician-supervised, and/or patient-self-directed exercise stress test assessment either with or without the use of ML/AI models. According to this feature, a pre-test safety assessment and/or other assessments are completed using the Q&A feature described above. A pre-configured and/or standardized set of physical tasks may be completed in scenes, sessions, and/or regimens using items within the Movement Module, ML/AI models, and/or other platform features. In other exemplary embodiments, the feature may be implemented using biometric data such as heart rate, blood pressure, pulse oximetry, EKG data, heart rate variability, and expired carbon dioxide levels. A pre-configured feedback/results report may automatically populate with any relevant data obtained during the assessment.

Automated Movement Assessment Feature

An automated movement assessment feature of the exemplary Movement Module may enable semi-supervised and/or automated movement activity assessment. The exemplary assessment may comprise positional data from XR and/or through the use of a web portal and/or companion application. The exemplary assessment may further comprise successfully completing XR scenes and/or sessions with the scenes and/or sessions having content that, if successfully completed, equates to or approximates one or more assessments relating to physical activity. The exemplary assessment may further comprise participating in two or more XR scenes and/or sessions over a period of time. The exemplary assessment may further comprise ML/AI models and platform data points. The exemplary assessment may further comprise summative and/or qualitative assessments of points of movement and/or positional data, either with or without the utilization of other platform features and/or additional points of platform data. This feature may include qualitative and/or summative determinations of the total amount of movement per unit of time for patients. This feature may further include qualitative and/or summative determinations of the lack of movement and/or inactivity per unit of time for patients. This feature may further include qualitative and/or summative determinations of mannerisms, gestures, poses, and/or body language expressions of patients and/or clinicians. This feature may be combined with facial, eye, and/or other points of biometric tracking data and/or other points of platform data.

Adaptive Physical Activity Feature

An adaptive physical activity feature of the exemplary Movement Module may adaptively determine and/or configure the intensity and/or duration of one or more physical activity-related features in a scene, session, and/or regimen using features and/or modules described herein. This feature is applied in or upon one or more use-cases and/or events, such as warm-up and/or cool-down, physical activity assessment as described herein, physical fitness assessment as described herein, movement activity assessment as described herein, exercise stress test as described herein. The exemplary feature may also be applied to determine and/or help ensure that a recommended amount and/or adequate amount of physical activity has been achieved over timespans. The exemplary feature may also be applied as set by a clinician when configuring a scene, session, and/or regimen. The exemplary feature may also be applied if a patient indicates that they are experiencing discomfort or pain. This may be determined using the pain with movement detection feature within the Movement Module, the automatic pain assessment feature within the Pain Module, or any other platform feature that may be utilized for the purposes of indicating that pain and/or discomfort are being experienced.

Adaptive Physical Activity Feedback Feature

An adaptive physical activity feedback feature of the exemplary Movement Module may adaptively determine, configure, and/or deliver communications of personalized feedback and/or instructional information during a physical activity scene, session, and/or regimen. According to this feature, the content, timing, frequency, intensity and/or medium (text vs. audio vs. visual content vs. tactile, etc.) of the communications may be determined by ML/AI models, platform data, and/or as configured by clinicians.

Movement Tactile Feedback Feature

A movement tactile feedback feature of the exemplary Movement Module is applicable for delivering feedback on the form of a patient's movements by tactile feedback (using one or more of the features described in the Tactile Module discussed above and/or visual and/or auditory stimuli). This feature may indicate the minimum and/or maximum displacement positions of movements, the outer bounds of movements, the inner bounds of movements, the duration of which static positions should be held by the patient, when the patient should transition from a static pose to a movement and vice-versa, the speed at which a patient should carry out movements, and the physical direction in which movements and/or a portion of one or more movements are to be carried out.

Gross and Fine Movement Assessment Feature

A gross and fine movement assessment feature of the exemplary Movement Module may be utilized for gross- and/or fine-movement tracking and/or assessment in XR. The exemplary feature may incorporate computers, XR devices, a web portal and/or a companion application, and 3D positional tracking of a patient and/or clinician in static positions and/or a series of positions over time. Positional tracking may utilize three dimensional positional and/or rotational tracking data from XR hardware, biometric data, video and/or a series of images from cameras, ML/AI models, audio data through the use of microphones, and simultaneous localization and mapping (SLAM) technology.

3D Positional Tracking Feature

A 3D positional tracking feature of the exemplary Movement Module may use positional and/or rotational information for locations on a patient's body. This information may be obtained using three dimensional positional and/or rotational tracking data from XR hardware. In other exemplary embodiments, the information may be obtained using ML/AI models, including computer vision models applied to an image, images extracted from a video, and/or a series of images captured from cameras. In other exemplary embodiments, the information may be obtained using the application of ML/AI models that are not computer vision models. In other exemplary embodiments, the information may be obtained using biometric data. In other exemplary embodiments, the information may be obtained using acoustic and/or sound data through the use of microphones.

Real-Time Movement Biofeedback Feature

A real-time movement biofeedback feature of the exemplary Movement Module may be used for real-time biofeedback where the scoring in one or more gamified XR experiences is at least partially determined by establishing and/or maintaining physical movements and/or positions. The movements and/or positions are determined as described herein, and whereby visual and/or auditory stimuli provide real-time feedback in terms of the correctness or incorrectness of the movements and/or physical positions. This correctness or incorrectness results in a higher or lower score, respectively. In one embodiment of this feature, scores are proportional to the angle and height of the controllers relative to the HMD as well as the length of time that this position is maintained. For example, if the patient holds his arms straight out in front of him at eye level, the score goes up proportionally to the time that this position is maintained.

Movement Creation Feature

A movement creation feature of the exemplary Movement Module may be used for the creation of movements to be tracked in XR. Clinician selects locations on a virtual human avatar for the purposes of generating points of sequential 3D positional tracking data. The exemplary feature comprises capturing and/or generating movement animations on a human virtual avatar. The exemplary feature may further comprise capturing and storing 3D positional tracking data representing static human positions, and/or a series of human positions over time generated by clinicians and/or ML/AI models. The exemplary feature may further comprise transferring the 3D positional tracking data from storage and applying the data to a virtual human avatar and/or a portion of a human avatar to generate one or more 2D and/or 3D animations of the avatar and storing the animations in one or more databases. The exemplary feature may further comprise generating and storing 2D and/or 3D animations representing a virtual human avatar and/or portions of a human avatar in one or more static positions, and/or a series of positions over time.

In other exemplary embodiments, the present feature may be based on diagnostic and/or therapeutic tasks. Appropriate locations on a virtual human avatar are selected by a clinician. An animation is then run with the selected locations on the virtual human avatar being tracked in virtual 3D space. Virtual objects may be generated at the position and/or rotation of the locations on the virtual human avatar as a function of time during the animation. Data are generated for each instance of a generated virtual object. Exemplary data may include the 3D positional data relative to the virtual human avatar, the 3D rotational data relative to the virtual human avatar, and the timestamps and/or relative times at which each virtual object was generated during each animation. The virtual object data is then reprocessed and stored such that, when recalled programmatically, the 3D positional data can be made relative to any object.

Fine Motor Feature

A fine motor feature of the exemplary Movement Module may be used to assess and/or improve the fine motor skills of patients using patient input methods. The input methods may be combined with XR and/or other platform features, such as the use of other features within the Movement Module, ML/AI models, points of platform data, and features described in the Tactile, Audio, Light, Neurological, Pain, and/or Mental Health Modules described herein.

In one embodiment, patient tasks to be carried out in XR may include copying, tracing, and/or manipulation of 2D or 3D objects. In another embodiment, patient tasks to be carried out in XR may include imitation of the movements and/or routines of a virtual human avatar. In yet another embodiment, patient tasks to be carried out in XR may include movement instructions delivered through audio, visual, and/or tactile means. In yet another embodiment, patient tasks to be carried out in XR may include object sorting into progressively smaller containers/buckets. In another embodiment, patient tasks to be carried out in XR may include completing a "loop and wire" type simulation where there is a ringed loop that encircles a wire going from one location to another, and where the patient is to move the ringed loop from the start location to the end location without letting the edge of the ring touch the wire. In another embodiment, patient tasks to be carried out in XR may include completing a "marble and maze" type simulation where the patient moves a marble through a maze without letting the marble fall into holes within the maze. In another embodiment, patient tasks to be carried out in XR may include completing a "peg and hole" type simulation where the patient picks up pegs from a receptacle and places the pegs into the holes on a surface and vice-versa.

Position Change Feature

A position change feature of the exemplary Movement Module may be used to assess and/or improve the ability of patients to re-orient and/or assess a change in 2D and/or 3D perspective, position, and/or rotation within XR. This feature may include a simultaneous and/or temporally-related change in one or more of the features described within the Audio, Light, Tactile, Mental Health, Neurological And/or Clinical Platform Modules; for example, one or more changes in three-dimensional spatial sound characteristics, changes in lighting, tactile stimuli, and the like.

Movement Integration Feature

A movement integration feature of the exemplary Movement Module may utilize and/or integrate features within the Movement Module in diagnostic, therapeutic, and/or other clinically related uses. This includes capabilities for creating, deriving, configuring, teaching, modifying, deploying and/or controlling physical movements and/or physical activities for diagnostic and/or therapeutic purposes. Using a graphical user interface, clinicians and/or ML/AI models may configure diagnostic and/or therapeutic tasks to be completed by a patient. Based on the clinically-related tasks selected, pre-configured sets of animations and instructional audio clips appropriate for the tasks may be automatically loaded from a stored library of previously captured and/or computer-generated 2D and/or 3D animations, along with their corresponding text-to-speech instructional audio clips. Based on diagnostic and/or therapeutic tasks selected, appropriate virtual object data may be automatically imported. Animations pre-configured as appropriate for the tasks may be automatically loaded from a stored library of previously captured and/or computer-generated 2D and/or 3D animations. At runtime, prior to each movement carried out by the patient, the corresponding pre-configured animation with any clinician modifications may be loaded onto an instructional virtual human avatar and played to demonstrate to the patient how to correctly complete the movement. Each instructional avatar movement may be preceded by instructional and/or educational audio clips which are played in XR and appear to the patient to be recited by the instructional avatar. At runtime, imported virtual object data may be used to instantiate virtual objects as a function of time based upon the preconfigured set of animations determined to be appropriate for each diagnostic and/or therapeutic task. At runtime, each virtual object may be instantiated as a function of time at a position and/or rotation relative to the patient using the system, such that a time-dependent series of one or more virtual waypoints appears in the appropriate proximity to the patient. At runtime, three-dimensional positional tracking of the patient may be used to guide the patient through movements and/or to traverse virtual waypoints with either a particular anatomical structure and/or XR hardware. The tracking, biometric, and/or other platform data may also be used to evaluate, measure and/or detect a range of motion of a particular anatomical structure and/or set of anatomical structures and/or other features, and a maximum distance that a particular anatomical structure has traversed relative to its starting position. The maximum distance may be determined during a series of movements or during an XR session.

The exemplary movement integration feature may also comprise variations where three-dimensional objects, two-dimensional overlays, and/or camera filters are instantiated one or more times in XR as a feedback mechanism for the patient. This may occur if the patient fails to traverse waypoints; and/or if the patient fails to traverse waypoints with the appropriate anatomical structure(s) and/or appropriate XR hardware; and/or upon hyperextension of an anatomical structure and/or skeletal joint; and/or upon hyperflexion of an anatomical structure and/or skeletal joint; and/or to encourage the patient to complete a greater percentage of movements; and/or to complete movements and/or series of movements.

The exemplary movement integration feature may also comprise variations combined with the telecommunication module for real-time voice, and/or video, and/or text interactions between the patient in XR and clinicians using a companion application, and/or web portal, and/or in XR.

The exemplary movement integration feature may also comprise variations where avatar silhouettes are used for producing visual biofeedback for the patient, and where the color, size, texture, and/or shader on the avatar silhouette may be used to indicate the level of correctness or incorrectness of physical movements being performed by the patient.

The exemplary movement integration feature may also comprise variations including any of the items within the movement customization feature described below.

Movement Customization Feature

The exemplary Movement Module may also comprise a movement customization feature. Using a companion application, web portal, and/or using XR, one or more clinicians and/or ML/AI models may configure clinically-related XR scenes and/or sessions for patients. In one embodiment, this is achieved by configuring virtual objects/waypoints to change shape, size, texture, text labels, associated audio, and/or color as an indicator. The indicator may represent events and/or desired patient actions, such as which virtual object/waypoint to traverse next; a change of direction; whether the patient is at the beginning, middle, or nearing the end of, or has successfully completed a series of movements; whether the patient should hold positions for a specified amount of time; and whether movements are to be performed on the right or left side of the patient's body.

According to the exemplary feature, spatial audio may be configured to indicate location of next waypoint and/or edge and/or outer bounds appropriate for configured movements. Clinicians may create custom instructional audio clips corresponding to one or more movements using a companion application, and/or web portal, and/or in XR. Clinicians may modify and/or carry out certain tasks using a web portal, companion application, and/or in XR. Exemplary tasks may comprise the selection of locations on a virtual human avatar for the purposes of delivering 3D positional tracking feedback to a patient and/or clinicians and/or ML/AI models, minimum and/or maximum displacement positions of movements, speed at which a movement is carried out, the duration of time that a patient needs to maintain his position at certain positions before the next waypoint in the sequence appears and/or before the movement should resume, and configuring if summative reports regarding movements and/or movement sessions over time can be exported. Individual session and/or individual movement reports can be exported by clinicians via a web portal and/or companion application and/or in XR.

Automatic Movement Configuration Feature

An automatic movement configuration feature of the exemplary Movement Module may be used for automatic configuration of movement features by ML/AI models to progress towards goals and/or to accomplish clinically-related tasks by combining one or more platform features with one or more of the ML/AI models. Exemplary movement features may comprise triggering movement-encouraging platform actions, making movement selections, setting the sequence of movements, and/or the frequency at which movement-related scenes or sessions occur.

Movement Replay Feature

A movement replay feature of the exemplary Movement Module may be used to create, configure and/or deliver instructional, educational, and/or therapeutic replays of patient movements performed by an instructional avatar. This feature comprises qualitative and/or quantitative auditory, tactile and/or visual feedback to show meaningful deviations from instructor standards. When a deviation occurs, the clinician has option to alter the playback speed, camera angle, and/or perspective of the replay. For the replay, clinician also has the option to alter the position of anatomical locations on the instructional avatar. In addition to the replay features already described, the replay functionality also gives the clinician the option to show the timing and identification of any patient input method-related events on controllers and/or other input devices along with any labels corresponding to the names of any patient inputs executed (such as buttons pressed). The clinician may export patient movement replays to share with the patient and/or other clinicians caring for that patient.

One embodiment of the movement replay feature includes the ability to read a patient's positional data output and use it for replay. In another embodiment of the movement replay feature, an admin, clinician, or patient can load a patient's replay data from a completed scene or session via file selection or API request. Once loaded, the replay data will show a replay of the patient's movements from third person perspective. In yet another embodiment of the movement replay feature, positional data is saved and retrieved as JSON with the following information: time stamp, scene time, scene position, scene rotation, head position, head rotation, left hand position, left hand rotation, right hand position, right hand rotation, and buttons pressed.

Once this information is loaded, the JSON is parsed and the replay is started. The replay system uses the Scene Position and Scene Rotation to place the patient's overall object in the scene. Then, using relative positioning, the feature uses the Head Position/Rotation, and Hand Position/Rotations to place models representing the patient and his movements. The replay functionality also keeps track of buttons pressed so that his actions can be emulated and the admin or clinician can get a better idea of what was done.

One exemplary embodiment of a workflow utilizing the present replay functionalities comprises a series of steps utilizing items within the movement replay feature. Replay positional JSON data is first retrieved from an API or by other means. Positional data is then parsed and loaded into a collection of scenes. A first scene is then loaded and the replay for the scene is started. The collection of positional data is iterated over on a co-routine that is based on the gather interval specified in the JSON data. During each iteration, the user's head and hands are placed in accordance with data for the particular point in time. This is repeated until the scene's positional data is exhausted, and the next scene is started where the positional data is parsed again until all scenes are exhausted.

Ecological Movement Intervention Feature

The exemplary Movement Module may further comprise an ecological movement intervention feature. In addition to all of the interventions mentioned herein, one or more of the following ecological interventions may be created, selected, modified, configured, and/or delivered using the functionalities, platform features, and/or modules described herein. These interventions may be used in scenes, sessions, and/or regimens by patients via a web portal, companion application, and/or in XR.

In one exemplary embodiment, the present feature employs a "multi-player" tool to engage with other patients and/or clinicians in exercise and/or physical activity. In another exemplary embodiment, educational, instructional, and/or therapeutic content and/or features may be delivered as set using features and or functionalities of the Configuration Module. These may include activities that can be done without others; safety guides for various different physical activities; education regarding the benefits of physical activity; illness-specific information regarding physical activity; education/instruction on how to complete movements as described herein; education/instruction on how to complete physical activities; short high-yield physical activities; physical activities that can be done anywhere; physical activities that do not require any equipment; physical activities that can be done at home; physical activities that further elucidate self-knowledge of time constraints; activities relating to scheduling and/or planning exercises and/or tasks; pre-configured movement scenes, sessions, and/or regimens as described herein; text snippets delivered either as text and/or voice as described herein; low impact exercises that can be completed while in pain and/or with limited ability; and the use of features described in the Audio Module to encourage participation in physical activity.

One embodiment of the present feature achieves additional configuration by adjusting content based on body locations of pain, body locations with limited ability, and/or body locations suffering from disease, with these body locations being identified by patients through patient input methods using features and/or items within the Anatomy Module.

In another exemplary embodiment, the present module comprises physical activity features relating to sleep optimization. In yet another exemplary embodiment, the present module comprises a patient self-completed scheduling tool for developing a self-directed physical activity regimen. This tool may utilize integrated email and/or text message (SMS) reminders. In yet another exemplary embodiment, the present module comprises a patient self-completed tool that assists with identifying and/or participating in scenes, sessions, and/or regimens that a patient finds as fun, enjoyable, potentially fun, and/or potentially enjoyable. In yet another exemplary embodiment, the present module utilizes other features in the Anatomy and/or Pain Modules described herein to identify and/or configure a scene, session, and/or regimen with physical activities that may be tolerable with respect to pain, an injury, and/or a disease. In yet another exemplary embodiment, the present module comprises a feature wherein desirable content is played (e.g. a movie or TV show) so long as patient continues to do physical activities as instructed, and if the patient ceases to perform the activities for a preset amount of time, the desirable content stops playing. In yet another exemplary embodiment, the present module comprises a feature that integrates local weather data. If local weather is, or is expected to be, "bad" as determined through the use of ML/AI models, an increased amount, frequency, and/or intensity of notifications/reminders to partake in physical activity using the platform may be delivered.

Fall Risk Feature

A fall risk feature of the exemplary Movement Module may be utilized to perform a fall risk assessment and/or mitigate fall risk using the features described in this module, the Q&A feature, points of platform data, and/or other platform features as described herein. In addition to any other features relating to fall risk assessment and/or fall risk mitigation mentioned elsewhere herein, the exemplary XR Health Platform may additionally comprise steps and/or features to assess a patient's flexibility, balance, strength, agility, and/or coordination. Based on the above assessment, scenes, sessions, and/or regimens may be configured by clinicians and/or using ML/AI models to mitigate fall risk.

This is accomplished by targeting the highest priority aspects of the patient's flexibility, balance, strength, and/or coordination for this purpose. Any of the features described in this module may additionally be used to track movements, deliver therapeutic interventions, and/or feedback.

A variation on the fall risk and/or mitigation feature additionally incorporates computer vision ML/AI models. Through the use of a web portal, companion application, and/or XR, the patient can scan his house to identify fall risks. These fall risks are then addressed through using ML/AI models to deliver appropriate messages/instructions on what actions to take and how to take them, and/or through interactions with clinicians using the communications feature described herein. In this variation, computer vision models may also be utilized to delineate, demarcate, and/or highlight real-world objects representing a fall risk to a patient in XR.

Using computer vision ML/AI models either with or without the use of one or more additional platform features and/or additional points of platform data, certain fall-risk-related assessments and/or tests may be completed autonomously or semi-autonomously. These exemplary assessments/tests may determine if a patient is able to sit unsupported. The exemplary assessments/tests may also determine if a patient is able to safely go from sitting to a standing position, and/or go from standing to sitting. Other exemplary assessments/tests may determine if a patient is able to transfer items between hands. Other exemplary assessments/tests may determine if a patient is able to safely stand without support, stand with transiently attenuated vision, stand with feet together, stand with feet in tandem, and/or stand on one leg. Other exemplary assessments/tests may determine if a patient is able to pick a virtual and/or real-world item/object up from the floor. Other exemplary assessments/tests may determine if a patient is able to turn one's torso to either side while seated, and/or turn 360 degrees while standing. Other exemplary assessments/tests may determine if a patient, while seated or standing, is able to lift one leg up and tap it on a stool in front of him and then repeat this process with the other leg and/or evaluate the performance on a seated step test. Other exemplary assessments/tests may determine if a patient is able to reach forward while standing, climb stairs, and/or turn on light switches. Other exemplary assessments/tests may comprise a back-scratch test where the patient demonstrates flexibility and/or coordination by scratching his back. Other exemplary assessments/tests may comprise a sit-to-stand test where a patient goes from a seated position to standing and then back again three or more times. Other exemplary assessments/tests may evaluate the performance of a patient on a 30 second chair-stand test. Other exemplary assessments/tests may evaluate the performance of a patient on a get up and go test, a timed up and go test, and/or a modified 30-second sit to stand test. Other exemplary assessments/tests may determine an individual's walking speed. Other exemplary assessments/tests may comprise a general balance assessment through analysis of videos, sets of positional tracking data, and or other points of platform data obtained through the use of XR and/or as a patient goes about daily life.

One embodiment of the exemplary fall risk and mitigation feature utilizes various other tests, each with their implementations in XR. A modified functional reach test may be implemented wherein a patient grabs a series of cans off of a shelf and then places them into a shopping basket with each can being incrementally further away from the patient. In this test, the present feature may estimate and/or access fall risk among individuals with Parkinson's disease. A basic sit and reach test and/or a gamified sit and reach sling shot test may be employed to encourage patients to reach as far as possible in order to hurl a virtual object in XR using a virtual slingshot. Leg and/or arm-matching tests may be used wherein the patient loses any visual feedback with respect to the position of his arms or legs while in XR. In this test, the patient is subsequently instructed hold his arms or legs out away from his body with the positional differences between the arms or legs being measured. A get up and go test, timed up and go test, and/or a modified 30-second sit to stand test may be used wherein the patient's performance on the test(s) is autonomously or semi-autonomously evaluated by ML/AJ models. A relevant co-morbidity assessment may be used to evaluate for the presence of any patient issues that may confer a higher risk of falling.

Additional experience-based fall risk assessments may be completed in XR. One example may include an assessment of the patient's ability to navigate a virtual house and/or a virtual neighborhood in dim lighting conditions and/or in other lighting conditions. Another example may include an assessment of the patient's ability to walk down a narrow virtual corridor. Yet another example may use a simulator for testing proper use of assistive devices. Yet another example may comprise practical XR-based medication management testing.

Once fall-risk assessments are completed, tailored treatment regimen(s) to mitigate fall risk may be synthesized by clinicians and/or ML/AI models. These regimen(s) may utilize features from the Movement Module as well as other platform features and/or other points of platform data to eliminate hazards, improve strength, improve flexibility, and improve balance.

XR Functional Reach Feature

An XR functional reach feature of the exemplary Movement Module may use an XR implementation of a functional reach test and/or modified functional reach test and other platform features to guide therapy, progress, and/or prognosis in total knee replacement.

Pain with Movement Detection Feature

A pain with movement detection feature of the exemplary Movement Module may use platform features selected and/or configured through the use of a web portal, companion application, and/or XR GUI. The GUI integrates points of platform data (such as facial tracking, biomarker tracking, Q&A, and the like) to detect any patient pain and/or discomfort during movements and/or while using the platform. Patients may also use patient input methods to indicate that they are experiencing pain and/or discomfort using movements while in XR.

Pre-Configured Movement Set Feature

Using a pre-configured movement set feature of the exemplary Movement Module combined with other features described herein, clinicians have the ability to automatically generate a pre-configured and clinician-approved set of diagnostic, therapeutic, and/or clinically-related movements. Such movements may be based on inputs including identification of the anatomic structures or regions involved in the movements, clinical use cases, a patient's initial range of motion (ROM) capability for anatomical joints (e.g. knee extension of x number of degrees, and the like) a patients ROM goal for anatomic joints (with or without the desired % increase between sessions), and patient anthropometric data.

Movement Configuration Feature

According to a movement configuration feature of the exemplary Movement Module, for any movement-related feature described herein, clinicians and/or ML/AI models may carry-out certain configuration functionalities. Examples of configuration functionalities include the selection and/or modification of clinically-related movements, and the selection and/or modification of clinically-related sets of movements.

In one embodiment, features within the Movement Module are included in a sequential workflow. According to this workflow, an admin and/or clinician loads single repetition (rep) exercise animations into an exercise creator console and adds them to a list of base exercises to choose from. The admin and/or clinician then creates exercises using an exercise creator companion application. The admin and/or clinician then assigns newly created exercises to a patient's exercise regimen. The patient then starts a movement or exercise-related session and/or scene. The scene configuration is loaded as JSON via API and the patient's exercises are parsed and loaded accordingly. The patient mimics the instructor in front of him while actively 'touching' each exercise sphere as they appear until the exercise is complete. Once an exercise is completed, the next exercise is started. This process is repeated until all exercises are completed by the patient.

The following workflow demonstrates one embodiment of an end-to-end exercise system using items within the Movement Module. An admin and/or clinician first chooses a series of exercises from a list of potential exercises using a front-end web application. Using the front-end web application, the admin and/or clinician next configures the number of reps, the number of example repetitions, whether the exercise contains a mid-repetition hold, and the goal range of motion for each exercise. Using the front-end web application, the admin and/or clinician may configure the exercise scene and/or session to simultaneously launch positional tracking libraries using a webcam upon launch of the scene and/or session. Using the front-end web application, the admin and/or clinician next assigns the newly created exercise scene configuration to a session configuration specific to patients. The patient then starts an exercise-related session in XR. If the session was previously configured to simultaneously launch positional tracking libraries, a web portal webcam stream of a pose estimation library is also started. The session ID (generated by the XR software) is sent to the API with the web portal launch. The patient-facing XR program then loads the exercise scene configuration as JSON via an API, and the patient's exercises are parsed and loaded in the XR program accordingly. The exercise scene starts and a virtual human avatar instructor recites the instructions to the patient and does the configured amount of practice repetitions demonstrating proper exercise form to the patient. If configured as such, positional tracking data is streamed from the patient's webcam to the API via Websocket connection. The first exercise set starts, and the patient mimics the virtual human avatar instructor in front of him while actively exercising. Additional virtual human avatars may additionally mirror the movements of the patient. The additional virtual human avatars may be overlaid on top of the instructor virtual human avatar to provide real-time feedback to the participating patient by visualizing the similarity of the patient's movements to those of the virtual human avatar instructor. After all repetitions and/or sets, the first exercise is completed and the next exercise is started. This process is repeated until all exercises are completed by the patient.

In one exemplary embodiment, the Movement Module may further comprise a clinician console (e.g., a clinician-facing companion application) applicable for implementing a variety of module functionalities. Using the clinician console, clinicians can select a movement from a list of single repetition movements that will be applied to an animated instructor virtual human avatar for preview and used for creating an XR movement.

Using the exemplary console, clinicians can also spawn a collection of customizable spheres (a type of virtual object waypoint) that will be used by the patient as an interactive guide to perform the movement. Spawned sphere customizations may include spawn interval and sphere size. Spheres are spawned at the location of the instructor virtual human avatar's hands or feet positions during the movement repetition, so the patient can accurately reproduce. Spawned spheres can be individually selected so a clinician can precisely choose the best positions for the patient to perform the movement intuitively and accurately. When selecting spheres, the clinician can choose to mirror his selections, so a sphere is spawned on the opposite side of the body (e.g. opposite hand, opposite leg, etc.) at the same time of selected spheres. When selecting spheres, the clinician can deactivate/reactivate spheres that are unselected for ease of use.

Using the clinician console, the clinician can also choose the number of repetitions of the movement for a patient to carry-out. Once spheres and number of repetitions are selected, the clinician can preview the movement. During the preview, the spheres will turn semitransparent. As the avatar instructor does the movement, the spheres will "activate" by turning green as the avatar instructor's hand or foot passes through to emulate performing the movement to the patient. Once satisfied with the movement, the clinician can then export the movement as a JSON configuration file that can be imported via API and/or directly into the patient movement scene.

The patient experience is described below.

A movement regimen is loaded via API and/or directly from a JSON file that was created using the clinician console. The patient will be positioned facing a male and/or female animated avatar instructor based on his choosing. The animated avatar instructor will explain the movement via text and/or spoken voice/audio before beginning the movement. Once the patient begins the movement, spheres will begin spawning as specified by the clinician in the JSON configuration. The spheres are spawned (in locations relative to where they spawned on the avatar instructor during the creation phase) on the user and spawned in sequence for a configurable time threshold as the avatar instructor completes the movement in front of the patient.

There will be at least two visible spheres per hand or foot. One sphere will be a solid material. This will be the next sphere in the sequence for the user to touch. Once touched, this sphere will turn into a "touched" material that will let the user know they have successfully made the correct movement at that point in the movement. The second visible sphere will be a semitransparent material. This is the following sphere in the sequence. It will become the solid material once it is time for the user to move onto that part of the sequence. This sphere is here for ease of use to let the user know which direction his hands/feet should be moving.

The above sequence will repeat until the repetition is complete. Once the repetition is complete, the sequence will repeat until the number of repetitions specified by the clinician has completed. Once a movement is complete, the next movement in the regimen is explained via text and/or spoken voice/audio and then started by the avatar instructor. Then everything repeats as stated. This continues until each movement in the regimen is completed.

K. Neurological Module

In exemplary embodiment, the present XR Health Platform further comprises a Neurological Module. The module contains features that, either alone or in combination with other platform features, enable the screening for, detection of, diagnosis of, treatment of, optimization of, and/or rehabilitation from, issues and/or diseases relating to and/or involving the nervous system. The methods, systems, and/or features within the Neurological Module may utilize other platform features described herein, points of platform data, and/or ML/AI models. Additionally, the Neurological module may comprise one or more various other features described below.

Vision Assessment Feature

A vision assessment feature of the exemplary Neurological Module may involve simulations, screening, and testing of a patient.

In one exemplary embodiment, the present module comprises acuity testing using a standardized visual acuity chart (such as a "tumbling E" chart) placed at a fixed virtual distance away from a patient in XR. Instructions are provided to complete visual acuity tasks being delivered to the patient as text and/or recited out loud using the TTS feature and/or through visual means. The patient responses are either recited out loud and/or are delivered by patient input methods.

In another exemplary embodiment, the present module comprises a contrast sensitivity simulation wherein a patient in XR is asked to align a visual contrast line indicator with the main contrast demarcation in each image in a series of images, each containing differing levels of contrast demarcation. The patient accomplishes this using patient input methods. A scoring algorithm automatically determines the degree of correctness by which the contrast line indicator aligns with the contrast demarcation in each image. After the scene and/or session is completed, metrics of visual contrast sensitivity may be reported to the patient and/or clinician.

In yet another exemplary embodiment, the present module further comprises tests utilizing oculokinetic perimetry technique(s) and tests that utilize monoscopic vision testing techniques.

In yet another exemplary embodiment, the present module further comprises tests in XR that leverage the Pulfrich phenomenon, the stereoscopic visual capabilities of XR, and/or neutral density filters. Such tests may include relative afferent pupillary defect testing and/or stereoscopic vision testing.

In yet another exemplary embodiment, the present module further comprises color vision testing using standardized sets of related color images in XR. According to this test, instructions are provided to arrange a series of color images according to their hue, with the instructions being delivered as text, recited out loud using the TTS feature, and/or through visual means. The patient completes the test using patient input methods. Once the patient is finished arranging the color images, a scoring algorithm stratifies the patient according to his likelihood of having color vision deficits.

One embodiment utilizes the color vision testing feature to additionally screen for, confirm, and/or diagnose specific types of color blindness. For example, a patient completes the color vision testing feature and is determined to have a high likelihood of having color vision deficits. The patient is then given text-based, voice-based, and/or visually-based instructions to complete tests to identify the specific word, letter, object or number contained within each image in a set of images using patient input methods. Each image has color and pattern characteristics that would make it difficult for someone with specific types of color blindness to identify the appropriate word, letter, object or number. This testing may then be repeated with camera filters and/or visual effects being applied to simulate, amplify, and/or attenuate specific types of color blindness to serve as a confirmatory test and/or an additional test that yields greater confidence in the overall testing result. The above testing may again be repeated with camera filters and/or visual effects being removed to simulate, amplify, and/or attenuate specific types of color blindness to serve as a further confirmatory test and/or an additional test that yields greater confidence in the overall testing result.

In yet another exemplary embodiment, the present module further comprises visual field testing intended to assess the patient's visual fields. In a gaze-following task, the patient is instructed to follow virtual objects while remaining stationary and/or without moving his head as the virtual objects traverse through all of the patient's visual fields. One or more ML/AI models, and/or gaze tracking, and/or positional tracking, and/or pupil tracking, and/or eye tracking are used to autonomously monitor the patient's ability to visually traverse the visual fields. In an extraocular muscle test, the patient is instructed to follow virtual objects while remaining stationary and without moving his head as the virtual objects traverse through all of the patient's visual fields. One or more ML/AI models and/or gaze tracking and/or positional tracking and/or pupil tracking and/or eye tracking are used to autonomously monitor the patient's ability to utilize his extra-ocular muscles associated with cranial nerves 3, 4, and 6. The visual field testing may further comprise tests and/or features involving the use of oculo-kinetic perimetry or similar technique.

In yet another exemplary embodiment, the present module further comprises passive visual disturbance and/or spatial neglect detection and identification. Visual disturbances (including spatial neglect) may be detected and/or identified in scenes and/or sessions through a passive assessment. According to this assessment, a patient's eye tracking data and/or gaze tracking data are analyzed by using "heat map" type visualizations. When ML/AI models and/or points of platform data and/or clinician interpretation of the visualizations are applied, the presence of and/or identities of visual deficiencies (including spatial neglect) are declared, detected, and/or identified.

In yet another exemplary embodiment, the present module further comprises spatial neglect detection and/or identification. Detection of spatial neglect may be determined through the use of ML/AI models and/or gaze tracking and/or positional tracking and/or pupil tracking and/or eye tracking. Instructions to complete tasks are delivered to the patient as text and/or recited out loud using the TTS feature and/or through visual means. Features, scenes, and/or sessions may assess for the presence of spatial neglect by instructing the patient to complete one or more tasks. In one exemplary task, using patient input methods, the patient is instructed to assemble a clock with each number in the appropriate position given a circular and/or disk-shaped clock template, and 2D and/or 3D models of the numbers one through twelve. One variation of this task may additionally include giving the patient an additional "second", "minute", and/or an "hour" hand. The patient may then be instructed to indicate the time on the clock template after being given the time either through visual and/or spoken means. In another exemplary task, labeled 2D and/or 3D objects are instantiated into a scene with each object instance being logged. The patient is then instructed to select each object that they can see using patient input methods.

The labels of each object selected are logged. Alternatively, the patient may be instructed to recite out loud the names of each object that the patient can see. The labels of each object recited may be logged through the use of ML/AI models (such as STT) as described herein. The exemplary task may be performed under one or more of the following conditions: (a) where there is only a singular instance of each object; (b) where a plurality of the labeled objects are scattered about two or more of the areas comprising the visual fields of a normal healthy adult with the positional data for each object, as well as the positional data relative to the patient's virtual head and/or eye position for each object being logged; (c) where the positional and/or relative positional data of each object is mapped to the various visual fields being assessed and labeled using a text description of its respective visual field by ML/AI models, and/or using any other feature described herein; (d) where the object instance log is compared to the object selection log and/or the objects recited log; (e) where the visual field mapping data for any instantiated objects that were not either selected and/or recited ("missed objects") are also logged with each entry being converted to a labeled description of the visual field in which the "missed object" was instantiated, and (f) where a summative report is generated containing one or more visualizations and/or summary descriptions of the names and/or visual field locations of each "missed object".

Hearing Assessment Feature

A hearing assessment feature of the exemplary Neurological Module may be used for the assessment of hearing using mono sound, stereo sound, and/or spatial/3D sound features, and/or ML/AI models. This feature may be implemented either with or without the use of points of other platform data to assess and/or perform one or more of hearing tests in either the right ear, the left ear, and/or in both ears. Exemplary tests include hearing acuity, sound frequency detection, sound discrimination, sound localization, spatial sound detection, spatial sound discrimination, spatial sound localization, evaluation of auditory rehabilitation progress, and hearing aid testing.

Another exemplary hearing test may comprise a pure tone test. According to this test, sounds and/or tones at various frequencies are played in the right, left, or both ears for the patient with the patient indicating if and/or when they hear the sound, and/or which side they hear the sound on using patient input methods. This test may be repeated multiple times with the frequency of each sound and/or tone, which ear(s) the tone was heard in, as well as the amount of time it took for each response (in milliseconds) all being recorded for each iteration. A variation of the above test may allow for modifying the intensities, lengths, frequencies, and/or patterns of each sound and/or tone that is played.

Another exemplary hearing test may comprise loudness balance test. According to this test, sounds and/or tones are played for the patient with each sound and/or tone be played alternatively to both ears with the sound intensity being fixed in one ear. Using patient input methods, the patient increases the intensity of the sound heard in one ear until the sounds/tones are perceived to be of equal intensity in both ears. This test may be repeated multiple times with the actual initial intensity of each sound and/or tone, the intensity at which the sound and/or tone was perceived to be equal in both ears, as well as whether the right ear or the left ear had the fixed tone or not being recorded for each iteration.

Another exemplary hearing test may comprise a synthetic sentence test. This test uses functionalities within the Q&A feature described above and/or other platform features. According to this test, sentences are recited out loud to the patient and at the conclusion of each sentence recited out loud, the patient must identify each sentence heard by selecting it from a list of sentences with each response being recorded.

Another exemplary hearing test may comprise a filtered speech test. This test uses functionalities within the Q&A feature described above and/or other platform features. According to this test, words are recited out loud to the patient while audio filters are simultaneously applied to remove one or more frequencies of sound. At the conclusion of each word recited out loud to the patient, the patient is asked to recite the word back. The word recited back is analyzed using ML/AL models and/or using other platform features for a match with the original word recited out loud to the patient.

Another exemplary hearing test may comprise an escalating hearing test. According to this test, sounds and/or tones are played for the patient with the patient indicating if and/or when they hear the sound using patient input methods. This test may be repeated multiple times with each iteration of the test playing the sound with an escalating level of intensity. The sound frequency and sound intensity, as well as each response may be recorded for each iteration.

Another exemplary hearing test may comprise a decay hearing test. According to this test, constant intensity sounds and/or tones are played for a fixed period of time for the patient. The patient indicates if they hear the sound and/or tone at a constant intensity for as long as they appreciate this to be the case using patient input methods. If the patient thinks that the sound fades at any time while a sound and/or tone is being played, the patient is instructed to indicate so using other patient input methods. For example, for as long as a patient hears a sound/tone at a constant intensity they pull the trigger, and then as soon as they appreciate the sound starting to fade and/or stop, they let go of the trigger. This test may be repeated multiple times with each iteration of the test playing a sound/tone with an escalating level of intensity for the same fixed period of time. For each iteration, the sound/tone frequency, the sound/tone intensity, the fixed period of time that the sound/tone was used, as well as the patient inputs, and the times during which each patient input was given are all recorded.

Another exemplary hearing test may comprise staggered word testing. According to this test, using one or more of the functionalities within the Q&A feature and/or other platform features, words are recited out loud to the patient in either the right or left ear. Either the same word or a different word is simultaneously played in the opposite ear. At the conclusion of each word and/or words recited out loud to the patient, the patient is asked to recite the word and/or words back as well as indicate which ear(s) each word and/or words were heard in using patient input methods. The word/words recited back as well as the laterality of each word as indicated by the patient are analyzed for a match and/or correctness with the original word(s) recited out loud to the patient in the right and/or left ears. The analysis may be conducted using ML/AL models and/or one or more other platform features.

Another exemplary hearing test may comprise speech in noise testing. According to this test, using functionalities within the Q&A feature and/or other platform features, sentences are recited out loud to the patient with each sentence containing "key words" while additional audio tracks play one more distracting sounds and/or tones simultaneously. At the conclusion of each sentence, the patient is asked to recite the sentence back. The sentence recited back may be analyzed using ML/AL models and/or one or more other platform features for the presence of any "key words" that were in the original sentence recited out loud to the patient.

Each of the above hearing tests (or assessments) may be pre-loaded, selected, and/or configured for the patient by clinicians and/or ML/AI models. Upon engaging with hearing assessments within a scene and/or session, the patient will be given instructions as text, as spoken voice recited out loud, and/or through visual means using platform features described herein. After completing the instructions, sounds and/or tones are played for the patient in either the right ear, the left ear, and/or both ears, and the patient indicates if they can hear the sounds and/or tones using patient input methods. If the patient can hear the sounds and/or tones, the patient indicates where in 3D space (and/or on a 2D representation of 3D space) they think the sounds and/or tones are originating from using patient input methods.

In another exemplary embodiment, the patient is asked to discriminate between two or more sounds and/or tones and/or discriminate between differences in sounds and/or tones heard in the right ear verses the left ear based on the frequency, tone, volume, pattern, and/or right verses left. The patient indicates one or more of these parameters through the use of patient input methods.

Cranial Nerve Assessment Feature

The exemplary Neurological Module may further comprise a cranial nerve assessment feature. According to this feature, autonomous and/or semi-autonomous cranial nerve assessment is made through the use of ML/AI models, voice and/or vocal biomarker analysis, facial tracking, pupil and/or eye tracking, other platform data points and/or supplemental hardware where indicated. The exemplary module may further utilize one or more of the assessments discussed below.

In one exemplary embodiment, the present module uses an assessment of cranial nerve 1. This embodiment comprises a rapid assessment of gross ability to smell using Q&A and/or STT features and incorporating the "Box" hardware device described below. During scenes and/or sessions, a smell is released by the "Box" at a pre-configured time and/or following feature-, scene- and/or session-related triggering events configured by clinicians and/or ML/AI models using the functionalities of the Configuration Module described herein. After appropriate instructions (using one or more text-based, auditory, and/or visual prompts), the patient either indicates the presence of any new smell and/or identifies of the name of any new smell appreciated using patient input methods. The cranial nerve 1 assessment may also be obtained through direct interaction with a clinician via the communications feature.

In another exemplary embodiment, the present module uses an assessment of cranial nerve 2. Successful use of the XR Health Platform passively tests gross vision upon each use. For a more complete exam, in addition to one or more of the other methods described herein, the patient is instructed to remain stationary while various common objects are instantiated at various areas within the patient's visual fields. The visual field location of each instantiated object is logged, and the patient is asked (using text-based, auditory, and/or visual prompts) to recite out loud what the name of each object is when it is instantiated. The audio of the words repeated out loud by the patient are subsequently processed by STT ML/AJ models. The text transcript output may then be compared to the original text "tags" and/or labels of the objects that were instantiated. The comparison may be made using eye tracking and/or gaze tracking and/or pupil tracking and/or through direct interaction with the clinician via the communications feature described here.

In another exemplary embodiment, the present module uses an assessment of cranial nerve 3, 4, 6. This assessment may be completed using the 'extraocular muscle test' mentioned herein and/or visual field test mentioned herein, either with or without gaze and/or eye tracking; and/or through direct interactions with a clinician via the communications feature; and/or after auditory, visual, and/or text-based requests to perform actions relating to visual fields is delivered to the patient, with the subsequent patient actions being assessed using ML/AJ models in combination with points of data provided by cameras, and/or, through the use of other points of platform data, and/or using eye and/or gaze tracking as described herein.

In another exemplary embodiment, the present module uses an assessment of cranial nerve 5. This embodiment may be achieved by detecting, assessing, and/or identifying muscle wasting of temporalis muscle and/or masseter muscle and/or jaw asymmetry identified through the use of ML/AJ models in combination with points of data provided by cameras; and/or through direct questioning regarding jaw asymmetry, muscle wasting, and/or facial sensation using the Q&A feature; and/or confirming intact facial sensation using tactile module functionalities; and/or through direct interactions with a clinician via the communications feature; and/or through the use of points of biometric data and/or points of other platform data.

In another exemplary embodiment, the present module uses an assessment of cranial nerve 7. This assessment may be completed using facial asymmetry identified through the use of one or more ML/AI models in combination with points of data provided by one or more cameras during the same session; and/or direct questioning regarding hearing sensitivity using the Q&A feature; and/or through direct interactions with a clinician via the communications feature; and/or given text-based, auditory, and/or visual prompts assessing a patients ability to smile symmetrically, and/or puff his cheeks, and/or raise his eyebrows, and/or close his eyes tightly shut after a verbal/auditory and/or text-based request to perform the actions is delivered to the patient. Any subsequent patient actions may be assessed using one or more ML/AI models in combination with the use of cameras and/or through the use of points of biometric data and/or points of other platform data.

In another exemplary embodiment, the present module uses an assessment of cranial nerve 8. This assessment passively tests gross hearing upon each use. In addition to other hearing tests described herein, as well as one or more of the other features described herein, another hearing assessment can be implemented as described below.

Using the clinician configured TTS functionality described herein, the audio output of one or more words are recited at low volume into the patients left or right ear or both ears. The patient subsequently repeats what is heard out loud which is detected by the patient's microphone. The audio of the words repeated out loud by the patient are subsequently processed by STT ML/AI models, and the text transcript output is compared to the original text inputs configured by the clinician for accuracy. The same process is repeated for the opposite ear and/or both ears.

A sub-test for hearing symmetry may be implemented by playing a single sound in one ear followed by the opposite ear at the same volume and assessing if the patient perceives the sound, and if so, if the sound was louder in one ear verses the other. The patient response may be assessed using the Q&A feature, and/or through patient vocalizing his response followed by the processing and analysis of the response through STT and/or natural language processing, and/or other ML/AJ models; and/or using other patient input methods; and/or through direct interaction with a clinician via the communications feature.

A sub-test for conductive and/or sensorineural hearing loss may be implemented using one or more testing activities. In one example, the test activity includes administering a fade-out type tactile stimulus to the patients right or left styloid process using tactile module functionalities. The patient is then instructed to indicate when they can no longer hear the sound. The activity assesses if the patient heard the sound for less then, equal to, or longer than the actual tactile stimulus duration with each response being logged. The patient response is assessed using the Q&A feature, and/or through patient vocalizing his response followed by the processing and analysis of the response through STT and/or natural language processing, and/or other ML/AJ models, and/or indicating the response using other patient input methods. The same process is repeated for the opposite ear. A similar process can be carried out through direct interaction with a clinician via the communications feature.

In one example, the test activity includes administering a fade-out type tactile stimulus to the middle of the patient's forehead using tactile module functionalities and instructing the patient to indicate whether they hear the sound equally in both ears or more on one side with each response being logged. The patient response is assessed using the Q&A feature, and/or through patient vocalizing his response followed by the processing and analysis of the response through STT and/or natural language processing, and/or other ML/AJ models, and/or indicating the response using other patient input methods. A similar process can be carried out through direct interaction with a clinician via the communications feature.

In another exemplary embodiment, the present module uses an assessment of cranial nerve 9, 10, and 12. Using the clinician configured TTS functionality described herein and/or through text-based, auditory, and/or visual prompts, the patient may be instructed to protrude his tongue and say words and/or sounds with tongue protrusion asymmetry and/or asymmetrical palatal movement and/or a uvula that is not in the midline position being identified through the use of ML/AI models in combination with a video and/or photos generated by cameras during this assessment. The patient's voice quality is either subjectively assessed after a visual, text-based, and/or auditory prompt through direct questioning using the Q&A feature and/or through a comparison of a recording of the patients voice to a previous recording using one or more ML/AI models; and/or performing of the aforementioned tests through direct interaction with a clinician via the communications feature.

In another exemplary embodiment, the present module uses an assessment of cranial nerve 11. Using the clinician configured TTS functionality described herein and/or through text-based, auditory, and/or visual prompts, the patient may be instructed to shrug his shoulders and slowly shake his head from side to side multiple times. Shoulder shrug asymmetry and/or inability to move his head and/or asymmetry in the ability to move his head an appropriate distance to one or both sides may be identified through the use of ML/AI models in combination with a video and/or photos generated by one or more cameras during this assessment. The assessment may also use the Q&A feature to ascertain the patient's subjective responses to direct questioning regarding shoulder shrug and/or head shaking. The assessment may also include performing one or more of the aforementioned tests through direct interaction with a clinician via the communications feature.

Motor Assessment Feature

A motor assessment feature of the exemplary Neurological Module may comprise an assessment of patient motor functions, such as the assessment of strength, gross-motor skills, fine-motor skills, physical coordination, and/or gait. Patient motor assessment may be completed using the methodologies of motor assessment described above in the Movement Module or may comprise or combine one or more of the various methods described below.

In one embodiment, the present module comprises a passive motor assessment. During a session, intact motor function of one or more of the patient's core (e.g. abdominals/back), neck, arms, and/or legs may be assessed using ML/AI models in combination with a video and/or photos of the patient generated by cameras during the same session, and/or using positional tracking data with or without the use of additional points of platform data.

In another embodiment, the present module comprises a formal/active motor assessment. Using the clinician configured TTS functionality described herein and/or through text-based, auditory, and/or visual prompts, the patient may be instructed to perform various different motor-requiring tasks ("such as raise your right arm") with the appropriate action being identified using ML/AI models in combination with a video and/or photos of the patient generated by cameras during this assessment. Alternatively, identifying if the appropriate action was carried out may be determined using positional tracking data with or without the use of additional platform data points, and/or using the Q&A feature to ascertain the patient's subjective responses to direct questioning regarding each movement that they are instructed to carry out, and/or performing one or more of the aforementioned tests through direct interactions with a clinician via the communications feature.

Sensory Assessment Feature

A sensory assessment feature of the exemplary Neurological Model may comprise one or more of the various assessment methods discussed below.

According to a first sensory assessment method ("method 1"), during a session intact sensory function of one or more anatomical areas on the patient's body are assessed using one or more of ML/AI models in combination with pieces of 3rd party hardware to deliver one or more tactile stimuli as described in the Tactile Module herein, and as set using one or more of the functionalities of the Configuration Module as described herein. This may be completed either with or without the use of points of additional platform data.

Whenever a stimulus is appreciated, immediately after the stimulus the patient indicates the number of stimuli in a series of stimuli, after a known number of serial stimuli are delivered; the location on the patient's body where each stimulus was appreciated; the location spread of each stimulus appreciated; the nature and/or character of each stimulus appreciated; the intensity of each stimulus appreciated; and/or the duration of each stimulus appreciated.

According to another sensory assessment method ("method 2"), using the clinician configured TTS functionality described herein and/or using text-based, auditory, and/or visual prompts, the patient may be instructed to place controllers and/or any other device capable of delivering a tactile stimulus, against anatomical areas on his body. As set using one or more of the functionalities of the configuration and/or tactile modules as described herein, stimuli are then delivered to the patient via the controllers and/or other devices. Using patient input methods, the patient indicates one or more of the following as instructed regarding each stimulus: whenever a stimulus is appreciated; immediately when a stimulus is terminated; the number of stimuli in a series of stimuli, after a known number of serial stimuli are delivered; the location on the patient's body where each stimulus was appreciated; the location spread of each stimulus appreciated; the nature and/or character of each stimulus appreciated; the intensity of each stimulus appreciated; and the duration of each stimulus appreciated. Each patent input is logged and sent to the API.

According to another sensory assessment method ("method 3"), using the clinician configured TTS functionality described herein and/or through text-based, auditory, and/or visual prompts, the patient is instructed to fasten the controllers to respective "controller clip/harness" devices described herein, and to then fasten the combined controller and "controller clip/harness" devices to anatomical areas on his body. As set using one or more of the functionalities of the Configuration and/or Tactile Modules described herein, stimuli are delivered to the patient via the controllers and/or other devices. Using patient input methods, the patient indicates one or more of the following as instructed regarding each stimulus: whenever a stimulus is appreciated; immediately after the stimulus; the number of stimuli in a series of stimuli, after a known number of serial stimuli are delivered; the location spread of each stimulus appreciated; the nature and/or character of each stimulus appreciated; the intensity of each stimulus appreciated; and the duration of each stimulus appreciated. Each patent input is logged and sent to the API.

Yet another sensory assessment method ("method 4") combines the items within sensory assessment methods 1, 2, and/or 3 above, either with or without other platform features and/or other points of platform data.

Arousal Assessment Feature

An arousal assessment feature of the exemplary Neurological Model comprises a passive assessment of arousal level using positional tracking data, eye tracking data, pupil size data, biometric data (including heart rate, heart rate variability and/or galvanic skin response data), the Q&A feature to ascertain the patient's subjective responses to direct questioning regarding his level of arousal, through direct interactions with clinicians via the communications feature, through the use of ML/AI models (including vocal biomarker analyses, speech analyses, and/or computer vision models), and/or through the use of other platform features.

Mental Status and Orientation Feature

A mental status and orientation feature of the exemplary Neurological Module may be utilized to assess whether a patient is alert and/or oriented to person, place, and/or time. Using the clinician configured TTS functionality described herein and/or through one or more text-based, auditory, and/or visual prompts, the patient may be instructed to state out loud the following: his name, where they are, and what year, date, and/or time it is. The patient's responses may be assessed through the use of STT and/or natural language processing, and/or other ML/AI models with the text transcript outputs of these responses compared to the patient's name and zip code on file as well as the timestamp at which the responses were generated to determine the accuracy of each patient response. The patient responses may also be obtained and/or assessed using the Q&A feature, and/or through direct interactions with a clinician via the communications feature, and/or using patient input methods as described herein, and/or using other platform modules and/or other platform features.

Cognitive Domains Feature

A cognitive domains feature of the exemplary Neurological Model comprises diagnostic, therapeutic, care delivery, and/or other clinically-oriented solutions relating to the assessment, management, treatment, and/or care relating to cognitive domains. Within the XR Health Platform, cognitive domains represent cognitive, intellectual, and/or neurological capabilities associated with human thought and/or mentation. The cognitive domains and related feature functionalities may comprise a system to autonomously, semi-autonomously, and/or manually create, configure, and/or perform assessments of certain cognitive domains either in XR and/or via a web portal and/or using a companion application. The exemplary cognitive domains discussed below are applicable in this module and may also be referenced elsewhere. Each cognitive domain below may be assessed and/or used to treat patients through the application of platform features and/or ML/AI models. Any required patient inputs, responses and/or interactions to test, assess and/or treat any cognitive domain may be achieved using patient input methods. Any of the items, features, and/or content listed below may be applied within other platform features, objects, scenes, sessions, and/or regimens. In one exemplary embodiment, the cognitive domains and cognitive domain functionalities may include long-term memory/long delay recall/crystallized memory.

In another exemplary embodiment, the cognitive domains and cognitive domain functionalities may include short-term memory/short delay recall.

In another exemplary embodiment, the cognitive domains and cognitive domain functionalities may include working memory; for example, way-finding tasks, N-back tasks and/or sentence evaluation.

In another exemplary embodiment, the cognitive domains and cognitive domain functionalities may include visual-spatial reasoning; for example, way-finding tasks, and/or the assessment of a patient's orientation in two- or three-dimensional space.

In another exemplary embodiment, the cognitive domains and cognitive domain functionalities may include episodic memory; for example, asking a patient about what had happened during previous scenes, sessions, and/or regimens using Q&A functionalities with the correct answers being pre-populated based on the tags of features and/or labels of the previously experienced scenes, sessions, and/or regimens.

In another exemplary embodiment, the cognitive domains and cognitive domain functionalities may include sorting/inductive reasoning; for example, having patients determine which object does not belong in a set of otherwise similar objects; or having patients indicate probable scenarios from a list of possible answer choices, given the visual, auditory, tactile, and/or situational context of a scene.

In another exemplary embodiment, the cognitive domains and cognitive domain functionalities may include attention; specifically (a) sustained attention; for example, using a prolonged psychomotor vigilance task, and (b) divided attention; for example, tasks requiring a patient to keep track of two or more objects, and (c) selective attention; for example, tasks requiring a patient to keep track of certain objects and ignore others.

In another exemplary embodiment, the cognitive domains and cognitive domain functionalities may include inhibition; for example, tasks requiring a patient response when one event happens but not when other events happen.

In another exemplary embodiment, the cognitive domains and cognitive domain functionalities may include reaction time/response time; for example, using reaction time testing. In this example, visual and/or auditory stimuli may appear in XR, and a patient in XR presses a button whenever particular stimuli appear. Timestamps of all stimuli and all button presses may be logged, and an algorithm used to automatically calculate the difference in time between the appearance of each stimulus and any subsequent appropriate button press.

In another exemplary embodiment, the cognitive domains and cognitive domain functionalities may include manual dexterity; for example, having patients sort two or more two- or three-dimensional objects into progressively smaller containers/buckets.

In another exemplary embodiment, the cognitive domains and cognitive domain functionalities may include knowledge; for example, a general trivia game where questions are asked using Q&A functionalities and/or other platform features, and where patient responses are delivered using patient input methods.

In another exemplary embodiment, the cognitive domains and cognitive domain functionalities may include conceptual flexibility.

In another exemplary embodiment, the cognitive domains and cognitive domain functionalities may include praxis/applying learned concepts and/or knowledge; for example, teaching a task and then having the patient demonstrate it.

In another exemplary embodiment, the cognitive domains and cognitive domain functionalities may include language comprehension; for example, questions using Q&A functionalities after the patient is instructed to read a paragraph of text and/or listen to the recited version of a paragraph of text.

In another exemplary embodiment, the cognitive domains and cognitive domain functionalities may include language production; for example, an assessment through analysis of audio recordings and/or patient inputs using ML/AI models.

In another exemplary embodiment, the cognitive domains and cognitive domain functionalities may include verbal reasoning; for example, delivering a brief story to a patient through written, spoken voice and/or visual means, and then using the Q&A feature and/or other platform features to subsequently ask questions that require language abstraction and/or verbal reasoning to correctly answer.

In another exemplary embodiment, the cognitive domains and cognitive domain functionalities may include reasoning/computation; for example, using puzzles testing reasoning and/or computation and/or other form of deductive reasoning in order to progress through scenes.

In another exemplary embodiment, the cognitive domains and cognitive domain functionalities may include processing speed and accuracy; for example, for logic-based tasks and math-based tasks.

In another exemplary embodiment, the cognitive domains and cognitive domain functionalities may include planning; for example, task sequence testing, speed anticipation testing, and simulations requiring the use of a calendar.

In another exemplary embodiment, the cognitive domains and cognitive domain functionalities may include decision making/problem solving; for example, task sequence testing and the assessment of ADLs and/or IADLs as described herein.

In another exemplary embodiment, the cognitive domains and cognitive domain functionalities may include judgement/evaluation. Examples include: (a) the assessment of likely physical characteristics of an object given virtual representations of the object; (b) having a patient assess of different amounts of money (for example which is greatest, etc.); (c) having patients determine which object does not belong in a set of otherwise similar objects; and (d) having patients sort two or more two- or three-dimensional objects into two or more visually transparent containers, and where the patient subsequently assesses the degree to which one or more of the containers are full and/or empty.

In another exemplary embodiment, the cognitive domains and cognitive domain functionalities may include executive function; for example, practical task sequence testing (such as following a recipe and/or performing a basic repair) and assessment of ADLs and/or IADLs as described herein.

In another exemplary embodiment, the cognitive domains and cognitive domain functionalities may include capability to autonomously, semi-autonomously, and/or manually create, configure, and/or deliver therapeutic actions addressing cognitive domains. One or more patient input methods as described herein can be used to deliver input and/or interact as needed for any implementations utilizing any of the cognitive domains described herein.

The exemplary cognitive domains feature may further comprise a variety of cognitive tests discussed separately below. Any inputs, responses, and/or interventions required for any cognitive domain test may be achieved using patient input methods. Any cognitive domain test may be deployed within any scene, session, and/or regimen. The terms "user" and "patient" may be used interchangeably throughout.

(a) 3D Sorting Test

According to this test, a user is in a room in XR with a screen or UI canvas in front of him instructing him to sort all of the objects by color. There is a finite number of 3D cubes of different sizes in front of the user, which are either red, green, blue, or black. There are also four 3D numbers in front of the user—1, 2, 3, and 4. There are also four semitransparent 3D boxes in front of the user. There is also a "Touch to Finish" 3D Cube in front of the user. The user must grab the cubes using his controllers and the grab button on the controllers, and drop the colored cubes into the boxes, putting cubes of the same color together. The user must then rank the boxes by grabbing and placing the 3D numbers in the designated area (indicated with a semitransparent cube in front of the boxes), as follows:

Placing 1 in front of the box with the most cubes
Placing 2 in front of the box with the second most cubes
Placing 3 in front of the box with the third most cubes
Pacing 4 in front of the box with the least cubes The user then touches the "Touch to Finish" Cube to complete the test. The amount of time taken to complete the test, and the user's ability to sort the colors, and the user's ability to count the items per box are all logged for analysis. FIG. 37 comprises a diagram depicting an implementation of one embodiment of this test.

(b) Hole Peg Test

According to this test, the user is in a room in XR with a screen or UI canvas in front of him instructing him to place all of the pegs from the well to the holes, then move all the pegs back into the well once the holes are all plugged with his right hand. Using his controller on his right hand and the grab button, the user must pick up each peg, and place it into any hole. Once all the holes are plugged with a peg, using the controller on his right hand and the grab button, the user must remove the pegs from the holes and move them back into the well. Once all the pegs are back into the well, the board is rotated using an animation, and the user must repeat steps 2 and 3 with his left hand. Once this is completed, the test is complete. The amount of time taken to complete the test is logged.

(c) Abstract Letter Reading Test

According to this test, the user is in a room in XR with a screen or UI canvas in front of him instructing him to identify each letter as it is shown to him. There is also a QWERTY keyboard in front of him. When the test is started, a random "Abstract Letter" is shown to the user on the canvas. The letter closely resembles a letter in the alphabet. The user must decipher and choose the letter they believe the abstract letter represents. Using the laser pointer emitting from his controller and the trigger, the user must choose the letter on the keyboard. This process is repeated until the configured number of letters has been exhausted. The amount of time taken to decipher each letter, the actual letter, and his chosen letter, are all logged for each letter shown to the user for analysis.

(d) Color Sorting Test

According to this test, the user is in a room in XR with a screen or UI canvas in front of him instructing him to sort each color, and a color grid. There is also a start button as well as a submit button that appears after the test has been started. There are 4 different sets of color spectrums of 15 colors, each graded separately. Using the laser on his controller and trigger, the user must click and drag the colors to sort them. The user sorts each color by hue from left to right, using the color with the least hue on the left and the largest hue on the right as a guide for the user. The test is completed once the user clicks the submit button. To grade the spectrum, each color is iterated. If the color next to it has a starting index that's difference is 4 or more that of the current color, that counts as one incorrect color. The spectrum is failed if 3 or more colors are marked as failed. The spectrum is automatically failed if the 15th color is marked as incorrect. If color 7 and color 15 are next to each other, the incorrect combination is omitted from the test. The time taken to complete the test, and the results for each spectrum are logged. FIG. 38 comprises a diagram depicting an implementation of one embodiment of this test.

In one embodiment of the color vision test scoring system, there are 4 different sets of color spectrums of 15 colors, each graded separately. The user sorts each color by hue from left to right, using the color with the least hue on the left and the largest hue on the right as a guide for the user. To grade the spectrum, each color is iterated. If the color next to it has a starting index that's difference is 4 or more that of the current color, that counts as one incorrect color. The spectrum is failed if 3 or more colors are marked as failed. The spectrum is automatically failed if the 15th color is marked as incorrect. If color 7 and color 15 are next to each other, the incorrect combination is omitted from the test.

(e) Digit Span Memory Test

According to this test, the user is in a room in XR with a screen or UI canvas in front of him instructing him to say a keyword to begin the test. The screen/canvas also includes brief instructions for how to perform the test. There is also a metric displayed for longest span, which is updated every time the user reaches a new high score for number of digits in the span. Once user says the keyword, and it is recognized by the voice recognition system, the test starts. Once the test starts, the first random digit in the digit span sequence is shown for a short, configurable amount of time. After the digit is shown, it disappears, and a microphone icon with instructions to say the list of digits that was shown (in this case, just the one). The user should then say the number that was shown. If they say the correct number, a "correct sound" is played. If they say the final number in the sequence correctly, a "correct sequence sound" is played. As the user speaks, the microphone icon will fill with the microphone input's loudness, giving the user visual feedback that his voice is heard. The number said is then shown again, followed by a new random number. The user must then say both numbers in the sequence. This process repeats, and the sequence grows with each response until the user says a wrong number. Each response as well as whether the response was correct or not are logged for later analysis. When a wrong number is said, an "incorrect sound" is played, and the screen/canvas is taken back to the original text with the instructions to say the starting keyword once again. The process then repeats once the keyword is said.

(f) Divided Attention Test

According to this test, the user is in a room in XR with a screen or UI canvas in front of him informing the user to count the number of each object as it appears on the canvas. There is also a virtual number entry pad ("numpad") in front of the canvas that will appear when all the objects have been shown to the user. When the test is started, objects will start appearing on the canvas, on at a time, in random order, at a fixed rate. On one half of the canvas, gold stars will appear. On the other half, red X's. There will be a total of 50 objects shown to the user. Once all the objects are shown, the numpad will appear, and canvas will instruct the user to input how many stars they counted. Using the laser pointer (emitting from the controller once all the objects are shown), and trigger, the user must enter how many stars they counted, then press enter. Then, the instructions will tell the user to enter how many X's they counted. Using the laser pointer (emitting from the controller once all the objects are shown), and trigger, the user must enter how many X's they counted, then press enter. Then, the test is complete. Actual numbers of stars and X's and entered numbers of stars and X's are logged for analysis.

(g) Episodic Memory Test

According to this test, the user is in a room in XR with a screen or UI canvas in front of him informing the user to pay attention to the pattern shown on a matrix grid made of cubes, and that they will have to select the matching pattern. When the test is started, a matrix grid will be shown to the user with a random sequence of randomly colored cubes. The grid will disappear after a few moments, and three more grids will be shown to the user. One grid will have the same pattern as the first grid shown. The other two grids will be random sequences with random colors. Using the laser pointer emitting from the controller and the trigger, the user must select the matching grid. The amount of time taken to make a selection and whether or not the selection was correct is logged for analysis. FIG. 39 a diagram depicting an implementation of one embodiment of this test.

(h) Inductive Reasoning Test

According to this test, the user is in a room in XR with a screen or UI canvas in front of him informing the user to pay attention to the pattern shown on a matrix grid made of similar random 3D objects of a single category, and then they select an object from that grid's category from a list of objects that contains one item from the category and other random objects not in that category. When the test is started, a matrix grid made of similar random 3D objects of a single category (e.g. Sea Creatures), is shown to the user. Also, directly in front of the user is another matrix grid made of one random option from the category of the grid shown to the user and several random objects that are not of that category. Using the laser pointer emitting from the controller and the trigger, the user must pick the object that is in the correct category. This process is repeated a configured number of times. When the test is complete, time taken to complete all trials of the test and how many times the chose correctly is logged for analysis.

(i) Loop and Wire Test

According to this test, the user is in a room in XR with a screen or UI canvas in front of him instructing him to move the loop across the wire without touching the wire to the best of his ability. The test starts when the user uses his controller and the grab button to grab the handle of the loop. The user then must traverse the wire until the end. When the loop touches the wire, a buzzing sound effect will be played, and the amount of time the loop touches the wire is added to a running summation. When the user reaches the other end of the wire, the test is complete. Total time taken to complete the test, total time the loop touched the wire, and the percentage of time the loop touched the wire is all logged for analysis. FIG. 40 comprises a diagram depicting an implementation of one embodiment of this test.

(j) Marble in a Labyrinth Test

According to this test, the user is in a room in XR with a screen or UI canvas in front of him instructing him to move the ball across the maze into the hole on the other side of the box. In front of him, following his hand movements, is a maze in a semitransparent box. When the user's hands are stable and they pull the trigger on one of his controllers, the test starts and a ball is spawned at the starting location of the maze. Then, using hand movements and balancing, the user must navigate the ball to the other side of the maze and into the hole. The amount of time taken to complete the test is logged for analysis (k) Read Words Test According to this test, the user is in a room in XR with a screen or UI canvas in front of him instructing him to read the words out loud as they are shown to him, with instructions to say a certain word to begin the test. When the test starts a random pool of words of a configured count is generated and the first word is shown to the user. Speech recognition starts listening for any word that is spoken. When a word is recognized, it is compared to the word shown, and either added to a correct or incorrect list of words said. This process is repeated until all words in the random word pool are exhausted. When the test is complete, the actual words, the correct words spoken, and incorrect words spoken are logged for analysis.

(l) Repeat Words Test

According to this test, the user is in a room in XR with a screen or UI canvas in front of him instructing him to repeat the word they hear out loud as they are spoken to him by a narrator, with instructions to say a certain word to begin the test. When the test starts a random pool of words of a configured count is generated and the first word is said to the user by the narrator. Speech recognition starts listening for any word that is spoken. When a word is recognized, it is compared to the word that is spoken to the user, and either added to a correct or incorrect list of words said. This process is repeated until all the words in the random word pool are exhausted. When the test is complete, the actual words spoken to the user, the correct words spoken, and incorrect words spoken are logged for analysis.

(m) Repeat Items Test

According to this test, the user is in a room in XR with a screen or UI canvas in front of him instructing him to say the name of the object that appears is out loud as they are shown to him, with instructions to say a certain word to begin the test. When the test starts a random pool of objects of a configured count is generated and the first object is shown to the user. Speech recognition starts listening for any word that is spoken. When a word is recognized, it is compared to the name of the object shown, and either added to a correct or incorrect list of words said. This process is repeated until all objects in the random object pool are exhausted. When the test is complete, the actual object names, the correct words spoken, and incorrect words spoken are logged for analysis.

(n) Selective Attention Test

According to this test, the user is in a room in XR with a screen or UI canvas in front of him instructing him to pull the trigger on his controller as fast as they can when they see a certain object (e.g., a baseball). There are also instructions to count the number of times they see the certain object, as they will be asked at the end of the test for the count. There is also instructions to pull the trigger to start the test. When the test is started the user is shown a series of random objects shown to the user at a fixed rate at a fixed location. The number of objects shown, time shown, and time between objects is all configurable. When the user sees the specified object from the instructions, they must pull the trigger as fast as they can. If the user presses the trigger while the object is not showing, an errant trigger pull is logged. At the end of the test, they are shown a numpad, and asked to enter the number of times they were shown that specific object. The controller's lasers are activated and the user must enter the number of times they were shown they object using the numpad, laser, and trigger. Once this is complete, his best reaction time, worst reaction time, his average reaction time, number of errant trigger pulls, the actual number of times they were shown the object, the number they entered, and how many times they correctly pulled the trigger are logged for analysis.

(o) Serial N Test

According to this test, the user is in a room in XR with a screen or UI canvas in front of him instructing him to answer the math problem shown on the canvas until 0 is reached. There is also instructions to pull the trigger to start the test. When the test is started, the math problem is shown to the user. The problem is a simple subtraction question, with a configurable starting number that is subtracted by a configurable "Serial N" number.

For example, 100-7=?

In this case, 100 is the configured starting number, 7 is the "Serial N" number, and 93 is the answer. The user then must enter the correct answer to the subtraction problem on the numpad using the laser and trigger on his controllers before moving to the next question. A correct sound will be played if the correct number is entered, the new number is now the number that was entered and the "Serial N" number remains the same.

For example, 93-7=?

In this case, 93 is the new starting number, 7 remains the "Serial N" and 86 is the new answer. An incorrect sound will be played if an incorrect number is entered and the numpad is reset.

This process is repeated until 0 is either reached or passed. When the test is complete, total time taken to complete the test and times the incorrect number was entered is logged for analysis.

(p) Spatial Span Memory Test

According to this test, the user is in a room in XR with a screen or UI canvas in front of him instructing him to repeat the pattern, order and color, they see on the matrix grid made of cubes. When the test is started, the user will be shown two matrix grids. One matrix grid will show a random pattern with a configurable number of cubes. The pattern will comprise a cube at a random location in the grid comprised of a random color (from a finite list of colors) shown for a few moments. The next random cube will be next shown for a few moments and repeated until the configured starting number has been reached. Using his laser pointer and trigger, the user must replicate the pattern on the neighboring matrix grid. They start by selecting the first cube in the pattern. If this selection is wrong, his selection grid is reset and the pattern is shown to him again on the example grid. Then, the user must cycle through the colors by pulling the trigger multiple times while the laser is still on the cube until they reach his desired color. The user can then move onto the next cube in the pattern. If at any point the selected cube was not part of the pattern, his selection grid is reset and the pattern is shown to him again on the example grid. Once the pattern is matched, sequence and colors, the next pattern is moved onto. This process is repeated until the configured number of tests is exhausted and the user has successfully replicated each random pattern shown to him. The number of cubes in the sequence is incremented after each pattern completed. When the test is complete, total time taken to complete the test and how many times the grid was reset are logged for analysis.

(q) Spell Backwards Test

According to this test, the user is in a room in XR with a screen or UI canvas in front of him instructing him to spell the word on the canvas backwards. When the test is started, a random word is chosen from the word pool and displayed to the user. Also, the user's controllers' lasers are activated and a QWERTY keyboard appears in front of him. Using the laser pointer emitting from his controller and the trigger, the user must spell the word backwards. There is a click sound with each letter selection to let the user know they've made a selection. This process is repeated until the number of letters in the assigned word has been met, then the test is complete. The amount of time taken to choose all the letters, the word given to the user, and all his chosen letters, are all logged for analysis. FIG. 41 comprises a diagram depicting an implementation of one embodiment of this test.

(r) Sustained Attention Test

According to this test, the user is in a room in XR with a screen or UI canvas in front of him instructing him to pull the trigger on his controller as fast as they can when they see a certain number. There are also instructions to pull the trigger to start the test. When the test is started the user is shown a series of random 3D numbers at a fixed rate and at a fixed location, with an "X" or an "X" within a circle appearing in the time between when each 3D number is shown. The number of objects shown, time shown, and time between objects is all configurable. When the user sees the specified number from the instructions, they must pull the trigger as fast as they can. If the user presses the trigger while the object is not showing, an errant trigger pull is logged. Once this is complete, his best reaction time, worst reaction time, his average reaction time, number of errant trigger pulls, the actual number of times they were shown the object, and how many times they correctly pulled the trigger are logged for analysis.

(s) Finger Tapping Test

According to this test, the user is in a room in XR with a screen or UI canvas in front of him instructing him to pull the trigger on his controller as many times as they can in the allotted time. There are also instructions to pull the trigger to start the test. There is also a light bulb in front of him that will illuminate when they pull the trigger, until released. When the test is started, the user must pull the trigger as many times as they can in the allotted configurable amount of time. Once this is complete, the number of times the user pulled the trigger is logged for analysis.

(t) Time Guess Test

According to this test, the user is in a room in XR with a screen or UI canvas in front of him instructing him to wait until it is time for him to guess how many seconds have gone by since starting the test. There are also instructions to pull the trigger to start the test. There is also a numpad that will appear when the random amount of time (in a configurable range) has passed. When the test is started, the user is shown a waiting animation until the random time has passed. Once the random time has passed, the user must enter how many seconds they believe has passed since they first pulled the trigger to start the test. The amount of time they guessed and the actual amount of time that passed is logged for analysis.

(u) Visual Spatial Counting Test

According to this test, the user is in a room in XR with a screen or UI canvas in front of him instructing him to count the number of balls that appear in front of him as well as instructions to start by squeezing the trigger. When the test is started, a random number of balls (within a configurable range) will appear in front of the user. Instructions appear to let the user know to pull the trigger on his controller once they've counted all the balls and are ready to enter. When the user pulls the trigger, the balls will disappear, a numpad will appear and lasers will appear from his controllers to allow the user to enter the number on the numpad. After the user enters the number and presses enter, the test is complete. The amount of time taken to complete the test, the actual number of balls, and the number that they entered is logged for analysis.

(v) Visuospatial Matrix Test

According to this test, the user is in a room in XR with a screen or UI canvas in front of him instructing him to repeat the pattern, order and color, they see on the matrix grid made of cubes. When the test is started, the user will be shown two matrix grids. One matrix grid will show a random pattern with a configurable number of cubes. The pattern will comprise a configurable number of cubes at random locations in the grid comprised of a random color (from a finite list of colors) shown all together for a few moments. Using his laser pointer and trigger, the user must replicate the pattern on the neighboring matrix grid. Then, the user must select the desired cube and cycle through the colors by pulling the trigger multiple times while the laser is still on the cube until they reach his desired color. Once the pattern is matched and colors match as well, the test is complete. When the test is complete, total time taken to complete the test are logged for analysis.

(w) Working Memory Test

According to this test, the user is in a room in XR with a screen or UI canvas in front of him instructing him to repeat the pattern, order and color, they see on the matrix grid made of cubes. When the test is started, the user will be shown two matrix grids. One matrix grid will show a random pattern with a configurable number of cubes. The pattern will comprise a cube at a random location in the grid comprised of a random color (from a finite list of colors) shown for a few moments. The next random cube will be next shown for a few moments and repeated until the configured starting number has been reached. Using his laser pointer and trigger, the user must replicate the pattern on the neighboring matrix grid. They start by selecting the first cube in the pattern. If this selection is wrong, his selection grid is reset and the pattern is shown to him again on the example grid. Then, the user must cycle through the colors by pulling the trigger multiple times while the laser is still on the cube until they reach his desired color. The user can then move onto the next cube in the pattern. If at any point the selected cube was not part of the pattern, his selection grid is reset and the pattern is shown to him again on the example grid. Once the pattern is matched, sequence and colors, the test is complete. When the test is complete, total time taken to complete the test and how many times the grid was reset are logged for analysis.

(x) Digit Span Memory Test

According to this test, the user is in a room in XR with a screen or UI canvas in front of him instructing him to say a keyword to begin the test. The screen/canvas also includes brief instructions for how to perform the test. There is also a metric displayed for longest span, which is updated every time the user reaches a new high score for number of digits in the span. Once user says the keyword, and it is recognized by the voice recognition system, the test starts. Once the test starts, the first random digit in the digit span sequence is shown for a short, configurable amount of time. After the digit is shown, it disappears, and a microphone icon with instructions to say the list of digits that was shown (in this case, just the one). The user should then say the number that was shown. If they say the correct number, a "correct sound" is played. If they say the final number in the sequence correctly, a "correct sequence sound" is played. As the user speaks, the microphone icon will fill with the microphone input's loudness, giving the user visual feedback that his voice is heard. The number said is then shown again, followed by a new random number. The user must then say both numbers in the sequence. This process repeats, and the sequence grows with each response until the user says a wrong number. Each response as well as whether the response was correct or not are logged for later analysis. When a wrong number is said, an "incorrect sound" is played, and the screen/canvas is taken back to the original text with the instructions to say the starting keyword once again. The process then repeats once the keyword is said.

(y) Psychomotor Vigilance Test

According to this test, the user is in a room in XR with a screen or UI canvas in front of him instructing him to pull the trigger on his controller to begin. The screen/canvas also include brief instructions for how to perform the test. The screen/canvas in this scenario has several metrics including: current reaction time, average reaction time, best reaction time, and time left. Once the user begins the test, after a brief, random amount of time that falls within a configurable range, a light is shown on the screen/canvas. When the user sees the light, as instructed, they are to squeeze the trigger on either of his controllers. Once they do so the amount of time (to the nearest millisecond) taken to squeeze the trigger is displayed for current reaction time. If the time is less than his best reaction time in this sequence of lights, the best reaction time is updated. All the reaction times in this sequence of lights are averaged and displayed for average reaction time. This process is then repeated until a configurable amount of time is reached. Once the time limit is reached, the screen/canvas is then taken back to the original instructions, with their metrics from the last sequence still displayed. Reaction times are logged for later analysis. The metrics are then cleared when the next sequence is started by the user.

(z) Variation of the Psychomotor Vigilance Test

According to a variation of the above psychomotor vigilance test, the user is in a room in XR with a screen or UI canvas in front of him instructing him to pull the trigger on his controller to begin. The screen/canvas also include brief instructions for how to perform the test. The screen/canvas in this scenario has several metrics including: current reaction time, average reaction time, best reaction time, and time left. Once the user begins the test, after a brief random amount of time that falls within a configurable range, a light is shown on the screen/canvas. When the user sees the light, as instructed, they are to squeeze the trigger on either of his controllers. Once they do so, the time taken to pull the trigger since the light was shown is logged and a "ding" sound is played. This process is then repeated until a configurable amount of time is reached. If the user pulls the trigger and the light is not showing, an errant trigger pull is logged and an incorrect sound is played. Reaction times, average time, best time, and worst time, and any errant trigger pulls are logged for later analysis.

(aa) Stroop Test

According to this test, the user is in a room in XR with a screen or UI canvas in front of him instructing him so say a keyword to begin the test. The screen/canvas also include brief instructions for how to perform the test. The screen/canvas in this scenario have several metrics including: current reaction time, average reaction time, best reaction time, time left, and what the user should be saying. Once the user begins the test, after a brief, configurable amount of time, a random color word is shown. The color of the font the of the word is also random and may or may not match the actual spelled word. The random colors/words are chosen randomly from a configurable list that can contain any amount of colors/words. There are three different test modes including one where the user must say the color font of the words, a second where the user must say the actual words themselves, and a third where they must randomly say the font color or the word as instructed when the word is shown. The user then says a color.

If the color said was correct, a "correct sound" is played. The amount of time (to the nearest millisecond) the user took to say the word is displayed for current reaction time. If the time is less than his best reaction time in this sequence of lights, the best reaction time is updated. All the reaction times in this sequence of lights are averaged and displayed for average reaction time. The user is displayed the next color.

If the color said was incorrect, an "incorrect sound" is played. The user is displayed the next color. This process is then repeated until a configurable amount of time is reached. Once the time limit is reached, the screen/canvas is then taken back to the original instructions with their metrics from the last sequence still displayed. Metrics relating to the Stroop Test are logged for later analysis. The metrics are then cleared when the next sequence is started by the user.

(bb) Another variation of the Stroop Test

According to this variation, the user is in a room in XR with a screen or UI canvas in front of him instructing him to select the color of the text of the word shown to him. And instructions to pull the trigger to begin. Once the user begins the test, after a brief, configurable amount of time, a random color word is shown. The color of the font the of the word is also random and may or may not match the actual spelled word. The random colors/words are chosen randomly from a configurable list that can contain any amount of colors/words. The user then chooses a color using lasers emitted from his controllers and the trigger. The user has no indication of right or wrong answer. This process is then repeated until a configurable amount of time is reached. The average time per word, best time, worst time, and wrong selections are logged for analysis.

(cc) Trail Finder

According to this test, the user is started on a large platform in XR with a large screen/UI canvas out in the distance in front of him. The screen/canvas also include brief instructions for how to perform the test, a timer, and instructions for starting the test by squeezing the trigger. A configurable number of number-labeled objects are spawned in random locations within a confined, configurable amount of space. The user must point a laser coming from his controller at the object with the next label in the numerical sequence and squeeze the trigger. As the user's pointer enters the object's collider, regardless if the object is next in the sequence, the object is applied with a highlight shader to let the user know his laser is colliding with one of the objects. The object's shader is returned to normal if the user's laser exits the collider without correct selection. If the user correctly squeezes the trigger while his laser is colliding with the next object in the sequence a "correct sound" is played. A line is rendered, connecting the previous object in the sequence (if one exists) with the one just selected by the user. The object remains highlighted for the remaining time of the test. If the user incorrectly squeezes the trigger while his laser is colliding with an object that is not next in the sequence, an "incorrect sound" is played. Once each of the objects in the sequence are correctly selected by the user the timer displaying the amount of time the user took to complete the test is stopped. A "sequence correct" sound is played. The screen/canvas is returned to the original instructions with the timer from the sequence just completed by the user still there until the next sequence is started. Metrics relating to the test are logged for later analysis.

(dd) Variation of the Trail Finder Test

According to one variation of the Trail Finder Test, the user is in a room in XR with a screen or UI canvas in front of him instructing him to choose the numbered balls in order from least to greatest until all balls are exhausted as fast as they can. Instructions are provided for starting the test by squeezing the trigger. A configurable number of number-labeled balls are spawned in random locations within a confined, configurable amount of space. The user must point a laser coming from his controller at the object with the next label in the numerical sequence and squeeze the trigger as the user's pointer enters the object's collider, regardless if the object is next in the sequence. The object is applied with a highlight shader to let the user know his laser is colliding with one of the objects. The object's shader is returned to normal if the user's laser exits the collider without correct selection. If the user correctly squeezes the trigger while his laser is colliding with the next object in the sequence, a "correct sound" is played. A line is rendered, connecting the previous object in the sequence (if one exists) with the one just selected by the user. The object remains highlighted for the remaining time of the test. If the user incorrectly squeezes the trigger while his laser is colliding with an object that is not next in the sequence, an "incorrect sound" is played. Once each of the objects in the sequence are correctly selected by the user, a final correct sound is played. The test is ended. The total amount of time and the average time per ball is logged for analysis.

ADL, IADL, and Practical Task Feature

An ADL, IADL, and practical task feature of the exemplary Neurological Module may be use for the assessment of, treatment of, training in and/or rehabilitation in household tasks, ambulation-based tasks, one or more tasks relating to home safety and/or personal safety, tasks relating to fall risk, tasks relating to Activities of Daily Living (ADLs), and/or tasks relating to Instrumental Activities of Daily Living (IADLs). According to this exemplary feature, one or more of the above tasks may be performed using one or more of the items described in the patient decision support feature with the Clinical Platform Module. The exemplary feature may comprise a system for XR decision support in the day-to-day lives of individuals using platform features and/or using any combination of such features, and/or ML/AI models, and/or patient input methods, and/or points of platform data to accomplish certain tasks, such as nudging and/or influencing a patient towards healthy decisions and/or actions by delivering timely, specific, and actionable messages, notifications, and/or communications recommending actions that are both realistic and measurable. Other exemplary tasks may include shielding the patient from, and/or decreasing the odds of, unhealthy decisions and/or actions. Such tasks may further include shielding the patient from and/or decreasing the odds of injury. The exemplary feature may be deployed either in the real-world (for example using augmented reality glasses), and/or using a real-life simulation (such as in a simulated house and neighborhood virtual environment), and/or using XR.

Neuroplasticity Feature

A neuroplasticity feature of the exemplary Neurological Module may be utilized for leveraging neuroplasticity to educate and/or instruct patients on topics and/or issues related to their health. Upon the delivery of items of educational content, the patient may indicate that the content is of educational interest using one or more patient input methods. The content is then tagged as interesting. One or more items may be tagged as priority educational content for the patient by clinicians and/or ML/AI models. Any interesting and/or priority educational content may be added to a que of important items of educational content. Each item may be subsequently re-delivered in future scenes and/or sessions (either as a snippet and/or as other content) at a specific timing and/or frequency while leveraging characteristics of neuroplasticity to maximize comprehension and long-term retention.

Health Literacy Feature

The exemplary Neurological Module may further comprise a health literacy feature. According to this feature, the health literacy and/or health efficacy and/or patient ability to navigate the healthcare system of patients are assessed and/or improved through spoken, written, and/or visually-based interactions with clinicians, using the Q&A feature, and/or through other interactions controlled by ML/AI models and/or clinicians.

Alzheimer's and Dementia Feature

An Alzheimer's and dementia feature of the exemplary Neurological Module may be used for detecting and/or screening for Alzheimer's disease and/or dementia using ML/AI models, voice and/or vocal biomarker analysis features, facial tracking, facial computer vision analyses, pupil and/or eye tracking, positional tracking, the Q&A feature, Movement Module features, Mental Health Module features, Clinical Platform Module features, Neurological Module features, other platform features, and/or using other platform data points. In one exemplary embodiment, this exemplary feature comprises neurocognitive assessments wherein features of the Neurological Module and/or as described in the Clinical Platform Module may be performed (either intentionally and/or passively), and patient inputs and/or actions are logged and stored in a database. In another exemplary embodiment, the present feature comprises movement assessments wherein features of the Neurological Module and/or Movement Module and/or as described in the Clinical Platform Module may be performed (either intentionally and/or passively). Patient inputs and/or actions are logged and stored in a database.

Any the logged datasets from assessments are compared to repeat assessments and/or population normal values (customized for the age and gender of the patient) by clinicians and/or ML/AI models. According to one exemplary embodiment, this comparison is implemented to identify if patient has had significant changes and/or remarkable results indicative of Alzheimer's and/or dementia in cognitive domains, movement assessments, and/or other neurological characteristics and/or features as described herein. The changes and/or clinically remarkable results may include (a) change and/or clinically remarkable results in voice features detectable through vocal analysis, NLP, STT, and/or similar ML/AI models; (b) change and/or clinically remarkable results in facial features detectable through computer vision algorithms, and/or other ML/AI models; (c) change and/or clinically remarkable results in performance on one or more cognitive domain tests with or without using ML/AI models; (d) change and/or clinically remarkable results in performance on one or more assessments of ability to carry out ADLs and/or IADLs with or without using ML/AI models; (e) change and/or clinically remarkable results in performance on one or more assessments of movement, and in particular gait and/or ability to ambulate using ML/AI models; (f) change and/or clinically remarkable results in patterns of patient inputs using data obtained from patient input methods during sessions using ML/AI models; (g) clinically remarkable results relating to other platform data points; and (h) clinically remarkable results relating to other platform features.

In another exemplary embodiment of the present module, any of the logged datasets from baseline assessments as well as repeat assessments are processed and/or analyzed by ML/AI models to identify any significant differences between any two or more assessments.

In another exemplary embodiment, the present module utilizing one or more of the features described for the patient decision support feature described herein.

In another exemplary embodiment, the present module comprises a feature wherein a patient completes way-finding, spatial orientation, and/or other navigational tasks and/or questions in XR.

In another exemplary embodiment, the present module uses functionalities of the Q&A Module to assess the patient's ability to recall details of the virtual environment experienced in the previous and/or current scenes including the position, rotation, and/or location of objects, content and/or feature(s) in XR (including the position, rotation, and/or location of the patient within the XR scenes).

In another exemplary embodiment, the present module comprises a feature wherein a patient completes tests of the patient's sense of smell.

In another exemplary embodiment, one modified implementation of the present module focuses on the detection and/or screening for Parkinson's disease. The implementation may include one or more of the above items, and additionally with tasks requiring patients to draw objects in XR using patient input methods, and where the drawing(s) produced by the patient are used as inputs and/or outputs for one or more ML/AI models and/or used by clinicians for the purposes of detecting and/or screening for the presence of Parkinson's disease.

Stroke Feature

A stroke feature of the exemplary Neurological Module may be used for detecting and/or screening for stroke and/or to monitor stroke recovery and/or to assist in stroke rehabilitation. This feature may utilize ML/AI models, voice and/or vocal biomarker analysis features, facial tracking, pupil and/or eye tracking, positional tracking, Q&A functionalities, Movement Module functionalities, one or more Audio Module functionalities, Tactile Module functionalities, Clinical Platform Module functionalities, other Neurological Module functionalities, and/or one or more other platform data points.

In one exemplary embodiment, the present module comprises a baseline neurocognitive assessment. Other features of the Neurological Module and as described in the Clinical Platform module are performed (either intentionally and/or passively) and patient inputs and/or actions that can be captured are logged and stored in a database.

In another exemplary embodiment, the present module comprises a baseline movement assessment including features of the Neurological Module and/or Movement Module, and as described in the Clinical Platform Module. These features are performed (either intentionally and/or passively), and patient inputs and/or actions are logged and stored in a database.

Over time, repeat neurocognitive assessments including features of the Neurological Module and/or as described in the Clinical Platform Module are performed (either intentionally and/or passively), and patient inputs and/or actions logged and stored in a database. Over time, repeat movement assessments including features of the Neurological Module and/or Movement Module and/or as described in the Clinical Platform Module are performed (either intentionally and/or passively), and patient inputs and or actions logged and stored in a database.

Any of the logged datasets from baseline assessments are compared to one or more repeat assessments and/or population normal values (customized for the age and gender of the patient) by clinicians and/or ML/AI models. The clinicians and/or ML/AI models are used to determine if the patient has had significant changes indicative of stroke. The changes indicative of a stroke may include: change in voice; change in performance on the hearing assessment described above; change in performance on of the vision assessments described above, including assessments of visual fields and/or spatial neglect; change in facial and/or pupil features; change in performance on cognitive domain tests; change in cranial nerve assessment scores; change in performance on mental status assessments; change in performance on arousal assessments; change in performance on assessments of ability to carry out ADLs and/or IADLs; and/or change in performance on assessments of movement and/or sensation.

Any of the logged datasets from baseline assessments as well as repeat assessments may be processed and/or analyzed by ML/AI models to identify any significant differences between any two or more assessments.

L. Mental Health Module

In exemplary embodiments, the present XR Health Platform may further comprise a Mental Health Module. This module contains features that, either alone, or in combination with one or more other platform features, enable the screening for, detection of, diagnosis of, treatment of, optimization of, and/or rehabilitation from, issues and/or diseases relating to and/or involving mental health. Aspects of the present Mental Health Module may utilize platform features, points of platform data and/or ML/AI models. Additionally, the Mental Health Module may incorporate one or more of the features described below.

Emotional Intelligence Feature

An emotional intelligence feature of the exemplary Mental Health Module may be utilized for Emotional Intelligence (EQ) assessment and/or training through examining and/or addressing a patient's self-awareness, self-regulation, situational awareness, motivation, social skills, and/or empathy (EQ constructs). Exemplary embodiments may comprise a feature where points of platform data and/or changes in platform data and/or interactions, triggers changes to one or more platform features and/or features and/or content within a scene in order to assess and/or treat a patient's self-awareness, self-regulation, situational awareness, motivation, social skills and/or empathy. The triggered changes may be configured by clinicians and/or ML/AI models.

Insight from Replay Feature

According to an insight from replay feature of the exemplary Mental Health Module, a patient is shown replays of himself from 1st and/or 3rd person perspectives during scenes and/or sessions using a variation of the replay feature. Alternatively, the patient may be shown altered replays of himself from the 1st and/or 3rd person perspectives during scenes and/or sessions using a variation of the replay feature. The alterations to replays may be configured by clinicians and/or ML/AI models.

In a variation on this feature, characteristics of the avatar featured in the replay are altered (such as changing the avatars shape, size, color, texture, shader, the avatar's voice, and/or other characteristics) to deliver insight and elicit one or more emotional, neurocognitive, pain, and/or health-related responses.

In a second variation on this feature, an altered and/or unaltered avatar replay is delivered as a "video vignette" showing the replay from a 3rd person perspective. Using ML/AI models, additional virtual human avatars and/or other platform features, the patient is simultaneously shown and/or taken through a vignette showing how maladaptive/negative thoughts can lead to negative feelings or emotions which in turn can lead to cognitive distortions and eventually mental health-related illness. This variation may or may not include other points of platform data, content, and/or utilize other platform features to yield additional therapeutic value, patient educational value and/or patient insight.

Insight from Audio Replay Feature

According to an insight from audio replay feature of the exemplary Mental Health Module, a patient is played audio recordings of his own voice with one or more of the features described in the Audio Module described herein being incorporated and/or as originating from 3rd person locations (including one or more virtual human avatars) during scenes and/or sessions. In a variation on this feature, characteristics of the playback audio are altered to deliver insight and/or to deliver insight and elicit one or more emotional, neurocognitive, pain, and/or health-related responses.

Social Simulation Feature

According to a social simulation feature of the exemplary Mental Health Module, a scene and/or feature within scenes triggers changes to one or more of the avatars. The scene or feature within scenes may comprise social simulation scenarios created using a plurality of configurable virtual human avatars with platform data points and/or changes in platform data and/or interactions. The configurations and/or changes may be configured by clinicians and/or one or more ML/AI models.

Second Person Perspective Feature

According to a second person perspective feature of the exemplary Mental Health Module, two perspectives are shared between two patients and/or clinicians with one seeing an XR perspective and the other seeing a real-world perspective. One participant may have exclusive control over XR objects, and the other participant may have exclusive control over a separate set of XR objects within the same scene.

Mental Health Diagnosis Feature

A mental health diagnosis feature of the exemplary Mental Health Module may comprise a system to screen for, identify, detect and/or diagnose mental health, psychological, psychiatric, cognitive, and/or behavioral issues or diseases.

In one exemplary embodiment, this module feature utilizes Q&A functionalities. In another exemplary embodiment, this module feature utilizes positional tracking functionalities for the detection and/or identification of psychomotor agitation, and/or restlessness, and/or any other movement-related manifestation of psychological, psychiatric, or mental health-related issues, illnesses, and/or diseases. In another exemplary embodiment, this module feature utilizes analysis of biometric data, with or without the use of ML and/or AI models. In another exemplary embodiment, this module feature utilizes patient actions and/or patient platform actions within one more XR scenes and/or sessions, and/or patient interactions with features, avatars, and/or objects within the scenes and/or sessions. In another exemplary embodiment, this module feature utilizes communications between a patient and clinician(s) through the use of the communications feature described herein. In another exemplary embodiment, this module feature utilizes text, audio, voice, and/or visually based interactions between patients and virtual human avatars, items of platform content, and/or other platform features that are controlled and/or configured by ML/AI models. In another exemplary embodiment, this module feature utilizes analysis of points of platform data, either during or between sessions, with or without the use of ML and/or AI models. In another exemplary embodiment, this module feature may utilize analysis and/or assessment of a patient's level of arousal, pain, pleasure, stress, emotion, and/or mood. This assessment may comprise positional tracking data, facial tracking data, eye tracking data, temporal data, biometric data, voice/vocal biomarker data, platform metadata, points of any other platform data, and ML/AI models.

Automatic Thought Record Feature

An automatic thought record feature of the exemplary Mental Health Module may be used for facilitated and/or automated completion of an automatic thought record and/or to determine a patients attributional style (e.g., how someone explains to himself why certain things happen) and whether the attributional style tends to be more positive and/or negative. This may be completed through spoken, text-based, visually-based, and/or movement-based interactions with a virtual human avatar in XR, a web portal, a companion application, and/or through direct or asynchronous interactions with a clinician using the communications feature, and/or using ML/AI models.

In one exemplary embodiment of this module feature, a clinician and/or ML/AI model creates, selects, configures, and/or modifies text-based questions relating to automatic thoughts. Questions are converted from text to spoken audio files using ML/AI models. Audio files are converted to appropriate format for consumption in XR. When the patient either begins a new XR session and/or next logs on to a web portal and/or uses a companion application, and/or when pre-configured times, interactions, or events occur within a scene, a call is made to the API which in turn delivers any needed audio files as set by a clinician and/or ML/AI models. Audio representing questions are played from a virtual human avatar and/or media player for the patient.

After each question, any subsequent spoken statements are either converted to text on a local computer using ML/AI models, and/or recorded with the audio files themselves being uploaded to a database for analysis and/or transcription. Patient responses to questions are compared to normative databases and/or analyzed through other means using clinicians and/or ML/AI models to populate the patient's autonomic thought record and/or to identify the patient's attributional style during scenes and/or sessions. Based on the patient's responses to questions, certain additional actions may occur to either get more information and/or as a therapeutic action, either in near-real-time and/or asynchronously. Exemplary additional actions may include: patient gets additional questions (snippets) recited and/or delivered to him; patient has statements (snippets) recited and/or delivered to him; changes to the platform content and/or features; and/or changes to the configuration of platform features, platform modules, scenes, sessions, and/or regimens; actions utilizing one or more of the steps or items outlined in any other feature described herein. In one variation of this feature, a clinician and/or ML/AI models creates, selects, configures, and/or modifies statements designed to elicit one or more automatic thoughts, negative thoughts, negative emotions, negative feelings and/or cognitive distortions. Any subsequent patient responses may then be examined by clinicians, virtual human avatars, and/or ML/AI models to yield additional diagnostic and/or clinically relevant information.

Automatic Identification of Feelings Feature

An automatic identification of feelings feature of the exemplary Mental Health Module may be used for automatic identification of patient feelings. According to this module feature, snippets, platform features, items of XR content, interactions and/or events designed to evoke one or more automatic thoughts may be applied to elicit certain feelings at certain times. The parameters surrounding attempts at eliciting these feelings may be configured by clinicians and/or by ML/AI models. The snippets, platform features, items of XR content, interactions and/or events may include open-ended questions asked by virtual human avatars which are controlled and/or configured by clinicians and/or ML/AI models. The snippets, platform features, items of XR content, interactions and/or events may further include open-ended questions asked within XR controlled and/or configured by clinicians and/or ML/AI models. Open-ended questions may also be asked using the Q&A feature and/or by clinicians using the communications feature.

In another exemplary embodiment, the present module feature may comprise a process for identification of single-word feelings expressed by one or more patients in scenes, sessions, and/or regimens. The patient engages in a spoken, written, and/or visually-based dialogue with one or more clinicians, ML/AI models, virtual human avatars, and/or other platform features. Any patient speech data is converted to text and the speech data (e.g. audio data) is logged. Sentiment analysis is performed on the speech and/or text data to indicate if portions of the dialogue were either positive or negative in nature, and to screen for the potential presence of negative statements and/or single-word feelings. By comparison against a reference list/database of single-word feelings, ML/AI models are applied to any text transcript(s) and/or speech data to identify if any single-word feelings were expressed, and if so, which ones were expressed. For each instance of an identified single-word feeling, the sentences and/or paragraphs containing identified single-word feelings may be logged.

Each single-word feeling in the reference list/database has an associated arousal/intensity annotation (tag), and an associated valence (degree of positivity or negativity) annotation that are logged and/or returned to ML/AI models. Each negative single-word feeling is annotated (tagged) with a list of possible cognitive distortions and/or maladaptive thoughts that are logged and/or returned to ML/AI models. Each instance of a single-word feeling may be associated with one or more identified and/or possible cognitive distortions that are logged and/or returned to ML/AI models.

Any audio and/or text containing any identified single-word feelings, along with any results from any annotations returned per one or more items above may be used as an input and/or output for ML/AI models to yield further insights. Such insights may include possible or likely negative thought patterns used by the patient; possible or likely cognitive distortions used by the patient; aspects, elements, and/or features relating to the mental health and/or mental state of the patient; features associated with and/or relating to positive experiences and/or positive outcomes for the patient; features associated with and/or relating to negative experiences and/or negative outcomes for the patient; the effect and/or influence of therapeutic and/or treatment efforts of the platform; the effect and/or influence of other platform features; and the effect, influence, and/or contextualization of points of platform data with respect to the patient.

Single Word Feelings Feature

A single word feelings feature of the exemplary Mental Health Module is applicable for the identification of single-word feelings or emotions using items of text, Q&A responses, voice and/or video data, and using ML/AI models. This feature compares any text and/or STT model outputs from a patient to a reference list/normative database including single-word feelings or emotions along with any associated tags, labels, and/or annotations ("emotion tags") for each single-word feeling or emotion. The emotion tags either describe characteristics of, and/or identify, specific feelings or emotions, and may also reference related cognitive distortions (for use by the cognitive distortion feature and/or any other platform feature). Exemplary emotion tags may represent qualitative and/or quantitative measurements representing the positive or negative valence/directionality. Exemplary emotion tags may also represent qualitative and/or quantitative measurements representing items consistent with or relating to the level of arousal of a patient. Exemplary emotion tags may also represent qualitative and/or quantitative measurements representing items consistent with, relating to, or found within standardized models of emotional classification and/or classification of feelings or emotions. Exemplary emotion tags may also classify an emotion or feeling as of the following types: related to the properties of objects; related to future appraisal; event-related; related to being introspective or self-appraising; related to social and/or relationship-based issues; related to love; related to hate; related to distress or suffering; related to pleasure; and/or related to any other characteristic or type of emotion or feeling.

Cognitive Distortion Feature

A cognitive distortion feature of the exemplary Mental Health Module may be used for the identification of cognitive distortions used by a patient during scenes, sessions, and/or interactions. XR scene(s), platform features, and/or one or more other items (e.g. snippets, content objects, lighting items, audio items) within a scene or session may be designed to result in exposures of psychologically or mentally stimulating content, and/or elicit psychological responses to evoke the outward manifestation (as text-based, behaviorally based, and/or as a vocal and/or audio manifes-
tation) of various cognitive distortions. Such cognitive dis-
tortions may include all-or-nothing thinking, overgeneral-
ization, global labeling/judgement, catastrophizing, jumping
to conclusions/mind reading, "i should have"/regret orien-
tation, personalization, control fallacy, fallacy of fairness,
fallacy of change, blaming (self or others), projection,
emotional reasoning, heaven's reward fallacy, discounting
the positive/filtering, underestimating coping ability, and
repeating same behavior expecting different results.

ML/AI models and/or other platform features herein may
be used to identify and extract any sentences containing
single-word feelings, and to identify the most likely cogni-
tive distortions, if any, being applied in each sentence
containing single-word feelings. ML/AI models may be
used to compare any transcripts of spoken and/or written
text from a patient to a normative database containing
sentences and/or parts of sentences annotated as being
consistent with the use of cognitive distortions, and to return
any matches. The matches may be an indicator that the
corresponding cognitive distortion was used. Over time
and/or through continued and/or repeat use, patients may
consistently use cognitive distortions more than others,
increasing confidence in any results.

ML/AI models may also be used to determine and/or
extract emotional and/or affective features from available
platform data to identify, detect, and/or determine the use or
potential use of specific cognitive distortions by patients
using the platform.

Mental Health Feature Extraction Feature

A mental health feature extraction feature of the exem-
plary Mental Health Module may be used to capture, extract,
identify, assess, and/or interpret features and/or characteris-
tics relevant to mental health. This feature may use points of
facial tracking, audio tracking and/or audio data (including
intonation, inflection, speed of vocalization, and/or any
other feature which may be extracted and/or derived from
audio and/or voice data), positional tracking, body language
tracking and/or body language data, and/or other points of
platform data. This may be completed either with or without
summative and/or qualitative determinations utilizing points
of facial tracking data, audio tracking data, positional track-
ing data, body language tracking data and/or other points of
platform data. One or more platform features, ML/AI mod-
els, and/or additional points of platform data may also be
utilized to identify, detect, and/or assess features and/or
characteristics related to mental-health. For clarity, any of
the features described within this exemplary feature may
also be used to capture, extract, identify, detect, assess,
and/or interpret emotional and/or affective features and/or
characteristics from patients. Any of the features described
within this exemplary feature may also be used to apply
virtual representations of the emotional and/or affective
features and/or characteristics to virtual human avatars in
XR.

Values Personality and Needs Feature

A values personality and needs feature of the exemplary
Mental Health Module may be used for autonomously
and/or semi-autonomously ascertaining values, personality
traits, and/or needs of patients by combining one or more of
the features described herein.

According to one exemplary embodiment, the present
module feature is implemented using the Q&A feature(s)
described herein to explicitly ask questions and receive any
patient generated answers produced through the use of
patient input methods.

According to another exemplary embodiment, the present
module feature is implemented using ML/AI models to carry
out text-based, spoken, audio-based, and/or visually based
interactions as described elsewhere herein. Additional
ML/AI models may be utilized to identify, annotate, and/or
recognize one or more features in the content produced by
patients. These features may include items relating to
beliefs; items related to and/or indicating what language
style is used (e.g. whether such language tends to be
analytical, confident, or tentative, and the like); items related
to the degree of openness, conscientiousness, extraversion,
agreeableness, and/or neuroticism or emotional range; and
items related to motivational constructs and/or statements
with explicit or implied motivational meaning. These fea-
tures may also include platform data derived using ML/AI
models to contextualize question responses (obtained using
the Q&A feature) based on longitudinal points of platform
data obtained over time to determine if and/or how often the
responses occur within similar contexts. These features may
also include platform data relating to selections or evalua-
tions of patient actions, policies, and/or events occurring
during platform use, and where the Q&A feature, ML/AI
models, or other platform features may be used to elicit such
selections and/or evaluations. These features may also
include patient rankings and/or assessments of the relative
importance of various values, personality traits, and/or needs
obtained using the Q&A feature. These features may also
include platform data relating to any other responses
obtained using the Q&A feature.

According to another exemplary embodiment, the present
module feature is implemented through the use of ML/AI
models to create, modify, and/or configure one or more
scenes where the focus of content, features and/or objects
within the scenes are for the purposes of identifying, anno-
tating, and/or or recognizing one or more characteristics
and/or features relating to values, personality traits, and/or
needs.

Cognitive Bias Feature

A cognitive bias feature of the exemplary Mental Health
Module may be used for the identification and/or treatment
of cognitive biases used by a patient during an XR session
and/or health encounter. XR scene(s) and/or features within
scene(s) may be designed to result in exposures of psycho-
logically stimulating content, and/or elicit psychological
responses to evoke the outward manifestation of one or more
of the cognitive biases. Exemplary cognitive biases may
include fundamental attribution error/correspondence bias
(over-emphasize personality-based explanations for behav-
iors observed in others), confirmation bias, self-serving bias
(claim more responsibility for successes compared to fail-
ures), belief bias, framing (too narrow approach/description
of a situation or issue), and hindsight bias.

The presence and/or outward manifestation of cognitive
biases may be detected and/or identified by patient admis-
sion, and/or through the Q&A feature, and/or through par-
ticipation in XR scenes or sessions. Actions consistent with
biases may be logged through direct interactions with a
clinician (e.g. using the communications feature). Any of the
aforementioned may occur either with or without the utili-
zation of biometric data and/or points of other platform data
to corroborate the biases.

If and/or when cognitive biases are identified, a timely
text-based, video-based, and/or audio-based message may
be delivered to the patient identifying the detected bias along
with insights and/or educational points regarding each bias.
XR scenes and/or platform features designed to deliver
insights and/or educational points regarding the biases may be automatically delivered to the patient in XR either in near-real-time and/or upon engaging in scenes and/or sessions in the future. The selection of scenes and/or features, as well as the timing and frequency of the scenes and/or features may be configured by clinicians and/or ML/AI models.

Mental Health Treatment Feature

A mental health treatment feature of the exemplary Mental Health Module may be used to treat mental health, psychological, psychiatric, cognitive, and/or behavioral issues and/or diseases.

In one exemplary embodiment, this module feature is implemented through the use of XR scenes and/or sessions that change dynamically to attenuate negative or counterproductive thoughts or feelings, as identified using any of the methods contained herein or any other platform features.

In another exemplary embodiment, this module feature is implemented through the use of XR scenes and/or sessions that change dynamically to enhance positive or productive thoughts or feelings, as identified using any of the methods contained herein or any other platform features.

In another exemplary embodiment, this module feature is implemented through the use of platform features relating to scene and/or session creation, selection, modification and/or configuration to produce scenes and/or sessions that attenuate negative or counterproductive thoughts or feelings, and/or enhance positive or productive thoughts or feelings.

In another exemplary embodiment, clinicians and/or ML/AI models may configure, select, create, modify, and/or deploy XR scenes and/or sessions utilizing balanced thinking techniques to address identified automatic thoughts used by a patient.

In another exemplary embodiment, this module feature comprises patient exposure to certain fears, environments, and events. Fears, environments, and/or events may or may not be identified without the need for clinician involvement through the use and/or analysis of points of platform data, either alone, or in combination with ML/AI models.

In another exemplary embodiment, this module feature is implemented using controlled desensitization. Real-world tasks, places, and/or things may be identified by a patient and/or clinician as causing significant stress, fear, angst, and/or any other negative thought pattern or cognitive distortion. Virtual object model approximations of the tasks, places, and/or things may be created and/or obtained by clinicians, admins, and/or ML/AI models, which in turn may be deployed as part of features, scenes, sessions, and/or regimens as configured using one or more items within the Configuration Module. In addition, the features, scenes, sessions, and/or regimens may be configured in such a way that the patient is gradually exposed to escalating intensity of the tasks, places, and/or things identified.

In another exemplary embodiment, this module feature uses points of platform data and/or patient input methods in combination with ML/AI models or other platform features to monitor patient responses while using the platform, and/or to adaptively configure features, scenes or sessions for a patient to improve one or more aspects of mental health.

Cognitive Behavioral Therapy Feature

A cognitive behavioral therapy feature of the exemplary Mental Health Module may be used for automated, semi-automated, and/or manual delivery of personalized cognitive behavioral therapy in XR. This may include other platform features, points of platform data, and/or one or more of the items below.

In one exemplary embodiment, the present module feature comprises identification of cognitive distortion(s) through the use of the Q&A feature, through platform actions, and/or through detecting or identifying patient platform actions or patient behaviors in XR.

In another exemplary embodiment, the present module feature comprises identification of cognitive distortion(s) through the related features and/or other functionalities described within the Mental Health Module.

In another exemplary embodiment, the present module feature comprises a method to select, prioritize, deliver appropriate therapeutic statements (as snippets and/or content objects) and/or address cognitive distortion(s), automatic/maladaptive thought(s), negative feeling(s), and/or emotion(s) with TTS. This may be completed by utilizing one or more of the related features described herein.

According to one exemplary embodiment, therapeutic sentences/statements/questions (which may be snippets and/or content objects) are entered by clinicians as voice or text using XR, a web portal, and/or a companion application. Each sentence/statement is associated with at least one tag which may represent cognitive distortion(s), automatic/maladaptive thought(s), negative feeling(s), and/or emotion(s), diseases, disease criteria, and/or other health related parameter(s) or item(s).

According to another exemplary embodiment, text sentences/statements/questions are converted to audio files using one or more text-to-speech ML/AI models, and/or spoken voice sentences/statements/questions are converted to text using speech-to-text STT ML/AI models, and each sentence/statement/question text and/or audio is stored in a database alongside any tags, annotations, and/or labels identifying any cognitive distortion(s), automatic/maladaptive thought(s), negative feeling(s), negative emotion(s), diseases, disease criteria, and/or other health related parameter(s).

According to another exemplary embodiment, when cognitive distortion(s), automatic/maladaptive thought(s), negative feeling(s), and/or negative emotion(s) are identified as likely to have been used either in the present session or in a previous session (by meeting qualitative and/or qualitative criteria, and/or using of the methods outlined herein), therapeutic snippets may be played as an audio track and/or displayed as text to combat the cognitive distortion(s), automatic/maladaptive thought(s), negative feeling(s), and/or negative emotion(s). The therapeutic snippets may also deliver insights by highlighting how identified cognitive distortion(s), automatic/maladaptive thought(s), negative feeling(s), and/or negative emotion(s) are a mutation of reality and/or may not actually be the case in reality. The therapeutic snippets may also reassure the patient that this is a positive experience. The therapeutic snippets may also explicitly describe to the patient how he/she is completely in control. The therapeutic snippets may also set expectations about the length, intensity, and nature of the scene and/or session. The therapeutic snippets may also recap on past objective success from using platform by combining the above method with platform data from previous scenes or sessions.

According to another exemplary embodiment, patient expectations prior to, during, or after a scene and/or session may be obtained through the use direct questioning regarding expectations using the Q&A feature. Patient expectations may also be obtained through interactions with a clinician as described herein. Patient expectations may also be obtained through spoken dialogue and/or interactions via of the relevant platform features described herein.

According to another exemplary embodiment, once detected and/or identified cognitive distortion(s), automatic/maladaptive thought(s), negative feeling(s), and/or negative emotion(s) may be addressed by selecting from a library of clinician-created or ML/AI model-derived snippets, and by delivering them to patients for teaching or practicing emotional education and skills training concepts such as explaining how and/or why cognitive distortion(s), automatic/maladaptive thought(s), negative feeling(s), and/or negative emotion(s) are bad for one's health, and the like.

XR Mental Health Treatment Feature

A XR mental health treatment feature of the exemplary Mental Health Module may be used to select, prioritize, and deliver appropriate assessment, diagnostic, therapeutic and/or health-related scenes. This feature may also address cognitive distortions with XR scenes and/or features within XR scenes (such as virtual objects, interactive virtual human avatars, virtual environment features, and the like).

Exemplary scenes and/or features may include XR scene(s) and/or features within XR scenes to evoke the application of flexible thinking and/or the realization that "there are no absolutes".

Other exemplary scenes and/or features may include XR scene(s) and/or features within XR scenes where the same event and/or same behavior does not repeat.

Other exemplary scenes and/or features may include XR scene(s) and/or features within XR scenes where forward progress relies on labeling or judging (e.g. something bad happens and make it clear that it was the virtual environment, situation, and/or the context rather than the people involved).

Other exemplary scenes and/or features may include XR scene(s) and/or features within XR scenes where a "safe space" is applied and/or where problem(s) are identified, and based on patient responses to generic contextual questions and/or available platform data, the problem(s) are then reframed to the patient using sentence/statement/thought provoking rhetorical questions (which may be snippets or content objects) selected from a database (e.g. delivering insights to a patient illustrating how a particular issue may not be a big deal, may not be the case, or may be temporary in nature, etc.).

Other exemplary scenes and/or features may include XR scene(s) and/or features within XR scenes where a patient is asked to predict what will happen using the Q&A feature, and then select from a list of options, and where the negative option(s) on the list either never happen and/or fail to achieve positive results. The assertion that negative predictions/responses/actions are never rewarded may or may not be included.

Other exemplary scenes and/or features may include XR scene(s) and/or features within XR scenes where something with potential negative consequences occurs and the patient is given the option to use a virtual time machine to "go back in time" and change decisions and/or actions and/or go "forward in time". If the patient elects to use the time machine to go back in time something negative and/or nothing changes. If the patient elects to use the time machine to go forward in time something positive occurs.

Other exemplary scenes and/or features may include XR scene(s) and/or features within XR scenes where a patient is evoked to examine his language. Patient's spoken language is converted to text using speech-to-text (STT) ML/AI models, and/or one or more other features described herein. Text is analyzed and the sentiment, single-word emotion(s) or feeling(s), and/or other cognitive-behavioral elements are labeled using natural language processing and/or other ML/AI models along with the content object and snippet feature and/or the content object and snippet ML feature as described herein. Upon meeting a certain qualitative and/or quantitative threshold, the patient's own spoken language is recited as audio and/or displayed as text back to him, either with or without additional clinician sentences/statements. If spoken language is recited, features described within the Audio Module may be utilized.

Other exemplary scenes and/or features may include XR scene(s) and/or features within XR scenes where past accomplishment(s), achieved goal(s), and/or positive progress are highlighted. The past accomplishment(s), achieved goal(s), and/or positive progress may be highlighted using sentences/statements, snippets, content objects, audio items, video items, 2D or 3D effects, animations, and/or replays of previously experienced scenes or sessions showing an avatar representing the patient to him/herself in 3rd person. Other exemplary scenes and/or features may include application of Socratic questioning/dialogue to identify negative thought patterns and/or cognitive distortions, and/or to attenuate negative or counterproductive thoughts or feelings, and/or to enhance positive or productive thoughts or feelings as described above.

Other exemplary scenes and/or features may include the prioritization/order in which thoughts, feelings, cognitive distortions, and/or mental health related issues are addressed, with this being determined by the patients list of medical problems, health risk factors, health goals and/or priorities, by one or more clinicians using the communications feature, using the Q&A feature, and/or by using other points of platform data with or without the use of ML/AI models or other platform features.

Other exemplary scenes and/or features may include XR scene(s) and/or features within XR scenes where the patient is asked to take on a seemingly impossible or difficult task (such as pushing a "large" or "heavy" block up a steep incline), and where attempts to complete the task and/or continued engagement are rewarded with success and/or positive reinforcement (through the selection and deployment of appropriate snippets, and the like).

Other exemplary scenes and/or features may include XR scene(s) and/or features within XR scenes where the patient's sense of control, sense of lack of control, and/or need for control of the situation are evoked (e.g. a volcanic island scenario where the volcano erupts and yet the patient is positioned in the only area that stays unharmed) and the patient's sense of control, sense of lack of control, and/or need for control are assessed, refuted, and/or appropriately reinforced using positive feedback.

Other exemplary scenes and/or features may include XR scene(s) and/or features within XR scenes where unfair situations or scenarios are carried out and/or occur.

Other exemplary scenes and/or features may include XR scene(s) and/or features within XR scenes with or without additional programmatically controlled virtual human avatars where something potentially negative occurs and the patient is asked to attribute the potentially negative event to someone or something in an open-ended question.

Other exemplary scenes and/or features may include XR scene(s) and/or features within XR scenes where "mean-looking" and/or "adversarial" looking virtual human avatars help the patient to complete tasks, and if one or more tasks are completed, the "mean-looking" and/or "adversarial" virtual human avatars delivers the insight that the patient actually helped him and/or deliver other insights.

Other exemplary scenes and/or features may include XR scene(s) and/or features within XR scenes where the patient is given an avatar guide to assist him/her through a difficult task or tasks, and where the guide avatar is somehow unable to help the patient after a certain proportion of tasks have been completed.

Other exemplary scenes and/or features may include XR scene(s) and/or features within XR scenes where forward progress depends on positive behaviors, actions, and/or choices; and/or negative behaviors, actions, and/or choices are associated with temporally-related but brief negative elements.

Other exemplary scenes and/or features may include XR scene(s) and/or features within XR scenes where the overall experience remains overwhelmingly positive as long as the patient continues to engage and/or participate.

Other exemplary scenes and/or features may include XR scene(s) and/or features within XR scenes to refute positive beliefs about worrying.

Other exemplary scenes and/or features may include XR scene(s) and/or features within XR scenes to deliver insights surrounding the need to tolerate uncertainty.

Other exemplary scenes and/or features may include a singular XR scene with all of the above XR scenes and/or features above incorporated into it, along with a clinician and/or "embodied agent" and/or virtual human avatar which, through the application of ML/AI models, Q&A features, and/or points of platform data, engage in dialogue with as well as escort the patient to optimal therapeutic location(s) for that individual within the virtual environment. A variation of this feature wherein the same "embodied agent" technology described above is utilized to assist clinicians and/or patients in completing a voice-based worry outcome journal.

Other exemplary scenes and/or features may include XR sessions where worry outcomes are assessed at the beginning, during, and/or at the end of the session.

Other exemplary scenes and/or features may include XR scene(s) and/or features within XR scenes where factual evidence and/or educational content is used to support positive or productive thoughts or statements, and/or, where factual evidence and/or educational content is used to refute negative or counterproductive thoughts or statements, and/or where the neuroplasticity feature described herein may be utilized to enhance the effectiveness in comprehending and/or retaining the educational content.

Other exemplary scenes and/or features may include a method to autonomously and/or semi-autonomously deliver and/or engage in a personalized Socratic dialogue with an individual patient. The Socratic dialogue is triggered/activated when a patient answers questions using the Q&A feature, when a patient makes negative/concerning health-related statements, when triggered/activated by ML/AI models, and/or if points of platform data exceed set thresholds. Once activated, the Socratic dialogue feature delivers appropriate open-ended questions and/or therapeutic statements (e.g. content objects and/or snippets) to the patient. The selection of appropriate open-ended questions and/or therapeutic statements to deliver to the patient is determined by one or more factors. One exemplary determination factor comprises points of platform data previously produced by the patient. This includes any statements made by the patient that triggered and/or contributed to the triggering of the Socratic dialogue feature. This determination may also be made by clinicians, ML/AI models, other points of platform data, or other platform features. Once appropriate open-ended questions and/or therapeutic statements are deliver to the patient, the Socratic dialogue feature then waits for either the next vocalized or text-based statement made by the patient, or will wait for the next Socratic dialogue trigger as described above. Once any of these criteria are met, the Socratic dialogue then selects the next appropriate response(s) to deliver to the patient as described above. The above process continues to iterate in a loop until the scene and/or session ends, until a certain amount of time has passed, until the patient indicates a desire to "turn off" the Socratic dialogue feature, and/or until points of platform data meet or exceed pre-configured thresholds for deactivating the Socratic dialogue feature.

FIG. 42 provides an illustration of the architecture of one embodiment of the platform to assess and/or treat issues related to mental health. This embodiment utilizes several items within this feature as well as other platform features (including the automatic identification of feelings feature, the single word feelings feature, and/or the mental health feature extraction feature) to detect items relating to the mental health state of individuals in XR as well as to deliver items to influence the mental health state of these individuals.

Supplementary XR Mental Health Treatment Feature

A supplementary XR mental health treatment feature of the exemplary Mental Health Module may comprise a variation of the XR mental health treatment feature described above. According to this present feature, the treatment and/or diagnostic features and capabilities remain the same as previously described, but the content of any therapeutic features, scenes, and/or regimens mentioned above are instead focused exclusively on one or more of: developing a sense of mindfulness and/or a sense of presence; evaluation of patient's experiences; reducing the tendency to dwell or re-hash over thoughts, feelings, and/or memories; allowing negative thoughts to be transient instead of trying to deal with them; determining a patient's values; and setting goals and developing a course of action.

Attention-Bias Feature

An attention-bias feature of the exemplary Mental Health Module may be used to deliver personalized attention-bias assessment, attention-bias modification therapy, and/or attentional retraining. This may be completed using platform data, platform interactions, and/or through one or more of the following tasks within XR: dot-probe task, visual-probe task, visual-search task, cognitive bias interpretations, and/or one or more other tasks designed to assess and/or modify subtypes of attention bias and/or subtypes of cognitive bias. This exemplary feature may additionally comprise one or more of steps indicated below.

A patient completes assessments using the Q&A feature which indicate that the patient may have issues amendable to treatment with attention-bias modification (such as affective disorders, tobacco abuse, substance abuse, and the like). Clinicians may also determine that the patient may have issues amendable to treatment with attention-bias modification, either with or without the aid of ML/AI models. Upon next use of the platform, the patient is asked to read several sentences out loud and/or make facial expressions while posing in front of a camera, with the respective audio, image, video, and/or other data obtained by a camera being uploaded to the API. The patient's next scene, session, and/or regimen is configured to contain one or more of tasks described above within the attention-bias feature (such as the visual-probe task, sentence reading, and the like), and the audio, images, video, and/or other data obtained from the previous use of the camera are preconfigured to appear within appropriate tasks at the appropriate times. Upon completing scenes and/or scenes containing the tasks, the results of the tasks are uploaded to the API. Clinicians and/or one or more ML/AI models may use the results and/or other platform data when configuring the next scene, session, and/or regimen to optimize clinical results.

A variation of the above process may be completed within real-world scenarios using augmented reality and/or XR with pass-through video combined with ML/AI models to utilize real-world objects, facial expressions, and/or places, as subject matter for either personalized attention-bias assessment and/or attention-bias modification therapy.

Eye Movement Desensitization and Reprocessing Feature

According to an eye movement desensitization and reprocessing feature of the exemplary Mental Health Module, clinicians and/or ML/AI models deliver eye movement desensitization and reprocessing (EMDR) to patients within scenes and/or sessions. This is completed by exposing a patient to brief sequential doses of emotionally stressful material (the "exposure stimulus") achieved through the use of images, video, audio, rendered content and/or by stimulating the patient's imagination. The exposure stimulus is presented alongside a separate visual, auditory, and/or tactile stimulus (the "non-exposure stimulus"). The present module may also use one or more of the steps, data points, and/or features described below.

According to one exemplary embodiment, the present feature uses the communications feature. According to another exemplary embodiment, the present feature uses points of other platform data (including points of eye tracking, gaze tracking, and/or other biometric data). According to another exemplary embodiment, the present feature uses the Q&A feature described herein. According to another exemplary embodiment, the present feature uses features within the Tactile, Sound, Audio, Neurological, and/or Mental Health Modules.

In yet another exemplary embodiment, the present feature uses exposure stimulus item selection and configuration. Clinicians and/or ML/AI models may select the exposure stimulus from a list of available content objects and/or snippets. The content objects and/or snippets may be tagged/labeled for use in EMDR by clinicians and/or ML/AI models. Clinicians and/or ML/AI models may select and/or modify the exposure duration (in milliseconds) for each selected content item once loaded in XR. Clinicians and/or ML/AI models may modify and/or configure the exposure stimulus using platform features and/or by configuring image-based or video-based exposure stimuli to coincide with audio clips by indicating which images/videos and audio clips to deploy simultaneously using one or more items within the Configuration Module.

According to another exemplary embodiment, non-exposure stimulus item selection and configuration may be determined through the use of platform features and/or through other steps, data points, and/or features described herein. Clinicians and/or ML/AI models may select the non-exposure stimulus from a list of available content objects and/or snippets. The content objects and/or snippets may be tagged for use in EMDR (or specific EMDR scenarios) by clinicians and/or ML/AI models. Clinicians and/or ML/AI models may select and/or configure the non-exposure stimulus by selecting and/or configuring one or more items. One exemplary item may include relative speed of a "light bar" non-exposure stimulus wherein a linearly arranged series of lights illuminates in predefined patterns. Another exemplary item may include the color of lights on the light bar. Another exemplary item may include other auditory, tactile, image-based, video-based, and/or rendered object stimuli.

According to another exemplary embodiment, an EDMR item sequence configuration feature allows clinicians and/or one or more ML/AI models to place items in a preferred sequence through the use of one or more platform features and/or through steps, data points, and/or features discussed herein. The exemplary feature may determine the duration after scene starts before first exposure stimulus and subsequent non-exposure stimulus. The exemplary feature may determine the duration of time to expire between the first exposure and each subsequent set of exposure and/or non-exposure stimuli. The exemplary feature may use the selection of any, one, or more event(s) while in XR, any patient platform action, or any platform interaction to trigger and/or delay sets of exposure and/or non-exposure stimuli. Such events may also include events resulting from patient input methods. Such events may also include points of biometric data and/or points of other platform data including: electro-dermal activity data; skin conductance and/or galvanic skin response data; pupil size data; respiratory rate data; and heart rate data, including heart rate variability data. For any delay that is created and/or configured, clinicians and/or ML/AI models may specify the length of delay after which sets of exposure and/or non-exposure stimuli may be deployed. When clinicians and/or ML/AI models complete the above steps, they may also select and/or configure when the applicable scene and/or session may be terminated. Termination may occur based on the length of time expired from the scene and/or session start, using one or more patient input methods, based on patient platform actions, based on events or platform interactions, or based on the number of sets of exposure and/or non-exposure stimuli that have been deployed since the scene or session start.

In addition to utilizing features within the EMDR method and system, one embodiment is carried out through history taking involving an inventory of traumatic or negative past events using the Q&A feature and/or the communications feature with clinicians, and/or involving a determination of treatment goals using the Q&A feature and/or the communications feature with clinicians. The exemplary embodiment may further be carried out using patient educational content on methods to manage anxiety. The exemplary embodiment may further be carried out through application of the EMDR feature in scenes or sessions, and wherein one or more of the tasks described herein are additionally carried out. Exemplary tasks may include a voiceover or text object asking the patient to recall past trauma and/or negative thoughts. Other exemplary tasks may include determining what negative thoughts a patient has about himself due to those experiences and what positive thoughts the patient would like to have about himself going forward using the Q&A feature and/or the communications feature with clinicians. Other exemplary tasks may include determining how bad things feel to the patient at that moment using the Q&A feature and/or the communications feature with clinicians.

The exemplary embodiment may further be carried out using the application of a treatment regimen with sessions that are approximately 7 to 10 days apart. Upon each follow up session, the patient may be asked to reflect back on the positive thoughts they would like to have about himself. The patient may be reevaluated for any positive and/or negative thoughts or sensations at one or more points during this treatment regimen.

Ecological Mental Health Feature

An ecological mental health feature of the exemplary Mental Health Module may incorporate any other feature and/or module described herein, and comprising ecological intervention methods, strategies, techniques, and/or systems to assess, diagnose, and/or treat issues relating to mental health.

In one exemplary embodiment, the present module features comprise the application of classical conditioning techniques to features, scenes, sessions, and/or regimens.

According to another exemplary embodiment, the present module feature comprises the application of operant conditioning techniques to features, scenes, sessions, and/or regimens.

According to another exemplary embodiment, the present module feature comprises guided and/or instructional behavioral therapy exercises. Guidance may be in the form of visual content, auditory content (e.g. voice instructions), physical movements from virtual human avatars and/or in the form of tactile stimuli. The exemplary guidance may employ various approaches including self-reflection, mindfulness, meditation, hypnosis, rhetorical questions, Socratic dialogue, prompting patient to think about hypothetical scenarios and/or questions, physical movements, and guided imagery techniques as described herein.

According to another exemplary embodiment, the present module feature comprises gradual stimulus control and/or gradual exposure exercises.

According to another exemplary embodiment, the present module feature comprises cognitive restructuring.

According to another exemplary embodiment, the present module feature comprises worry outcome monitoring.

According to another exemplary embodiment, the present module feature comprises present-moment focus.

According to another exemplary embodiment, the present module feature comprises motivational interviewing.

According to another exemplary embodiment, the present module feature comprises acceptance and commitment therapy.

According to another exemplary embodiment, the present module feature comprises intolerance of uncertainty education, education regarding the dangers and/or uncontrollability of worrying, and education relating to techniques to refute positive worry beliefs.

According to another exemplary embodiment, the present module feature comprises evaluating beliefs about worry.

According to another exemplary embodiment, the present module feature comprises improving how one is oriented towards problems, education relating to belief reframing, emotional skills training, improving attitudes towards dealing with problems, and/or addressing cognitive avoidance.

According to another exemplary embodiment, the present module feature comprises using other scenes, sessions, regimens, content objects (including audio, video, rendered objects, and/or avatars).

According to another exemplary embodiment, the present module feature comprises using other platform data points and/or other platform features.

M. Pain Module

The exemplary XR Health Platform may further incorporate a Pain Module. In exemplary embodiments, the present Pain Module contains features that, either alone, or in combination with other platform features, enable the screening for, detection of, diagnosis of, treatment of, mitigation of, management of, and/or rehabilitation from, issues relating to acute and/or chronic pain. Chronic pain in particular is a multifactorial disease that requires the application of a multifaceted approach for successful management and/or treatment. FIG. 43 illustrates how the XR Platform is capable of addressing multifactorial issues relating to health, using pain as an example. One or more of the methods, systems, and/or features within the Pain Module may utilize platform features, points of platform data, and/or ML/AI models. Additionally, the Pain Module may comprise one or more of the various features described below.

Chronic Pain Diagnosis Feature

A chronic pain diagnosis feature of the exemplary Pain Module may be used to autonomously or semi-autonomously assess for and/or diagnose chronic pain. In one embodiment, the present feature uses certain data and/or patient or clinician input to determine if a patient has had pain causing distress for a period of 6 months or more. In another embodiment, the present feature uses certain data and/or patient or clinician input to determine if a patient has had pain causing impairment for a period of 6 months or more. In each case, the data and inputs may comprise platform data resulting from repeated XR scenes, sessions, and/or regimens completed over a period of time (e.g. data including data obtained through patient use of patient input methods, data obtained using the Q&A feature, and/or any other points of platform data).

Automatic Pain Assessment Feature

An automatic pain assessment feature of the exemplary Pain Module may be used to autonomously and/or semi-autonomously assess the levels and/or nature of acute and/or chronic pain. This may be completed by a patient using patient input methods, by a clinician, and/or by ML/AI models. Pain may be assessed using any points of platform data relating to pain in a particular patient including which movements have been utilized by a patient in previous scenes, sessions, and/or regiments and, if applicable, during which movements and in which positions during the movements did the patient indicate that they were having pain using the pain with movement detection feature. Pain may also be assessed using other features within the Movement, Neurological, and/or Mental Health Modules, and/or using other platform features. Pain may also be assessed based on which scenes, sessions, and/or regimens have been used in the past to address the individual's pain as well as any available timestamps and/or configuration settings that were used for the scenes, sessions, and/or regimens.

In one exemplary embodiment, the present module feature comprises the selection and/or identification of anatomical areas of pain using one or more anatomical models in XR, and upon selecting and/or identifying areas of pain, a subsequent set of questions utilizing features within the history of present illness feature described herein may be administered to further characterize the pain with any responses being produced by a patient using patient input methods, a clinician, and/or by ML/AI models. The items collecting the selections and/or responses may be prepopulated using appropriate points of platform data.

In another exemplary embodiment, the present module feature may utilize other questions and/or other items within the Q&A feature configured to identify and/or characterize anatomical sites of pain.

In another exemplary embodiment, the present module feature may utilize ML/AI models to automatically characterize anatomic locations of pain, duration of pain, severity pain, date and time of onset of pain, and/or other aspects of pain. This may be completed using analyses of points of biometric data, for example, vocal biomarkers identifying a painful scream upon the onset or exacerbation of pain; aspects of pain identified through analysis of spoken and/or written dialogue obtained from patients while in XR; computer vision models identifying aspects of images that are consistent with or related to the body language, posturing, and/or facial expressions of someone that is experiencing pain; and/or the inputs and/or outputs of other ML/AI models In another exemplary embodiment, the present module feature may utilize other points of platform data and/or other platform features described herein. Items within this feature may be repeated multiple times within one or more scenes, sessions, and/or regimens.

Pain Management Feature

A pain management feature of the exemplary Pain Module may be used to assess, treat, diagnose, manage, and/or prevent acute and/or chronic pain. This may be completed using scenes, sessions, and/or regimens created, modified, configured, and/or deployed by clinicians, ML/AI models, and/or other platform features.

In one exemplary embodiment, this module may utilize platform data fields.

In another exemplary embodiment, the present module may utilize guided imagery techniques, which may include one or more of the following: the application of content objects (such as text snippets, audio clips, etc.) containing therapeutic statements and/or thought-provoking rhetorical questions that invite and/or direct the patient to experience desirable feelings and/or sensations; the use of virtual human avatars that guide the patient and/or invite the patient to experience desirable feelings and/or sensations through spoken, visual, haptic, and/or text-based interactions; and the use of other platform features that invite and/or direct the patient to experience desirable feelings and/or sensations.

In another exemplary embodiment, the present module may use any other platform feature, including the features of the Tactile, Light, Audio, Mental Health, Neurological, Movement, and/or Clinical Platform Modules.

In another exemplary embodiment, the present module may use platform features configured and/or utilized to assess pain sensitivity and/or pain tolerance in individuals.

In another exemplary embodiment, the present module may use features of the Tactile, Light, Audio, Mental Health, Neurological, Movement, and/or Clinical Platform Modules, and/or one or more other platform features to assess for, treat, and/or prevent co-morbid issues including: anxiety, depression, circadian disruption, sleep disturbance, seasonal affective disorder, inactivity, cigarette smoking, alcohol abuse and/or substance abuse. In another exemplary embodiment, the present module may use platform features related to obtaining a "history of present illness", a past medical history, a surgical history, and/or a social history.

In another exemplary embodiment, the present module may use features within the Movement and/or Neurological Modules to target one or more anatomical areas in need of increased strength, coordination, flexibility, and/or range of motion.

In another exemplary embodiment, the present module may comprise features utilizing distraction, and integrating: a "cold" virtual environment, a nature based virtual environment, a fantasy based virtual environment, soothing and/or distracting audio, distracting gameplay, distracting visual content elements, scents using the "Box" device, tactile or haptic stimuli, features from the light module, other platform features, and/or features or content that incorporates the use of a Transcutaneous Electrical Nerve Stimulation (TENS) device.

In another exemplary embodiment, the present module may utilize the aforementioned features to avoid injury, re-injury, and/or injury exacerbation as described herein.

In another exemplary embodiment, the present module may use items within the A-B testing feature to adjust any features and/or content, and/or any other platform features.

In another exemplary embodiment, the present module may use the platform features described herein whereby the features are combined and/or utilized to change the amount, timing, frequency, intensity, and/or any other characteristics of features and/or objects within scenes, sessions, and/or regimens in order to increase the likelihood of one or more pain-related goals being achieved and/or desired actions being completed.

In another exemplary embodiment, the present module may use other platform features and/or other platform data points not otherwise mentioned herein.

In another exemplary embodiment, the present module may use a "pain loading scene" that utilizes features of the Q&A feature and/or features of the Anatomy Module. One or more of the items discussed herein can be completed by a patient, clinician, and/or by ML/AI models. A patient can select anatomical areas where they are having pain. Upon the patient selecting an area in which they are having pain, a subsequent set of questions utilizing features within the history of present illness feature described herein are given to the patient to further characterize the pain. Data relating to anatomical areas of pain, response data from related "history of present illness" questioning, as well as other points of platform data are utilized by clinicians and/or one or more ML/AI models. This data may be used to determine which physical therapy exercises will be deployed to the patient in subsequent scenes, sessions, and/or regimens. The feature may also be further utilized to determine the number of repetitions per set of exercises, the number of sets of exercises, and any other feature and/or parameter described within the Movement Module herein. The data may also be used to determine which educational items will be deployed to the patient in subsequent scenes, sessions, and/or regimens. The data may also be used to determine which set of platform features, platform data, and/or platform content may comprise and/or be utilized within subsequent scenes, sessions, and/or regimens. For clarity, this includes determining which scenes and/or scene configurations may comprise future sessions and/or regimens. This process may be repeated multiple times within sessions and/or regimens.

N. Procedural and Digital Anesthetic Module

The exemplary XR Health Platform may further incorporate a Procedural and Digital Anesthetic Module. In exemplary embodiments, this module offers solutions for the creation, selection, modification, configuration, personalization, automated titration, and/or deployment of procedure-based care and/or "digital anesthetics". The exemplary module is a digital therapeutic approach to anesthesia, "Monitored Anesthesia Care", mild sedation, moderate sedation, deep sedation, procedural care, procedure-based care, and/or peri-operative care. The module may be utilized as either the sole anesthetic for procedures, and/or as an adjunct treatment modality that is combined with other approaches. The exemplary module may utilize hardware agnostic XR programs, a clinician companion application, and/or a web portal. In one embodiment of a system utilizing features within this module, patients experience and/or interact with XR programs, while clinicians simultaneously monitor, interact, and/or communicate with the patient(s) using a clinician companion application or web portal. Other embodiments of system using any feature(s) within this module may also include other platform features described herein.

Digital Anesthetic Feature

A digital anesthetic feature of the exemplary Procedural and Digital Anesthetic Module enables the integration and/or use of one or more capabilities of the platform in peri-operative and/or peri-procedural contexts and/or settings. The feature is implemented with patients in XR and with clinicians using a companion application and/or web portal (but either clinicians and/or patients may utilize any XR device). Using the companion application, clinician(s) may interact with patient(s) by creating, altering, and/or deploying items of content and/or platform features to the patient in XR. FIGS. 44 and 45 illustrate two embodiments of a companion application to be used for this purpose, along with some example functionalities. Additionally, the feature may comprise one or more of the various steps discussed below, either carried out in the indicated sequence and/or in other sequences.

The devices with the XR program and clinician companion application on them are first turned on. A clinician and/or the patient completes pre-procedure forms. FIG. 46 provides an illustration and visual description of one embodiment of a pre-procedure form. The clinician may alternatively utilize questions using the survey functionality.

The clinician selects an appropriate "procedure template" using the clinician companion application. FIG. 47 provides an illustration and visual description of one embodiment of a procedure template. The clinician may then modify and/or remove elements within the procedure template to achieve greater personalization of the digital anesthetic.

The patient is then placed into the appropriate position for the procedure (the starting position). A head-mounted display is then placed onto the patient's head. A brief (30 seconds to 1 minute) tutorial and safety education (this step may be completed at any time prior to the start of the procedure) teaches controls, educates the patient on what to do if safety related events or scenarios occur, and describes what is about to take place. This description may use text, audio, images, and/or video entered, modified, selected, configured, and/or communicated by a clinician using the clinician companion application or web portal. The description may also use the default content for the procedure template selected as described herein. After the description, the tutorial may include the use of "Guides" that are in the form of a virtual human avatar and/or a virtual animal avatar. Once the tutorial and safety education is completed, the procedure is started.

During the procedure, any of the features described herein may be applied and/or triggered in XR (experienced and/or viewed the patient) by one or more clinicians, the patient, and/or automatically using the "Dynamic titration of XR content and/or features" system as described herein.

At point(s) in time near the completion of the procedure, the patient may be notified that the procedure will end soon and/or that the procedure will end in X minutes, with X being a number set in procedure templates. Alternatively or in addition, the patient may be notified by clinicians using the clinician companion application.

At any point during the procedure, music and/or audio may change using crescendos, fades, reverse-fades, and/or other effects. Audio may provide positive messages and/or pleasant sounds. Visual effects may also be displayed and/or experienced at any point during the procedure.

At completion of the procedure, a brief visual, audio, and/or text-based notification is delivered to the patient indicating that the procedure is over. The patient then may complete survey questions. The patient may then be sent an email with information allowing him to benefit from further personalization in any future procedures.

Two-Way Communication Feature

A two-way communication feature of the exemplary Procedural and Digital Anesthetic Module enables direct communication between a patient and clinician(s). This feature is designed to be used when both the patient and the clinician(s) are in the same real-world space and/or within the same real-world facility.

In one embodiment, patient audio is "always on" such that any audio generated by the patient is automatically transmitted to and played by the clinician companion application or web portal. Any audio transmitted from the clinician companion application or web portal is to be played for the patient by the XR program. Clinician audio may be accomplished using a "push to talk" approach wherein the clinician must press a button on the clinician companion application to be able to transmit any audio to the patient-facing XR program. Alternatively, clinician audio may be "always on" wherein any audio generated by the clinician is automatically transmitted to and played by the patient-facing XR program. Any audio transmitted from the patient-facing XR program may be automatically played by the clinician companion application or web portal.

In another embodiment, the clinician may create, select, modify, and/or send text-based messages to the patient-facing XR program.

In another embodiment, preset text-based and/or audio notifications of upcoming procedural events may be selected and/or sent to the patient by clinicians using a clinician companion application or web portal, automatically using programmatic methods, and/or using ML/AI models. Examples of notifications include:

"Numbing medicine coming momentarily, you may feel some pressure, pain, or a pinch"

"Finishing up momentarily!"

"Are you doing OK?"

"Please remain still, and let us know if you are uncomfortable in any way"

"You may feel warmth, liquid, or wetness"

Procedure Template Feature

A procedure template feature of the exemplary Procedural and Digital Anesthetic Module may be used for pre-configuring content tailored for a particular patient undergoing a particular procedure type. Brief pre-procedure forms and/or survey questions may be completed by one or more clinicians prior to the start of the procedure to query for appropriate procedure templates given the information obtained, and clinicians may select procedure templates from the queried results for use in a patient procedure.

"Procedure templates" may include one or more XR configuration, content, and/or feature settings. Exemplary settings include procedure name, estimated length of case, and procedural setting. The template may auto populate safety related scenarios related to the procedural setting, and clinicians may create and/or modify these "safety related" scenarios for use as part of the tutorial/safety education feature as described above. Other exemplary template settings may include patient type (adult vs pediatric); gender; pertinent items within patients past medical, surgical, and/or social histories; patient's first use of system, Yes or No; default position to place virtual content in relative to the HMD; and if there is a planned use of adjunct medications, and if so, their names.

Clinicians may create, select, configure, and/or modify settings within procedure templates using the clinician companion application or web portal. Selection, modification, and/or configuration of "procedure templates" may be completed automatically through code, programming, and/or ML/AI models, using points of patient and/or procedure information available. Different content and/or features may populate the procedure templates for different procedures, different estimated procedure lengths, different settings, for adults verses pediatric patients, and/or based on other patient characteristics.

Procedural Content Control Feature

A procedural content control feature of the exemplary Procedural and Digital Anesthetic Module uses programming and/or code to create, enable, modify, select, and/or configure one or more features and/or content elements. The features and/or elements may be deployed, instantiated, and/or triggered at points during a health-related and/or medically-related procedure, surgery, and/or operation. Deployment, triggering, and instantiation of these features and/or elements may occur through various methods discussed herein. In one embodiment, this occurs automatically using functionalities of the "Dynamic titration of XR content and/or features" system. In another embodiment, this occurs manually by clinicians using the clinician companion application or web portal. In another embodiment, this occurs by the patient via features within the XR program. In another embodiment, this occurs by using ML/AI models.

In another exemplary embodiment, the present module comprises interactive features including distracting tasks (such shooting, crushing, or popping 2D and/or 3D objects); cognitive tasks and/or puzzles; education-based tasks; interactive and/or passive mindfulness, breathing, hypnosis, and/or meditation exercises, and/or other related activities and/or content.

In another exemplary embodiment, the present module comprises patient self-selection of changes in XR content and/or features from within the XR program.

In another exemplary embodiment, the present module comprises changes in XR content and/or features triggered by points of biometric data exceeding thresholds as set in the clinician companion application, the web portal, and/or as set in procedural templates.

In another exemplary embodiment, the present module comprises changes in XR content and/or features starting just prior to, and/or synchronously with procedure-related events that are expected to be painful, loud, and/or uncomfortable, and the like. Exemplary XR content changes include changes to the weather and/or skybox within the virtual XR environment, such as a lightning storm, snowstorm, and/or strong wind gusts, and the like; and other audio and/or visual features and/or virtual 2D and/or 3D objects.

In another exemplary embodiment, the present module comprises a "Default Mode" feature wherein all of the default values for selected procedure templates are executed, unless modified by clinicians.

In another exemplary embodiment, the present module comprises populating procedure templates with different content and/or features based on the information entered by clinicians prior to starting a procedure using one or more pre-procedure forms and/or similar questions.

In another exemplary embodiment, the present module comprises an "End Session" button on the clinician companion application that terminates the XR program instance.

In another exemplary embodiment, different content and/or features may populate the procedure templates and/or be applied for different procedures, different estimated procedure lengths, different settings, and/or for adults verses pediatric patients.

In another exemplary embodiment, the present module comprises other graphical user interface elements, such as virtual buttons, main menus, and the like to allow patients to navigate about the program as well as to allow for the proper functioning of any features described herein which may require the elements.

Procedural XR Feature

A procedural XR feature of the exemplary Procedural and Digital Anesthetic Module uses a patient facing XR program comprising features and/or content which may be selected, deployed, and/or triggered at various points during a procedure.

In one exemplary embodiment, the present feature uses voice guided mindfulness, breathing, hypnosis, and/or meditation exercises either with or without additional relaxing, distracting, and/or immersive audio, and/or guided by voice, text-based, and/or visual instructions.

In another exemplary embodiment, the present feature uses procedurally generated "endless" experiences for patients to explore.

In another exemplary embodiment, the present feature uses interactions with virtual human avatars. For example: the patient may see a virtual human avatar, and the virtual human avatar may direct patient to points of interest within the XR environment.

In another exemplary embodiment, the present feature uses audio selections and/or interactive and/or passive audio visualizations.

In another exemplary embodiment, the present feature uses interactive and/or passively experienced visual features.

In another exemplary embodiment, the present feature uses interactive features including distracting tasks (such shooting, crushing, or popping 2D and/or 3D objects); cognitive tasks and/or puzzles, education-based tasks; interactive and/or passive mindfulness, breathing, hypnosis, and/or meditation exercises; and/or other related activities and/or content.

In another exemplary embodiment, the present feature uses other content items and/or platform features described herein.

Repeat Procedural Use Feature

A repeat procedural use feature of the exemplary Procedural and Digital Anesthetic Module is applicable for continued patient engagement personalization, and efficacy applicable for any patient repeat use of the platform utilizing one or more of the other features within the Procedural and Digital Anesthetic Module.

According to this exemplary feature, at the conclusion of any use, the patient and/or the patient's legal guardian may be given a unique and/or one-time use code that may be linked to electronic medical records. This allows the patient to utilize data in subsequent procedures to further optimize and/or personalize his digital anesthetic. This use code may also identify any patient preferences and/or characterize the patient's dynamic titration profile from previous usages of the system. The unique identifier may be delivered via a scratch off card with the code or by email. Alternatively, the above functions may be enabled without the "unique and/or one-time use code", but through integration with electronic medical records and/or one or more similar programs handing patient data.

Minimizing Movement Feature

A minimizing movement feature of the exemplary Procedural and Digital Anesthetic Module may be used to facilitate individuals with minimizing and/or mitigating movement while using XR. In one exemplary embodiment, this feature comprises a gaze control system. Content may be static in position and "front facing" only. The clinician may remotely adjust the content-facing position and/or rotation using the clinician companion application, the web portal, and/or using XR. The clinician may also remotely adjust other settings relating to the patient-facing XR content using the clinician companion application the web portal, and/or using XR. The patient may re-adjust the forward position using patient input methods. The gaze control system may further comprise a static and/or constrained user interface and/or content position and/or rotation which mitigates the risk of nausea. The gaze control system may also comprise an integrated feature to minimize the likelihood of nausea and/or disorientation occurring with any head movements by subtly moving content elements to compensate.

In another exemplary embodiment, the present module feature comprises a passive positional control system using audio, tactile, and/or visual elements. Optimal audio and/or visual content and/or features are predicated upon the patient and/or XR devices being within a certain proximity to the starting position and/or the patient capsule (as described within the safety features section), with the degree and/or proportion of positional and/or rotational movement away from the starting position and/or patient capsule. This may result in a disproportional and/or proportional change in the quality and/or volume of audio within the XR program. This may further result in a disproportional and/or proportional change in the clarity, color composition and/or visual quality of visual elements within the XR program. This may further result in the application of items of audio and/or visual content, and/or effects, each with or without features that are proportional to the degree of positional and/or rotational movement away from the starting position and/or from the patient capsule. This may further result in the application of tactile and/or vibrational stimuli (delivered through XR devices), each with or without an intensity, duration, and/or frequency proportional to the degree of positional and/or rotational movement away from the starting position and/or from the patient capsule. Features of the passive positional control system may incorporate and/or be triggered by, other elements within this feature.

In another exemplary embodiment, items within the present module feature may utilize, incorporate, modify, be triggered by, and/or be configured by points of platform data.

In another exemplary embodiment, the present module feature comprises items within the peri-operative safety feature.

In another exemplary embodiment, the present module feature comprises features within the Movement and/or XR Platform Modules.

In another exemplary embodiment, the present module feature comprises other items included and/or within other platform features described herein.

Peri-Operative Safety Feature

The exemplary Procedural and Digital Anesthetic Module may further comprise a peri-operative safety feature.

In one embodiment, this safety feature comprises a "max distance" feature that delivers safety prompts to the patient and/or clinician through voice, text-based, tactile (vibration), and/or visual means whenever the patient's head and/or other anatomical body parts travel beyond a preset maximum distance threshold in either the X, Y, and/or Z directions.

In another embodiment, the exemplary safety feature comprises a "max rotation" feature that delivers safety prompts to the patient and/or clinician through voice, text-based, tactile (vibration), and/or visual means whenever the patient's head and/or other anatomical body parts rotate beyond a preset maximum rotation threshold in either the X, Y, and/or Z axis.

In another embodiment, the exemplary safety feature comprises direct voice and/or text-based communication between the patient and clinician as described in the two-way communications feature herein.

In another embodiment, the exemplary safety feature comprises an "End Session" button on the clinician companion application or web portal that terminates the XR program.

In another embodiment, the exemplary safety feature comprises patient movement and movement tolerance capability. Once the patient is placed in the appropriate position for his procedure, clinician may set a virtual representation of the position using the clinician companion application or web portal, with the virtual representation being a capsule (the patient capsule) and/or any other 3D shape that approximates the size and/or shape of a human, and/or 3D shapes that approximates the size and/or shape of one or more anatomical parts on a human. The size of the patient capsule may be automatically made larger or smaller based on the patient height and/or weight as entered into the clinician companion application or web portal by the clinician prior to or during the procedure.

After the patient capsule is set, the clinician selects a movement tolerance for the patient undergoing a particular procedure using the clinician companion application with the selected movement tolerance being converted to a virtual representation of a separate capsule (the movement tolerance capsule) that is larger than, and encompasses, the patient capsule in such a way that the directionality of the patient and the movement tolerance capsules are aligned (see FIG. 48).

If at any point during the remainder of the session, the patient capsule touches, enters, and/or traverses the movement tolerance capsule, sounds, visual elements and/or vibrations may be administered. See FIGS. 49 and 50. A gentle reminder may be given to keep patient in, or close to, a desired position. This reminder may be effected by: (a) using one or more of the features described within the passive positional control system, (b) manually creating and/or triggering the reminders through one or more clinicians using the clinician companion application or web portal, or (c) automatically creating and/or triggering the reminders programmatically, and/or through the utilization of ML/A. Safety prompts may also be administered to either the patient in XR and/or to the clinician via the clinician companion application or web portal.

In another embodiment, using the clinician companion application or web portal, a clinician may see a first- and/or third-person view of the patient-facing XR program while in use by a patient, allowing for continuous and/or real-time monitoring of the patient experience.

In another embodiment, the exemplary safety feature may comprise one or more items within the minimizing movement feature.

In another embodiment, the exemplary safety feature may comprise other items of and/or within other platform features.

Dynamic Titration Feature

In another exemplary embodiment, the Procedural and Digital Anesthetic Module may comprise a feature applicable for dynamic titration of XR content and/or features to achieve patient goals, patient-centered objectives, and/or to address health-related problems based on patient characteristics and/or points of platform data.

One exemplary embodiment of this feature uses integration of patient input methods (including button presses, joystick movements, touchpad movements and/or clicks, controller movements, gaze changes, eye movements, voice commands, and the like). For example, the patients may indicate if they are having pain and/or anxiety by vocalizing and/or communicating either. Patients may also select and/or press virtual buttons appearing within an XR program user interface (for example, a button for "I am having pain"). Alternatively, instead of pressing virtual buttons, patients may instead select and/or interact with features within the XR program with the selections and/or feature interactions resulting in the same actions as pressing the buttons described above.

In another exemplary embodiment, patients may be instructed to press buttons on XR devices to indicate that they are having pain, anxiety, heightened and/or depressed levels of arousal, level of consciousness, and/or agitation (any instructions regarding the pressing of the buttons may be given during the tutorial).

In another exemplary embodiment, whenever one of the features described herein indicate that a patient is in a state of pain, anxiety, discomfort, agitation, and/or any other non-ideal state, appropriate content items and/or features within the XR program as described herein may be selected, triggered, activated, instantiated, modified, removed, and/or configured. This may be accomplished either manually by clinicians using the clinician companion application or web portal, or automatically through either programmatic means and/or by utilizing one or more ML/AI models.

In another exemplary embodiment, the present module feature uses points of biometric data as described herein with preset thresholds for selecting, configuring, triggering, instantiating, modifying, and/or removing items of content and/or features. The thresholds may be set by clinicians using the clinician companion application or web portal, programmatically, and/or by ML/AI models.

In another exemplary embodiment, at the conclusion of the procedure, a dynamic titration profile may be generated which contains data related to the features, content, and/or configurations experienced by the patient during the procedure, along with changes in biometric data, as well as any survey questions and responses. This may allow patients to get further personalization during future procedures and/or to enable the "continued engagement feature" as described herein.

Standalone Enabling Feature

A standalone enabling feature of the exemplary Procedural and Digital Anesthetic Module may use a set of system enabling capabilities comprised of minimalist and/or optimized versions of other platform features and/or capabilities. When added to and/or integrated with other platform features, these versions allow for the standalone application of the platform feature for the purposes of the assessment, diagnosis, screening, therapy, rehabilitation, and/or treatment of issues relating to the health of an individual. The peri-procedural and/or peri-operative embodiment of the standalone enabling feature may comprise minimalist and/or optimized versions of their similarly named and respective features and/or capabilities (as described elsewhere herein).

According to one such minimalist and/or optimized version, ML/AI models may be applied as follows: (a) computer vision models may be utilized one or more times to determine, evaluate, and/or assess patient position, movement, levels of arousal, pain, anxiety, level of consciousness, agitation, orientation, amnesia and/or any other measure relating to intra-operative anesthesia and/or sedation; (b) ML/AI models may be utilized one or more times to adaptively determine, select, and/or configure the most efficacious set of features to include, apply, and/or utilize in the XR program; and (c) for analysis, integration, and/or utilization of biomarkers, ML/AI models, points of platform data, and/or platform features as described herein.

Another exemplary minimalist and/or optimized version in the standalone enabling feature may utilize application programming interfaces (APIs) for requesting and/or retrieving one or more surveys/questions, submitting and/or saving survey responses, submitting, saving, and/or retrieving points of biometric data, running asynchronous tasks related to other platform features, running ML/AI models, as well as querying against, saving, updating, and/or ascertaining pre-configured procedure templates.

Another exemplary minimalist and/or optimized version in the standalone enabling feature may utilize the question and answer (Q&A) feature to assess aspects of the patient experience. Clinicians may create, save, and/or deploy single-selection and/or multi-selection-type questions using the clinician companion application or web portal. Clinicians may also create, save, and/or deploy surveys comprising one or more single-selection and/or multi-selection type questions using the clinician companion application or web portal. Each procedure template may have pre-made surveys associated with it. The surveys may be the default surveys loaded upon selecting procedure templates. Alternatively, instead of utilizing the default surveys, clinicians may select other pre-made and/or previously made surveys to deploy to patients. Using the clinician companion application or web portal, clinicians may set the timing of when surveys are deployed to patients. Clinicians may also select particular questions within pre-made and/or previously made surveys to deploy to patients using the clinician companion application or web portal.

Another exemplary minimalist and/or optimized version in the standalone enabling feature may utilize platform features related to biometric and/or platform data integration. In addition to any data points produced by, relating to, and/or resulting from one or more of the features described herein, another feature contains the code and/or programming for the integration of points of additional biometric and/or platform data. This may include points of biometric data and/or any other measure relating to intra-operative anesthesia and/or sedation and/or other points of platform data as described herein. The biometric and/or platform data integration may also comprise ML/AI models using and/or deriving points of platform data as described herein. When any biometric or platform data value is obtained and/or assessed, certain aspects may be calculated and/or carried out using platform features, ML/AI models, and/or through any other method. One exemplary aspect may include a relative change in biometric and/or platform data values after the start of a procedure. Another exemplary aspect may include a relative change in biometric and/or platform data values from previous measurements. Quantitative biometric and/or platform data measurements and/or data points may be converted to qualitative measures of arousal, pain, level of consciousness, agitation, orientation, anxiety, amnesia, and/or any other measure which may then be displayed and/or updated on the clinician companion application or web portal.

Another exemplary minimalist and/or optimized version in the standalone enabling feature may comprise other platform features configured and/or optimized for stand-alone use and/or to be part of standalone applications of the platform.

O. Billing Module

The exemplary XR Health Platform may further comprise a Billing Module. The Billing Module extracts relevant data needed for successful medical billing claims. Methods, systems, and/or features within the Billing Module may utilize platform features, points of platform data, and/or ML/AI models. Additionally, the Billing Module may comprise one or more of the features discussed below.

Auto Billing Feature

According to an auto billing feature of the exemplary Billing Module, for each clinical use-case, medical billing specialists, clinicians and/or ML/AI models tag and/or label certain platform data fields that may be required for submitting a claim for payment based on any medical billing coding convention.

According to one embodiment, the content, scenes, features, and other platform elements needed to elicit, collect, and/or curate the data are auto-populated into a platform pre-configuration using platform features, including features or items within the Integration and/or Configuration Modules. Items of documentation required for billable medical encounters, billable medical procedures and/or billable facility fees may be completed when the pre-configuration is utilized in the care of patients.

According to another embodiment, upon completion of sessions and/or encounters determined to contain the items of content and/or documentation necessary for billable scenarios, this information may be auto-populated into claim-related documents.

According to another embodiment, if upon competition of the sessions and/or encounters, all of the necessary information required to file claims may be auto-populated onto the appropriate claim-related documents. The documents may then be automatically submitted to appropriate entities in order to automatically file a medical payment claim.

Payment Processing Feature

A payment processing feature of the exemplary Billing Module allows payments to be made using a credit card, debit card, blockchain-based currency, and/or any other method of electronic payment. The payments may be made using the web portal, the companion application, and/or using XR.

P. Hardware Module

The exemplary XR Health Platform may further comprise a Hardware Module. Features and/or devices within the Hardware Module may be integrated into the overall XR Health Platform, and/or may be utilized on an "as needed" basis. One or more features and/or devices within the Hardware Module may utilize platform features, one or more points of platform data, and/or ML/AI models. Additionally, the Hardware Module may include one or more of the features described below.

Box Device

Referring to FIG. 51, an exemplary "Box" device 10 of the present Hardware Module incorporates one or more hardware, software, firmware, and technologies including a CPU 11, computer, Bluetooth and/or Wi-Fi connectivity, power supply, low frequency or other type of speaker 12, ultraviolet light source, fan 14, and an aroma diffuser 15. These may be combined with cameras 16, rotating and/or articulating camera mount 16A, and/or microphones 17, and an amplifier. FIG. 51 comprises an illustration of one embodiment of the exemplary device.

The exemplary Box may be used to increase immersiveness in XR through emulation of features consistent with weather patterns and/or sounds and/or smells of various real-world or virtual-world environments and/or when various different events occur in XR. The fan may help to reduce nausea. Sensors, computers, and/or Bluetooth and/or Wi-Fi connectivity may be incorporated and utilized to send and/or receive points of platform data to and/or from other platform features and/or modules. Cameras may be incorporated and utilized for positional tracking and/or patient monitoring and/or the use of the communications feature and/or for any other purpose mentioned herein where cameras may be utilized. The cameras may be attached to rotating and/or articulating camera mounts incorporated into the Box device. Microphones may be incorporated for positional tracking and/or patient monitoring and/or the use of the communications feature and/or for any other purpose mentioned herein where microphones may be utilized. Ultraviolet light sources may or may not be included for purposes of sanitizing real world objects.

O.R. Box Device

Referring to FIG. 52, exemplary hardware, software, firmware, and technologies may further comprise an "O.R. Box" device 20. The exemplary O.R. Box device 20 comprises computers 21 (each with a motherboard, CPU, memory, hard drive, Bluetooth, Wi-Fi, and power supply), cameras 22 and/or microphones 23. FIG. 52 illustrates one embodiment of this exemplary device. The cameras 22 may be incorporated for positional tracking and/or patient monitoring and/or for any other purpose mentioned herein where cameras may be utilized. The cameras 22 may be attached to rotating and/or articulating camera mounts incorporated into the device 20. Microphones 23 may be incorporated for positional tracking and/or patient monitoring and/or for any other purpose mentioned herein where microphones may be utilized. Additionally, ultraviolet light sources may or may not be included for purposes of sanitizing real world objects.

Controller Clip/Harness Device

Referring to FIG. 53, exemplary hardware may also comprise a controller clip/harness device 30. The controller clip/harness device functions to hold an XR controller to anatomical body parts or to any other physical object. The exemplary device may have the ability to alter the angle and/or orientation of the controller with respect to the clip. FIG. 53 illustrates one embodiment of this exemplary device 30. The exemplary device 30 may comprise an articulating mechanism 31, an optional articulating arm 32 of any length, a latching mechanism 33 including plastic "teeth" and fixed latch with release tab, a rotation adjustment nob 34 to screw down to hold the articulating ball in a fixed position, and an adjustable strap 35 with a plastic loop for a free end of strap to pass through and fasten (using hook and loop, or other). The articulating mechanism 31 may comprise ball (as shown), or disc that rotates along a single axis, or a disc that rotates at discrete intervals along a single axis.

One variation of the present controller clip/harness uses a disc instead of a ball and socket design for the attachment between the upper assembly and the patient strap (which results in a device that only rotates a controller along singular axis).

In another exemplary variation, the present device may have bright and/or saturated green or other color plastic spheres, attached directly to the device, and/or bright green or other color plastic spheres attached to articulating arms, which are in turn, attached to the device. The articulating arm may be ridged or flexible, may be of any length, may be telescoping to allow for a variety of lengths, or may not be present.

In another exemplary variation, the present device may have retro-reflective markers.

In another exemplary variation, instead of bright and/or saturated green or other color plastic spheres, the present device may use saturated/bright green or other color plastic pyramids with different colored points on each pyramid.

In another exemplary variation, the present device may comprise different latching/attaching mechanisms (for where the controller is affixed to the clip/harness and/or patient strap). Such mechanisms may include plastic teeth and clip design, as in FIG. 53, hook and loop (e.g., Velcro®), button snap, magnetic, or zipper (for example, if incorporated into clothing).

In another exemplary variation, the present device may comprise different patient strap designs. Such designs may comprise or incorporate cloth and similar materials, hook and loop (e.g., Velcro®), leather or synthetic leather, or plastic.

In another exemplary embodiment, the present device may comprise sensors, transceivers, computers, and/or Bluetooth and/or Wi-Fi connectivity. This wireless technology may be used to send and/or receive points of platform data to and/or from other platform features and/or modules.

Measuring Tape Device

Referring to FIG. 54, a flexible non-elastic measuring tape device 40 (and/or scale) may be used to quickly assess the circumference and/or magnitude of a variety of body measurements. One exemplary embodiment of the present measuring tape device is illustrated in FIG. 54. The exemplary device 40 may comprise a clip 41 and/or affixing component (may be made out of metal, hook and loop, an adhesive, a snap, or other material) to attach device to an anatomical body part and/or physical object and/or strap. The tape device 40 may further comprise a flexible, non-elastic scale 42 with regularly spaced markers adhering to one or more conventions. The exemplary device 40 may also comprise a plastic sphere 44 colored bright green or other color.

In one variation, the exemplary device may comprise retro-reflective markers.

In another variation, the exemplary device may comprise plastic spheres colored bright green or other color and attached directly to the device. Alternatively, bright green or other color plastic spheres may be attached to articulating arms, which are in turn, attached to the device.

In another variation, fastener mechanisms may be used for affixing the measuring tape device to straps. Such fastener mechanisms may include a plastic teeth and clip design, hook and loop (e.g., Velcro®), button snap, magnetic, and zipper (for example, if incorporated into clothing).

In another variation, once the measuring tape devices are affixed to a strap, they may then be strapped to anatomical body parts for use as motion capture markers and/or devices.

In another variation, the exemplary device may incorporate sensors, transceivers, computers, and/or Bluetooth and/or Wi-Fi connectivity. Wireless technology may be used to send and/or receive points of platform data to and/or from other platform features and/or modules.

HMD Cushion Device

Referring to FIG. 55, the exemplary module may further utilize a HMD cushion device 50. This exemplary device 50 comprises a plastic and/or airtight tube 51 sealed with air, or inert gas, or non-flammable gas. Pieces of affixing material 52 may be located on one-side to create a sanitary, disposable, and universal HMD cushion. The affixing material affixes to the HMD, and may utilize hook and look (e.g., Velcro®), a button snap material, magnetic material, tape, and/or other adhesive and/or affixing materials. FIG. 55 illustrates one embodiment of this exemplary device 50.

In one variation, the exemplary device may include electrodes on the HMD and/or facial side and/or patient-facing of the HMD cushion. The electrodes may be connected in series and/or in parallel using conductive materials.

In another variation, the exemplary device may include sensors, transceivers, computers, and/or Bluetooth and/or Wi-Fi connectivity. Wireless technology may be used to send and/or receive points of platform data to and/or from other platform features and/or modules.

In another variation, the exemplary device may comprise one or more LED lights.

In another variation, the exemplary device may comprise colors and/or light-blocking materials applied to the plastic layer.

Controller Handle Sensor Device

Referring to FIG. 56, the present module may further incorporate a controller handle sensor device 60. The exemplary controller handle sensor device 60 comprises a thin, elastic, and/or flexible device primarily constructed of plastic or other material that is designed to be applied to the handle of controller devices and/or to other XR devices. The device has adhesive materials and/or properties in areas to adhere to an XR device. Additionally, the device may comprise conductive, piezoelectric, and/or resistive materials in areas in or on the device, and an electronics unit located at any position on the device. The electronics unit may comprise one or more of various items including: central processing units, processing units, memory, electronic storage, transceivers, Bluetooth connectivity, Wi-Fi connectivity, inertial movement units, accelerometers, microphones, cameras, dynamometers, potentiometers, transistors, and/or items of software, computer programming, and/or code (such as an operating system for example).

In one exemplary embodiment, the device 60 comprises an electronics unit incorporating a processing unit, memory, additional electronic storage, Bluetooth and/or Wifi, inertial measurement unit and/or accelerometer, microphone, camera, dynamometer, potentiometer, transistor, and operating system. In the exemplary embodiment shown, there is a "loop" composed of plastic or other material for the band to encircle one or more XR devices and/or one or more anatomic body parts on an individual.

When in use, the exemplary device senses, collects, processes, and/or transmits points of platform data, including points of biomarker data (such as grip strength, heart rate, points of electro-cardiographic data, temperature, galvanic skin response, and the like), vocal biomarkers, points of movement data, points of data produced by ML/AI models on the device, and/or points of other platform data. FIG. 56 illustrates the features and/or capabilities of one embodiment of the controller handle sensor device.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under 35 U.S.C. § 112(f) [or 6th paragraph/pre-AIA] is not intended. Additionally, it is not intended that the scope of patent protection afforded the present invention be defined by reading into any claim a limitation found herein that does not explicitly appear in the claim itself.

We claim:

1. A computer-based extended reality health system adapted for electronically rendering patient sessions within an XR environment comprising immersive scenes, said XR health system comprising:

an XR device adapted for being employed by a patient to visually display the immersive scenes during a patient session within the XR environment, and wherein said XR device comprises a head-mounted display;

an input device adapted for electronically interacting with objects, content and features visually displayed in the immersive scenes of the XR environment;

a plurality of software modules operable in a computing environment comprising a computing device and a processor communicating with said head-mounted display, and utilizing data and control signals of said input device to generate system data applicable in the patient session, and wherein one of said software modules comprises a billing module configured to auto-populate medical claim-related documents upon completion of a patient session; and at least one of an aroma diffuser communicating with said head-mounted display and adapted for emitting selected scents to a patient at pre-configured times during the patient session, a camera communicating with said head-mounted display and adapted for capturing a perspective of a patient, a speaker communicating with said head-mounted display and adapted for enabling audio communication to a patient, and a microphone communicating with said head-mounted display and adapted for capturing audio data relating to a patient.

2. The computer-based extended reality health system according to claim 1, and comprising an HMD cushion operatively connected to said head-mounted display and adapted to reside between said head-mounted display and a head of the patient.

3. The computer-based extended reality health system according to claim 1, wherein said plurality of software modules are further selected from a group consisting of clinical platform module, XR platform module, configuration module, integration module, light module, audio module, tactile module, anatomy module, movement module, neurological module, mental health module, pain module, and procedural and digital anesthetic module.

4. The computer-based extended reality health system according to claim 1, and comprising a positional tracking device communicating with said head-mounted display and adapted for capturing positional tracking data for positional tracking of the patient, and wherein said positional tracking device comprises at least one of a camera and a microphone.

5. The computer-based extended reality health system according to claim 4, wherein said positional tracking data comprises data selected from a group consisting of gaze tracking, pupil tracking, eye tracking, facial tracking, hand tracking, audio tracking, and body language tracking.

6. The computer-based extended reality health system according to claim 1, and comprising a releasable device fastener attached to said head-mounted display and adapted for releasably securing said head-mounted display to the patient.

7. The computer-based extended reality health system according to claim 1, and comprising a flexible measuring tape including spaced markings and adapted for being carried by the patient.

8. The computer-based extended reality health system according to claim 1, wherein said XR device further comprises a controller.

9. The computer-based extended reality health system according to claim 8, and comprising a controller handle sensor device operatively connected to said controller and adapted for being gripped by the patient to capture biomarker data.

10. The computer-based extended reality health system according to claim 9, wherein said biomarker data comprises data selected from a group consisting of grip strength, heart rate, points of electro-cardiographic data, temperature, and galvanic skin response.

11. The computer-based extended reality health system according to claim 1, and comprising at least one adaptive learning model programmatically implemented to generate system data applicable in the patient session within the XR environment.

12. The computer-based extended reality health system according to claim 1, and comprising software for rendering a virtual human avatar adapted for influencing the patient in immersive scenes during the patient session within the XR environment.

13. A method utilizing a computer-based extended reality health system adapted for electronically rendering patient sessions within an XR environment comprising immersive scenes, the method comprising:

employing an XR device to visually display the immersive scenes during a patient session within the XR environment, and wherein the XR device comprises a head-mounted display;

using an input device, electronically interacting with objects, content and features visually displayed in the immersive scenes of the XR environment; and utilizing data and control signals of the input device, generating system data applicable in the patient session; and during the patient session, effecting at least one of emitting selected scents to a patient at pre-configured times, capturing a perspective of a patient using a camera communicating with the head-mounted display, communicating with a patient using a speaker, and capturing audio data relating to a patient using a microphone communicating with the head-mounted display; and upon completion of a patient session, auto-populating medical claim related documents.

14. The method according to claim 13, and comprising using at least one of a camera and a microphone, capturing positional tracking data for positional tracking of the patient.

15. The method according to claim 14, wherein the positional tracking data comprises data selected from a group consisting of gaze tracking, pupil tracking, eye tracking, facial tracking, hand tracking, and body language tracking.

16. The method according to claim 13, and comprising rendering a virtual human avatar adapted for interacting with the patient in immersive scenes during the patient session within the XR environment.

17. The method according to claim 13, wherein the XR device further comprises a controller.

18. The method according to claim 17, and comprising a controller handle sensor device operatively connected to the controller and adapted for being gripped by the patient to capture biomarker data.

19. The method according to claim 18, wherein the biomarker data comprises data selected from a group consisting of grip strength, heart rate, points of electro-cardiographic data, temperature, and galvanic skin response.

20. The method according to claim 13, and comprising employing at least one adaptive learning model programmatically implemented to generate system data applicable in the patient session within the XR environment.

\* \* \* \* \*